United States Patent
Wang et al.

(10) Patent No.: US 10,222,368 B2
(45) Date of Patent: *Mar. 5, 2019

(54) ALZHEIMER'S DISEASE ASSAY IN A LIVING PATIENT

(71) Applicant: Pain Therapeutics, Inc., Austin, TX (US)

(72) Inventors: Hoau-Yan Wang, Philadelphia, PA (US); Lindsay Burns Barbier, Austin, TX (US)

(73) Assignee: Pain Therapeutics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,370

(22) Filed: May 27, 2016

(65) Prior Publication Data

US 2016/0266149 A1    Sep. 15, 2016

Related U.S. Application Data

(63) Continuation of application No. 13/942,326, filed on Jul. 15, 2013, now Pat. No. 9,354,223.

(60) Provisional application No. 61/671,445, filed on Jul. 13, 2012.

(51) Int. Cl.
  *G01N 33/50* (2006.01)
  *G01N 33/68* (2006.01)
  *G01N 33/94* (2006.01)

(52) U.S. Cl.
  CPC ......... *G01N 33/50* (2013.01); *G01N 33/6896* (2013.01); *G01N 33/94* (2013.01); *G01N 2333/70571* (2013.01); *G01N 2800/2821* (2013.01); *G01N 2800/52* (2013.01)

(58) Field of Classification Search
  CPC ....... G01N 2800/2821; G01N 2800/52; G01N 33/6896; G01N 2800/50; G01N 2800/56; G01N 2333/70571; G01N 33/50; G01N 33/94
  See application file for complete search history.

(56) References Cited

U.S. PATENT DOCUMENTS

| | | |
|---|---|---|
| 3,203,992 A | 8/1965 | Kunz et al. |
| 5,593,846 A | 1/1997 | Schenk et al. |
| 5,852,029 A | 12/1998 | Fisher et al. |
| 6,441,049 B2 | 8/2002 | Reitz et al. |
| 6,630,492 B1 | 10/2003 | Bauer |
| 7,049,321 B2 | 5/2006 | Fisher et al. |
| 7,560,468 B2 | 7/2009 | Sundermann et al. |
| 7,951,815 B2 | 5/2011 | Sundermann et al. |
| 8,048,890 B2 | 11/2011 | Buschmann et al. |
| 8,153,795 B2 | 4/2012 | Sundermann et al. |
| 8,273,731 B2 | 9/2012 | Heldman |
| 8,492,349 B2 | 7/2013 | Wang et al. |
| 8,580,808 B2 | 11/2013 | Barbier et al. |
| 8,580,809 B2 | 11/2013 | Barbier et al. |
| 8,614,324 B2 | 12/2013 | Barbier et al. |
| 8,653,068 B2 | 2/2014 | Barbier et al. |
| 2002/0013374 A1 | 1/2002 | Reitz et al. |
| 2005/0075505 A1 | 4/2005 | Gandhi et al. |
| 2007/0111970 A1 | 5/2007 | Cruz et al. |
| 2007/0117824 A1 | 5/2007 | Berk et al. |
| 2007/0149543 A1 | 6/2007 | Stockwell et al. |
| 2010/0279997 A1 | 11/2010 | Barbier et al. |
| 2010/0280061 A1 | 11/2010 | Barbier et al. |
| 2011/0312894 A1 | 12/2011 | Wu |

FOREIGN PATENT DOCUMENTS

| | | | |
|---|---|---|---|
| WO | WO 2001/40261 | 6/2001 | |
| WO | WO 2005095398 A1 * | 10/2005 | ........... C07D 471/10 |

OTHER PUBLICATIONS

Aboukhatwa et al. Antidepressants are a rational complementary therapy for the treatment of Alzheimer's disease. Mol Neurodegener. Mar. 12, 2010;5:10. doi: 10.1186/1750-1326-5-10.*
Petersen et al., *Arch Neurol* 56:303-308 (1999).
Naslund et al., *J Am Med Assoc* 283(12):1571-1577 (2000).
Wang et al., *J Biol Chem* 275, 5626-5632 (2000).
Wang et al., *J Neurochem* 75(3):1155-1161 (2000).
Liu et al., *Proc Natl Acad Sci, USA* 98(8):4734-4739 (2001).
Nagele et al., *Neuroscience* 110(2):199-211 (2002).
Clifford et al., *Brain Res* 1142:223-236 (2007).
ZINC12342403 Compound Summary—NCBI PubChem Chemical Database, (Nov. 2007).
CAS RN 1070805-65-0 Nov. 4, 2008.
Wang et al., *PLoS One* 3(2):e1554 (2008).
Borgmann-Winter et al., *Neuroscience* 158:642-653 (2009).
Sarasa et al., *Current Alzheimer Res.*, 6:171-178 (2009).
Wang et al., *J Neurosci* 29(35):10961-10973 (2009).
Wang et al., *PLos One* 4(1):e4282 (2009).
Burns et al., *Recent Patents on CNS Drug Discovery* 5:210-220 (2010).

(Continued)

*Primary Examiner* — Gregory S Emch
(74) *Attorney, Agent, or Firm* — Husch Blackwell LLP

(57) ABSTRACT

An assay for Alzheimer's disease (AD) pathology in a living patient is disclosed wherein an amount of α7nAChR or TLR4 in a FLNA-captured protein complex or α7nAChR in an Aβ-captured protein complex or α7nAChR-FLNA, TLR4-FLNA and/or α7nAChR-Aβ$_{42}$ complex present as a protein-protein complex in a sample is compared to the amount in a standard sample from a person free of AD pathology. An amount greater than in the standard sample indicates AD pathology. Also disclosed is an assay predictive of prognosis for treatment with a medicament in which the amount of an above protein or protein complex is compared to an amount in the presence of a medicament that binds to a FLNA pentapeptide and contains at least four pharmacophores of FIGS. 7-12. An amount of protein or protein complex determined in the presence of the medicament that is less than the first amount indicates a favorable treatment prognosis.

8 Claims, 49 Drawing Sheets
Specification includes a Sequence Listing.

(56) References Cited

OTHER PUBLICATIONS

Arnold et al., *Ann Neurol* 67(4):462-469 (2010).
Wang et al., *J Neurosci* 32(29):9773-9784 (Jul. 18, 2012).
International Search Report WO 2014/012054; Published Jan. 16, 2014.
Jones et aql., *J Mol Neurosci* 30(1-2):83-84 (2006).
Wang et al., *J Biopsych* 67(6):522-530 (2010).
Supplementary European Search Report for EP 13 81 6628 (dated Nov. 26, 2015).
*Remingtom: The Science and Pracrice of Pharmacy*, 20$^{th}$ ed., Gennaro ed., Lippincott, Williams and Wilkins, Philadelphia, PA (2000), pp. 552-553.
US PTO Action in U.S. Appl. No. 14/137,374 dated Sep. 11, 2015.
CAS RN 1170830-83-7 (entered into STN on Jul. 13, 2009).
International Search Report WO 2013/050368, dated Oct. 21, 2013.
Amended claims as filed in Europe for EP 13 18 6628.
Wang et al. Manuscript submitted to *Neurobiol Aged*.
Sachdev, *Dementia News*, Jan. 21, 2012.
Weintraub et al., *Am J Geriatric Psychiatry*, (Apr. 2010) 18(4):332-340.
Banerjee et al,. *The Lancet*, (Jul. 30-Aug. 11, 2011), 378(9789):403-411.
Bui, *Am Fam Physician* (Jan. 1, 2012) 85(1):20-22.

\* cited by examiner

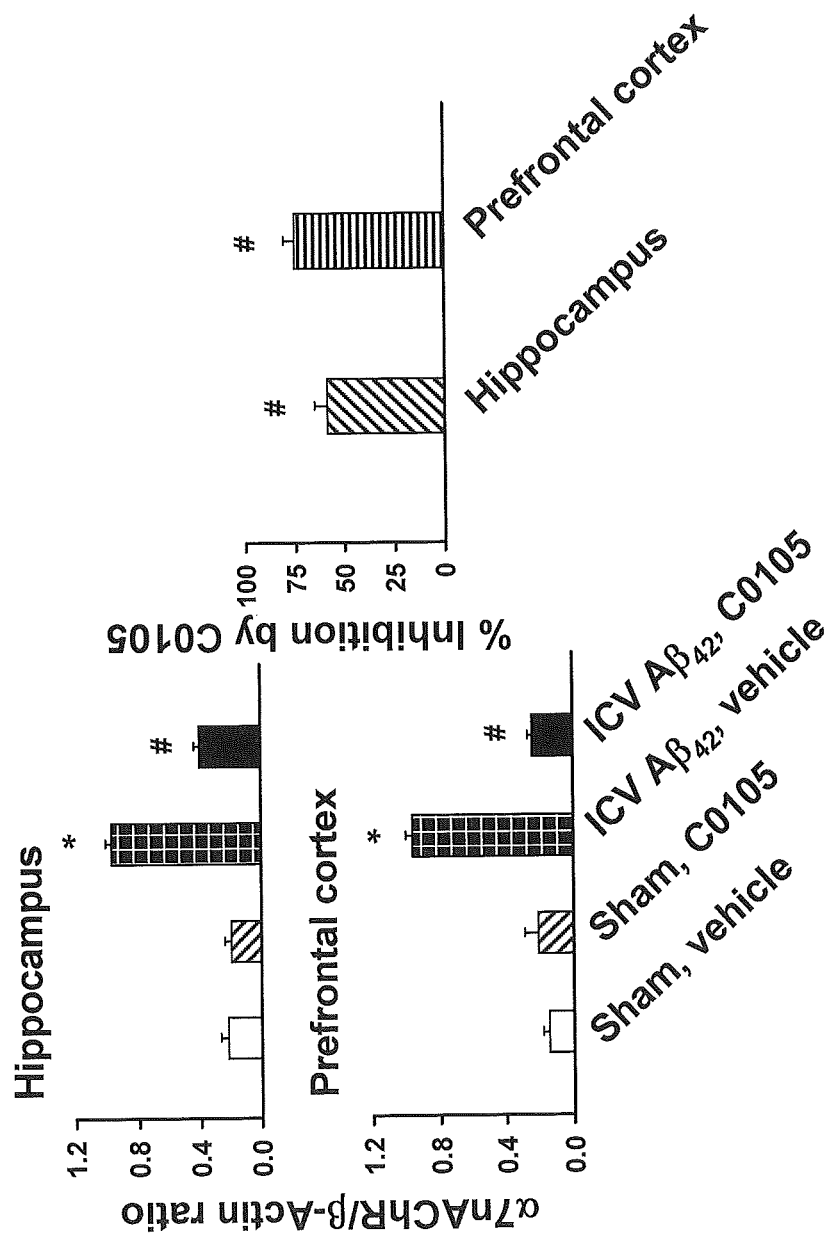

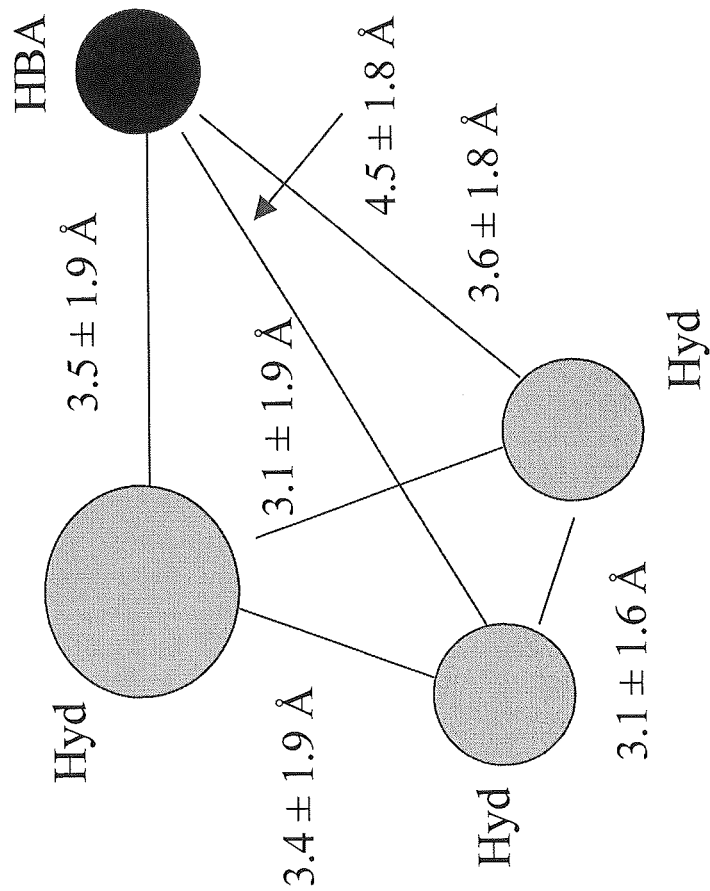
Fig. 9 Pharmacophore 3

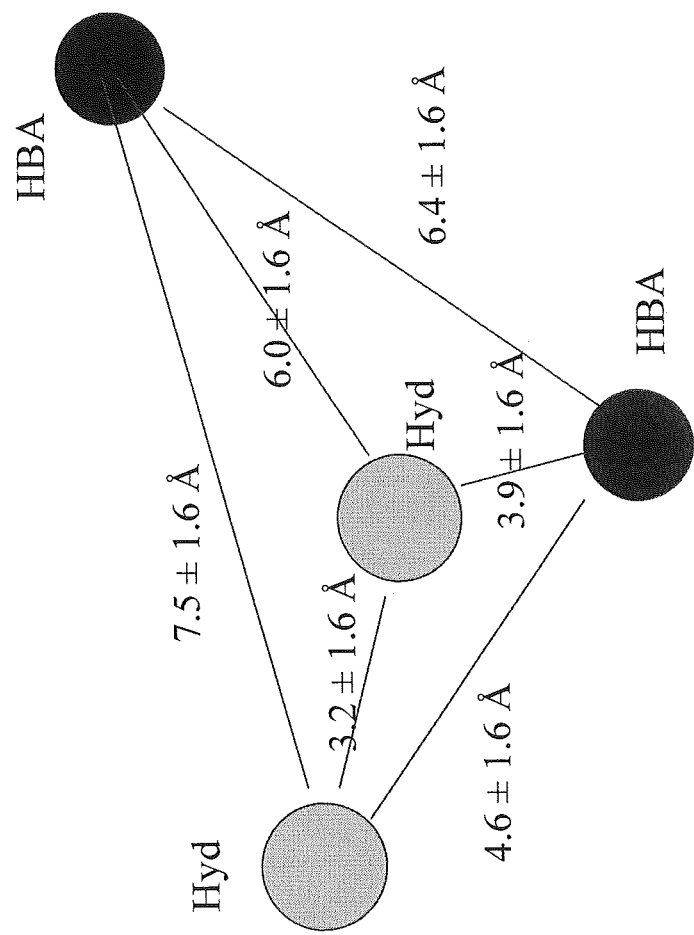
Fig. 10 Pharmacophore 4

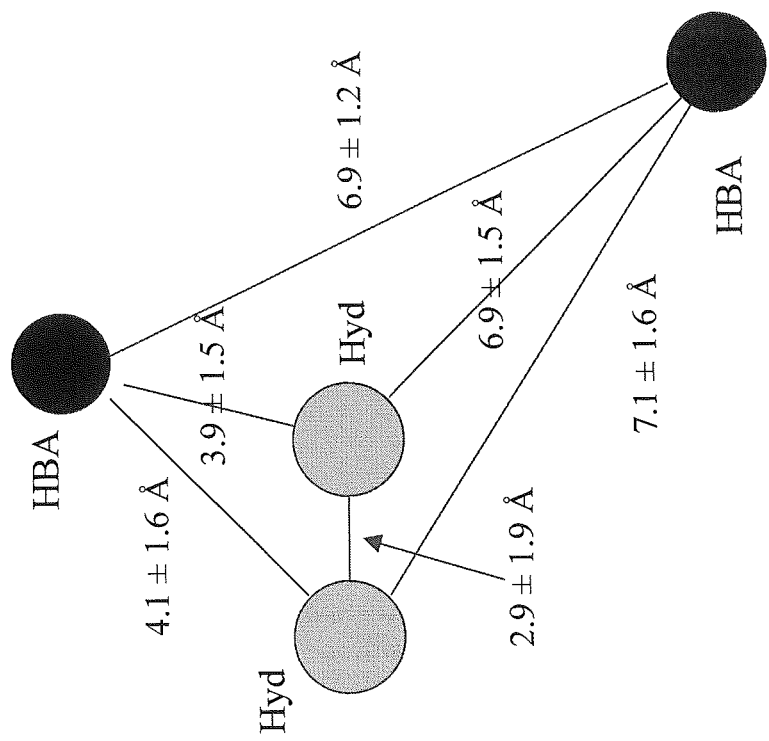
Fig. 11 Pharmacophore 5

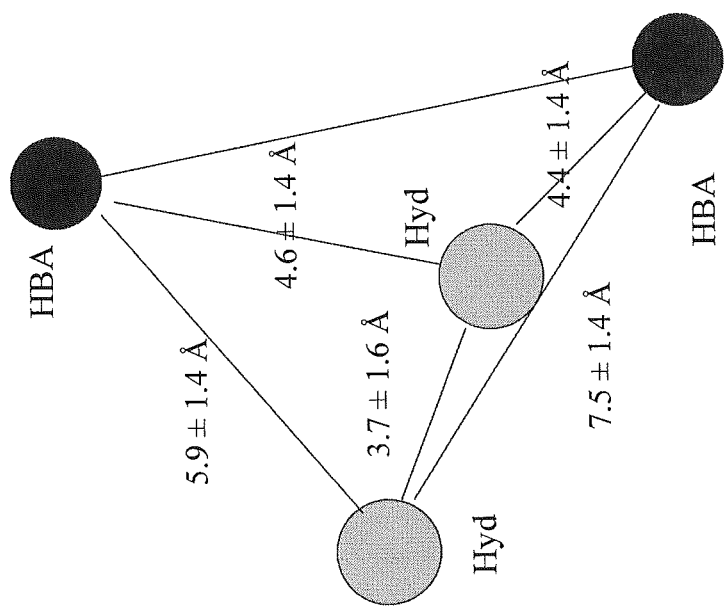
Fig. 12 Pharmacophore 6

ALZHEIMER'S DISEASE ASSAY IN A LIVING PATIENT

CROSS-REFERENCE TO RELATED APPLICATIONS

This application is a continuation of application Ser. No. 13/942,326, now U.S. Pat. No. 9,354,223, that was filed on Jul. 15, 2013, and claims priority from application Ser. No. 61/789,180 that was filed on Mar. 15, 2013, and from application Ser. No. 61/671,445 that was filed on Jul. 13, 2012, whose disclosures are incorporated herein by reference.

TECHNICAL FIELD

The present invention relates to Alzheimer's disease (AD), and more particularly in one aspect, to an assay that can detect the disease (AD pathology) in a living patient, whereas in another aspect, an assay is contemplated that is predictive of the prognosis for treatment with a particular medicament type in a patient that exhibits symptoms of AD, and in yet another aspect, an assay is contemplated that indicates the efficacy of such a patient's treatment.

BACKGROUND ART

Alzheimer's disease (AD) represents one of the greatest health care burdens, with 35 million affected individuals worldwide, a population estimated to increase to 115 million by 2050. [Wimo, *Alzheimer's Disease International World Report* 2010. *The Global Economic Impact of Dementia*, Alzheimer's Disease International (2010).] AD is a devastating dementia that first presents as progressive memory loss and later can include neuropsychiatric symptoms such as depression, paranoia, agitation and even aggression. Currently, available AD treatment is limited to cognitive enhancers with limited and short-lived efficacy.

Previously, diagnosis of AD could only be confirmed at autopsy by the presence of amyloid deposits and neurofibrillary tangles (NFTs) containing the microtubule-associated protein tau. Current clinical diagnoses of AD satisfy the DSM-IV TR and the NINCDS-ADRDA Work Group criteria for probable AD in McKhann et al., *Neurology* 34(7):939-944 (1984). Initial diagnostic criteria based mostly on subjective assessments set out in McKhann et al., above, require that the presence of cognitive impairment and a suspected dementia syndrome be confirmed by neuropsychological testing for a clinical diagnosis of possible or probable AD; although they need histopathologic confirmation (microscopic examination of brain tissue) for the definitive diagnosis.

The criteria specify as well eight cognitive domains that may be impaired in AD. Those cognitive domains that may be impaired in AD are: memory, language, perceptual skills, attention, constructive abilities, orientation, problem solving and functional abilities. These criteria have shown good reliability and validity, and are those used herein as the basis for assertion of clinical diagnosis of AD.

Clinical criteria for the diagnosis of Alzheimer's disease include insidious onset and progressive impairment of memory and other cognitive functions. There are no motor, sensory, or coordination deficits early in the disease. The diagnosis could not heretofore be determined by laboratory assays. Such assays are important primarily in identifying other possible causes of dementia that must be excluded before the diagnosis of Alzheimer's disease can be made with confidence. Neuropsychological tests provide confirmatory evidence of the diagnosis of dementia and help to assess the course and response to therapy. The criteria proposed by McKhann et al. are intended to serve as a guide for the diagnosis of probable, possible, and definite Alzheimer's disease; these criteria will likely be revised as more definitive information become available.

Diagnostic criteria have more recently been refined to include the prodromal phase (early symptoms that occur before the full-blown symptoms of the disease hit) termed "Mild Cognitive Impairment (MCI) due to AD." This new diagnosis reflects a desire to treat the disease earlier because the neuropathology is estimated to start 10 years prior to appearance of symptoms. [Trojanowski et al., *Alzheimers Dement* 6, 230-238 (2010)] Clinical trials of potential disease-modifying treatments have been hugely disappointing, possibly in part because even an "early-stage" patient already has a massive amyloid-beta (Aβ) burden and substantial pathologies with significant synaptic defects and inflammation.

According to Petersen et al., *Arch Neurol* 56(3):303-308 (1999), the primary distinction between control subjects and subjects with MCI is in the area of memory, whereas other cognitive functions are comparable. However, when the subjects with MCI were compared with the patients with very mild AD, memory performance was similar, but patients with AD were more impaired in other cognitive domains as well. Longitudinal performance demonstrated that the subjects with MCI declined at a rate greater than that of the controls but less rapidly than the patients with mild AD.

Patients who meet the criteria for MCI can be differentiated from healthy control subjects and those with very mild AD. They appear to constitute a clinical entity that can be characterized for treatment interventions.

Amyloid-beta (Aβ), a peptide of 39-42 amino acids that is generated in vivo by specific, proteolytic cleavage of the amyloid precursor protein (APP) by β- and γ-secretases. $A\beta_{42}$ comprises residues 677-713 of the APP protein, which is itself a 770-residue transmembrane protein having the designation P05067 in the UniProtKB/Swiss-Prot system. Aβ, and in particular the $A\beta_{42}$, is commonly believed to be the principal causative agent in AD, although its mechanism underlying AD neuropathologies is debated.

Cognitive impairment and the magnitude of synaptic deficit in AD brain is more highly correlated with soluble Aβ than with the abundance of amyloid plaques, suggesting it is the soluble Aβ that causes active impairment. [Naslund et al., *JAMA* 283, 1571-1577 (2000)] Robust evidence demonstrates that soluble Aβ can elicit a toxic signaling cascade via the α7nAChR leading to impaired synaptic activities and subsequent $A\beta_{42}$ intraneuronal aggregates and cognitive deficits. [Wang et al., *J Neurosci* 35, 10961-10973 (2009); Liu et al., *PNAS* 98, 4734-4739 (2001); Pettit et al., *J Neurosci* 21, RC120-RC125 (2001); Chen et al., *Neuropharmacology* 50, 254-268 (2006); and Dziewczapolski et al., *J Neurosci* 29, 8805-8815 (2009)] $A\beta_{42}$ binds the α7nAChR with extraordinarily high (high femtomolar) affinity [Wang et al., *J Biol Chem* 275, 5626-5632 (2000); and Wang, et al., *J Neurochem* 75, 1155-1161 (2000)] and this interaction activates the kinases ERK2 and JNK1, which phosphorylate tau protein, leading to the formation of neurofibrillary tangles (NFTs). [Wang et al., *J Biol Chem* 278, 31547-31553 (2003)]

Pharmacotherapies have attempted to disrupt $A\beta_{42}$-elicited toxic signaling by preventing $A\beta_{42}$ from binding to α7nAChRs, a difficult task for two reasons: first, surpassing the sub-picomolar affinity of the interaction requires an even higher affinity interaction, and second, directly targeting the receptor with chronic receptor agonists or antagonists can alter its sensitivity or cell surface expression level. In fact, the desensitization of acetylcholine receptors following enhanced and prolonged stimulation due to administration of acetylcholinesterase inhibitors, the only approved therapy for AD, is thought to be the primary reason that this class of drugs provides only short-lived cognitive enhancement.

The present invention utilizes that sub-picomolar interaction (protein-protein complex formation) between $A\beta_{42}$ and α7nAChR, and similar newly found protein associations (complexes), between α7nAChR and FLNA, and also TLR4 and FLNA as bases for a contemplated objective assay that can diagnose the presence of AD in a living person using the relatively non-invasive technology of body sampling. In another aspect, those same $A\beta_{42}$-α7nAChR, α7nAChR-FLNA, and TLR4-FLNA interactions are utilized as bases for a contemplated objective prognostic and biomarker assay that can indicate the prognosis of treatment as well as track disease progression and treatment efficacy in a living, presumed AD patient using the relatively non-invasive technology of body sampling and a compound that exhibits particular binding activity similar to those of a compound used for treatment.

BRIEF SUMMARY OF THE INVENTION

In one aspect, the present invention contemplates a method for determining the likelihood of the presence of Alzheimer's disease (AD) or "mild cognitive impairment due to AD" in a living patient. The method comprises the steps of determining the amount of α7nAChR or TLR4 in a FLNA-captured protein complex or α7nAChR in an Aβ-captured protein complex [also referred to herein as i) α7nAChR/FLNA, ii) TLR4/FLNA and iii) α7nAChR/Aβ protein ratios] in a standard body sample preparation from a living, typically adult, typically cognitively-impaired patient to be assayed for the presence of AD. The value (amount or level) so determined is compared with the value of the same determination in a standard body sample preparation from a person free of AD pathology. The value (amount or level) so determined is compared with the value of the same determination established from a standard body sample preparation from a person free of AD pathology.

It is preferred to utilize a ratio of one or more of the amounts of i) α7nAChR/FLNA, ii) TLR4/FLNA and iii) α7nAChR/Aβ protein complexes. However, an amount of α7nAChR or TLR4 from one of those complexes can also be used, although possibly with some loss of accuracy and/or precision. A value of a protein amount or ratio present from the assayed patient that is significantly greater than the value present in the standard body sample preparation from a person without AD pathology is consistent with and therefore indicates the presence of AD pathology.

A body sample is preferably olfactory neuroepithelial cells, lymphocytes, or cells from a brain biopsy. Lymphocytes are a particularly preferred body sample for this assay because of the ease in obtaining those cells and are used illustratively herein.

More preferably, the assay is carried out in two stages, but in no particular order. For convenience in description, in a first stage, a first portion of a body sample preparation as above is assayed as described above to determine the amount of one or more of α7nAChR or TLR4 or of i) α7nAChR/FLNA, ii) TLR4/FLNA and iii) and α7nAChR/Aβ protein ratios present in a captured complex such as one or both of an anti-FLNA immunoprecipitate, or in the latter case, in an anti-Aβ immunoprecipitate. An excess of Aβ free of complexed protein over that normally present in a body sample preparation from a patient free of AD pathology is admixed (exogenously supplied Aβ) with a second portion of the body sample and the amount of one or more of α7nAChR or TLR4 or of i) α7nAChR/FLNA, ii) TLR4/FLNA and iii) and α7nAChR/Aβ ratios is determined in preferably the same manner as the first determination, as in a respective anti-FLNA or anti-Aβ immunoprecipitate. The excess Aβ can also be referred to as a "α7nAChR-saturating amount" of Aβ in that α7nAChR is a receptor whose binding site for Aβ can be fully occupied and therefore be saturated.

An illustrative excess of Aβ free of complexed protein is an amount sufficient to provide a concentration in the sample preparation portion of about 1 nM or greater. Admixture of an amount sufficient to provide a concentration of at least about 100 nM is preferred. A determined amount of α7nAChR or TLR4 or of a complex ratio value present in the first body sample preparation portion that is significantly greater than the value established in the body sample of a person free of AD pathology and/or comparable to the value present in the second sample (added Aβ-containing sample) is consistent with and therefore indicates the presence of AD pathology or "mild cognitive impairment due to AD". It is to be understood that "Aβ free of complexed protein" describes the state of the Aβ prior to admixture in that the Aβ can form a protein-protein complex after admixture.

In another embodiment of a more preferred aspect of the invention, the first body sample preparation portion is assayed as discussed above. The second body sample preparation portion is admixed with a FLNA-binding effective amount of a compound that binds to the FLNA pentapeptide of SEQ ID NO: 1, rather than admixture with Aβ as discussed above. A contemplated FLNA-binding compound inhibits at least about 60 percent of the FITC-labeled naloxone binding when present at a 10 μM concentration and using unlabeled naloxone as the control inhibitor at the same concentration, and preferably inhibits about 70 percent. A FLNA-binding effective amount is typically that amount that provides a compound concentration of about 0.1 nM to about 10 nM. The FLNA-binding compound preferably contains at least four of the six pharmacophores of FIGS. 7-12, and preferably contains at least five of those six pharmacophores, and is preferably an opioid receptor antagonist or mixed agonist/antagonist (collectively referred to as an antagonist compound) or one or more of a compound of Series A, B, C-1, C-2, D or E described hereinafter, or a pharmaceutically acceptable salt thereof.

A significant lessening of the determined value of the α7nAChR or TLR4 or of the protein complex ratio in the presence of that FLNA-binding compound compared to the amount determined in the compound's absence is consistent with the patient from whom the sample was obtained having AD pathology or "mild cognitive impairment due to AD". On the other hand, the value of the ratio of proteins obtained from a normal patient free of AD pathology symptoms is substantially unchanged (not significantly different) from the amount determined in the absence of the contemplated compound.

Another embodiment of the present invention contemplates a method for determining the prognosis of treatment of a living, typically adult, cognitively-impaired patient that may have AD with an effective amount of compound or a pharmaceutically acceptable salt thereof that binds in an aqueous composition to a pentapeptide of filamin A (FLNA)

of SEQ ID NO: 1 and contains at least four of the six pharmacophores of FIGS. 7-12 as discussed above.

The method comprises the steps of: a) determining the amount of α7nAChR or TLR4 or of one or more of α7nAChR-FLNA, TLR4-FLNA and α7nAChR-Aβ [or i) α7nAChR/FLNA, ii) TLR4/FLNA and iii) α7nAChR/Aβ protein ratios in a protein-protein complex such as that present in an anti-FLNA or anti-Aβ immunoprecipitate] in a first body sample preparation portion from the living patient; b) a second body sample preparation portion from that living patient is provided that further contains an exogenously provided binding-effective amount of an antagonist compound or one or more of a compound of Series A, B, C-1, C-2, D or E or its salt as described above, and the value of the same one of the α7nAChR or TLR4 or the one or more of α7nAChR-FLNA, TLR4-FLNA and α7nAChR-Aβ protein association ratios as in the first portion is determined in that second body sample; c) the values determined in steps a) and b) are compared. A significant lessening of the determined value in the presence of that FLNA-binding compound compared to the amount determined in the compound's absence is consistent with a prognosis of a benefit to the patient from whom the sample was obtained through use of the treatment.

Yet another contemplated assay indicates the efficacy of the treatment for improving cognition given to a living, typically adult, cognitively-impaired patient. That method comprises the steps of: a) determining a first value of α7nAChR or TLR4 or one or more of α7nAChR-FLNA, TLR4-FLNA and α7nAChR-Aβ protein association ratios in a body sample preparation from that living patient. b) Treating the patient with a therapeutic composition such as a composition containing an effective amount of an antagonist compound or a compound of Series A, B, C-1, C-2, D or E or a pharmaceutically acceptable salt thereof that binds to the FLNA peptide of SEQ ID NO: 1 as described hereinafter, a cholinesterace inhibitor such as one or more of those sold under the name donepezil, rivastigmine tartrate, galantamine hydrobromide, or tacrine, or a NMDA receptor antagonist such as memantine, or an investigational or commercially available therapeutic whose mechanism of action results in a reduction of amyloid deposits in the brain. c) Thereafter, a second value of the same of α7nAChR or TLR4 or one or more of α7nAChR-FLNA, TLR4-FLNA and α7nAChR-Aβ protein association ratio in a body sample preparation determined in step a) is (are) determined. d) The levels of α7nAChR or TLR4 or of the one or more protein association ratios determined before, periodically during and after the treatment are compared. In that comparison, a subsequently determined value that is significantly less than the first determined value (treated less than untreated) is consistent with the therapeutic treatment being effective in providing an improvement in the patient's disease state. Alternately, a patient undergoing treatment whose lymphocytes become less responsive to an FLNA-binding compound or more responsive to Aβ as determined in the above embodiments, is consistent with the therapeutic treatment being effective in providing improvement in the patient's disease state.

In some embodiments, a contemplated assay is carried out as a solid phase assay. In one embodiment, the assay is carried out using a first, capture receptor affixed to the well of an assay plate. In another embodiment, the assay is carried out with the first, capture receptor affixed to water-insoluble surface or particles.

BRIEF DESCRIPTION OF THE DRAWINGS

In the drawings forming a part of this disclosure,
FIG. 1, in three panels, illustrates that FLNA associations with α7nAChR and TLR4 (FIG. 1A) and Aβ$_{42}$ and α7nAChR linkage (FIG. 1B) are markedly increased in lymphocytes from AD patients and Aβ$_{42}$-incubated lymphocytes from control subjects compared to those in Kreb's-Ringer (K-R) vehicle-treated lymphocytes from age-matched control subjects. Additionally, Compound C0105 incubation for 30 minutes in the lymphocyte preparation prior to determining the amount of complex present significantly decreased these associations in AD lymphocytes and in control lymphocytes incubated simultaneously with exogenous Aβ$_{42}$. Western blots (FIGS. 1A and 1B) were quantified by densitometric scanning (FIG. 1C). Data are means±SEM of the levels of α7nAChR or TLR4 in an anti-FLNA immunoprecipitate or α7nAChR in an anti-Aβ immunoprecipitate. n=2. **p<0.05, *p<0.01 vs. vehicle-treated control; ##p<0.05, #p<0.01 vs. Aβ$_{42}$-treated control or vehicle-treated AD. Numerals outside of and to the left of the blots of this and the remaining figures are molecular weight positions within the blots.

FIG. 2 also demonstrates that Compound C0105 can reduce all three associations in AD lymphocytes or in control lymphocytes treated with exogenous Aβ$_{42}$. Because exogenous Aβ$_{42}$ was used with control lymphocytes to show treatment effects of Compound C0105, the level of Aβ$_{42}$ was normalized to β-actin. *p<0.01 compared to vehicle-treated control; #p<0.01 compared to Aβ$_{42}$-treated control or vehicle-treated AD.

FIG. 7 through FIG. 12 represent schematic pharmacophores (Pharmacophores 1-6, respectively) showing relative locations of chemical features such as a hydrogen bond acceptor (HBA), an aromatic/hydrophobe (ARO/HYD) center, and the intramolecular distances there between in Angstroms for a compound that binds to the pentameric peptide of FLNA of SEQ ID NO: 1.

FIG. 14 in three panels.

FIG. 15, in two panels.

FIG. 16, in four parts as FIGS. 16A, 16B, 16C and 16D, are graphs that illustrate the binding of radio-labeled naloxone [$^3$H]NLX in the presence of naltrexone (NTX) or illustrative Compound C0105 to the filamin A (FLNA) or the filamin A (FLNA) pentamer of SEQ ID NO. 1 determined by a displacement assay as reported in Wang et al., *PLoS One.* 3(2):e1554 (2008).

FIG. 17, in two panels as FIG. 17A and FIG. 17B, are graphs showing amounts of α7nAChR assayed by ELISA as an α7nAChR/FLNA protein-protein complex measured by optical density ($OD_{450}$) present in varying amounts of lymphocyte lysates.

FIG. 18, in five panels as FIG. 18A, FIG. 18B, FIG. 18C and FIG. 18D, show the ELISA assay results as in FIG. 17, using indicated amounts per well of lysate from lymphocytes obtained from an Alzheimer's disease patient (FIG. 18A, X's) and lymphocyte lysate from that patient to which was added sufficient Compound C0105 (filled circles) to provide a 10 µM concentration, whereas FIG. 18C is similarly prepared using lymphocyte lysate from a YCI subject (X's) and the same lysate to which a saturating amount of A$\beta_{42}$ (100 nM final concentration) was added (filled circles), whereas

FIG. 21, in five panels as FIG. 21A-FIG. 21E, shows the effects or lack thereof of 1 nM of illustrative Compound C0105 on the amounts of the protein-protein complexes α7nAChR/FLNA, TLR4/FLNA and α7nAChR/A$\beta_{42}$ present in lymphocyte preparations from young cognitively intact (YCI) subjects and patients exhibiting AD symptoms.

ABBREVIATIONS AND SHORT FORMS

Figure 1A:
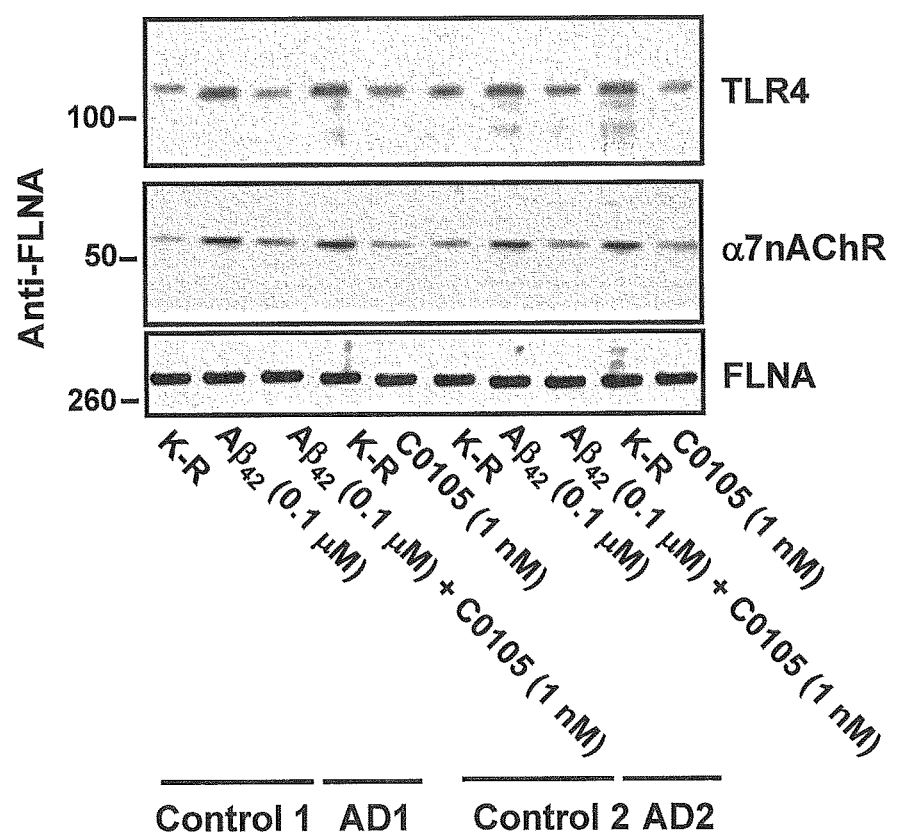

The following abbreviations and short forms are used in this specification.

"Aβ" means amyloid-beta and indicates a 39-42 residue sequence of the 770-residue amyloid precursor protein (APP) protein (A$\beta_{39}$=positions 672-710, A$\beta_{40}$=positions 672-711, A$\beta_{41}$=positions 672-712)

"A$\beta_{42}$" means a 42-residue peptide that has the sequence of positions 677-713 of the amyloid precursor protein (APP) protein "α7nAchR" means alpha-7 nicotinic acetylcholine receptor "DAMGO" means [D-Ala2, N-MePhe4, Gly-ol]-enkephalin "ERK2" means extracellular signal-regulated kinase 2

"FCX" means frontal cortex or prefrontal cortex

"FLNA" means filamin A

"FITC" means fluorescein isothiocyanate

"Gs" means G protein stimulatory subtype, stimulates adenylyl cyclase

"HP" means hippocampus

"IHC" means immunohistochemistry

"IR" means insulin receptor

"MOR" means µ. opioid receptor

"NLX" means naloxone

"NTX" means naltrexone

"NFTs" means neurofibrillary tangles

"NMDA" means N-methyl-D-aspartate

"NMDAR" means NMDA receptor

"pERK2" means phosphorylated ERK2

"pTau" means hyperphosphorylated tau protein

"TLR4" means toll-like receptor-4

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed hereinafter to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. An aralkyl substituent group such as benzyl is deemed an aromatic group as being an aromatic ring bonded to an X group, where X is $CH_2$. A substituent group containing both an aliphatic ring and an aromatic ring portion such as tetralin (tetrahydronaphthalene) that is linked directly through the aliphatic portion to the depicted ring containing the W group is deemed a non-aromatic, hydrocarbyl group. On the other hand, a similar group bonded directly via the aromatic portion, is deemed to be a substituted aromatic group. Where a specific aliphatic hydrocarbyl substituent group is intended, that group is recited; i.e., $C_1$-$C_4$ alkyl, methyl or dodecenyl. Exemplary hydrocarbyl groups contain a chain of 1 to about 12 carbon atoms, and preferably 1 to about 8 carbon atoms, and more preferably 1 to 6 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl, decyl, dodecyl and the like. Cyclic alkyl radicals such as cyclo propyl, cyclobutyl, cyclopentyl, cyclohexyl and cycloheptyl are also contemplated, as are their corresponding alkenyl and alkynyl radicals. Examples of suitable straight and branched chain alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of straight and branched chain alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups. On the other hand, a hydrocarbyl group containing a —C(O)— functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as acetyl and acetoxy, acryloyl and acryloyloxy.

Carboxyl-related linking groups between the central spiro ring system and an aromatic or heteroaromatic ring system, circle A, include several types of ester and amide bonds. Illustrative of such bonds are sulfonamide, sulfonate and thiosulfonate esters that can be formed between a $SO_2$-containing group [also sometimes shown as a $S(=O)_2$ group] and an amine, oxygen or sulfur atom, respectively. Amide, ester and thioester links can be formed between an aromatic or heteroaromatic ring containing a C(O) [also sometimes shown as (C=O)] group and a nitrogen, oxygen or sulfur atom, respectively. Similarly, a guanidino linker can be formed between an aromatic or heteroaromatic ring containing a NHC(NH) [NHC(=NH)] group and a nitrogen, a urethane, carbonate or thiocarbonate can be formed between an aromatic or heteroaromatic ring containing a OC(O) [or OC(=O)] group and a nitrogen, oxygen or sulfur, respectively. A compound containing a urea linker, urethane linker or isothiourea linker [NHC(O)S] {or [NHC(=O)S]} can be formed between an aromatic or heteroaromatic ring containing a NHC(O) group and a nitrogen, oxygen or sulfur, respectively. A thiourea linkage is also contemplated.

A "carboxyl" substituent is a —C(O)OH group. A $C_1$-$C_6$ hydrocarbyl carboxylate is a $C_1$-$C_6$ hydrocarbyl ester of a carboxyl group. A carboxamide is a —C(O)$NR^3R^4$ substituent, where the R groups are defined elsewhere and are numbered here as 3 and 4 for ease in further discussion, but need not be so numbered in the following chemical formulas. Similarly, a sulfonamide is a —S(O)$_2NR^3R^4$ substituent, where the R groups are defined hereinafter. Illustrative $R^3$ and $R^4$ groups that together with the depicted nitrogen of a carboxamide form a 5-7-membered ring that optionally contains 1 or 2 additional hetero atoms that independently are nitrogen, oxygen or sulfur, include morpholinyl, piperazinyl, oxathiazolyl, 1,2,3-triazolyl, 1,2,4-triazolyl, pyrazolyl, 1,2,4-oxadiazinyl and azepinyl groups.

As a skilled worker will understand, a substituent that cannot exist such as a $C_1$ alkenyl or alkynyl group is not intended to be encompassed by the word "hydrocarbyl", although such substituents with two or more carbon atoms are intended.

The term "aryl", alone or in combination, means a phenyl, naphthyl or other radical as recited hereinafter that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O-arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

As used herein, the term "binds" refers to the adherence of molecules to one another, such as, but not limited to, the interaction of a ligand with its receptor, or a polypeptide of SEQ ID NO: 1 with a small molecule such as the compounds disclosed herein.

As used herein, the term "FLNA-binding compound" refers to a compound that binds to the scaffolding protein filamin A, or more preferably to a polypeptide comprising residues -Val-Ala-Lys-Gly-Leu-(SEQ ID NO: 1) of the FLNA sequence that correspond to amino acid residue positions 2561-2565 of the FLNA protein sequence as noted in the sequence provided at the web address: UniProtKB/Swiss-Prot entry P21333, FLNA-HUMAN, Filamin-A protein sequence. A FLNA-binding compound can inhibit the MOR-Gs coupling caused by agonist stimulation of the μ opioid receptor via interactions with filamin A, preferably in the $24^{th}$ repeat region.

As used herein, the term "opioid receptor" refers to a G protein-coupled receptor located in the CNS that interacts with opioids. More specifically, the μ opioid receptor is activated by morphine causing analgesia, sedation, nausea, and many other side effects known to one of ordinary skill in the art.

As used herein, the term "opioid agonist" refers to a substance that upon binding to an opioid receptor can stimulate the receptor, induce G protein coupling and trigger a physiological response. More specifically, an opioid agonist is a morphine-like substance that interacts with MOR to produce analgesia.

As used herein, the term "opioid antagonist" refers to a substance that upon binding to an opioid receptor inhibits the function of an opioid agonist by interfering with the binding of the opioid agonist to the receptor.

As used herein the term "ultra-low-dose" or "ultra-low amount" refers to an amount of compound that when given in combination with an opioid agonist is sufficient to enhance the analgesic potency of the opioid agonist. More specifically, the ultra-low-dose of an opioid antagonist is admixed with an opioid agonist in an amount about 1000- to about 10,000,000-fold less, and preferably about 10,000- to about 1,000,000-fold less than the amount of opioid agonist.

As used herein an "FLNA-binding effective amount" or more simply an "effective amount" refers to an amount of a contemplated compound sufficient to bind to the FLNA pentapeptide of SEQ ID NO: 1 and perform the functions described herein, such as inhibiting at least about 60 percent, and preferably about 70 percent, of the FITC-labeled naloxone binding when present at a 10 μM concentration and using unlabeled naloxone as the control inhibitor at the same concentration. An effective amount of a contemplated compound is most easily determined using the in vitro assay of Example 1. Using that definition, an effective amount of a contemplated compound binds to a pentapeptide of SEQ ID NO: 1 with at least about 60 percent of the value obtained when using naloxone as the control inhibitor at the same concentration as the contemplated compound, and up to about twice (200 percent) the value obtained with naloxone as control.

As used herein the term "pharmacophore" is not meant to imply any pharmacological activity. A pharmacophore can be defined as the relevant groups on a molecule that interact with a receptor and are responsible for the activity of the compound. [R. B. Silverman, *The Organic Chemistry of Drug Design and Drug Action*, $2^{nd}$ ed., Elsevier Academic Press, Amsterdam, (2004), p. 17.] The term refers to chemical features and their distribution in three-dimensional space that constitutes the preferred requirements for molecular interaction with a receptor (See, U.S. Pat. No. 6,034,066). A pharmacophore is calculated by determining the shared aromatic/hydrophobic and hydrogen bond acceptor functions and the distances there between of a group of compounds that bind similarly to a particular receptor, here, pentapeptide of SEQ ID NO: 1.

As used herein, the term "receptor" is broadly used to refer to an entity with which another entity, a ligand, specifically binds. A receptor is generally a macromolecule and a ligand is generally a smaller, lower molecular weight molecule, but that distinction is not required. Some receptors discussed herein are specific proteins such as the Toll-like receptor 4, MOR and α7nAchR, and those receptors can themselves be ligands for other receptors such as antibodies. Other receptors include whole antibodies and antibody combining site portions (paratopes) that immunoreact with specific epitope ligands, as well as proteins such as Staphylococcal and Streptococcal proteins A and G, respectively, that bind to Fab and Fc antibody portions. Biotin and avidin (streptavidin) can also be viewed as a ligand-receptor pair, as can aptamers.

As used herein, the phrase "significantly different" and "significant difference" and like terms and phrases mean that if an assay is repeated, the compared results will differ by greater than one standard deviation of either measurement, preferably by greater than two standard deviations, and more preferably by three standard deviations.

DETAILED DESCRIPTION OF THE INVENTION

The present invention contemplates an assay method for determining the likelihood of the presence of Alzheimer's disease pathology (AD pathology) in a living patient, albeit, the assay is carried out extracorporeally. A contemplated assay method includes the steps of a) determining the amount of α7nAChR or TLR4 or one or more of an α7nAChR-FLNA, a TLR4-FLNA and an α7nAChR-Aβ [also referred to herein as i) α7nAChR/FLNA, ii) TLR4/FLNA and iii) α7nAChR/Aβ] protein ratios in a protein-protein complex present in a body sample preparation from a living (typically adult and typically cognitively-impaired) patient to be assayed for the presence of AD; and b) comparing that (those) amount(s) with the amount(s) of the same protein or ratio or ratios in a standard body sample from a person free of AD pathology.

A protein ratio refers to the level of one protein associated with (bound to) the other protein present in a protein-protein complex present within the body sample preparation. Usually, the proteins are co-precipitated in an immunoprecipitate formed by immunoreaction with an antibody to one or the other of the two proteins sought to be assayed. The protein amounts present are measured by Western blot probing of the co-immunoprecipitated proteins, or by ELISA or FITC detection of the proteins adhered to one another, or the like. An individual protein or a protein complex can also be obtained using affinity techniques as in a column or as in an antibody-combining site containing molecule bound to a bead.

A determined amount from an assayed patient that is statistically significantly greater than the amount present in the standard sample is consistent with and therefore indicates the presence of AD pathology or "mild cognitive impairment due to AD" in the patient at the time at which the sample was taken (obtained from the patient).

Thus, when determined by Western blot analysis, the α7nAChR/FLNA ratio amount in a lymphocyte body sample preparation from a person clinically determined to have AD pathology is about 0.4 to about 1.4 with an average value of about 0.8, whereas the α7nAChR/FLNA ratio in normal persons is typically about 0.1 to about 0.8, and the average value is about 0.4. The TLR4/FLNA ratio in a lymphocyte body sample preparation from a person clinically determined to have AD is about 0.5 to about 1.0, with an average value of about 0.7, whereas the TLR4/FLNA ratio in normal persons is typically about 0.45 to about 1.0, with an average value of about 0.8. The α7nAChR/Aβ ratio in a lymphocyte body sample preparation from a person clinically determined to have AD pathology is about 0.2 to about 1.0, with an average value of about 0.6, whereas the α7nAChR/Aβ ratio in normal persons is typically about 0.1 to about 0.8, with an average value of about 0.4. Preferably, the differences in amount are different by at least one standard deviation (significantly different), and more preferably by two standard deviations.

When a body sample preparation such as a lymphocyte body sample preparation is divided into at least two portions and one portion is admixed with an excess of exogenously supplied Aβ (an α7nAChR-saturating amount of Aβ) that is free of complexed protein and the other portion is not, the α7nAChR/FLNA ratio without and with the excess Aβ admixture for a clinically diagnosed AD patient changes by less than a significant amount. On the other hand, the difference in the determined α7nAChR/FLNA ratio without and with admixture of an exogenously supplied α7nAChR-saturating amount of Aβ is a significantly greater amount for a normal patient. Similar changes are noted when α7nAChR or TLR4 is assayed alone, and not in a ratio with FLNA.

The exogenously supplied α7nAChR-saturating amount of Aβ free of complexed protein utilized in an assay described herein can be any of the four $A\beta_{39-42}$ peptides. The $A\beta_{42}$ peptide is the most potent, is preferred and is generally used in the assays discussed herein. For example, $A\beta_{42}$-induced FLNA recruitment to α7nAChRs was mimicked by a 10-fold higher concentration of $A\beta_{40}$. See, Wang et al., *J. Neurosci*, 32(29):9773-9784 (Jul. 18, 2012).

Those differences in percentage of change in the protein ratio before and after admixture of Aβ to the lymphocyte sample preparation provide a further, preferred basis for diagnosis in that the α7nAChR/FLNA ratio data are consistent with the patient having or not having AD pathology (concluding that a patient has or does not have AD pathology), as are data from TLR4/FLNA and α7nAChR/Aβ ratio determinations or determinations of the individual protein amounts of TLR4 or α7nAChR.

Thus, following the procedure described above of dividing the body sample preparation into at least two portions and admixing a saturating amount of Aβ (an excess of Aβ free of complexed protein over that normally present in those cells) to one portion and not the other, one observes that the TLR4/FLNA ratio without and with the excess Aβ admixture for a clinically diagnosed AD patient does not change significantly. On the other hand, the difference in TLR4/FLNA ratio without and with admixture of excess Aβ is significantly greater for a normal patient.

Those differences in percentage of change in the protein ratio before and after admixture of excess free, uncomplexed Aβ to the lymphocyte sample preparation provide the basis for diagnosis in that the TLR4/FLNA ratio data are consistent with the patient having or not having AD (concluding that a patient has or does not have AD).

Again, following the procedure described above of dividing the body sample preparation into at least two portions and admixing a saturating amount of Aβ (an excess of Aβ over that normally present in those cells) to one portion and not the other, one observes that the α7nAChR/Aβ ratio without and with the excess Aβ admixture for a clinically diagnosed AD patient changes by less than a significant amount. On the other hand, the difference in α7nAChR/Aβ ratio without and with admixture of excess Aβ is significantly greater than for a normal patient.

Those differences in percentage of change in the protein complex amount before and after admixture of Aβ to the lymphocyte sample preparation again provide the basis for diagnosis in that the α7nAChR/Aβ ratio data are consistent with the patient having or not having AD pathology (concluding that a patient has or does not have AD pathology).

Thus, in a more preferred aspect of this embodiment, the assay is carried out in two stages, but in no particular order as to those stages. For convenience in description, in a first stage, a first portion of a body sample is assayed as described above to determine the amount(s) of α7nAChR or TLR4 or of one or more of i) α7nAChR/FLNA, ii) TLR4/FLNA and iii) and α7nAChR/Aβ. In the second stage, a saturating amount of Aβ (an excess of Aβ over that normally present in a body sample from a patient free of AD pathology) is admixed with a second portion of the body sample preparation and the value of the same α7nAChR or TLR4 amount or the same protein ratio of one or more of i) α7nAChR/FLNA, ii) TLR4/FLNA and iii) and α7nAChR/Aβ is determined. The saturating amount of Aβ (excess of exogenously supplied Aβ over that normally present in a body sample from a patient free of AD pathology) can be provided by admixing an amount of Aβ that is sufficient to provide a concentration of 1 nM or greater. Admixture of an amount sufficient to provide a concentration of at least about 100 nM is preferred.

A determined amount of α7nAChR/FLNA, TLR4/FLNA or α7nAChR/Aβ that differs between the assays of the first and second portions by an insignificant amount indicates that the patient has AD pathology. On the other hand, if the difference between the two determined values for any of the three protein ratios is significantly increased, the patient is free of AD pathology at the time of the assay. Similar degrees of change are noted for α7nAChR or TLR4 assayed alone. The magnitude of those differences is readily distinguished.

In another more preferred aspect of this embodiment, a first body sample preparation portion is assayed as discussed above and one or more of the above two individual proteins or the three protein ratios is determined. A second body sample preparation portion is admixed with an exogenously-provided FLNA-binding effective amount of a compound (one or more compounds) that binds to the FLNA pentapeptide of SEQ ID NO: 1 that contains at least four of the six pharmacophores of FIGS. 7-12, and preferably contains at least five of those six pharmacophores, such as an opioid receptor antagonist or mixed opioid receptor agonist/antagonist compound (collectively referred to as an antagonist compound) or a compound of Series A, B, C-1, C-2, D or E as discussed hereinafter, or a pharmaceutically acceptable salt of any of those compounds, rather than admixture with Aβ as discussed above. The same individual protein amount or protein ratio is determined after that admixture and equilibration time as noted hereinafter.

A significant lessening of the determined protein ratio amount in the presence of that FLNA-binding compound compared to the amount determined in the compound's absence is consistent with the patient from whom the sample was obtained having AD pathology. On the other hand, the value of the ratio of proteins obtained from a normal patient (AD pathology-free) is substantially unchanged from the amount determined in the absence of the contemplated compound. Looked at differently, an individual protein amount or a protein complex amount determined in the presence and absence of the contemplated FLNA binding compound differs significantly when the patient who provided the sample has AD pathology, and is not significantly different when obtained from a normal patient, thereby distinguishing the two patient types.

Yet another contemplated assay indicates the efficacy of the treatment for improving cognition given to a living, typically adult, cognitively-impaired patient. That method comprises the steps of: a) determining a first amount of one or both of α7nAChR or TLR4 or of one or more of i) α7nAChR/FLNA, ii) TLR4/FLNA and iii) and α7nAChR/Aβ protein complex amounts in a body sample preparation from that living patient. b) Treating the patient with an opioid receptor antagonist or mixed agonist/antagonist compound (an antagonist compound) or a compound of Series A, B, C-1, C-2, D or E or a pharmaceutically acceptable salt of such a compound that binds to the FLNA peptide of SEQ ID NO: 1 (Val-Ala-Lys-Gly-Leu) as described hereinafter, the one or more compound(s) or its(their) pharmaceutically acceptable salt preferably being present in a therapeutic composition. c) After that treatment (compound or compound salt administration), a second amount of the same individual protein or one or more of the i) α7nAChR/FLNA, ii) TLR4/FLNA and iii) α7nAChR/Aβ protein complex amounts is determined in a second body sample preparation as in step a). d) The amounts of the individual protein or one or more protein complex ratios determined before and after the treatment are compared. In that comparison, a later-determined (post treatment) amount that is significantly less than the first determined amount is consistent with the therapeutic treatment being effective in providing an improvement in the patient's cognition, and a slowed or inhibited disease progression. A significant increase in a protein or complex amount indicates an ineffective treatment, whereas an amount unchanged from a previous amount indicates no discernible change at the time of the assay.

One or a plurality of subsequent determinations of the amount of α7nAChR or TLR4 or of the one or more protein complexes can also be made, and each determined amount of α7nAChR or TLR4 or of the one or more complex compared to a prior determined amount. Because AD and other cognitive loss diseases are progressive diseases, the level of each of the two individual proteins or three protein complex ratios in lymphocytes, olfactory neuroepithelial cells and in the untreated brain can increase markedly over the course of the disease, particularly in earlier stages.

An assay for either or both of the two proteins and any of the above three protein complexes can be used to provide evidence that is consistent with a human patient having AD pathology or a lower animal patient with an AD-associated pathology. It is preferred that at least two of the three assays be performed and provide the same result. All three assays being carried out can provide further assurance of proper diagnosis.

Another embodiment of the invention contemplates a method for determining the prognosis (out-come) of treatment of a living patient presumed to have Alzheimer's disease pathology (AD pathology) using a compound or a pharmaceutically acceptable salt of such a compound that has particular binding and structural properties. A contemplated compound or its salt binds in an aqueous composition to a pentapeptide of filamin A (FLNA) having SEQ ID NO: 1 (Val-Ala-Lys-Gly-Leu) as discussed hereinafter, and contains at least four of the six pharmacophores of FIGS. 7-12. A currently particularly preferred compound also inhibits at least about 60 percent of the FITC-labeled naloxone binding to that SEQ ID NO: 1 pentapeptide when present at a 10 µM concentration and using unlabeled naloxone as the control inhibitor at the same concentration.

The method comprises the steps of: a) determining the amount of one or both of α7nAChR or TLR4 or of one or more of α7nAChR-FLNA, TLR4-FLNA and α7nAChR-Aβ protein complex in a body sample preparation from the living patient, as the words "body sample preparation" and "patient" was previously defined. b) Determining the amount of the same one or both of α7nAChR or TLR4 or of one or more of α7nAChR-FLNA, TLR4-FLNA and α7nAChR-Aβ complexes in a second portion of the body sample preparation from that same living patient. Those determinations can be carried out in either order or simultaneously. That second body sample preparation further contains an exogenously provided FLNA-binding effective amount (typically about 0.1 nM to about 10 nM) of the above compound or its salt, as discussed hereinafter. c) The amounts determined in steps a) and b) are compared, and if the amount determined in step b) is statistically significantly less than the value determined in step a), the prognosis for treatment of the patient with that compound or its salt is favorable. Additionally, if determinations of one or both of α7nAChR or TLR4 or one or more of α7nAChR-FLNA, TLR4-FLNA and α7nAChR-Aβ complexes in a body sample taken after a patient has been administered the compound or its salt for a period of time are also significantly less than the amounts initially determined in step a), these determinations serve as a biomarker illustrating efficacy of treatment, as is discussed below.

The word "patient" is intended to include a human patient as well as a lower animal model useful in studying AD. Illustrative lower animal models include laboratory animals such as the mouse and rat, in which AD-associated pathologies can be induced as illustrated hereinafter. Companion animals such as the dog and cat are also contemplated. Dogs can suffer from an age-related syndrome of cognitive dysfunction that naturally reproduces key aspects of AD including Aβ cortical pathology, neuronal degeneration and learning and memory disabilities, but dense core neuritic plaques and neurofibrillary tangles have not been consistently demonstrated in the dog. Other animals as are discussed in Sarasa et al., *Current Alzheimer Res.*, 6:171-178 (2009) are also contemplated.

Assay Procedures

A contemplated body sample for use in a contemplated method includes lymphocytes, olfactory neuroepithelial cells and cells obtained by biopsy of the brain, particularly the hippocampus and prefontal cortex. Lymphocytes are a preferred body sample from which a useful body sample preparation can be prepared as is discussed hereinafter.

In preferred practice, a useful body sample preparation is a cellular lysate such as a lymphocyte lysate prepared as discussed hereinafter. Typically, about 1 to about 50 µg of lymphocyte lysate is used per assay, and more preferably about 5 to about 20 µg are used.

A contemplated body sample preparation is the material that is actually used in an assay, and is an aqueous composition prepared from the body sample that contains a protein to be assayed. Illustratively, one body sample preparation is an aqueous composition containing a soluble or solubilized cell lysate that includes a protein or protein-protein complex to be assayed. Illustrative body sample preparations are illustrated hereinafter and typically contain buffer salts, one or more surfactants, and osmolality adjusting solutes such as salts and sugars.

Lymphocyte preparations often contain platelets. The lymphocyte assays utilized herein were carried out using a lymphocyte preparation free of platelets. However, platelets do not contain the protein complexes that are assayed herein, and platelets are typically present in small quantities in usual lymphocyte preparations so that a useful lymphocyte preparation need not be free of platelets.

Olfactory dysfunction is an early and common sign in various neurodegenerative diseases. Microsmia or anosmia is present in approximately 90% of patients with Alzheimer's disease and accumulating evidence suggests that this psychophysical biomarker predicts incident mild cognitive impairment and also correlates with severity of dementia and abundance of neurodegenerative disease pathology in the brain. [Arnold et al., *Ann Neurol.*, 67(4):462-469 (2010).]

As pointed out by Borgmann-Winter et al, *Neuroscience* 158:642-653 (2009), the olfactory epithelium constitutes a source of regenerating neural cells that can be obtained from a living human. As such, primary cultures derived from human olfactory epithelial biopsies can be utilized to study neurobiological characteristics of individuals under different conditions and disease states. The olfactory epithelium provides neural inputs to the olfactory bulb that is located in the forebrain.

Brain biopsies from living patients, particularly humans, are less easily obtainable, and are less desirable for use in repeated assays. Nevertheless, such biopsies can be obtained from living patients, and as is illustrated hereinafter using post mortem tissues, brain tissue can provide useful cells for carrying out a contemplated assay.

Perhaps surprisingly, cerebrospinal fluid (CSF) is not a source of a protein or protein complex assayed in a contemplated method. A principal reason for the lack of utility of CSF for a contemplated assay is that the blood-brain barrier (BBB) has to be compromised for whole proteins to escape from the brain itself into the CSF for subsequent analysis.

Rather, the CSF is presently used as a source of the tau protein and of Aβ that are used in current clinical assays for AD. As the disease progresses, the BBB becomes more porous and the ratio of total tau (phosphorylated plus non-phosphorylated tau) to Aβ increases. Aβ is produced throughout the body such as in the bone marrow, pancreas and gut.

The standard body sample preparation from a person free of AD symptoms can be prepared in many ways known to skilled workers. It is preferred that the standard be measured from the same sample source, e.g., a standard from lymphocytes used in an assay from lymphocytes, and the like. Such standards are readily prepared. It is also preferred that the standard sample be from age-matched individuals, wherein the age of the standard group is within about five years (about ±5 years) of that of the patient being assayed. Where laboratory animals are the patients, age-matching is of less import.

The standard value for a given protein ratio can be a known quantity for various age groups and sampled tissues. However, it is preferred that a sample from the standard be run with the assay sample, or that some other exogenously supplied normalizing standard that is correlatable to a standard amount of complex be run along with the assay to assure accuracy in the obtained result.

A variety of assay procedures can be utilized in carrying out a contemplated method. Western blot with and without quantification as by densitometric analysis, and a solid phase assay such as a plate-type assay wherein the walls of a multi-well plate are used as the solid phase, are exemplified hereinafter as illustrative. Further illustrative techniques for determining the amount of a protein or protein complex include without limitation radioimmunoassay as discussed in Berson et al., *Clin Chem Acta* 22:51-69 (1968) and Walsh et al., *J Infect Dis* 121:550-554 (1970); Flow Cytometry as described in Lisi et al., *Clin Chem Acta* 120:171-179 (1982); microparticle analysis as discussed in Al-Hakiem et al., *J Immunoassay* 3:91-110 (1982); ELISA assay as in Engvall et al., (1976); enzyme-linked immunosorbent assay (ELISA), p135-147, In X. Feldmarr (ed.), First international symposium on immunoenzymatic techniques (1976); Porstmann et al., *J Immunol Methods* 150:5-21 (1992); and Wolters et al., *J Clin Pathol* 29:873-879 (1976); chemiluminescent microparticles as discussed in Wolf-Rogers et al., *J Immunol Methods* 133:191-198 (1990); multianalyte microspheres as discussed in Earley et al., *Clinical Cytometry* 50:239-242 (2002); mass spectral analysis as discussed in Atmanen et al., *Anal. Chem.* 81 (15):6364-6373 (2009); Pandyey et al., *Proc Natl Acad Sci, USA* 97:179-184 (2000); and Nedelkov, *Expert Rev Mol Diagn.* 12(3): 235-239 (2012).

More particularly, in a solid phase plate-type assay, a first, capture receptor that specifically binds to one of the proteins of the complex is used to capture the protein complex, and a second receptor that specifically binds to the second protein of that complex is used in measuring the amount of complex captured. For example, biotinylated paratope-containing molecules (first or capture receptors) that specifically bind to FLNA can be affixed to the wells of an assay plate, as for example being bound to a streptavidin-coated plate well, to capture a FLNA-containing complex.

Second paratope-containing molecules (second receptors) specifically bind to the second protein of the complex or to a non-interfering epitope of the first protein, such as TLR4, for example, can then be used to bind to a TLR4 molecule complexed to FLNA. That second paratope-containing molecule can itself contain an indicator group such as an enzyme, FITC or a radioisotope, that can be used to determine the amount bound, or the amount bound can be determined by other means.

In another illustrative example, the first receptor can be affixed (chemically or physically bonded) to water-insoluble particles such as resin beads or magnetic particles. After admixture with a body sample preparation and a suitable maintenance time to permit binding (about 0.5 to about 24 hours), the particulate-bonded first, capture receptor specifically bound to an assayed complex can be separated from the remainder of the aqueous composition by physical means such as centrifugation or magnetic attraction. The complex and its constituents can themselves be separated by boiling in buffer, followed by separation by chromatography or electrophoresis, component identification by binding with appropriate second receptors and quantitation as desired, so that both proteins a complex or only one of them can be quantified.

One type of preferred receptor utilized herein is at least a paratope-containing polyamide portion of an antibody that binds to a protein of an assayed protein or protein complex. Intact antibodies are preferred receptors.

Paratope-containing polyamide portions (antibody combining sites) of antibodies are those portions of antibody molecules that include the paratope (binding site), and bind to the ligand. Such portions include the Fab, Fab', Fv and F(ab')$_2$ fragments prepared from antibodies by well-known enzymatic cleavage techniques. See for example, U.S. Pat. No. 4,342,566 to Theofilopoulos and Dixon, generally, and specifically, Pollack et al., [*Science*, 234:1570-1573 (1987)] who reported accelerated hydrolytic rates for Fab fragments were the same as those of the native immunoglobulin.

Inasmuch as the antibodies from which paratope- or antibody combining site-containing polyamides are obtained can themselves be described as raised against or induced by immunogens, paratope-containing polyamide receptors are discussed as being "raised" or "induced" with the understanding that a cleavage step is typically required to obtain an paratope-containing polyamide from an antibody. Intact antibodies are preferred, however, and are utilized as illustrative of the receptor molecules of this invention.

The antibody receptors useful in the present invention are preferably monoclonal antibodies, although polyclonal antibodies can also be used. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monoclonal antibodies are well known. Such receptors were first described by Kohler and Milstein, *Nature,* 256:495-497 (1975). Monoclonal antibodies are typically obtained from hybridoma tissue cultures or from ascites fluid obtained from mammals into which the hybridoma tissue was introduced.

Biological activity of a receptor molecule is evidenced by the binding of the receptor to its ligand upon their admixture in an aqueous medium, at least at physiological pH values and ionic strengths. Preferably, the receptors also bind to a ligand within a pH value range of about 5 to 9, and at ionic strengths such as that of distilled water to that of about one molar sodium chloride.

Receptors, and other binding reagents, can be utilized along with an indicator labeling means or "indicating group" or a "label". The indicating group or label is utilized in conjunction with the receptor as a means for signaling (determining) that a specific ligand, e.g., TLR4, has bound to or been bound by the receptor and quantifying the amount so bound.

The terms "indicator labeling means", "indicating group" or "label" are used herein to include single atoms and molecules that are linked to the receptor or used separately, and whether those atoms or molecules are used alone or in conjunction with additional reagents. Such indicating groups or labels are themselves well-known in biochemistry and particularly in immunochemistry.

The signal-providing label utilized is typically linked to another molecule or part of a molecule. As such, the label is operationally linked to that other molecule or molecule part such as a receptor so that the binding of the molecule to which the label is linked is not substantially impaired by the label and the desired signaling provided by the label is not substantially impaired.

The indicator labeling means can be a reactive fluorescent labeling agent that chemically binds to (reacts with) receptors or ligands without denaturing them to form a fluorochrome (dye) that is a useful immunofluorescent tracer. Suitable reactive fluorescent labeling agents are fluorochromes such as fluorescein isocyanate (FIC), flourescein isothiocyanate (FITC), dimethylamino-naphthalene-S-sulphonyl chloride (DANSC), tetramethylrhodamine isothiocyanate (TRITC), lissamine rhodamine B200 sulphonyl chloride (RB 200 SC) and the like. A description of immunofluorescence analysis techniques is found in DeLuca, "Immunoflourescence Analysis," in *Antibody As A Tool*, Marchalonis et al. eds., John Wiley & Sons Ltd., p. 189-231 (1982).

The indicator labeling means can be linked directly to a receptor or can comprise a separate molecule. It is particularly preferred that the indicator means be part of a separate molecule such as receptors that bind to a protein of a complex discussed herein.

*Staphylococcus aureus* Cowan strain protein A, sometimes referred to in the art as protein A, and/or *Streptococcus* protein G can also be used as a separate molecule indicator or labeling means where an intact or substantially intact antibody is utilized as a receptor. In such uses, the protein A itself contains a label such as a radioactive element or a fluorochrome dye. Alternatively, one or both of Protein A and Protein G can be used as a capture receptor as is shown hereinafter.

The indicating group can also be a biologically active enzyme, such as horseradish peroxidase (HRP) or glucose oxidase, or the like. Where the principal indicating group is an enzyme such as HRP or glucose oxidase, additional reagents are required to visualize the fact that a receptor-ligand complex has formed; i.e., the receptor has bound to a protein of the complex such as TLR4. Such additional reagents for HRP include hydrogen peroxide and an oxidation dye precursor such as diaminobenzidine. An additional reagent useful with glucose oxidase is 2,2'-azino-di-(3-ethylbenzthi-azoline-6-sulfonic acid) (ABTS).

Radioactive elements provide another class of label, and are used herein as exemplary of useful labels. An exemplary radio-labeling agent that can be utilized in the invention is a radioactive element that produces gamma ray emissions. Elements which themselves emit gamma rays, such as $^{124}$I, $^{125}$I, $^{128}$I, $^{131}$I, $^{132}$I, and $^{51}$Cr represent one class of gamma ray emission-producing radioactive element indicating groups. Particularly preferred is $^{125}$I.

Another class of useful indicating groups are those elements such as $^{11}$C, $^{18}$F, $^{15}$O, and $^{13}$N that themselves emit positrons. The positrons so emitted produce gamma rays upon encounters with electrons present in the analysis medium. Also useful is a beta ray emitter, such as 111-indium ($^{111}$In).

Radioactive monoclonal receptors can be made by culturing an appropriate hybridoma in a medium containing radioactive amino acids, as is well known. Both monoclonal and polyclonal receptors can be prepared by isolating the receptors and then labeling them with one of the above radioactive elements. Radiolabeling of proteins is well known in the art and will not be discussed further herein.

A "ligand" is defined herein as a molecule or portion thereof that binds specifically to a receptor. Where the receptor is an antibody combining site- (paratope-) containing molecule, that binding is an immunoreaction. Thus, one contemplated ligand is an epitope provided by a protein of an assayed complex.

Further useful assays and their methods or practice can be found in U.S. Pat. No. 4,761,382; 4,946,958; 5,656,207; EP 570518 B1; U.S. Pat. No. 4,016,043; and EP 2963 B1. Further disclosures can be found in the following published papers: Li et al., *JALA* (April 2010) 107-113; Mendoza et al., *BioTechniques* 27:778-788 (1999); Cai et al., *Anal. Chem.* 83(15):5844-5850 (2011); and Rosi et al., *Chem. Rev.* 105: 1547-1562 (2005).

FLNA Binding and Pharmacophore Determinations

One aspect of the invention is the use of a compound that binds to the FLNA pentapeptide of SEQ ID NO: 1 as described in Example 1 to inhibit formation of an assayed complex as a control. A contemplated compound inhibits at least about 60 percent and more preferably about 70 percent of the FITC-labeled naloxone binding to that FLNA pentapeptide when present at a 10 µM concentration and using unlabeled naloxone as the control inhibitor at the same concentration. In this aspect, the structure of a compound that effectively binds to a pentapeptide of SEQ ID NO: 1 is quite varied but can be unified through the calculation of a group of pharmacophores shared by those compounds that so bind.

A contemplated compound useful in this aspect of a method of the invention contains at least four of the six pharmacophores of FIGS. 7-12. In preferred practice, a contemplated compound contains five of the six pharmacophores of those figures, and more preferably, a contemplated compound contains all six of the pharmacophores. Aside from NLX, NTX, several other morphinan ring compounds such as nalorphine, nalbuphine and buprenorphine also bind well to the FLNA pentapeptide of SEQ ID NO: 1 (VAKGL). An illustrative list of similarly useful morphinan ring compounds is provided hereinafter along with a discussion of compounds of four structural series that are particularly preferred.

An ensemble pharmacophore model was prepared using the three-dimensional conformations of compounds in the training sets. Using 0.1 µM data from Example 1 as a starting point, 153 compounds out of the list of compounds in the tables of Example 1 have a binding activity to the FLNA pentapeptide that is less than the mean value of 45.54 percent. A "poor binding" compound or "poor binder" is defined as a compound whose binding inhibition is equal to or less than the mean value of 45.54 percent in an assay as conducted in Example 1, whose results are shown in the tables of Example 1. The training set consists of ten compounds known to bind to the FLNA pentapeptide, the above poor binding 153 compounds and also about 1000 random compounds selected from ZINC database at zinc.docking.org.

The selection of pharmacophores involves in the following steps: 1) Three-dimensional computer-generated conformations of all compounds were first prepared. 2) A set of 4-point pharmacophores present in most of known active compounds was derived. 3) Using known inactive and random selected compounds as reference compounds, only those pharmacophores that were not present in the most of the reference compounds were identified as relevant to FLNA binding activity. 4) Six 4-point pharmacophores were finally identified from those determined above to best represent the 10 active compounds.

An untested compound not having a structure of one of the four compound structural formulas shown hereinafter (i.e., Series A, Series B, Series C-1 or Series C-2), that contains four out of the six pharmacophores has about a 20 percent chance to be an active binder in FLNA pentapeptide. A compound containing five of the six pharmacophores has about a 32 percent chance to be an active binder in FLNA pentapeptide, and about a 60 percent chance when containing six of the six pharmacophores.

The Molecular Operating Environment (MOE) software from Chemical Computing Group, Montreal, Quebec, Canada, was used to program a general purpose computer to generate three-dimensional conformations, to derive 4-point pharmacophores from active compounds, and to test these pharmacophores against known inactive compounds and random selected compounds. Pharmacophore modeling as used herein is carried out as discussed and explained in Penzotti et al., *J. Med. Chem.*, 2002, 45(9):1737-1740 (2002); Siew et al., *Bioorganic & Medicinal Chemistry Letters*, 21(10):2898-2905 (15 May 2011); Leong, *Chem. Res. Toxicol.*, 20(2):217-226 (2007); and Lin, chemcomp.com/journal/ph4.htm.

The ten known FLNA pentapeptide-binding training set compounds are shown below along with their alpha-numeric designations used herein. Of the

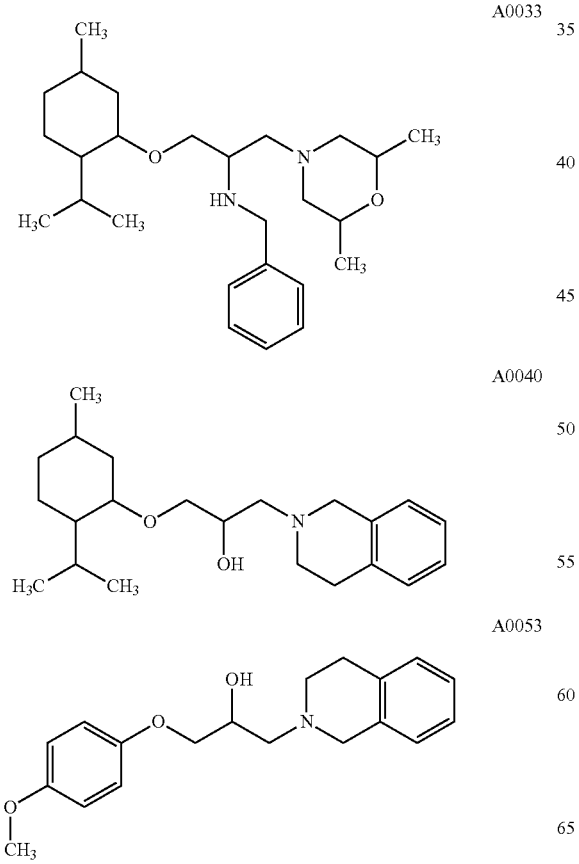

A0033

A0040

A0053

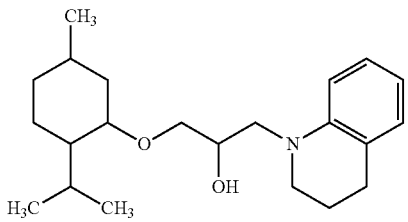

A0068

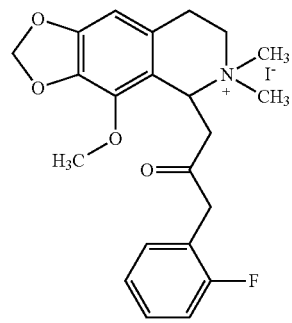

B0055

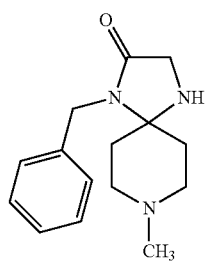

C0105 M

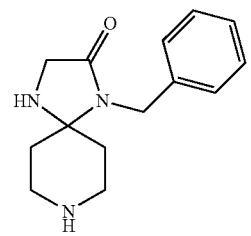

C0114M

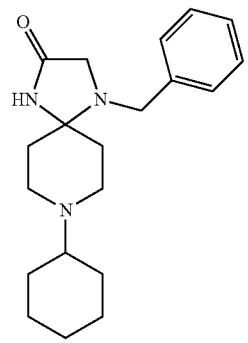

C0137 M

-continued

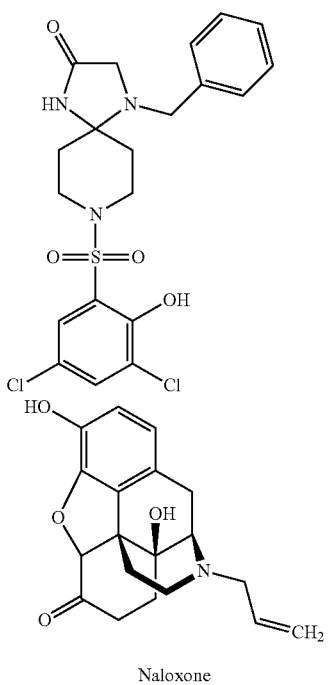

C0138 M

Naloxone above ten compounds used in the training set for determining the pharmacophores, nine contained all six pharmacophores. Naloxone contained to five of the six. Examining several more of the structures of the four groups of compounds (Series A, Series B, Series C-1 and Series C-2) shown in the tables and assayed in Example 1 hereinafter, twenty further compounds contained to five of the six pharmacophores, and another twenty contained four of the six.

Specifically Contemplated FLNA-Binding Compounds

A compound contemplated for use in a contemplated method can have a varied structure as noted before, and illustrated hereinafter. Regardless of that structural variance, a contemplated compound binds to the FLNA pentapeptide of SEQ ID NO: 1, inhibits the binding of labeled naloxone (FITC-NLX) to the biotinylated-VAKGL pentapeptide (Bn-VAKGL; SEQ ID NO: 1) bound to coated streptavidin plates to an extent that is at least about 60 percent, and preferably about 70 percent, of the value obtained when using naloxone as an inhibitor at the same concentration and under conditions defined hereinafter in Example 1, and can be about twice the value for naloxone at the same concentration.

In some embodiments, it is preferred that a FLNA-binding compound also be an opioid receptor antagonist or mixed agonist/antagonist, and particularly an antagonist for the mu opioid receptor (MOR). It is particularly preferred that the compound not be a MOR agonist. A compound is defined herein as not being a MOR agonist if it has less than about 80 percent the MOR agonist activity of [D-Ala2,N-MePhe4,Gly-ol]-enkephalin (DAMGO) at either of the two concentrations used in the Table of Example 2.

For purposes of brevity and clarity of disclosure, compounds that are an opioid receptor antagonist or a mixed opioid receptor agonist/antagonist are collectively referred to hereinafter as an "antagonist compound", unless otherwise described, or specifically named. A contemplated antagonist compound is a reversible antagonist at opioid receptors.

Binding studies of the naltrexone inhibition of tritiated-naloxone, [³H]NLX, binding to membranes from FLNA-expressing A7 cells (an astrocyte cell line produced by immortalizing optic nerve astrocytes from the embryonic Sprague-Dawley rat with SV40 large T antigen) has shown the existence of two affinity sites on FLNA; a high affinity site (H) with an $IC_{50}$-H of 3.94 picomolar and a lower affinity site (L) $IC_{50}$-L of 834 picomolar. [Wang et al., PLoS One. 3(2):e1554 (2008); Wang et al., PLoS One. 4(1):e4282 (2009).] The high affinity site was subsequently identified as the FLNA pentapeptide of SEQ ID NO: 1 (US Patent Publication 2009/0191579 and its predecessor application Ser. No. 60/985,086 that was filed on Nov. 2, 2007), whereas the lower affinity site has not yet been identified. The presence of two FLNA protein binding sites is illustrated in the graphs of FIG. 16.

A compound contemplated for use in the present invention inhibits the binding of fluorescein isothiocyanate-labeled naloxone (FITC-NLX) to biotin-linked SEQ ID NO: 1 (Bn-VAKGL) bound to coated streptavidin plates under conditions defined hereinafter in Example 1 to an extent that is at least about 60 percent, and more preferably about 70 percent, of the value obtained when using FITC-labeled naloxone present at a 10 µM concentration and using unlabeled naloxone as the control inhibitor at the same concentration, and up to about twice the value obtained with naloxone as control.

One group of preferred inhibitor compounds is a morphinan ring compound. Morphinan ring compounds are analogs of morphine. The structural formulas of morphine and a typical morphinan ring compound are shown below, where $R^1$ and $R^2$ are substituent groups.

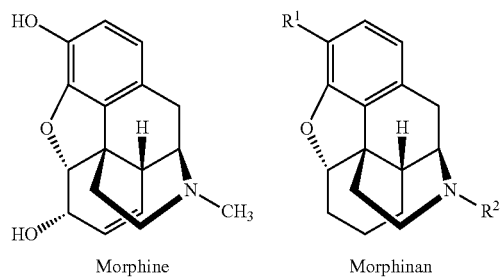

Morphine                Morphinan

Preferably, the opioid receptor antagonized is at least the mu opioid receptor (MOR), although one or both of the delta and kappa receptors can also be antagonized. Many of the morphinan ring compounds are analgesics that bind to the mu opioid receptor (MOR). The table below lists several antagonist compounds, the opioid receptor that they antagonize, and the relative potency of the antagonism as reported for a majority of the compounds in Goodman & Gilman's The Pharmaceutical Basis of Therapeutics, 11$^{th}$ ed., Brunton ed., McGraw-Hill Medical Publishing Division, New York, Table 21-3, page 552 (2011).

|  | OPIOID RECEPTOR* | | |
| --- | --- | --- | --- |
| OPIOID LIGAND | MU | DELTA | KAPPA |
| Naloxone | – – – | – | – – |
| Naltrexone | – – – | – | – – – |
| Diprenorphine | – – – | – – | – – – |
| Naloxonazine | – – – | – | – |
| nor-Binaltrophimine | – | – | – – – |

-continued

| OPIOID LIGAND | OPIOID RECEPTOR* | | |
|---|---|---|---|
| | MU | DELTA | KAPPA |
| Binaltrophimine | NR | | – – |
| Naltrindole | – | – – – | – |
| Naloxone benzoylhydrazone | – – – | – | – |
| Nalbuphine | – – | NR | ++ |
| Buprenorphine | P | NR | – – |
| Butorphanol | P | NR | +++ |
| Ethyl Ketocyclazcine | P | + | +++ |
| Nalorphine | – – – | NR | + |
| Cyprodime | NR | – – | |

*"–" = antagonist; "+" = agonist; "NR" = not reported in the published table; P = partial agonist; The number of symbols in an indication of relative potency; "#" = not reported in the published table, but otherwise reported to have both antagonist and agonist activities.

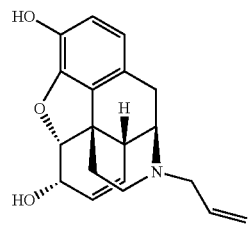

Nalorphine

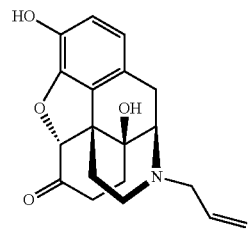

Naloxone

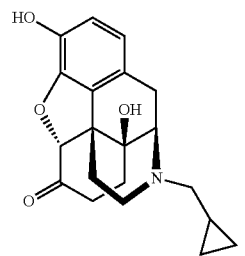

Naltrexone

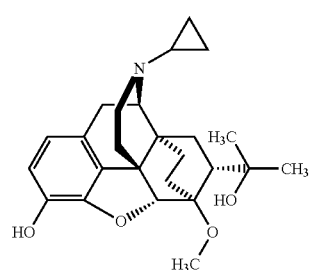

Diprenorphine

-continued

| OPIOID LIGAND | OPIOID RECEPTOR* | | |
|---|---|---|---|
| | MU | DELTA | KAPPA |

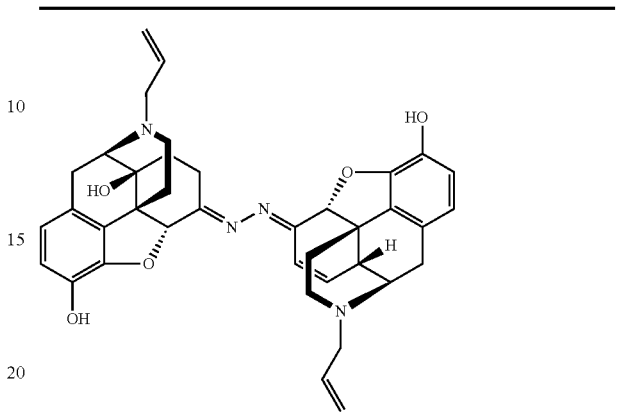

Naloxnazine

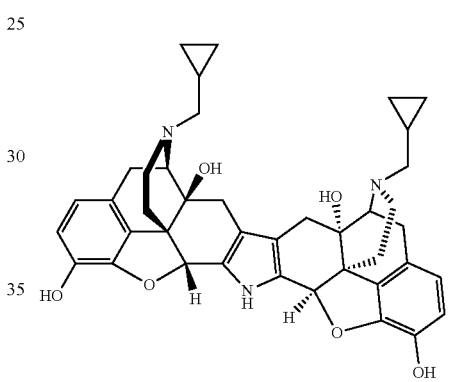

Nor-Binaltrophimine

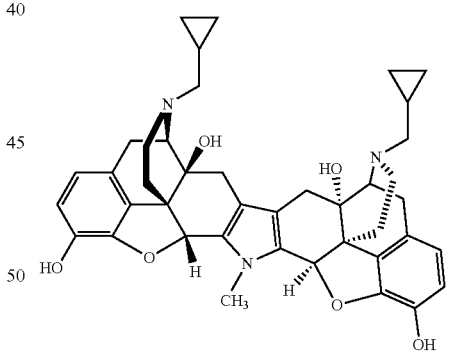

Binaltrophimine

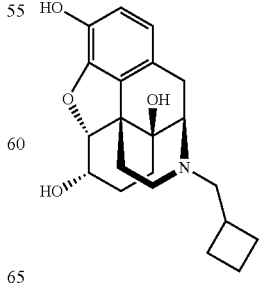

Nalbuphine

| OPIOID LIGAND | OPIOID RECEPTOR* | | |
|---|---|---|---|
| | MU | DELTA | KAPPA |
| 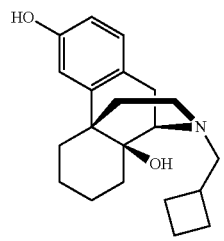 Butorphanol | | | |
| 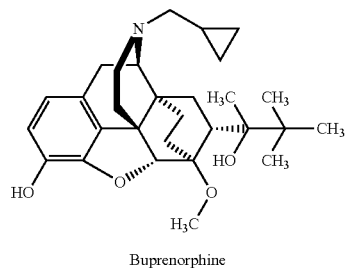 Buprenorphine | | | |
| 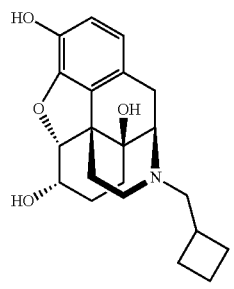 Nalbuphine | | | |
| 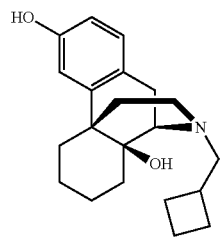 Butorphanol | | | |
| 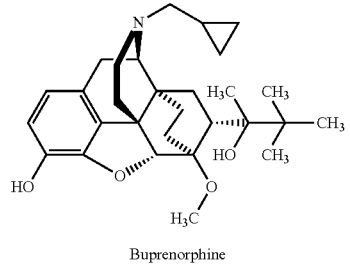 Buprenorphine | | | |

| OPIOID LIGAND | OPIOID RECEPTOR* | | |
|---|---|---|---|
| | MU | DELTA | KAPPA |
| 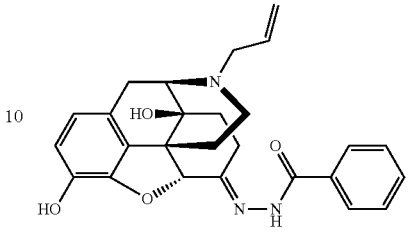 Naloxone Benzoylhydrazone | | | |

Morphinan ring compounds such as naloxone (NLX), naltrexone (NTX), nalorphine, nalbuphine and buprenorphine, and the like bind well to the high affinity FLNA pentapeptide of SEQ ID NO: 1 (VAKGL). However, when used at a dosage recited on the commercial product label, those compounds also bind to the lower affinity site on FLNA, and typically also bind to the MOR. Some of the compounds are MOR antagonists such as naloxone, naltrexone, nalbuphine, whereas others such as buprenorphine are full or partial agonists of MOR. Binding to that lower affinity FLNA site impairs the activity of the FLNA pentapeptide of SEQ ID NO: 1 to exhibit its activities as discussed, utilized and illustrated herein. As a consequence, opioid antagonist compounds such as naloxone, naltrexone, methadone, fentanyl, nalorphine, nalbuphine, buprenorphine and similar compounds that also bind to the lower affinity site on the FLNA protein are utilized in an amount that is about $100^{th}$ to about $1000^{th}$ or less than that normally used.

In addition, opioid agonists such as morphine itself do not bind to the FLNA pentapeptide. Consequently, compounds that are only opioid agonists are not contemplated herein.

Naltrexone (NTX) can also be used as a control inhibitor. Average inhibition values obtained using NTX rather than NLX tend to be 1 or 2 percent lower in absolute value than those obtained with NLX. Thus, for example, where an average inhibition value at a particular concentration of NLX is 40 percent, one can expect values obtained with NTX to be about 38 or 39 percent. The binding inhibition values for a contemplated compound are determined taking the expected NLX/NTX value difference into account.

Most of the above antagonist compounds are or can be chiral and can exist as enantiomers of each other. It is presently preferred to utilize an enantiomeric compound that exhibits the lesser analgesic activity over the enantiomer that is more analgesically potent for the present method.

Another related class of useful opioid compounds are the benzomorphans that include pentazocine, phenazocine, dezocine and cyclazocine. These compounds are partial agonists of opioid receptors and are less preferred than those compounds noted in the table above.

Additionally, compounds having four exemplary structures have been found to bind well to the pentapeptide of SEQ ID NO: 1. Those compounds are referred to herein as Series A, Series B, Series C-1, Series C-2, Series D and Series E. Inhibition of tau phosphorylation by Compounds A, B and C and Series D are illustrated herein and are representative of those structural series. Compounds of Series E overlap with those of Series C-1 and -2 and are therefore also included herein. The general structures of the compounds of each series are shown below, followed by more specific disclosures.

Series A

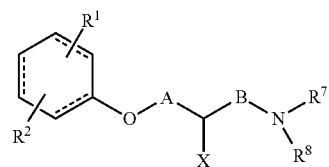

Series B

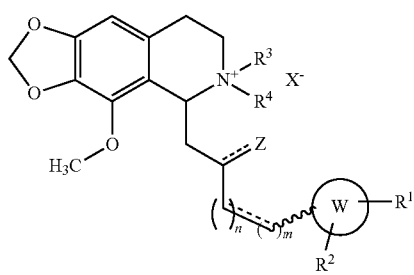

Series C-1

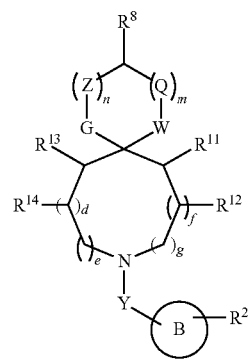

Series C-2

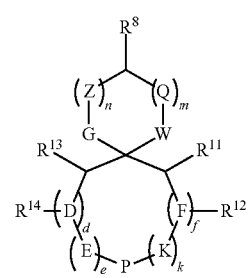

Series D

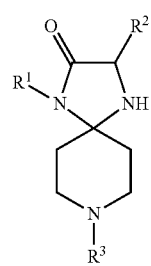

Series E

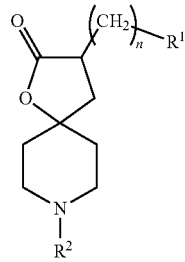

A pharmaceutically acceptable salt of a compound of each of the above Formulas is also contemplated. A compound having an asymmetrical (chiral) carbon or a salt of such a compound can exist in the form of stereoisomers, that are two enantiomers. The invention relates both to each enantiomer separately, and to their mixture; i.e., to both enantiomeric forms (d and l, or R and S) and to their mixture. Additionally, where two or more chiral centers are present, stereoisomers called diastereomers can form, and diastereomers are also contemplated.

As will be seen from the following definitions, a contemplated compound can contain one or more deuterated carbon, in which deuterium is designated by its usual chemical designation, D. Deuterated compounds can be useful in studying the mechanism of drug interactions with living organisms for the elucidation of metabolic and biosynthetic pathways. Deuteration can also extend the half-life of a contemplated compound in vivo because a carbon-deuterium (C-D) bond is stronger than a Carbon-hydrogen (C—H) bond thereby requiring more energy input for bond cleavage. See, Blake et al., 1975 *J. Pharm. Sci.* 64(3):367-391; and Nelson et al., 2003 *Drug Metab. Dispos.* 31(12): 1481-1498, and the citations therein. Contemplated deuterated compounds are prepared using well-known reactions.

More particularly, a compound of Series A corresponds in structure to Formula A, below,

A

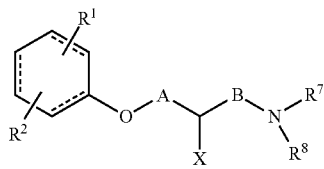

wherein $R^1$ and $R^2$ are the same or different and are independently H, halogen, $C_1$-$C_{12}$ hydrocarbyl, $C_1$-$C_6$ acyl, $C_1$-$C_6$ hydrocarbyloxy, $CF_3$ and $NR^3R^4$, wherein $R^3$ and $R^4$ are the same or different and are H, $C_1$-$C_4$ hydrocarbyl, $C_1$-$C_4$ acyl, $C_1$-$C_4$ hydrocarbylsulfonyl, or $R^3$ and $R^4$ together with the depicted nitrogen form a 5-7-membered ring that optionally contains 1 or 2 additional hetero atoms that independently are nitrogen, oxygen or sulfur;

A and B are the same or different and are $CH_2$, CDH or $CD_2$ (where D is deuterium);

X is OH or $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7- membered ring that optionally contains 1 or 2 additional hetero atoms that independently are nitrogen, oxygen or sulfur;

$NR^7R^8$, $R^7$ and $R^8$ are the same or different and are H, $C_1$-$C_6$ hydrocarbyl, $C_1$-$C_6$ acyl, $C_1$-$C_6$ hydrocarbylsulfonyl, or $R^7$ and $R^8$ together with the depicted nitrogen form a ring structure W;

W contains 5 to 14 atoms in the ring structure including the depicted nitrogen, and preferably up to 12 atoms. W can optionally contain:

a) 1 or 2 further hetero atoms that are independently oxygen, nitrogen or sulfur, and b) one or more substituent groups bonded to one or more ring atoms, in which the one or more substituents contain a total of up to 8 atoms, and preferably up to 6 atoms, selected from the group consisting of carbon, nitrogen, oxygen and sulfur, and mixtures thereof.

A dashed line (----) represents an optional double bond.

In regard to a contemplated compound, $R^1$ and $R^2$ are preferably other than methyl and isopropyl, respectively, when W is N-morpholinyl or dimethyl-N-morpholinyl and the optional double bonds are absent.

A preferred compound of Formula A is a compound of Formula I, below, in which A, B, X, W and $R^1$ and $R^2$ are as defined above.

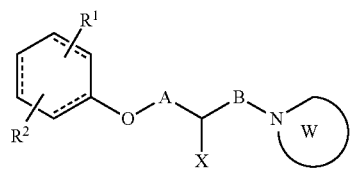

I

In one preferred embodiment, a contemplated compound corresponds in structure to Formula Ia

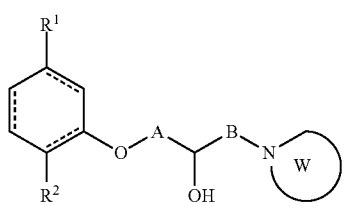

Ia

Here, $R^1$ and $R^2$ are the same or different and are independently H, or $C_1$-$C_6$ hydrocarbyl; A and B are the same or different and are $CH_2$, CDH or $CD_2$ (where D is deuterium); W is a ring structure that contains 5 to 14 atoms in the ring structure including the depicted nitrogen, and can optionally contain: a) 1, 2 or 3 further hetero atoms that are independently oxygen, nitrogen or sulfur, and b) one or more substituent groups bonded to one or more ring atoms, in which the one or more substituent contain a total of up to 14 atoms, preferably up to 12 atoms and more preferably up to 8 atoms selected from the group consisting of carbon, nitrogen, oxygen and sulfur, and mixtures thereof. The dashed line (----) represents 1, 2, or 3 optional double bonds. Preferably, $R^1$ and $R^2$ are other than methyl and isopropyl, respectively, when W is N-morpholinyl or dimethyl-N-morpholinyl, and the optional double bonds are absent.

In preferred practice for some embodiments of a compound of either Formula I or Formula Ia, W further includes one or more substituent groups bonded to one or more ring atoms, in which those one or more substituents contain a total of up to 8 atoms selected from the group consisting of carbon, nitrogen, oxygen and sulfur, and mixtures thereof. Hydrogen atoms bonded to those atoms are not counted.

In one preferred embodiment, a compound of Formulas I and Ia has the structure of Formula II, whereas in another preferred embodiment, a compound of Formulas I and Ia has the structure of a compound of Formula III.

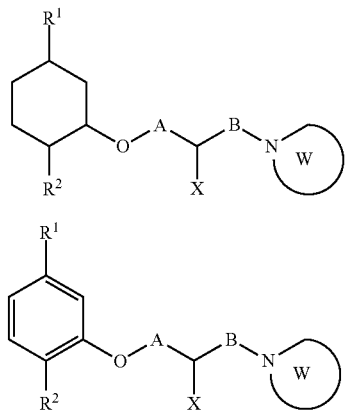

II

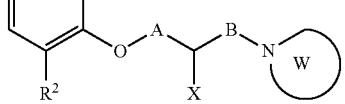

III

In a compound of both of Formulas II and III, A, B, W and X are as previously defined for a compound of Formulas I and Ia, above. $R^1$ and $R^2$ for a compound of Formula II are defined as $R^1$ and $R^2$ for a compound of Formula Ia, whereas $R^1$ and $R^2$ for a compound of Formula III are defined as $R^1$ and $R^2$ for a compound of Formula I.

More preferably, the $R^1$ and $R^2$ groups of a compound of Formula II contain 3 to 5 carbon atoms. For some compounds of Formula III, $R^1$ is H and $R^2$ is halogen, $C_1$-$C_6$ hydrocarbyl, $C_1$-$C_6$ acyl, $C_1$-$C_6$ hydrocarbyloxy or $NR^3R^4$, whereas for others, both R groups are other than H, but chosen as defined above.

In a compound of either Formula II or Formula III, W can optionally contain 1 or 2 further hetero atoms that are independently oxygen, nitrogen or sulfur, and more preferably still, contains at least one such hetero atom. It is also preferred that W further includes one or more substituent groups bonded to one or more ring atoms, in which the one or more substituents contain a total of up to 8 atoms selected from the group consisting of carbon, nitrogen, oxygen and sulfur, and mixtures thereof, and hydrogens bonded to those atoms are not counted.

A particularly preferred compound of Formulas II and III has a structure of Formulas IIa and IIIa, wherein the other groups A, B, W, $R^1$ and $R^2$ are as defined above.

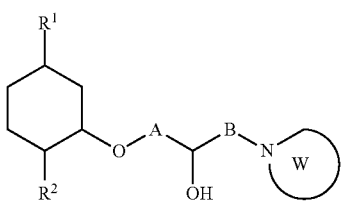

IIa

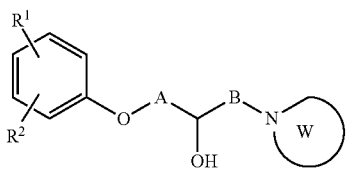

IIIa

A compound of Series B corresponds generally to the Formula I, below

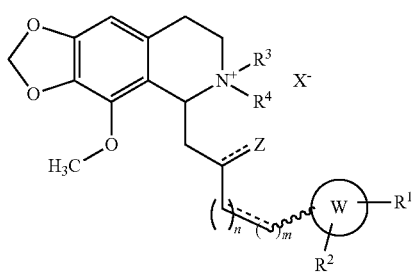

I wherein
n=0 or 1;
m=0 or 1;
m+n=0, 1 or 2;

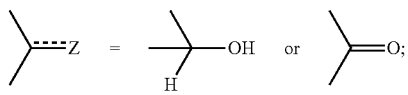

W is an aromatic ring containing 0, 1 or 2 hetero atoms that can be nitrogen, oxygen or sulfur, or mixtures thereof in the ring;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl;

$R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen;

$R^3$ is absent or $C_1$-$C_6$ hydrocarbyl;

$R^4$ is $C_1$-$C_6$ hydrocarbyl;

$X^-$=an anion or is absent when $R^3$ is absent;

the dashed line indicates an optional double bond between the depicted carbon atoms; and the wavy line indicates that the depicted phenyl substituent can be in the Z or E configuration when the optional double bond is present.

Illustrative anions can be monovalent or polyvalent. A contemplated anion is pharmaceutically acceptable and includes phosphate, hydrogen phosphate, dihydrogenphosphate, sulfate, bisulfate, chloride, bromide, iodide, acetate, formate, benzenesulfonate, methanesulfonate, toluenesulfonate and the like as are well known. These and other anions are listed in Berge et al., 1977 *J. Pharm Sci.* 68(1): 1-19.

It is preferred that m+n=1 or 2, and the optional double bond is absent, and is rather a saturated, single bond.

In preferred practice, W is a six-membered ring, although five membered rings are also contemplated. Thus, a contemplated aromatic ring that can include zero, one or two hetero atoms that are nitrogen, oxygen or sulfur or mixtures thereof include phenyl, pyridyl, furanyl, imidazyl, oxazolyl and the like. In some preferred embodiments, W is free of (has zero) ring nitrogen atoms. In other embodiments, preferred compounds have W groups that are free of ring hetero atoms, having only ring carbon atoms.

W preferably further includes one or more substituent groups ($R^1$ and $R^2$) to one or more ring atoms, in which those one or more substituents contain a total of up to 12 atoms selected from the group consisting of carbon, nitrogen, oxygen and sulfur, and mixtures thereof, with hydrogen atoms not being counted. Preferred substituent groups on ring W have an oxygen atom bonded to the W ring. Such compounds are preferably $C_1$-$C_6$ hydrocarbyloxy groups such as methoxy groups.

The Z-containing group can be a keto group or can be reduced to a hydroxyl group. Both groups are preferred.

In some embodiments, both $R^3$ and $R^4$ are $C_1$-$C_6$ hydrocarbyl groups that are both methyl. In other embodiments, one is an ethyl group and the other is methyl or absent. When $R^3$ is absent, a Series B compound is a tertiary amine.

In one preferred embodiment, a Series B compound of Formula I has the structure of Formula II,

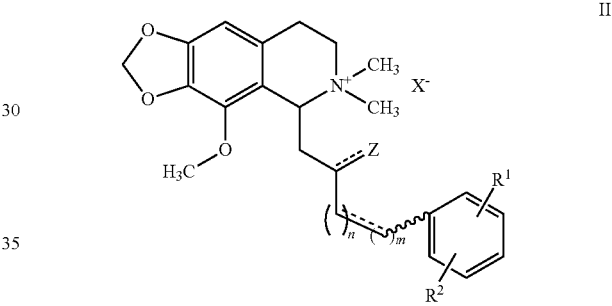

II wherein
n=0 or 1;
m=0 or 1;
m+n=0, 1 or 2;

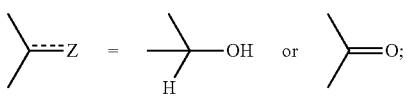

$X^-$=an anion;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl;

$R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen;

the dashed line indicates an optional double bond between the depicted carbon atoms; and the wavy line indicates that the depicted phenyl substituent can be in the Z or E configuration when the optional double bond is present.

In some preferred embodiments, $R^2$=H. In some such embodiments, $R^1$ includes an oxygen atom bonded to the depicted phenyl ring, and that oxygen is preferably part of a $C_1$-$C_6$ hydrocarbyloxy group. For many compounds, it is preferred that

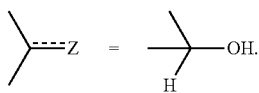

In yet other preferred embodiments, a contemplated Series B compound of has a structure that corresponds to Formula III, below

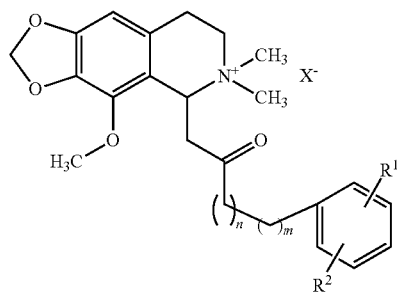

here,
n=0 or 1;
m=0 or 1;
m+n=0, 1 or 2;
$X^-$=an anion;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl; and $R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen.

As was the case for other Series B compound embodiments, $R^2$ is sometimes H, and one or both of $R^1$ and $R^2$ are $C_1$-$C_6$ hydrocarbyloxy groups such as methoxy. A pharmaceutically acceptable salt of a compound of Formula I, II and III and all of the remaining Series B formulas disclosed herein is also contemplated.

A compound of Series C-1 corresponds generally to the Formula A, below

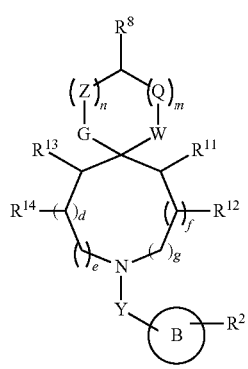

In Formula Series C-1 Formula A, G and W are selected from the group consisting of $NR^{20}$, $NR^7$, $CH_2$, S and O, where $R^7$ is H, $C_1$-$C_{12}$ hydrocarbyl, or $C_1$-$C_{12}$ hydrocarboyl (acyl) and $R^{20}$ is a group X-circle A-$R^1$ as defined hereinafter, and G and W are preferably $NR^{20}$ and $NR^7$. In one preferred embodiment, only one of G and W is $NR^7$ and one of G and W must be $NR^7$ or $NR^{20}$;

X and Y are the same or different and are $SO_2$, C(O), $CH_2$, $CD_2$ (where D is deuterium), OC(O), NHC(NH), NHC(S) or NHC(O);

Q is $CHR^9$ or C(O); Z is $CHR^{10}$ or C(O);

each of d, e, f and k is either zero or one and the sum of (d+e+f+k)=2. In some embodiments, e is zero when d is zero, and g is zero when f is zero. In other embodiments, d is zero when f is zero, or e is zero when g is zero.

Each of m, n and p is zero or one and the sum of m+n+p is 2 or 3 for all embodiments. Each of m and n is preferably 1, and p is preferably zero so that the sum of m+n+p is preferably 2.

The circles A and B are the same or different aromatic or heteroaromatic ring systems. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl (acyl), hydroxy-, trifluoromethyl- (—$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [S(O)$_2NR^3R^4$] wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl group as described previously, and $NR^5R^6$, wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms;

$R^{11}$, $R^{12}$, $R^{13}$ and $R^{14}$ are all H, or one of the pair $R^{11}$ and $R^{12}$ or the pair $R^{13}$ and $R^{14}$ together with the depicted ring form a saturated or unsaturated 6-membered ring, and the other pair are each H, or they are H and D as recited herein (in this subparagraph).

Also in the above preferred embodiment, $R^1$ and $R^2$ are not both methoxy when X and Y are both $SO_2$, W is O and p is zero.

In another preferred embodiment,
i) only one of G and W is $NR^{20}$,
ii) one of G and W must be $NR^{20}$,
iii) one of G and W is other than $NR^7$ in which $R^7$ is H or an aliphatic $C_1$ hydrocarbyl; i.e., methyl, when (a) the sum of m+n+p is 2, and (b) the other of G and W is $NR^{20}$ bonded to a Z or Q, respectively, that is C(O), and
iv) when X and Y are both $SO_2$, W is O, Q is $CH_2$, p is zero, and d and f are both 1, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen.

$R^1$ and $R^2$ are preferably also not both methoxy when X and Y are both $SO_2$, W is O and p is zero in the above-preferred embodiment.

A pharmaceutically acceptable salt of a compound of Series C-1 Formula A and all of the remaining Series C-1 formulas disclosed herein is also contemplated.

In one preferred Series C-1 embodiment, e and g are both zero and a compound of Series C-1 Formula A becomes a compound of Series C-1 Formula B, below

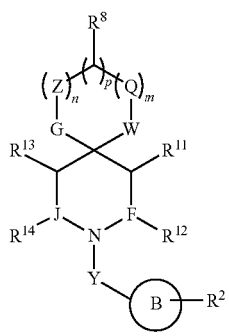

B

In Formula B, the letters of the formula G, J, E, F, K, W, Q, Z, d, e, f, k, n, m, p, X, Y, circle A and circle B and all R groups are as previously defined for a compound of Formula A of Series C-1. Preferably, $R^1$ and $R^2$ are not both methoxy when X and Y are both $SO_2$, W is O and p is zero.

In all of the following sub-generic formulas of a compound of Series C-1, the formula letters of G, J, E, F, K, W, Q, Z, d, e, f, k, n, m, p, X, Y, circle A and circle B and all R groups are as previously defined for a compound of Formula A of Series C-1, unless otherwise defined. Additionally, the previously stated preferences also apply unless a depicted structural formula precludes such a preference.

More preferably, a compound of Series C-1 Formula B corresponds in structure to Series C-1 Formula I, below

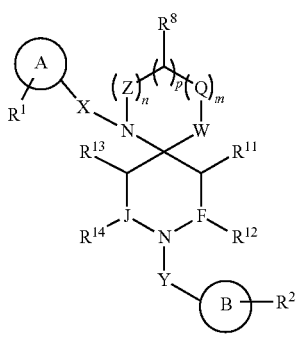

I

In Series C-1 Formula I, X and Y are the same or different and are $SO_2$, C(O), $CH_2$, $CD_2$, NHC(NH), OC(O), NHC(S) or NHC(O);

W is $NR^7$, $CH_2$, S or O, where $R^7$ is H, $C_1$-$C_{12}$ hydrocarbyl, or $C_1$-$C_{12}$ hydrocarboyl (acyl), and is preferably $NR^7$;

Q is $CHR^9$ or C(O);

Z is $CHR^{10}$ or C(O);

J and F are the same or different and are CH or CD (where D is deuterium);

each of m, n and p is zero or one and the sum of m+n+p is 2 or 3, preferably 2; and the circles A and B are the same or different aromatic or heteroaromatic ring systems that contain one ring or two fused rings. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, trifluoromethyl, trifluoromethoxy, $C_1$-$C_7$ hydrocarboyl (acyl), hydroxy-, trifluoromethyl- (—$CF_3$) or halogen-substituted $C_1$-$C_7$ hydrocarboyl, $C_1$-$C_6$ hydrocarbylsulfonyl, halogen (F, Cl or Br, and preferably Cl), nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$SO_2NR^3R^4$] wherein the amido nitrogen of either group (the carboxamide or sulfonamide) has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is where M is —$CH_2$—, —O— or —N=N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms; and $R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein (in this subpargraph).

Preferably, $R^1$ and $R^2$ are not both methoxy when X and Y are both $SO_2$, W is O and p is zero.

In other preferred embodiments, X and Y are the same. X and Y are preferably both C(O) or both $SO_2$, and more preferably are both $SO_2$. In those and other embodiments, W is preferably O. It is also preferred that p be zero.

A contemplated aromatic or heteroaromatic ring system of circle A or circle B can contain one ring or two fused rings, and preferably contains a single aromatic ring. An illustrative aromatic or heteroaromatic ring system is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, benzopyrimidinyl, and mixtures thereof. The mixtures of the previous sentence occur when circle A and circle B aromatic or heteroaromatic ring systems are different.

An illustrative single-ringed aryl group of substituent MAr is selected from the group consisting of phenyl, pyridyl, pyrazinyl, pyrimidinyl, pyridazinyl, triazinyl (1,3, 5-triazinyl, 1,2,4-triazinyl and 1,2,3-triazinyl), furanyl, thienyl, oxazolyl, isoxazolyl, thiazolyl and isothiazolyl.

Phenyl is a preferred aromatic or heteroaromatic ring system of circle A and circle B. Phenyl, pyridinyl and furanyl are preferred single-ringed aryl groups, Ar, of a MAr substituent, with phenyl being particularly preferred.

There are several independent and separate preferences regarding the substituent R groups. Thus, $R^1$ and $R^2$ are preferably the same single substituent other than hydrogen, so that circle A and circle B both contain a single substituent other than hydrogen. The single substituent of $R^1$ and $R^2$ is preferably located at the same relative position in their respective ring systems.

Thus, X and Y can form a sulfonamido, a carboxamido, a urea, a thiourea, a guanidino or methylene linkage from the circle A or circle B ring system to a depicted nitrogen atom of the central spiro ring. A compound having a central ring that is a spiro 6,6-ring system or a spiro 5,6-ring system, along with one nitrogen and one oxygen or two nitrogen atoms is contemplated. Illustrative central spiro rings are shown below where wavy lines are used to indicate the presence of covalent bonds to other entities, and where $R^7$ is defined above and $R^8$ is H.

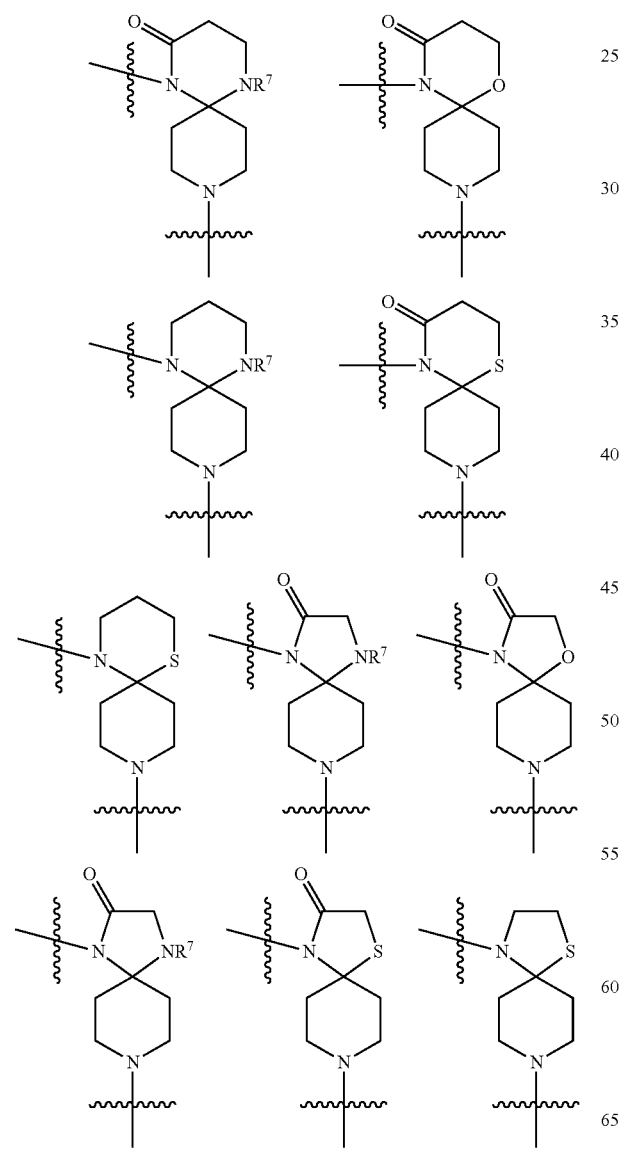

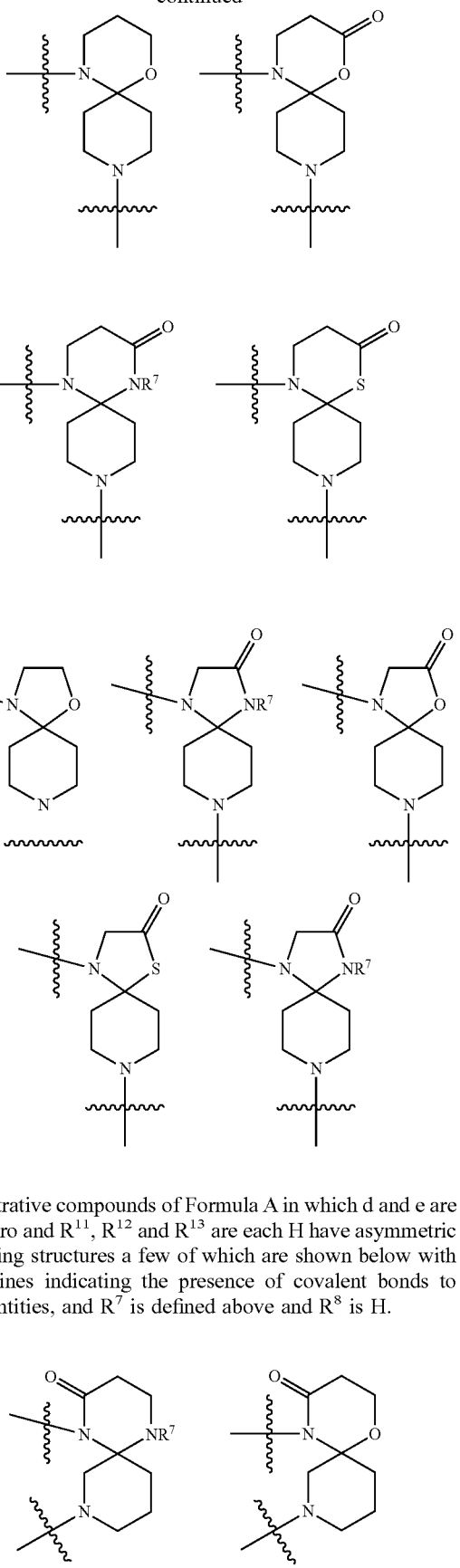

Illustrative compounds of Formula A in which d and e are each zero and $R^{11}$, $R^{12}$ and $R^{13}$ are each H have asymmetric Spiro ring structures a few of which are shown below with wavy lines indicating the presence of covalent bonds to other entities, and $R^7$ is defined above and $R^8$ is H.

-continued

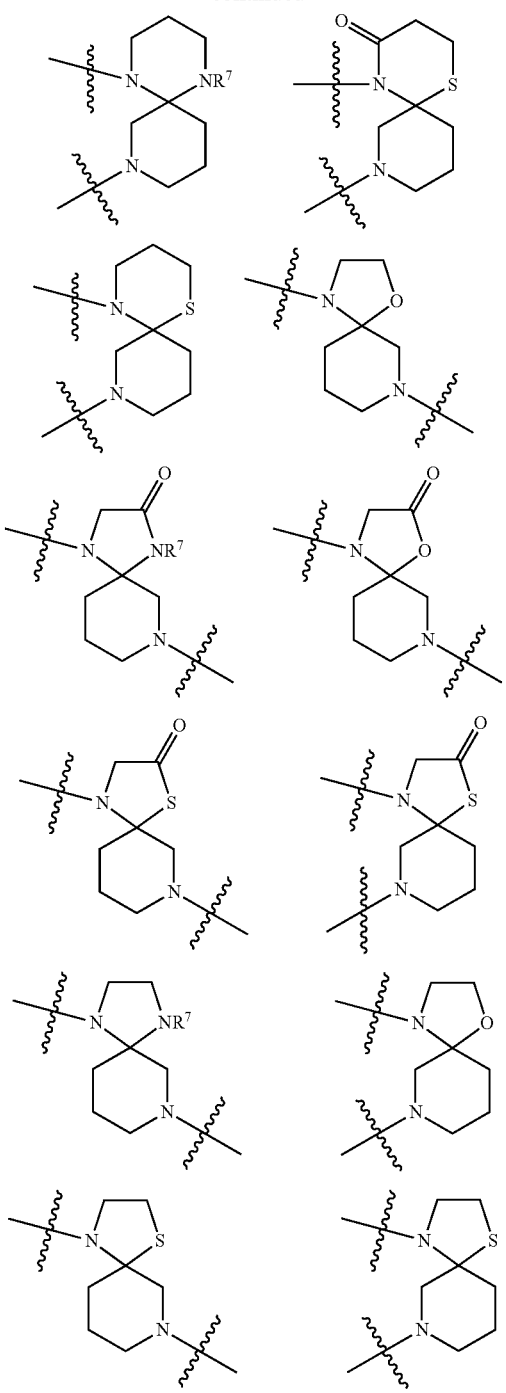

In preferred practice, p is zero, e and g are both zero and $R^{11}$, $R^{12}$ and $R^{13}$ are all H, so the central ring is a Spiro 5,6-ring system whose 6-membered ring is unsubstituted and in which the Spiro bonds are in the 4-position relative to the nitrogen of the 6-membered ring. It is separately preferred that W be O. A compound in which X and Y are the same is preferred. It is also separately preferred that X and Y both be $SO_2$ (sulfonyl).

A particularly preferred compound of Series C-1 Formula A that embodies the above separate preferences is a compound of Series C-1 Formula II

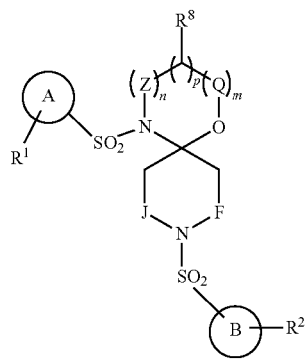

II wherein
circle A and circle B, Z, Q, m, n, p, $R^1$, $R^2$ and $R^8$ are as described above for a compound of Series C-1, unless the formula as shown precludes a definition provided for a compound of Formula A; and J and F are the same or different and are $CH_2$, CHD or $CD_2$ (where D is deuterium).

It is more preferred that circle A and circle B are each phenyl, furanyl or pyridyl and $R^1$ and $R^2$ is each a single substituent. There are several independent and separate preferences regarding the substituent R groups. Thus, $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n+p=2 so that the upper depicted ring contains 5-ring atoms.

Preferred $R^1$ and $R^2$ substituent groups do not themselves provide a positive or negative charge to a compound at a pH value of about 7.2-7.4.

In other embodiments, a particularly preferred compound of Series C-1 Formula A is a compound of Series C-1 Formula III

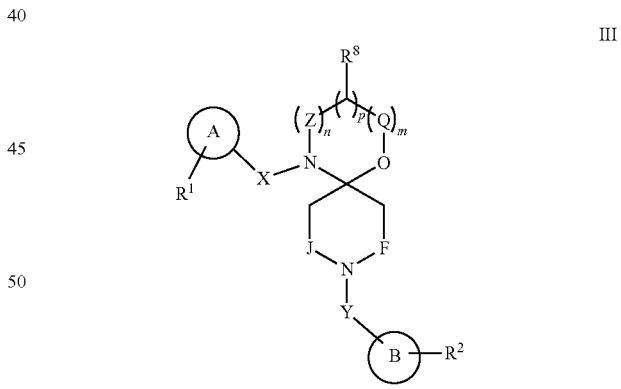

III wherein
circle A and circle B, Z, Q, m, n, p, $R^1$, $R^2$ and $R^8$ are as described previously for a compound of Series C-1 unless the formula as shown precludes a prior definition; J and F are the same or different and are $CH_2$, CHD or $CD_2$ (where D is deuterium); and X and Y are both CO, or X and Y are different and are $SO_2$, C(O), $CH_2$, $CD_2$ (where D is deuterium), OC(O), NHC(NH), NHC(S) or NHC(O). Previous preferences are also applicable unless precluded by the above structural formula.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that p=0, and that the sum of m+n+p=2, so that the upper depicted ring contains 5-ring atoms.

In still further embodiments, a particularly preferred compound of Series C-1 Formula A is a compound of Series C-1 Formula IV

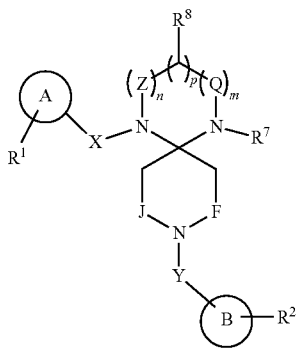

IV wherein
circle A and circle B, Z, Q, m, n, p, $R^1$, $R^2$, $R^7$ and $R^8$ are as described previously for a compound of Series C-1 unless the formula as shown precludes such a prior definition; J and F are the same or different and are $CH_2$, CHD or $CD_2$ (where D is deuterium); and X and Y are the same or different and are $SO_2$, C(O), $CH_2$, $CD_2$ (where D is deuterium), OC(O), NHC(NH), NHC(S) or NHC(O). Previous preferences are also applicable unless precluded by the above structural formula.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n=1, so that the upper depicted ring contains 5-ring atoms.

It is noted that the previously mentioned preferences regarding E, J, F, G, K, Q, W, X, Y, Z, d, e, f, k, n, m, p, circle A and circle B, and all of the R groups as are appropriate for a particular formula apply to a compound of Series C-1 Formulas A, B, and I-IV.

A compound of Series C-2 corresponds generally to the Formula A, below

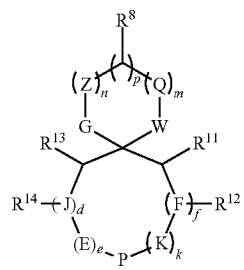

A

In Series C-2 Formula A,
Q is $CHR^9$ or C(O), Z is $CHR^{10}$ or C(O), and only one of Q and Z is C(O);
each of m and n and p is zero or one and the sum of m+n+p is 2 or 3, preferably 2;
each of G, P and W is selected from the group consisting of $NR^{20}$, $NR^2$, $NR^7$, S and O, where $R^7$ and $R^2$ are the same or different and are H, $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, (including aliphatic $C_1$-$C_{12}$ hydrocarbyl when q+r=0), aliphatic $C_1$-$C_{12}$ hydrocarbyl sulfonyl or aliphatic $C_1$-$C_{12}$ hydrocarboyl (acyl), and $R^{20}$ is X-circle A-$R^1$ as defined hereinafter.

Preferably, in one embodiment,
i) only one of G, P and W is $NR^{20}$,
ii) one of G, P and W must be $NR^{20}$,
iii) P is $NR^2$ when other than $NR^{20}$,
iv) one of G and W is other than $NR^2$ or $NR^7$ in which $R^2$ and $R^7$ is H or an aliphatic $C_1$ hydrocarbyl when (a) the sum of m+n+p is 2 and (b) the other of G and W is $NR^{20}$, $NR^2$, or $NR^7$ bonded to a Z or Q, respectively, that is C(O), and
v) P is $NR^2$ in which $R^2$ is other than $—S(O)_2C_1$-$C_3$-hydrocarbyl when (a) the sum of m+n+p is 2 and the Q or Z present is $CH_2$, (b) the G or W that is not $NR^{20}$ is O, and (c) $R^{20}$ is $—S(O)_2$phenyl-$R^1$, where $R^1$ is H, $C_1$-$C_3$-hydrocarbyl or halogen.

Each of d, e, f and k is either zero or one and the sum of (d+e+f+k)=2. In some embodiments, e is zero when d is zero, and k is zero when f is zero. In other embodiments, e is zero when k is zero, and f is zero when d is zero.

J and F are the same or different and are CH or CD (where D is deuterium).

E and K are the same or different and are $CH_2$, CHD or $CD_2$ (where D is deuterium).

X is $SO_2$, C(O), $CH_2$, $CD_2$, OC(O), NHC(NH), NHC(S) or NHC(O), preferably $SO_2$, C(O) or $CH_2$. In some embodiments, X is more preferably $CH_2$ or $SO_2$. In other embodiments, X is preferably $SO_2$, NHC(NH), NHC(S) or NHC(O).

Circle A is an aromatic or heteroaromatic ring system that preferably contains a single ring, but can also contain two fused rings. $R^1$ is H or represents up to three substituents, $R^{1a}$, $R^{1b}$, and $R^{1c}$, that themselves can be the same or different, wherein each of those three groups, $R^{1a-c}$, is separately selected from the group consisting of H, $C_1$-$C_6$ hydrocarbyl, $C_1$-$C_6$ hydrocarbyloxy, $C_1$-$C_6$ hydrocarbyloxy-carbonyl, trifluoromethyl, trifluoromethoxy, $C_1$-$C_7$ hydrocarboyl, hydroxy-, trifluoromethyl- ($—CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen (F, Cl, or Br, and preferably Cl) nitro, phenyl, cyano, carboxyl, $C_1$-$C_7$ hydrocarbyl carboxylate [C(O)O—$C_1$-$C_7$ hydrocarbyl], carboxamide [C(O)NR$^3$R$^4$] or sulfonamide [S(O)$_2$NR$^3$R$^4$], wherein the amido nitrogen in either amide group has the formula NR$^3$R$^4$ in which R$^3$ and R$^4$ are the same or different and are H, $C_1$-$C_4$ hydrocarbyl, or R$^3$ and R$^4$ together with the depicted nitrogen form a 5-7-membered ring that optionally contains 1 or 2 additional hetero atoms that independently are nitrogen, oxygen or sulfur, MAr, where M is —CH$_2$—, —O— or —N=N— and Ar is a single-ringed aryl or heteroaryl group and NR$^5$R$^6$ wherein R$^5$ and R$^6$ are the same or different and are H, $C_1$-$C_4$ hydrocarbyl, $C_1$-$C_4$ acyl, $C_1$-$C_4$ hydrocarbylsulfonyl, or R$^5$ and R$^6$ together with the depicted nitrogen form a 5-7-membered ring that optionally contains 1 or 2 additional hetero atoms that independently are nitrogen, oxygen or sulfur.

R$^8$, R$^9$, and R$^{10}$ are each H, which is preferred, or two of R$^8$, R$^9$, and R$^{10}$ are H and one is a $C_1$-$C_8$ hydrocarbyl group that is unsubstituted or is substituted with up to three atoms that are the same or different and are oxygen or nitrogen atoms (including hydrogens as appropriate).

R$^{11}$, R$^{12}$, R$^{13}$ and R$^{14}$ are all H, or R$^{11}$ and R$^{13}$ are H and R$^{12}$ and R$^{14}$ are H or D, or one of the pair R$^{11}$ and R$^{12}$ or the pair R$^{13}$ and R$^{14}$ together with the depicted ring form a saturated or unsaturated 6-membered ring, and the other pair are each H or they are H and D as recited herein (in this subparagraph).

In another preferred embodiment of a compound of Formula A, above, i) only one of G, P and W is NR$^{20}$, ii) one of G, P and W must be NR$^{20}$, and iii) P is NR$^2$ when other than NR$^{20}$.

Additionally, Q is CHR$^9$ or C(O); and

Z is CHR$^{10}$ or C(O), with the other of J, E, F, K, X, Z, d, e, f, k, n, m, p, circle A, and all of the R groups being defined as discussed above unless precluded by the structural formula.

A pharmaceutically acceptable salt of a compound of Series C-2 Formula A and all of the remaining formulas disclosed herein is also contemplated.

In preferred embodiments, a compound of Series C-2 Formula A corresponds in structure to either Formula B or Formula C, can be present as a pharmaceutically acceptable salt, and can optionally be present including both individual enantiomeric forms, a racemate, diastereomers and mixtures thereof.

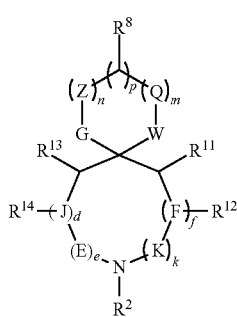

B

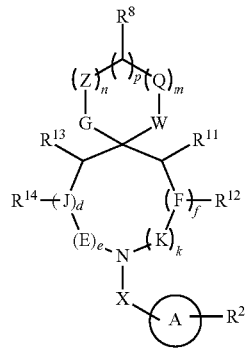

C

In a compound of Series C-2 that corresponds in structure to Series C-2 Formula B, G and W are selected from the group consisting of NR$^{20}$, NR$^7$, S and O, where R$^2$ and R$^7$ are the same or different and are C(H)$_v$(D)$_h$ (where D is deuterium) and where each of v and h is 0, 1, 2 or 3 and v+h=3, C(H)$_q$(D)$_r$-aliphatic $C_1$-$C_{11}$ hydrocarbyl (where D is deuterium) where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl, or R$^2$ and R$^{20}$ are the same or different, and R$^{20}$ is X-circle A-R$^1$.

Preferably in one embodiment, i) only one of G and W is NR$^{20}$, ii) one of G and W must be NR$^{20}$, iii) the G or W that is not NR$^{20}$ is other than NR$^2$ or NR$^7$ in which R$^2$ or R$^7$ is H or an aliphatic $C_1$ hydrocarbyl when (a) the sum of m+n+p is 2 and (b) the G or W that is NR$^{20}$ is bonded to a Z or Q, respectively, that is C(O), and iv) R$^2$ of the depicted NR$^2$ is other than —S(O)$_2$C$_1$-$C_3$-hydrocarbyl when (a) the sum of m+n+p is 2 and the Q or Z that is present is CH$_2$, (b) the G or W that is not NR$^{20}$ is O, and (c) R$^{20}$ is —S(O)$_2$phenyl-R$^1$, where R$^1$ is H, $C_1$-$C_3$-hydrocarbyl or halogen.

In another preferred embodiment:

i) only one of G and W is NR$^{20}$, ii) one of G and W must be NR$^{20}$, iii) the G or W that is not NR$^{20}$ is NR$^2$ or NR$^7$ in which R$^2$ or R$^7$ is H or an aliphatic $C_1$ hydrocarbyl, (iv) the sum of m+n+p is 2, and (v) the G or W that is NR$^{20}$ is bonded to a Z or Q, respectively, that is C(O).

In yet another preferred embodiment:

i) only one of G and W is NR$^{20}$, ii) one of G and W must be NR$^{20}$, iii) the G or W that is not NR$^{20}$ is NR$^7$ that is H or an aliphatic $C_1$ hydrocarbyl, (iv) the sum of m+n+p is 2, (v) the G or W that is NR$^{20}$ is bonded to a Z or Q, respectively, that is C(O), (vi) R$^2$ of the depicted NR$^2$ is the same or different R$^{20}$, and (vii) R$^{20}$ is X-circle A-R$^1$.

For a compound of Formula C, G and W are selected from the group consisting of NR$^2$, NR$^7$, S and O, where R$^2$ and R$^7$ are the same or different and are H, C(H)$_v$(D)$_h$ (where D is deuterium) and where each of v and h is 0, 1, 2 or 3 and v+h=3, C(H)$_q$(D)$_r$-aliphatic $C_1$-$C_{11}$ hydrocarbyl where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl.

Preferably, in another embodiment:

i) one of G and W must be $NR^2$ or $NR^7$, and ii) one of G and W is other than $NR^2$ or $NR^7$ in which $R^2$ or $R^7$ is H or an aliphatic $C_1$ hydrocarbyl when (a) the sum of m+n+p is 2 and (b) the other of G and W is $NR^2$ or $NR^7$ bonded to a Z or Q, respectively, that is C(O).

In both of Series C-2 Formulas B and C, the symbols X, Z, Q, d, e, f, g, n, m, circle A, and all of the R groups not otherwise defined in the paragraphs following their structural formulas are as defined previously for a compound of Series C-2 Formula A unless the formula as shown precludes a prior definition. The previously noted preferences are also as discussed before unless the formula as shown precludes a prior preference.

In one embodiment, a preferred compound of Series C-2 Formulas A and B has the structure of Formula I

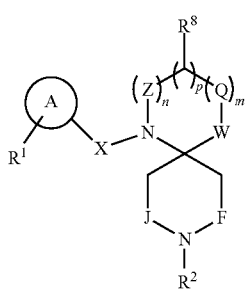

I wherein J and F are the same or different and are $CH_2$, CHD or $CD_2$ (where D is deuterium); and W, X, Z, Q, n, m, p, circle A, $R^1$, $R^2$, $R^8$ and the R groups therein defined are as described previously for a compound of Series C-2 Formula A, unless the formula as shown precludes a prior definition. Preferably, i) $R^2$ of the depicted $NR^2$ is other than —$S(O)_2C_1$-$C_3$-hydrocarbyl when (a) the sum of m+n+p is 2 and the Q or Z present is $CH_2$, (b) the G or W that is not $NR^{20}$ is O, and (c) $R^{20}$ is —$S(O)_2$phenyl-$R^1$, where $R^1$ is H, $C_1$-$C_3$-hydrocarbyl or halogen, and ii) W is other than $NR^2$ or $NR^7$ in which $R^2$ or $R^7$ is H or an aliphatic $C_1$ hydrocarbyl when (a) the sum of m+n+p is 2 and (b) Z is C(O).

In another preferred embodiment where $R^8$ is H, one of n and m is zero and the remaining Z or Q is $CH_2$, a compound of Series C-2 Formulas A, B and I has the structure of Series C-2 Formula II

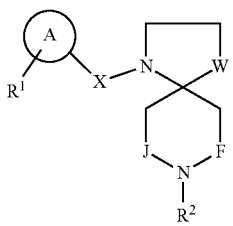

II wherein J and F are the same or different and are $CH_2$, CHD or $CD_2$ (where D is deuterium); and X, W, circle A, $R^1$, $R^2$ and the R groups therein defined are as described previously for a compound of Series C-2 Formula A, unless the formula as shown precludes a prior definition. Preferably, $R^2$ of the depicted $NR^2$ is other than —$S(O)_2C_1$-$C_3$-hydrocarbyl when W is O, and X-circle A-$R^1$ is —$S(O)_2$phenyl-$R^1$, where $R^1$ is H, $C_1$-$C_3$-hydrocarbyl or halogen.

In a further preferred embodiment, where $R^8$ is H, a compound of Series C-2 Formulas A, B and I has the structure of Series C-2 Formula III

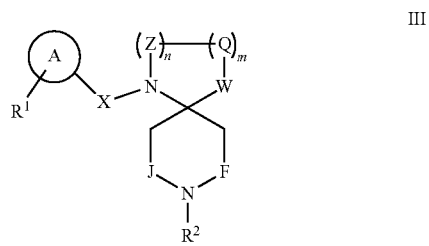

III wherein J and F are the same or different and are $CH_2$, CHD or $CD_2$ (where D is deuterium);

each of m and n is one; and

W, X, Z, Q, circle A, $R^1$, $R^2$ and the R groups therein defined are as described previously for a compound of Series C-2 Formula A, unless the formula as shown precludes a prior definition.

In one preferred embodiment, i) Z is C(O), ii) Q is $CH_2$, iii) W is NH, and $R^2$ is H or $C_1$-$C_{12}$ aliphatic straight, branched or cyclic hydrocarbyl, iv) X is preferably $CH_2$, $SO_2$, NHC(NH), NHC(S) or NHC(O), and more preferably $CH_2$. In another preferred embodiment, i) one of Z and Q is C(O), and ii) W is other than $NR^2$ or $NR^7$ in which $R^2$ and $R^7$ is H or an aliphatic $C_1$ hydrocarbyl when Z is C(O), iii) X is preferably $CH_2$, $SO_2$, NHC(NH), NHC(S) or NHC(O).

In a still further preferred embodiment, i) Z is C(O), ii) Q is $CH_2$, iii) W is NH, (vi) $R^2$ is the same or different $R^{20}$, and (vii) $R^{20}$ is X-circle A-$R^1$. In this embodiment, X is preferably $CH_2$, $SO_2$, NHC(NH), NHC(S) or NHC(O), more preferably $CH_2$.

A presently most preferred compound for carrying out a contemplated method corresponds in structure to Formula III, above, in which i) Z is C(O), ii) Q is $CH_2$, iii) W is NH, and $R^2$ is H or a $C_1$-$C_{12}$, preferably $C_1$-$C_8$, and more preferably a $C_1$-$C_6$, aliphatic straight, branched or cyclic hydrocarbyl group, iv) X is $CH_2$, and circle A-$R^1$ is unsubstituted phenyl so that the substituent X-circle A-$R^1$ is a benzyl group. Illustrative presently most preferred compounds include Compounds C0105M, C0115M and C0124M, whose structural formulas are shown below.

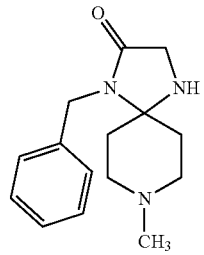

C0105M

-continued

C0114M

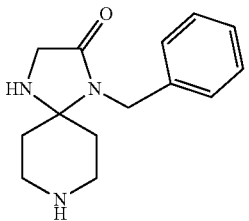

C0124M

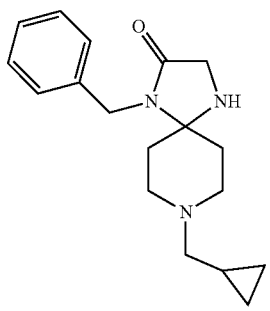

In a still further preferred embodiment, a compound of Series C-2 Formulas A and C has the structure of Series C-2 Formula IV

IV

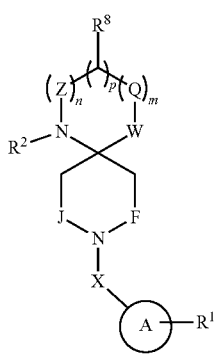

wherein J and F are the same or different and are CH$_2$, CHD or CD$_2$ (where D is deuterium); and W, X, Z, Q, circle A, R$^1$, R$^2$, R$^8$ and the R groups therein defined are as described previously for a compound of Series C-2 Formula A, unless the formula as shown precludes a prior definition.

In one preferred embodiment, i) W is other than NR$^2$ or NR$^7$ in which R$^2$ or R$^7$ is H or an aliphatic C$_1$ hydrocarbyl, when p is zero and the sum of m+n+p is 2 and Z is C(O), and ii) R$^2$ of the depicted NR$^2$ group is other than H or an aliphatic C$_1$ hydrocarbyl, when p is zero and the sum of m+n+p is 2, W is NR$^2$ or NR$^7$, and Q is C(O).

In yet another preferred embodiment where R$^8$ is H, one of n and m is zero and the remaining Z or Q is CH$_2$, a compound of Formulas A, C and IV has the structure of Series C-2 Formula V

V

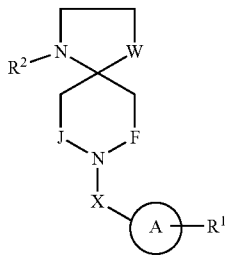

wherein J and F are the same or different and are CH$_2$, CHD or CD$_2$ (where D is deuterium); and X, W, circle A, R$^1$, R$^2$ and the R groups therein defined are as described previously for a compound of Series C-2, unless the formula as shown precludes a prior definition.

In still another preferred embodiment, where R$^8$ is H, a compound of Series C-2 Formulas A, C and I has the structure of Series C-2 Formula VI

VI

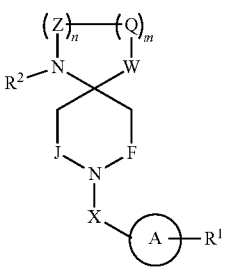

wherein J and F are the same or different and are CH$_2$, CHD or CD$_2$ (where D is deuterium); and each of m and n is one; W, X, Z, Q, circle A, R$^1$, R$^2$ and the R groups therein defined are as described previously for a compound of Series C-2, unless the formula as shown precludes a prior definition.

Preferably, i) one of Z and Q is C(O), ii) W is other than NR$^2$ or NR$^7$ in which R$^2$ or R$^7$ is H or an aliphatic C$_1$ hydrocarbyl when Z is C(O), and iii) R$^2$ of the depicted NR$^2$ group is other than H or an aliphatic C$_1$ hydrocarbyl when W is NR$^2$ or NR$^7$, and Q is C(O). In a compound of the above formula, X is preferably SO$_2$, NHC(NH), NHC(S) or NHC(O).

It is also noted that the previously mentioned preferences regarding apply to X, W, Z, Q, d, e, f, k, n, m, circle A, and all of the R groups apply to a compound of Series C-2 Formulas A, B, C, and I-VI, unless the formula as shown precludes a prior definition.

A contemplated aromatic ring (aryl) system of circle A of one of the contemplated compounds preferably contains a single aromatic ring, but can also contain two fused aromatic rings. An illustrative circle A aromatic ring system is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, and benzopyrimidinyl.

An illustrative single-ringed aryl or heteroaryl group of a circle A group or of a substituent of circle A, MAr, is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl and isothiazolyl groups.

Phenyl, pyridinyl and furanyl are a preferred aromatic or heteroaromatic ring system of circle A, with phenyl being more preferred. Phenyl, pyridinyl and furanyl are also preferred single-ringed aryl or heteroaryl groups, Ar, of a MAr substituent, with phenyl being particularly preferred.

From a depicted nitrogen atom of the central spiro rings to the circle A ring system, X and Y can form a sulfonamido (N—SO$_2$-circle A), a carboxamido [N—C(=O)-circle A), a urea [carbonyldiimino; N—C(=O)—NH-circle A], a thiourea [thiocarbonyldiimino; N—C(=S)—NH-circle A], a guanidino [N—C(=NH)—NH-circle A] or aminomethylene (N—CH$_2$-circle A) linkage.

Examining a compound of the above Series C-2 formulas more closely, it is seen that that formula defines a double ringed, substituted spiro compound that can have two six-membered rings or one six- and one five-membered ring, as when one of "m" and "n" is one and the other zero. One of those rings (the lower ring in the formulas) contains one nitrogen atom in the 6-membered ring and the remaining ring atoms are carbons. The ring that can contain 5- or 6-ring atoms (upper ring in the formulas) can contain one ring nitrogen and four or five carbons, or two nitrogens, a nitrogen and a sulfur or a nitrogen and an oxygen atom along with three or four ring carbons. Illustrative central spiro rings are shown below where wavy lines are used to indicate the presence of covalent bonds to other entities, and where R$^7$ is defined above and R$^8$ is H for clarity.

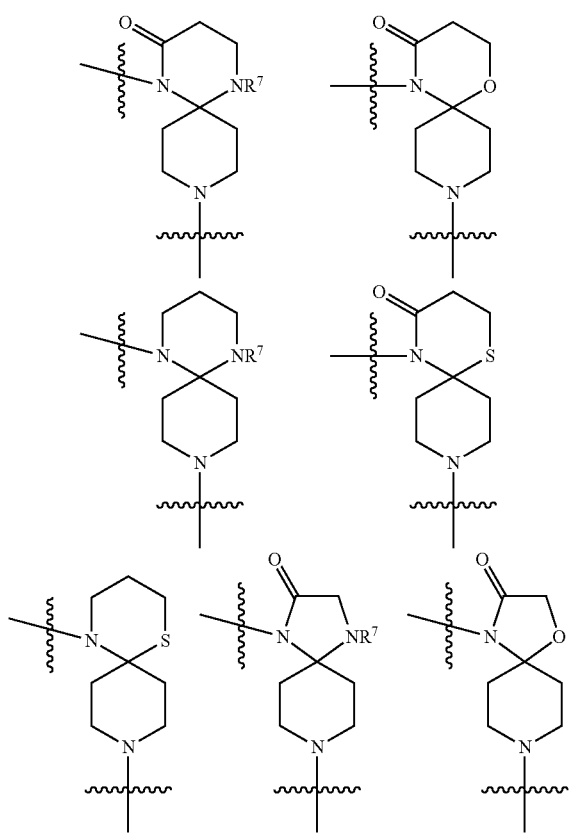

-continued

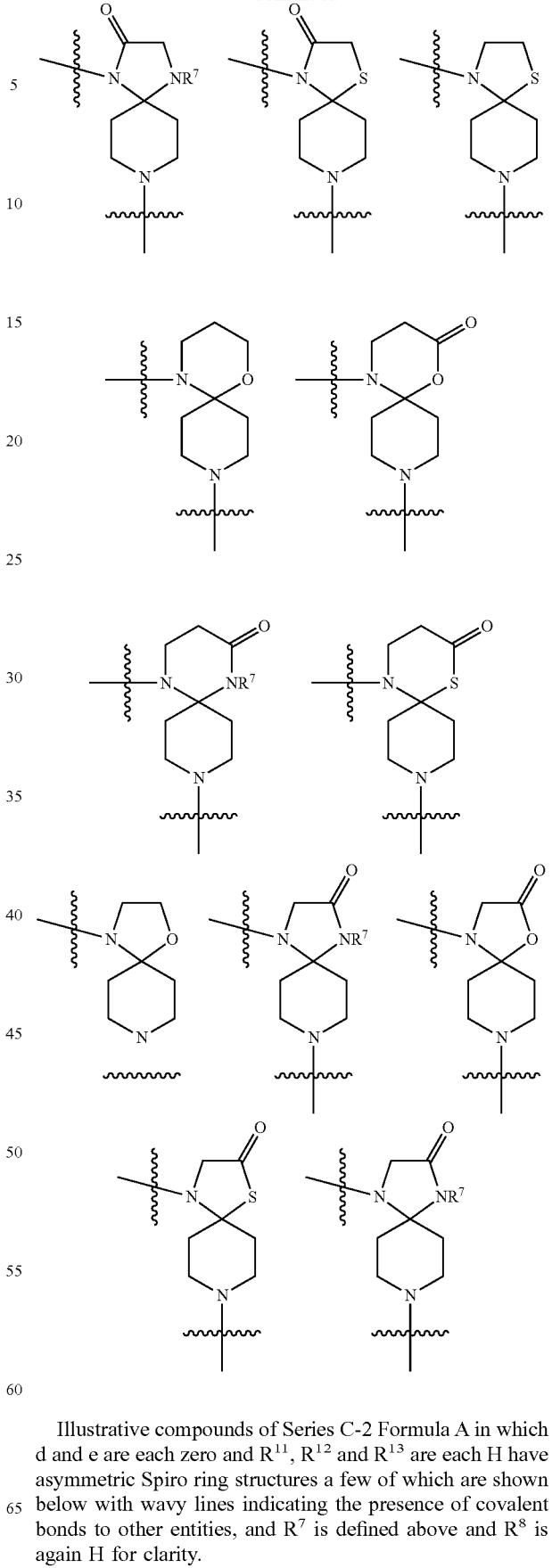

Illustrative compounds of Series C-2 Formula A in which d and e are each zero and R$^{11}$, R$^{12}$ and R$^{13}$ are each H have asymmetric Spiro ring structures a few of which are shown below with wavy lines indicating the presence of covalent bonds to other entities, and R$^7$ is defined above and R$^8$ is again H for clarity.

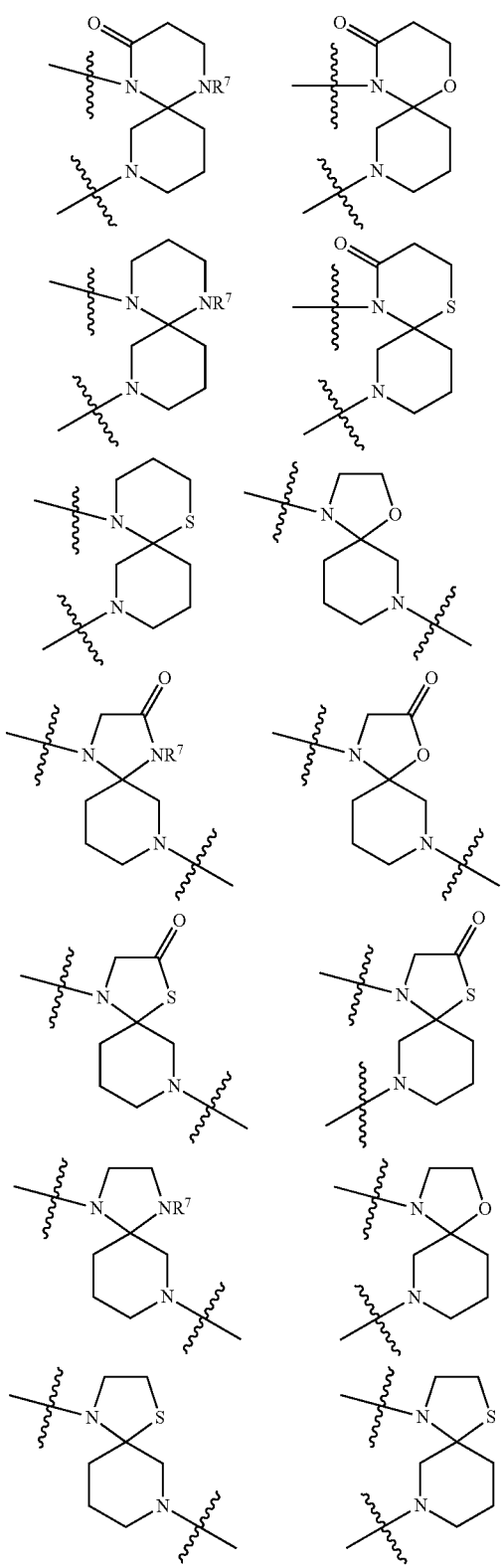

In preferred practice for the compounds of Series C-2 Formulas A, B and C, p is zero, e and g are both zero and $R^{11}$, $R^{12}$ and $R^{13}$ are all H, so the central ring is a spiro 5,6-ring system whose 6-membered ring is unsubstituted and in which the spiro bonds are in the 4-position relative to the nitrogen of the 6-membered ring. It is separately preferred that W be O, S or $NR^7$. It is also preferred that X be $SO_2$ (sulfonyl).

The aromatic substituent, the circle A, is linked to one nitrogen atom of the spiro rings by a X group that is $SO_2$, C(O), $CH_2$, $CD_2$, OC(=O), NHC(=NH), NHC(=S) or NHC(=O), preferably $SO_2$, C(O), $CH_2$, or $CD_2$, and most preferably $CH_2$ and $SO_2$. The resulting aromatic substituent is thereby linked to the spiro ring portion by a sulfonamide, an amide, a methylene, a urea, a thiourea or a guanidino linkage. Aryl sulfonamide bridges, aryl amide bridges and phenylmethylene bridges (benzyl compounds) are preferred, with aryl sulfonamide and phenylmethylene being particularly preferred.

Many of the compounds of Series A, Series B, Series C-1, and Series C-2, as well as compounds such as naloxone and naltrexone not only bind to the peptide of SEQ ID NO: 1, but also bind to MOR and activate or stimulate that receptor. Naloxone and naltrexone bind to MOR about 200 times more poorly than they bind to the pentapeptide of SEQ ID NO: 1. The tables of Example 2 illustrate relative binding abilities of exemplary compounds of Series A, Series B, Series C-1, and Series C-2 based on MOR stimulatory activity.

In some embodiments it is preferred that a compound useful in a contemplated method binds well to and activates MOR. In those cases, it is preferred that the compound bind to MOR to an extent of at least about ±20 percent as well as DAMGO at a concentration shown in the tables, indicating the compound is a complete agonist for the receptor. In other embodiments, it is preferred that a compound useful herein not bind well to MOR. In those embodiments, it is preferred that the compound exhibit less than about 80 percent the MOR stimulation provided by DAMGO at the same concentration, down to zero binding/stimulation. Illustrative binding percentages in the presence of stated concentrations of DAMGO are illustrated for exemplary compounds of Series A, Series B, Series C-1, and Series C-2 in the tables of Example 2, hereinafter.

A 1,4,8-triazaspiro[4,5]-decan-2-one compound of Series D corresponds in structure to the formula

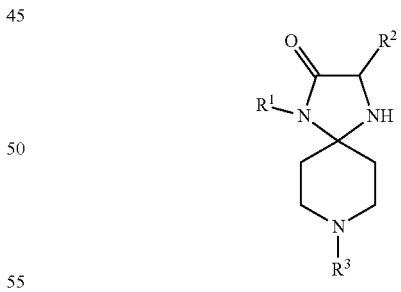

wherein $R^1$ represents hydrogen; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which aryl and heteroaryl groups may be bonded via a linear or branched alkylene group that can comprise at least one heteroatom as a link; or a —C(=O)OR$^7$ group that can be bonded via a linear or branched alkylene group;

R$^2$ represents hydrogen; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which aryl and heteroaryl group may be bonded via a linear or branched alkylene group that can comprise at least one heteroatom as a link;

R$^3$ represents a —S(=O)$_2$—R$^4$ group; a —C(=S)NH—R$^5$ group; or a —C(=O)NH—R$^6$ group;

R$^4$ represents a —NR$^{10}$R$^{11}$ group; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which groups may be bonded via a linear or branched unsubstituted or at least monosubstituted alkylene group that can comprise at least one heteroatom as a link and may be condensed with an unsubstituted or at least monosubstituted monocyclic ring system; an unsubstituted or at least monosubstituted cycloaliphatic group, that can comprise at least one heteroatom as a ring member and that can be bonded via a linear or branched unsubstituted or at least monosubstituted alkylene group that can comprise at least one heteroatom as a link and that can be bridged by a linear or branched unsubstituted or at least monosubstituted alkylene group;

R$^5$ represents a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which group may be bonded via a linear or branched unsubstituted or at least monosubstituted alkylene group that can comprise at least one heteroatom as a link; an unsubstituted or at least monosubstituted cycloaliphatic group, that can comprise at least one heteroatom as a ring member or that can be bonded via a linear or branched unsubstituted or at least monosubstituted alkylene group that can comprise at least one heteroatom as a link; a —C(=O)OR$^8$ group or a —C(=O)OR$^9$ group, that can, in either case, be bonded via a linear or branched alkylene group;

R$^6$ represents an unsubstituted or at least monosubstituted aryl group or an unsubstituted or at least monosubstituted heteroaryl group, which aryl and heteroaryl groups may be bonded via a linear or branched unsubstituted or at least monosubstituted alkylene group that can comprise at least one heteroatom as a link; or for an unsubstituted or at least monosubstituted cycloaliphatic group, that can comprise at least one heteroatom as a ring member or that can be bonded via a linear or branched unsubstituted or at least monosubstituted alkylene group that can comprise at least one heteroatom as a link;

R$^7$, R$^8$, R$^9$, R$^{10}$, and R$^{11}$, each independently represent a linear or branched alkyl group, a linear or branched alkenyl group, or a linear or branched alkynyl group, or a physiologically acceptable salt thereof.

Preferably for a 1,4,8-triazaspiro[4,5]-decan-2-one compound corresponding to the formula above, R$^1$ represents hydrogen; a linear or branched unsubstituted or at least monosubstituted C$_{1-10}$ alkyl group that can comprise at least one heteroatom as a link; a linear or branched unsubstituted or at least monosubstituted C$_{2-10}$ alkenyl group that can comprise at least one heteroatom as a link; a linear or branched unsubstituted or at least monosubstituted C$_{2-10}$ alkynyl group that can comprise at least one heteroatom as a link; an unsubstituted or at least monosubstituted five-membered to fourteen-membered aryl group or heteroaryl group, that can be bonded via a linear or branched C$_{1-5}$ alkylene group that can comprise at least one heteroatom as a link; a —C(=O)OR$^7$ group that can be bonded via a linear or branched C$_{1-5}$ alkylene group;

R$^2$ represents hydrogen; a linear or branched unsubstituted or at least monosubstituted C$_{1-10}$ alkyl group that can comprise at least one heteroatom as a link; a linear or branched unsubstituted or at least monosubstituted C$_{2-10}$ alkenyl group that can comprise at least one heteroatom as a link; a linear or branched unsubstituted or at least monosubstituted C$_{2-10}$ alkynyl group that can comprise at least one heteroatom as a link; an unsubstituted or at least monosubstituted five-membered to fourteen-membered aryl or heteroaryl group, that can be bonded via a linear or branched C$_{1-5}$ alkylene group that can comprise at least one heteroatom as a link;

R$^4$ represents an NR$^{10}$R$^{11}$ group; a linear or branched unsubstituted or at least monosubstituted C$_{1-10}$ alkyl group that can comprise at least one heteroatom as a link; a linear or branched unsubstituted or at least monosubstituted C$_{2-10}$ alkenyl group that can comprise at least one heteroatom as a link; a linear or branched unsubstituted or at least monosubstituted C$_{2-10}$ alkynyl group that can comprise at least one heteroatom as a link; an unsubstituted or at least monosubstituted five-membered to fourteen-membered aryl group or heteroaryl group, that can be bonded via a linear or branched unsubstituted or at least monosubstituted C$_{1-5}$ alkylene group that can comprise at least one heteroatom as a link and may be condensed with a five-membered or six-membered monocyclic ring system; an unsubstituted or at least monosubstituted C$_{3-8}$-cycloaliphatic group that can comprise at least one heteroatom as a ring member or that can be bonded via a linear or branched unsubstituted or at least monosubstituted C$_{1-5}$ alkylene group that can comprise at least one heteroatom as a link and that can be bridged by a linear or branched unsubstituted or at least monosubstituted C.sub.1-5 alkylene group;

R$^5$ represents a linear or branched unsubstituted or at least monosubstituted C$_{1-10}$ alkyl group that can comprise at least one heteroatom as a link; a linear or branched unsubstituted or at least monosubstituted C$_{2-10}$ alkenyl group that can comprise at least one heteroatom as a link; a linear or branched unsubstituted or at least monosubstituted C$_{2-10}$ alkynyl group that can comprise at least one heteroatom as a link; an unsubstituted or at least monosubstituted five-membered to fourteen-membered aryl or heteroaryl group, that can be bonded via a linear or branched unsubstituted or at least monosubstituted C$_{1-5}$ alkylene group that can comprise at least one heteroatom as a link; an unsubstituted or at least monosubstituted $C_{3-8}$-cycloaliphatic group that can comprise at least one heteroatom as a ring member and that can be bonded via a linear or branched unsubstituted or at least monosubstituted $C_{1-5}$ alkylene group that can comprise at least one heteroatom as a link; a —C(=O)OR$^8$ group or a —C(=O)OR$^9$ group either of that can be bonded via a linear or branched $C_{1-10}$ alkylene group;

R$^6$ represents an unsubstituted or at least monosubstituted five-membered to fourteen-membered aryl or heteroaryl group, which aryl or heteroaryl group may be bonded via a linear or branched unsubstituted or at least monosubstituted $C_{1-5}$ alkylene group that can comprise at least one heteroatom as a link; an unsubstituted or at least monosubstituted $C_{3-8}$-cycloaliphatic group that can comprise at least one heteroatom as a ring member, or that can be bonded via a linear or branched unsubstituted or at least monosubstituted $C_{1-5}$ alkylene group that can comprise at least one heteroatom as a link; and R$^7$, R$^8$, R$^9$, R$^{10}$, and R$^{11}$, independently represent a linear or branched $C_{1-5}$ alkyl group, a linear or branched $C_{2-5}$ alkenyl group, or a linear or branched $C_{2-5}$ alkynyl group.

Compounds A, B and C whose structural formulas are shown below are illustrative preferred compounds of Series D.

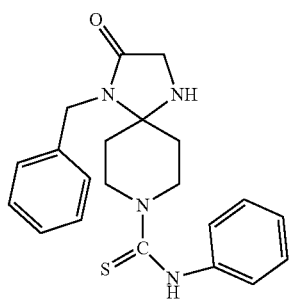

Compound A

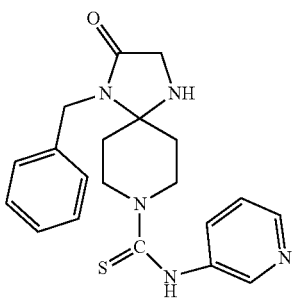

Compound B

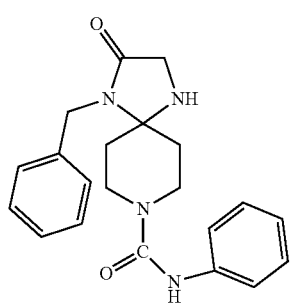

Compound C

A substituted 1-oxa-3,8-diazaspiro[4.5]-decan-2-one compound of Series E corresponds in structure to the formula

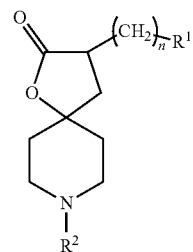

wherein
n is 1, 2, 3, 4 or 5;
R$^1$ denotes:
an optionally substituted 6- or 10-membered aryl group or an optionally substituted 5- to 14-membered heteroaryl group, wherein the aryl or heteroaryl group optionally can be fused with a saturated or unsaturated, optionally substituted mono- or bicyclic ring system;
R$^2$ denotes:
—C(=S)—NH—R$^3$; —C(=O)—NH—R$^4$;
—S(=O)$_2$—R$^5$; —(CH$_2$)—C(=O)—NH—R$^6$;
—(CH$_2$)-D$_{aa}$-(CH$_2$)$_{bb}$-E$_{cc}$-(CH$_2$)$_{dd}$—R$^7$, wherein
aa=0 or 1;
bb=0, 1 or 2;
cc=0 or 1; dd=0 or 1; and
the sum of aa and cc does not equal 0; and
D and E each independently denote O, S, NH, N(CH$_3$), N(C$_2$H$_5$) or N[CH(CH$_3$)$_2$];
—C(=O)—R$^8$, or —S(=O)$_2$—NR$^9$R$^{10}$;
R$^3$ denotes:
—(CHR$^{11}$)—(CH$_2$)$_w$—C(=O)—O—R$^{12}$, wherein w=0 or 1;
—(CHR$^{13}$)—(CH$_2$)$_a$—K$_b$—(CH$_2$)$_c$-L$_d$-R$^{14}$, wherein a=0, 1 or 2; b=0 or 1; c=0, 1 or 2; d=0 or 1, and K and L each independently denote O, S, NH, N(CH$_3$), N(C$_2$H$_5$) or N[CH(CH$_3$)$_2$];
a linear or branched, saturated or unsaturated, optionally substituted $C_{1-10}$ aliphatic group;
an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups or fused with a saturated, unsaturated or aromatic, optionally substituted mono- or bicyclic ring system, or both; or an optionally substituted 6- or 10-membered aryl group; or an optionally substituted 5- to 14-membered heteroaryl group, wherein the aryl or heteroaryl group optionally can be fused with a saturated or unsaturated, optionally substituted mono- or bicyclic ring system;
R$^4$ denotes:
—(CHR$^{15}$)—(CH$_2$)$_e$-M$_f$-(CH$_2$)$_g$—P$_h$—R$^{16}$, wherein e=0, 1 or 2; f=0 or 1; g=0, 1 or 2; h=0 or 1; and M and P each independently denote O, S, NH, N(CH$_3$), N(C$_2$H$_5$) or N[CH(CH$_3$)$_2$];
a linear or branched, saturated or unsaturated, optionally substituted $C_{1-10}$ aliphatic group;
an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups or fused with a saturated, unsaturated or aromatic, optionally substituted mono- or bicyclic ring system, or both;
or an optionally substituted 6- or 10-membered aryl group or optionally substituted 5- to 14-membered heteroaryl group, wherein said aryl or heteroaryl group optionally can be fused with a saturated or unsaturated, optionally substituted mono- or bicyclic ring system;

$R^5$ denotes:

—(CHR$^{17}$)—(CH$_2$)$_k$-Q$_l$-(CH$_2$)$_m$-T$_o$-R$^{18}$, wherein k=0, 1 or 2; l=0 or 1; m=0, 1 or 2; o=0 or 1; and Q and T each independently denote O, S, NH, N(CH$_3$), N(C$_2$H$_5$) or N[CH(CH$_3$)$_2$];

a linear or branched, saturated or unsaturated, optionally substituted C$_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted C$_{1-5}$ alkylene groups or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^6$ denotes:

a linear or branched, saturated or unsaturated, optionally substituted C$_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted C$_{1-5}$ alkylene groups or fused with a saturated, unsaturated or aromatic, optionally substituted mono- or bicyclic ring system, or both; an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^7$ denotes:

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally can be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_3$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or a group selected from the group consisting of phenyl, naphthyl, and [1,2,3,4]-tetrahydronaphthyl, wherein said group optionally can be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_3$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_3$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_3$—NH—CH$_3$, —S(=O)$_2$—NH$_2$, —S(=O)$_2$—NH-phenyl, phenyl and benzyl, wherein the cyclic moiety of the groups —S(=O)$_2$—NH-phenyl, phenyl and benzyl optionally can be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_3$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

$R^8$ denotes —(CHR$^{19}$)—V$_p$—(CH$_2$)$_q$—(CH$_2$)$_r$—W$_s$—R$^{20}$, wherein p=0 or 1;

q=0, 1 or 2;

r=0, 1 or 2;

s=0 or 1; and

V and W each independently denote O, S, NH, —NH—CH$_3$, —NH—C$_2$H$_5$, —NH—CH(CH$_3$)$_2$;

—(CH=CH)—R$^{21}$;

—(CR$^{22}$R$^{23}$)—Y$_t$—(CR$^{24}$R$^{25}$)$_u$—(CH$_2$)$_v$—C(=O)—OR$^{26}$, wherein t=0 or 1, u=0 or 1;

v=0 or 1, and Y denotes O, S, NH, —NH—CH$_3$, —NH—C$_2$H$_5$, —NH—CH(CH$_3$)$_2$;

—(CHR$^{27}$)—O—C(=O)—R$^{28}$;

—CH[(CH$_2$)R$^{29}$][NH—S(=O)$_2$—R$^{30}$];

—CH[(CH$_2$)R$^{31}$][NH—C(=O)—O—R$^{32}$];

a linear or branched, saturated or unsaturated, optionally substituted C$_{1-10}$ aliphatic group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl;

an unsaturated or saturated, optionally substituted 3-, 4-, 5-, 6-, 7-, 8- or 9-membered cycloaliphatic group that optionally can be bridged with 1 or 2 linear or branched, optionally substituted C$_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^9$ and $R^{10}$ each independently denote a linear or branched, saturated or unsaturated, optionally substituted C$_{1-10}$ aliphatic group;

$R^{11}$, $R^{13}$, $R^{15}$, $R^{17}$, $R^{19}$, $R^{22}$, $R^{23}$, $R^{24}$, $R^{25}$ and $R^{26}$ each independently denote a hydrogen or a linear or branched, saturated or unsaturated, optionally substituted $C_{1-10}$ aliphatic group;

$R^{12}$, $R^{28}$ and $R^{32}$ each independently denote a linear or branched, saturated or unsaturated, optionally substituted $C_{1-10}$ aliphatic group;

$R^{14}$, $R^{16}$, $R^{18}$ and $R^{20}$ each independently denote a linear or branched, saturated or unsaturated, optionally substituted $C_{1-10}$ aliphatic group;

an unsaturated or saturated, optionally substituted 3-, 4-, 5-, 6-, 7-, 8- or 9-membered cycloaliphatic group that optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system; and $R^{21}$, $R^{27}$, $R^{29}$, $R^{30}$ and $R^{31}$ each independently denote an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system; wherein the above-stated $C_{1-10}$ aliphatic groups each independently may optionally be substituted with 1, 2, 3, 4 or 5 substituents independently selected from the group consisting of F, Cl, Br, I, —CN, —NO$_2$, —OH, —SH and —NH$_2$;

the above-stated cycloaliphatic groups each independently can optionally be substituted with 1, 2, 3, 4 or 5 substituents independently selected from the group consisting of oxo (=O), thioxo (=S), F, Cl, Br, I, —CN, —CF$_3$, —SF$_5$, —OH, —O—C$_{1-5}$alkyl, —NH$_2$, —NO$_2$, —O—CF$_3$, —S—CF$_3$, —S—CF$_2$H, —S—CFH$_2$, —SH, —S—C$_{1-5}$alkyl, —C$_{1-5}$alkyl, —C(=O)—OH, —(CH$_2$)—C(=O)—OH, —C(=O)—O—C$_{1-5}$alkyl, —(CH$_2$)—C(=O)—O—C$_{1-5}$alkyl, —O—C(=O)—C$_{1-5}$alkyl, —NH—C$_{1-5}$alkyl, —N(C$_{1-5}$alkyl)$_2$, —NH-phenyl, —NH-pyridinyl, —N(C$_{1-5}$alkyl)-phenyl, —N(C$_{1-5}$alkyl)-pyridinyl, —NH—C(=O)—O—C$_{1-5}$alkyl, —C(=O)—H, —C(=O)—C$_{1-5}$alkyl, —C(=O)—C$_{1-5}$-perfluoroalkyl, —C(=O)—NH$_2$, —C(=O)—NH—C$_{1-5}$alkyl, C(=O)—N—(C$_{1-5}$alkyl)$_2$, —S(=O)$_2$—C$_{1-5}$alkyl, —S(=O)$_2$-phenyl, —NH—S(=O)$_2$—C$_{1-5}$alkyl, —S(=O)$_2$—NH—C$_{1-5}$alkyl, —S(=O)$_2$—NH$_2$, —S(=O)$_2$—NH-phenyl, cyclohexyl, cyclopentyl, pyridinyl, [1,2,5]-thiadiazolyl, pyridazinyl, —(CH$_2$)-benzo[b]furanyl, —O-phenyl, —O-benzyl, phenyl and benzyl, wherein the cyclic moiety of the groups —S(=O)$_2$—NH-phenyl, —NH-phenyl, —NH-pyridinyl, —N(C$_{1-5}$alkyl)phenyl, —N(C$_{1-5}$alkyl)pyridinyl, pyridinyl, cyclopentyl, [1,2,5]-thiadiazolyl, cyclohexyl, pyridazinyl, —S(=O)$_2$-phenyl, —O-phenyl, —O-benzyl, phenyl, —(CH$_2$)-benzo[b]furanyl and benzyl optionally can be substituted with 1, 2, 3, 4 or 5 substituents independently selected from the group consisting of F, Cl, Br, —OH, —CF$_3$, —SF$_5$, —CN, —NO$_2$, —C$_{1-5}$alkyl, —O—C$_{1-5}$alkyl, —O—CF$_3$, —S—CF$_3$, phenyl and —O-benzyl, and comprise 1, 2, 3, 4 or 5 heteroatom(s) mutually independently selected from the group consisting of oxygen, nitrogen and sulfur;

the above-stated $C_{1-5}$-alkylene groups each independently may optionally be substituted with 1, 2, 3, 4 or 5 substituents independently selected from the group consisting of F, Cl, Br, I, —CN, —NO$_2$, —OH, —SH and —NH$_2$;

the rings of the above-stated mono- or polycyclic ring systems each independently may optionally be substituted with 1, 2, 3, 4 or 5 substituents independently selected from the group consisting of oxo (=O), thioxo (=S), F, Cl, Br, I, —CN, —CF$_3$, —SF$_5$, —OH, —O—C$_{1-5}$alkyl —NH$_2$, —NO$_2$, —O—CF$_3$, —S—CF$_3$, —S—CF$_2$H, —S—CFH$_2$, —SH, —S—C$_{1-5}$-alkyl, —C$_{1-5}$alkyl, —C(=O)—OH, —(CH$_2$)—C(=O)—OH, —C(=O)—O—C$_{1-5}$alkyl, —(CH$_2$)—C(=O)—O—C$_{1-5}$alkyl, —O—C(=O)—C$_{1-5}$alkyl, —NH—C$_{1-5}$alkyl, —N(C$_{1-5}$alkyl)$_2$, —NH-phenyl, —NH-pyridinyl, —N(C$_{1-5}$alkyl)-phenyl, —N(C$_{1-5}$alkyl)-pyridinyl, —NH—C(=O)—O—C$_{1-5}$alkyl, —O(=O)—H, —C(=O)—C$_{1-5}$alkyl, —C(=O)—C$_{1-5}$-perfluoroalkyl, —C(=O)—NH$_2$, —C(=O)—NH—C$_{1-5}$alkyl, C(=O)—N—(C$_{1-5}$alkyl)$_2$, —S(=O)$_2$—C$_{1-5}$alkyl, —S(=O)$_2$-phenyl, —NH—S(=O)$_2$—C$_{1-5}$alkyl, —S(=O)$_2$—NH—C$_{1-5}$alkyl, —S(=O)$_2$—NH$_2$, —S(=O)$_2$—NH-phenyl, cyclohexyl, cyclopentyl, pyridinyl, —(CH$_2$)-benzo[b]furanyl, —O-phenyl, —O-benzyl, phenyl and benzyl, wherein the cyclic moiety of the groups pyridinyl, cyclopentyl, cyclohexyl, pyridazinyl, —S(=O)$_2$-phenyl, —S(=O)$_2$—NH-phenyl, —O-phenyl, —O-benzyl, phenyl, —(CH$_2$)-benzo[b]furanyl, optionally can be substituted with 1, 2, 3, 4 or 5 substituents independently selected from the group consisting of F, Cl, Br, —OH, —CF$_3$, —SF$_5$, —NO$_2$, C$_{1-5}$alkyl, —O—C$_{1-5}$alkyl, —O—CF$_3$, —S—CF$_3$, phenyl and -o-benzyl;

the rings of the above-stated mono- or bicyclic ring systems are each independently 5-, 6- or 7-membered and each independently may optionally comprise as ring member(s), 1, 2, 3, 4 or 5 heteroatom(s) independently selected from the group consisting of oxygen, nitrogen and sulfur; the above-stated aryl or heteroaryl groups each independently may optionally be substituted with 1, 2, 3, 4 or 5 substituents independently selected from the group consisting of F, Cl, Br, I, —CN, —CF$_3$, —SF$_5$, —OH, —O—C$_{1-5}$alkyl —NH$_2$, and the above-stated heteroaryl groups each independently may optionally comprise as ring member(s), 1, 2, 3, 4 or 5 heteroatom(s) independently selected from the group consisting of oxygen, nitrogen and sulfur; or a pharmaceutically acceptable salt or solvate thereof.

Preferably, in a contemplated compound, $R^1$ denotes a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl, oxazolyl, isoxazolyl, pyridazinyl, pyrazinyl, pyrimidinyl, indazolyl, quinazolinyl, quinolinyl and isoquinolinyl. That $R^1$ group can optionally be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —NH—C(=O)—CH$_3$, —NH—C(=O)—C$_2$H$_5$, —NH—C(=O)—C(CH$_3$)$_3$, —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_3$—CH$_3$, —S(=O)$_3$—C$_2$H$_5$, —NH—S(=O)$_2$—CH$_3$, —S(=O)$_3$—NH—CH$_3$, —S(=O)$_2$—NH$_2$, —S(=O)$_2$—NH-phenyl and -benzyl, wherein the cyclic moiety of each phenyl or benzyl group independently can optionally be substituted with 1,2,3,4, or 5 substituents independently selected from the group consisting of F, Cl, Br, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_3$, —O—CF$_3$, —S—CF$_3$, phenyl and —O-benzyl.

It is also preferred that the $R^2$ group of a contemplated compound denote C(=S)—NH—$R^3$; —C(=O)—NH—$R^4$; —S(=O)$_2$$R^5$; —(CH$_2$)—C(=O)—NH— $R^6$; —(CH$_2$)—O—$R^7$, —(CH$_2$)—S—$R^7$, —(CH$_2$)—NH—$R^7$, —(CH$_2$)—N(CH$_3$)—$R^7$, —(CH$_2$)—(CH$_2$)—O—$R^7$, —(CH$_2$)—(CH$_2$)—S—$R^7$, —(CH$_2$)—(CH$_2$)—NH—$R^7$, —(CH$_2$)—(CH$_2$)—N(CH$_3$)—$R^7$, —(CH$_2$)—(CH$_2$)—(CH$_2$)—O—$R^7$, —(CH$_2$)—(CH$_2$)—(CH$_2$)—S—$R^7$, —(CH$_2$)—(CH$_2$)—(CH$_2$)—NH—$R^7$, —(CH$_2$)—(CH$_2$)—(CH$_2$)—N(CH$_3$)—$R^7$, —(CH$_2$)—O—(CH$_2$)—$R^7$, —(CH$_2$)—S—(CH$_2$)—$R^7$, —(CH$_2$)—NH—(CH$_2$)—$R^7$, —C(=O)—$R^8$, or —S(=O)$_2$—NR$^9$R$^{10}$.

Illustrative α7nAChR-FLNA, TLR4-FLNA and Aβ$_{42}$-α7nAChR Complex Inhibiting Compounds Certain compounds discussed hereinafter have been found to bind to a pentapeptide region of FLNA having the sequence VAKGL (SEQ ID NO: 1) at picomolar to nanomolar concentrations, and can activate MOR. These compounds can also inhibit or reverse FLNA complex formation with α7nAChR or TLR4. On the other hand, the presence of Aβ$_{42}$ can induce an increase in the amount of complex containing FLNA and α7nAChR and FLNA and TLR4, as well as increase the levels of cytokines IL-6, TNFα and IL-1β.

Admixture of a FLNA-binding amount of a FLNA-binding compound to an aqueous composition containing a complex between FLNA and one or the other of α7nAChR or TLR4 can decrease these Aβ$_{42}$-induced increases in FLNA-containing complexes. That admixture can also almost abolish the production of those three cytokines as measured by a fluorescence ELISA assay using FITC.

In some embodiments, it is preferred that a FLNA-binding compound also be a MOR agonist. In other embodiments, it is preferred that the FLNA-binding compound not be a MOR agonist. A compound is defined herein as not being a MOR agonist if it has less than about 80 percent the MOR activation of [D-Ala2,N-MePhe4,Gly-ol]-enkephalin (DAMGO) at either of the two concentrations used in the Table of Example 2.

Discussion

Although much AD research has focused on Aβ$_{42}$ signaling via α7nAChR, the present invention is the first to make use of the fact that this signaling requires recruitment of FLNA coupling to α7nAChR, and that there is a profound increase in FLNA coupling to α7nAChR in AD lymphocytes, AD postmortem tissue or following Aβ$_{42}$ treatment in lower animal model systems (FIG. 1). By binding FLNA instead of the receptor, Compound C0105 blocks Aβ$_{42}$'s toxic signaling without disrupting α7nAChR's physiological activation by acetylcholine or altering its sensitivity or cell surface expression. Compound C0105's efficacy in a mouse model and in human AD lymphocytes, human postmortem AD and Aβ$_{42}$-treated control tissue on numerous AD-related neuropathologies both validates the FLNA pentapeptide target and reinforces Aβ$_{42}$'s aberrant signaling via α7nAChR as a predominant mechanism of AD pathology.

Figure 6:
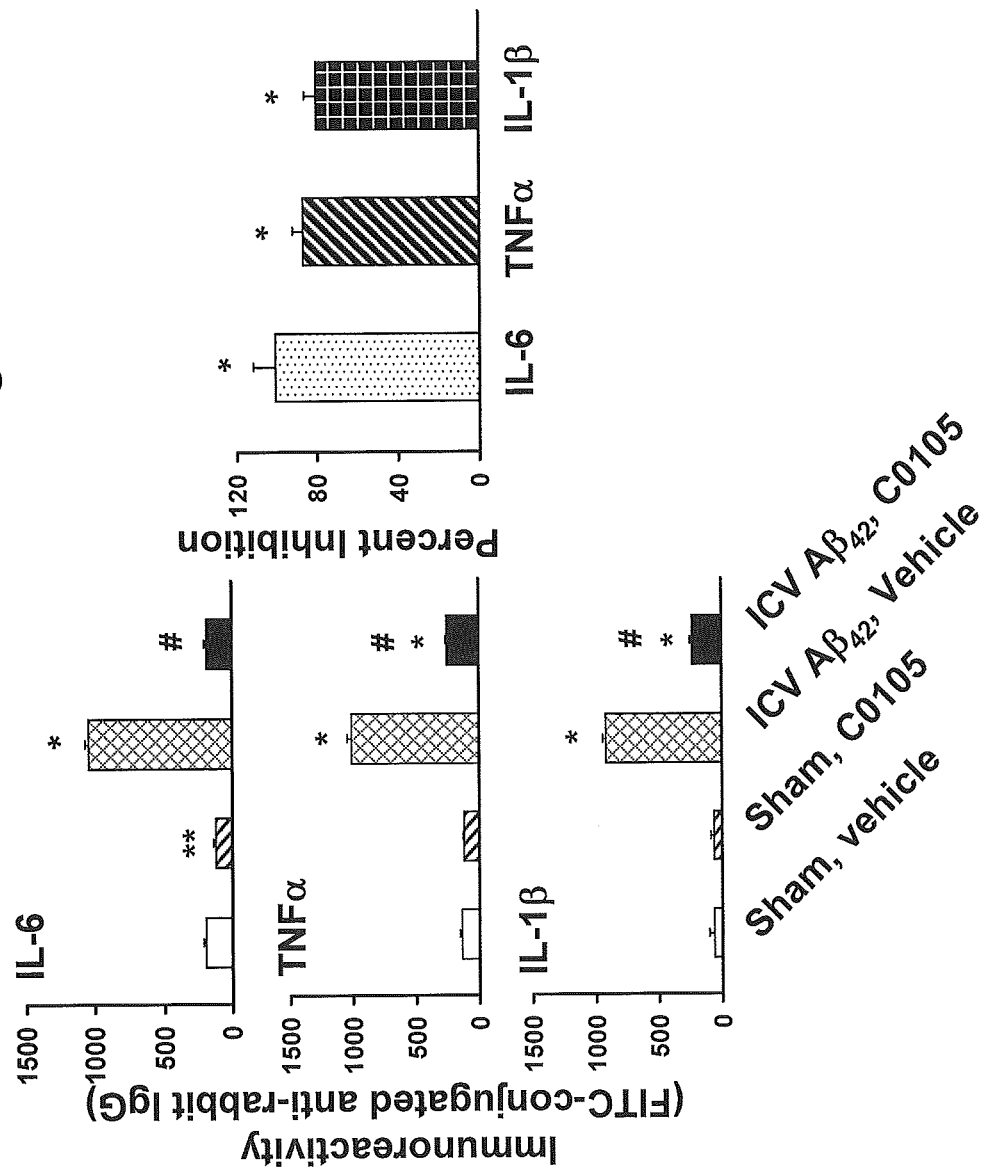
FIG. 6 illustrates that Compound C0105 treatment of mice nearly abolishes $A\beta_{42}$-induced cytokine production. $A\beta_{42}$ increased levels of cytokines IL-6, TNFα and IL-1β as measured by a fluorescence ELISA assay using FITC. Compound C0105 almost abolished the production of these 3 cytokines. n=7 or n=8. Data are means±SEM. *p<0.01 vs. respective cytokine level in sham, vehicle group; #p<0.01 vs. respective cytokine level in ICV $A\beta_{42}$, vehicle group.
Figure 7:
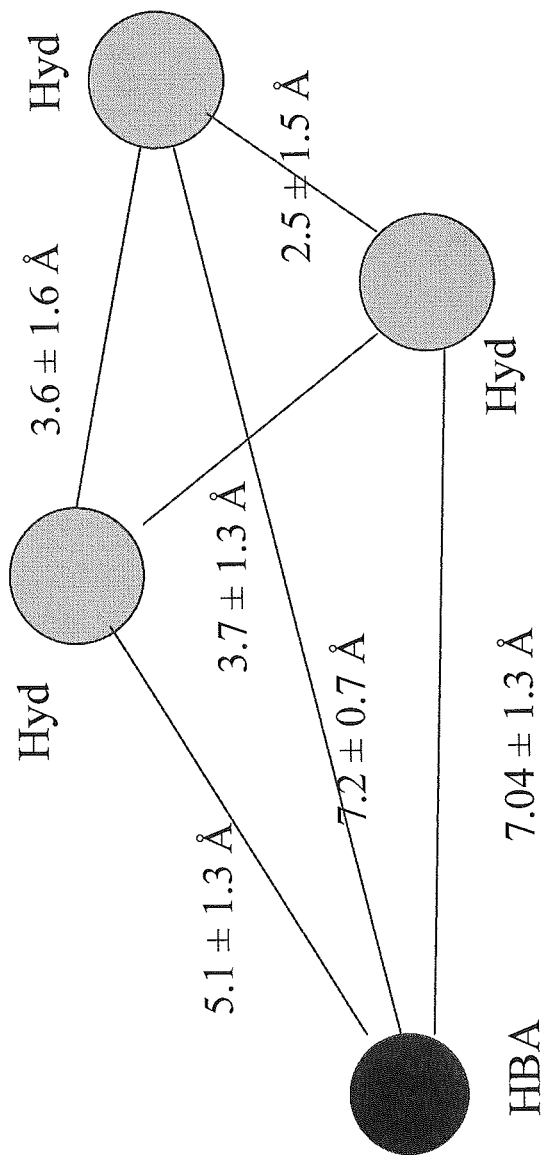
Figure 8:
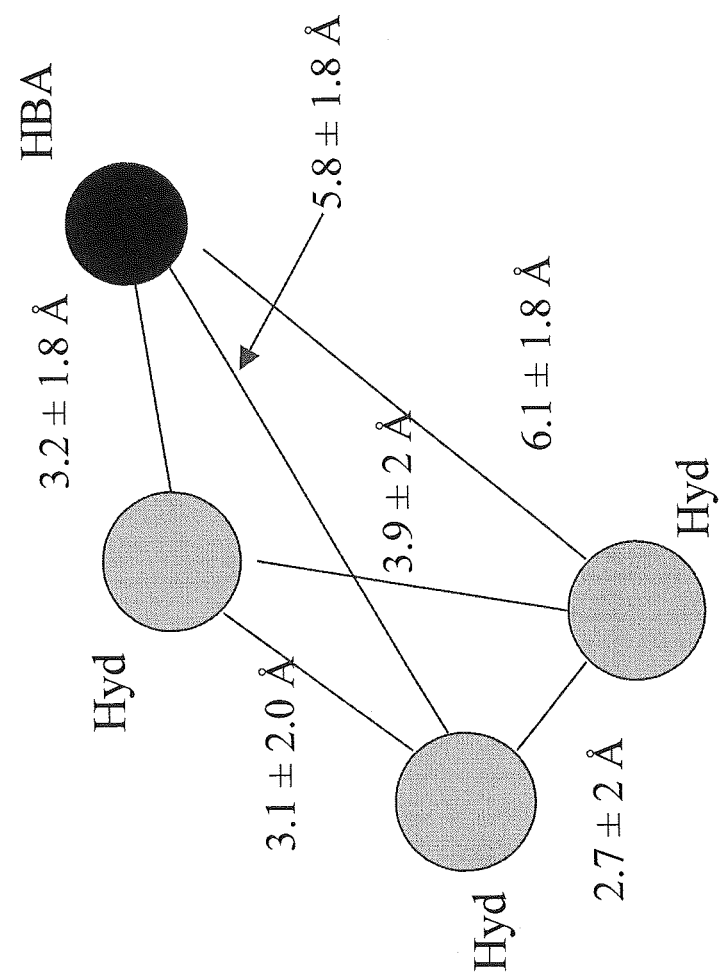
Figure 13A:
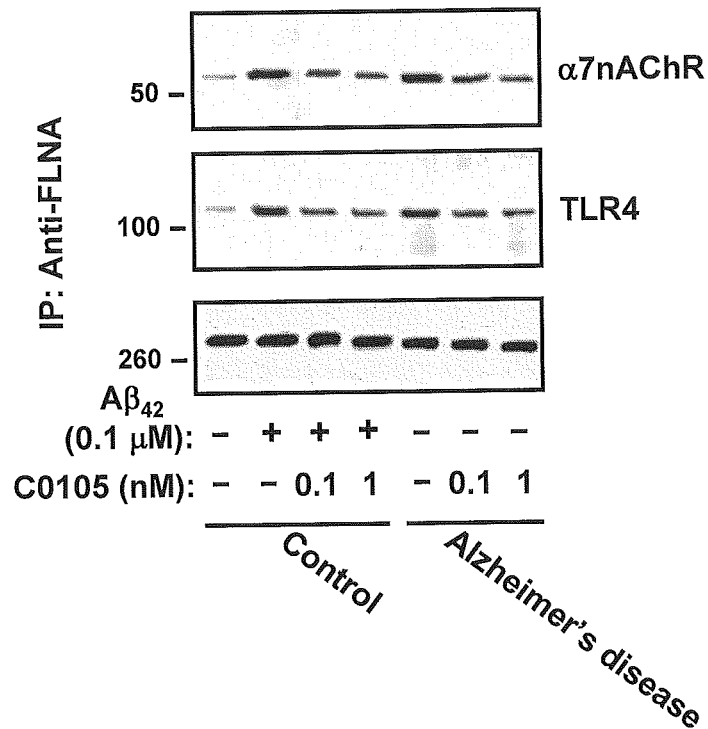
FIG. 13 in five panels illustrates that Compound C0105 decreased $A\beta_{42}$-induced FLNA association with both α7nAChR and TLR4 in human postmortem AD and control brain tissue. AD and age-matched control brain slices were treated with 0.1 or 1 nM concentrations of Compound C0105, and control brain slices were simultaneously treated with $A\beta_{42}$. The extent of FLNA association with α7nAChR or TLR4 was assessed in the solubilized synaptosomes by immunoprecipitation with immobilized anti-FLNA and Western blot detection (FIG. 13A) using antibodies specific to each receptor, and wherein numerals outside of and to the left of the blots are as discussed before. Blots were analyzed by densitometric quantitation (FIG. 13B and FIG. 13D). AD tissue and $A\beta_{42}$-treated control tissue showed a markedly increased association of α7nAChR and TLR4 with FLNA, and Compound C0105 reduced these associations. Percent inhibition is depicted in FIG. 13C and FIG. 13E. n=11. Data are means±SEM. *p<0.01 vs. vehicle-treated control, #p<0.01 vs. $A\beta_{42}$-treated control or vehicle-treated AD.
Figure 13B:
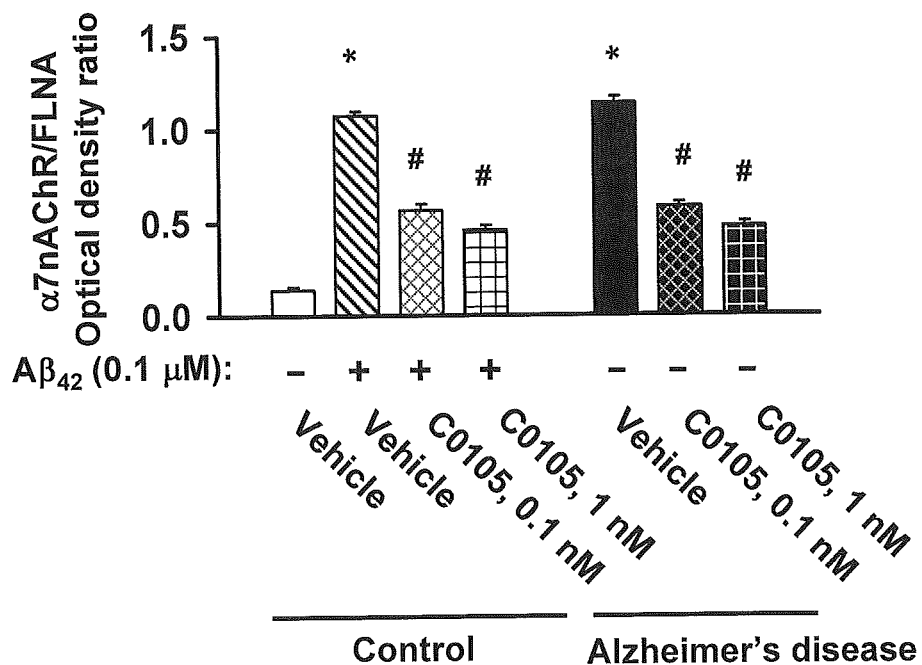
Figure 13C:
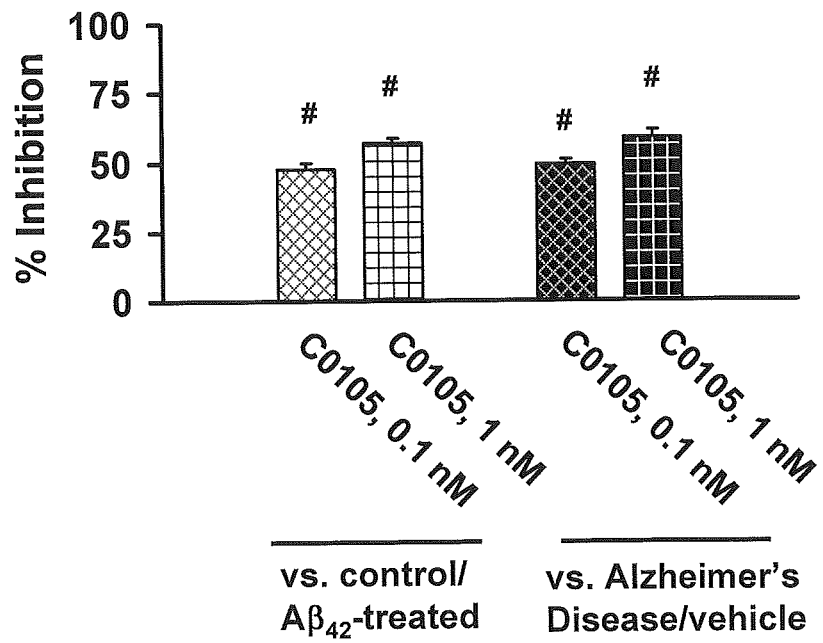
Figure 13D:
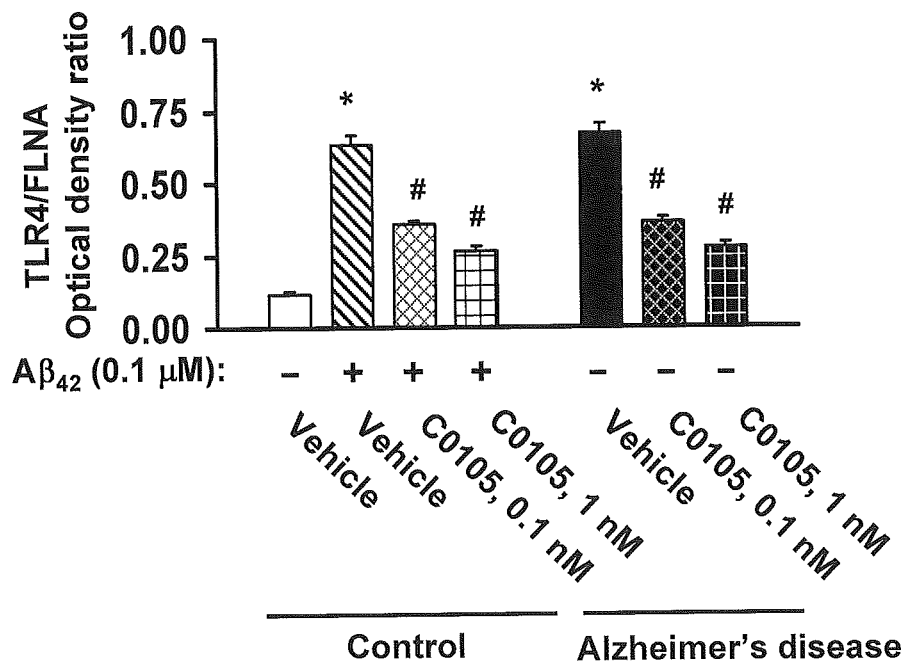
Figure 13E:
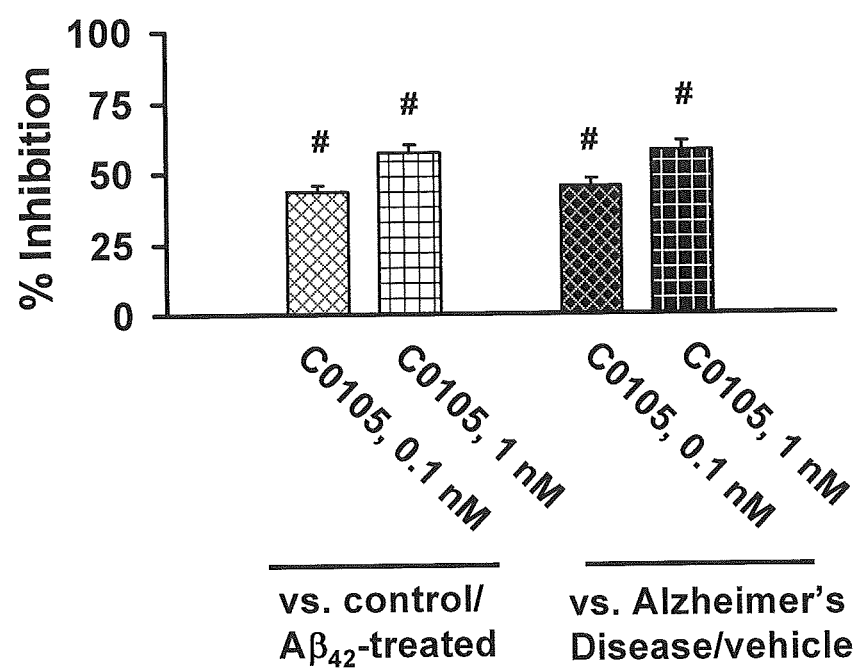
Figure 14A:
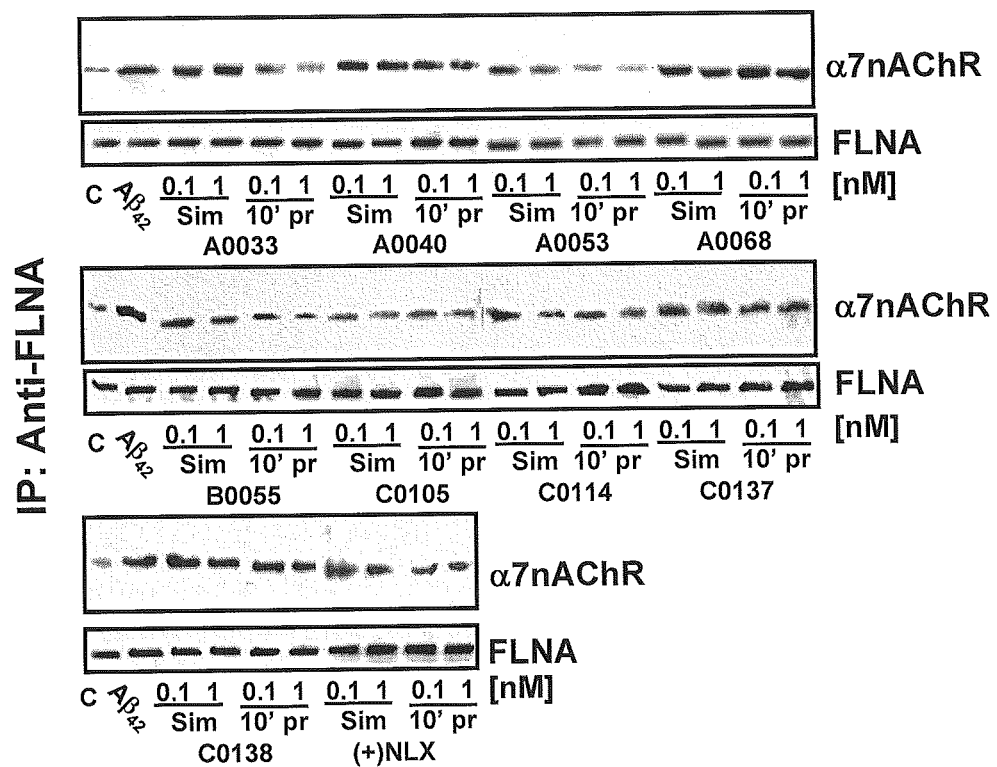
FIG. 14A, FIG. 14B, and FIG. 14C, illustrates high-affinity FLNA-binding compounds reduce α7nAChR-FLNA association. Frontal cortical synaptosomes from 2-month-old rats (n=4) were treated with 0.1 or 1 nM concentrations of compounds [A0033, A0040, A0053, A0068, B0055, C0105M, C0114M, C0137M, C0138M and (+)naloxone ((+)NLX)] either simultaneously (Sim) with or 10 minutes prior (10' pr) to $A\beta_{42}$ and were analyzed for their α7nAChR-FLNA complex contents. The α7nAChR-FLNA complexes in the solubilized synaptosomes were immunoprecipitated with immobilized anti-FLNA and the α7nAChR and FLNA levels in the anti-FLNA immunoprecipitates determined by Western blotting (FIG. 14A) and quantified by densitometry for illustrative compounds (FIG. 14B). n=3. Data are means±SEM. **p<0.05, *p<0.01 vs. $A\beta_{42}$ alone.
Figure 14B:
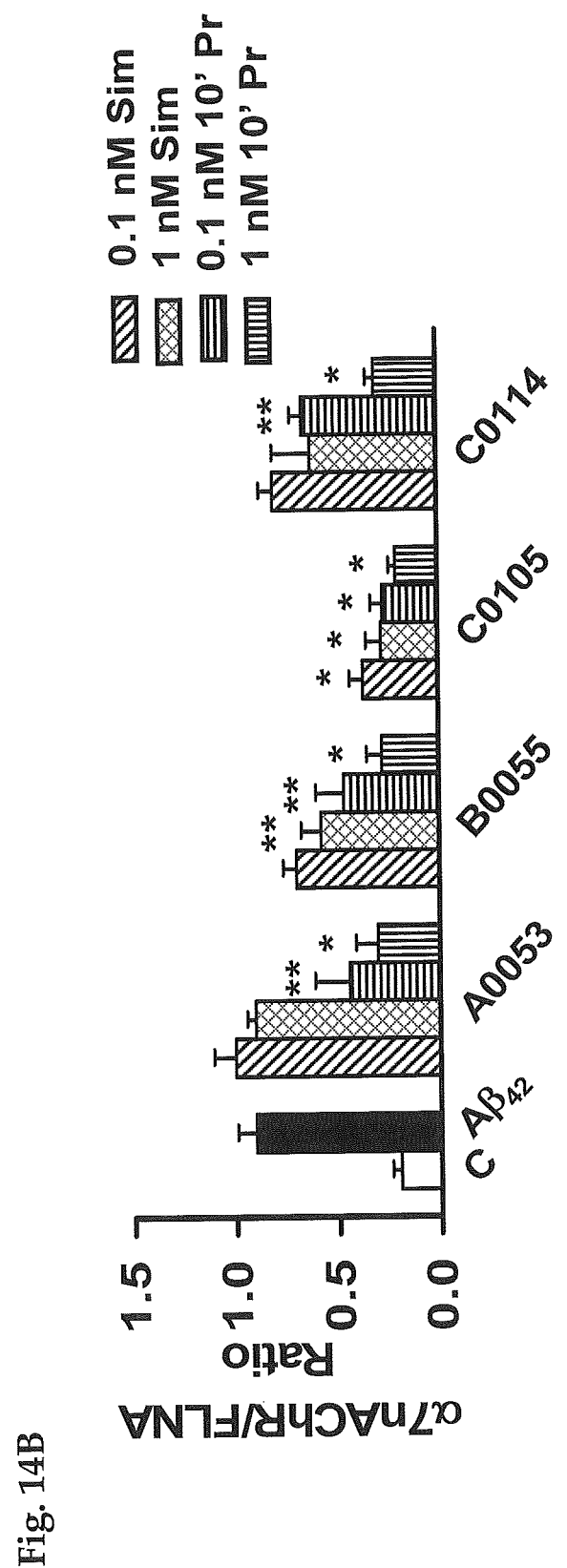
Figure 14C:
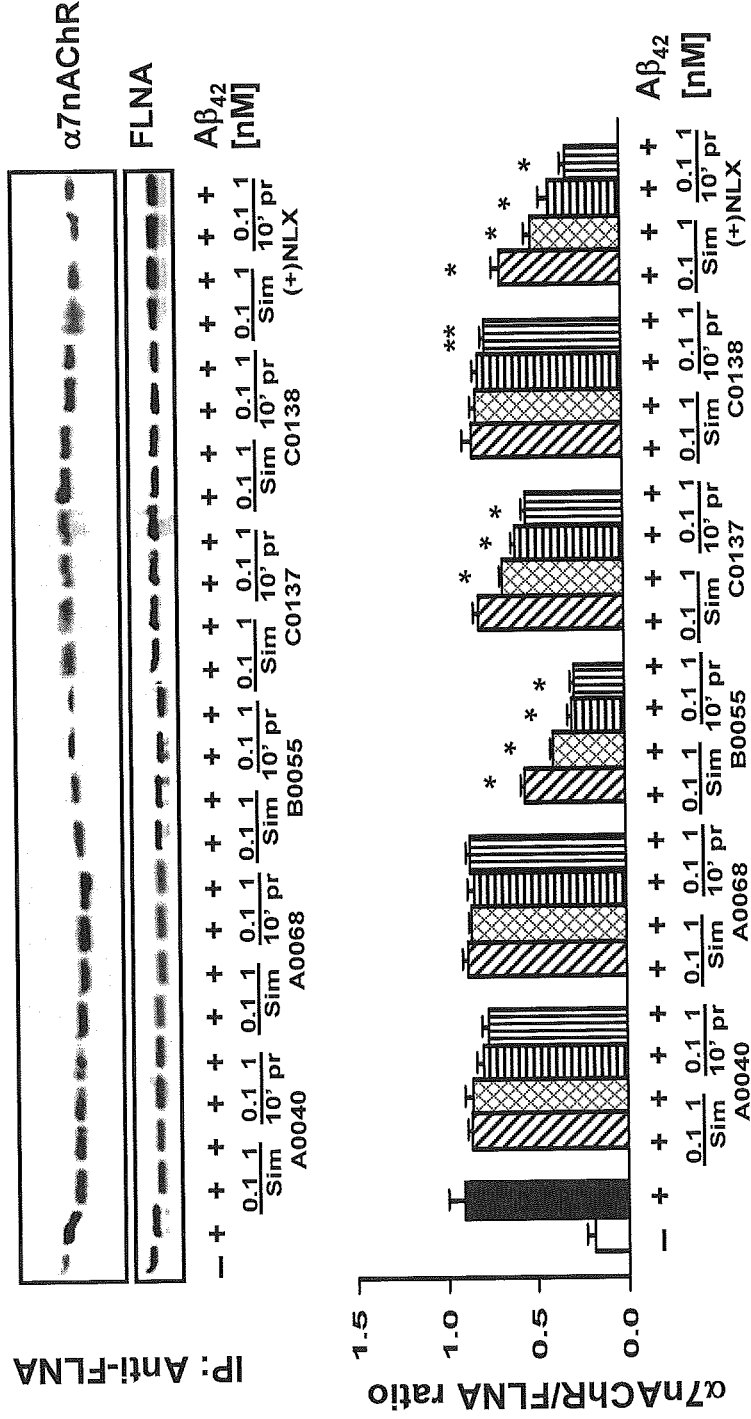
Figure 15A:
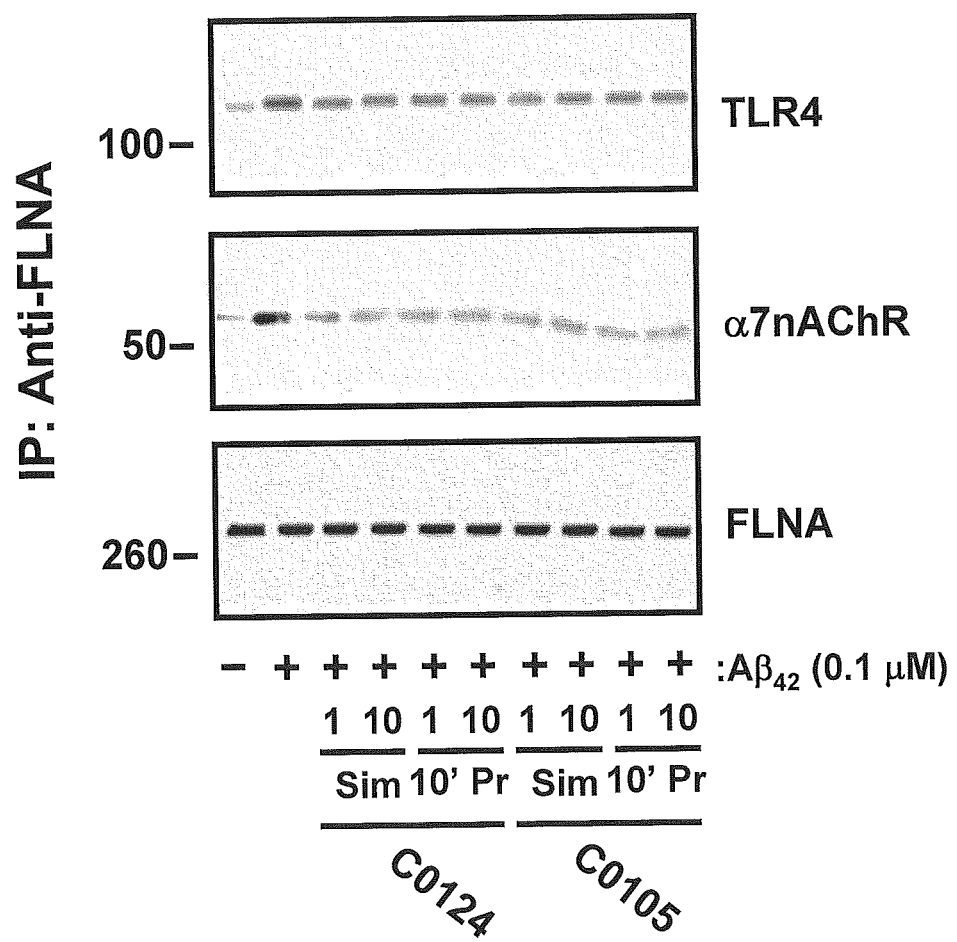
FIG. 15A and FIG. 15B, illustrates further high-affinity FLNA-binding compounds that reduce α7nAChR-FLNA association assayed as in FIG. 14. Frontal cortical synaptosomes from 2-month-old rats were treated with 1 or 10 nM concentrations of Compound C0124, using Compound C0105 as a control, either simultaneously (Sim) or 10 minutes prior (10' pr) to $A\beta_{42}$ (0.1 μM) and were immunoprecipitated with immobilized anti-FLNA. The complexes in the solubilized synaptosomes, and α7nAChR, TLR4 and FLNA levels in the anti-FLNA immunoprecipitates were determined by Western blotting (FIG. 15A) in which numerals outside of and to the left of the blots are as discussed before. Amounts present in the blots were quantified by densitometry (FIG. 15B). Ratios of α7nAChR/FLNA and TLR4/FLNA were statistically different from $A\beta_{42}$ alone with **p<0.05, *p<0.01 for the compounds as shown using Dunnett's test. Structural formulas of the compounds used in this and the other figures are provided hereinafter.
Figure 15B:
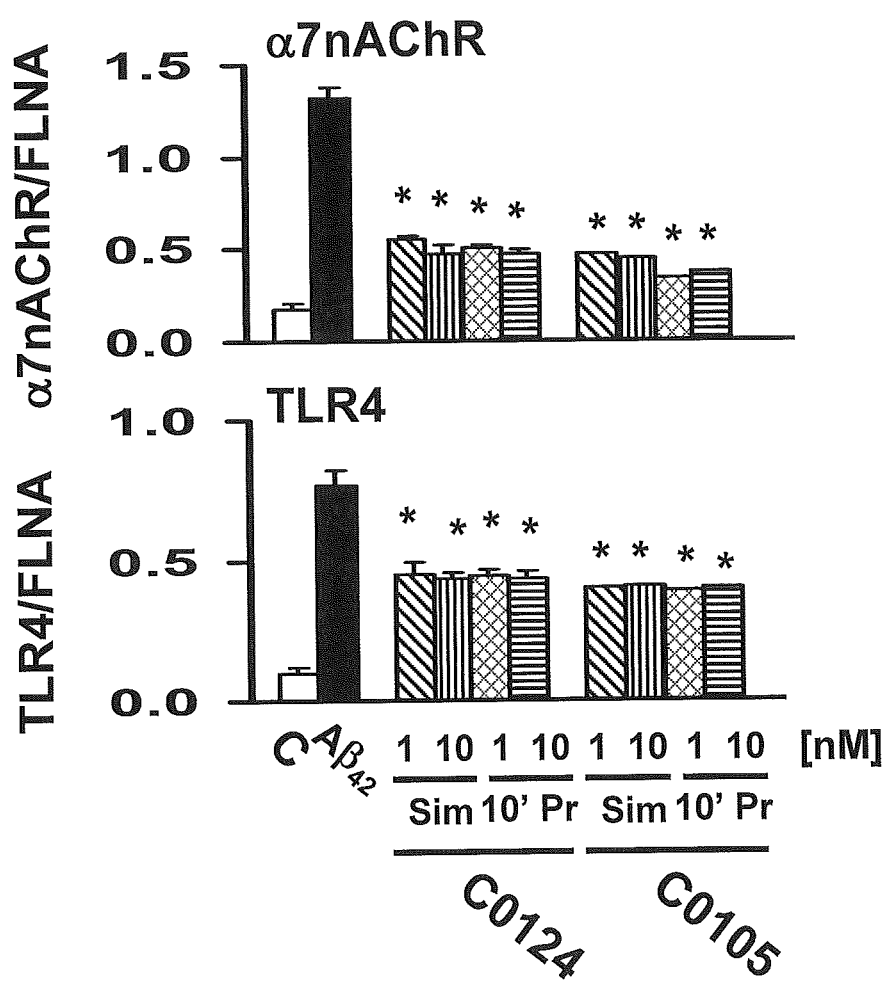

AD lymphocytes, AD postmortem brain tissue or Aβ$_{42}$ treatment also show a dramatic increase in FLNA association with TLR4, the innate immune receptor responsible for inflammatory cytokine release. ICV Aβ$_{42}$ infusion into a mouse brain increases IL-6, TNF-α and IL-1β production. Because FLNA recruitment is similarly aiding signaling of TLR4, Compound C0105 also blocks this FLNA-TLR4 association and the Aβ$_{42}$-induced inflammatory cytokine release. Thus, Compound C0105 treatment completely abolished the Aβ$_{42}$-induced IL-6 production and suppressed TNF-α and IL-1β levels by 86 and 80%, respectively (FIG. 6). Although Aβ$_{42}$ does not itself interact with TLR4, it binds to CD14, which in turn binds TLR4 to produce the inflammation noted in AD. [Reed-Geaghan et al., *J Neurosci* 29:11982-11992 (2009).]

(ICV) Infusion

In an intracerebroventricular (ICV) Aβ$_{42}$ infusion mouse model of AD, Aβ$_{42}$ induced robust FLNA associations with both α7nAChR and TLR4 that were almost completely blocked by Compound C0105. Remarkably, Compound C0105 also reversed this FLNA-α7nAChR association in postmortem AD brain slices, as well as in age-matched control brain tissue incubated with Aβ$_{42}$. Evidence that the FLNA-TLR4 association is critical to Aβ$_{42}$-induced TLR4 signaling is that, by disrupting this FLNA-TLR4 association, Compound C0105 almost completely blocks IL-6, TNF-α and IL-1β release in ICV Aβ$_{42}$-infused mice.

Specific FLNA-Binding Compounds

Compounds were synthesized and provided by Medicilon, Shanghai. Aside from the three syntheses described herein, more detailed syntheses are set out in one or more of US Patent Publications No. 2009/0191579 A1, No. 2010/

0279996 A1, No. 2010/0279997 A1, No. 2010/0280061 A1, No. 2011/0105481 A1, 2011/0105484 A1, No. 2011/0105487 A1, and No. 2011/0105547 A1, whose disclosures are incorporated by reference.

A compound having an asymmetrical (chiral) carbon or a salt thereof can exist in the form of two enantiomers. The invention relates both to each enantiomer and to their mixture; i.e., to both enantiomeric forms and to their mixture. Additionally, where two or more chiral centers are present, diastereomers can form.

Where a contemplated compound or a pharmaceutically acceptable salt of a compound of Series A, B, C-1 or C-2 or any of the other formulas herein is obtained in the form of a mixture of the stereoisomers, preferably in the form of the racemates or other mixtures of the various enantiomers and/or diastereoisomers, they can be separated and optionally isolated by conventional methods known to the person skilled in the art. Illustratively, for example, chromatographic separation processes are useful, particularly liquid chromatography processes under standard pressure or under elevated pressure, preferably MPLC and HPLC methods, and also methods involving fractional crystallization. This can particularly involve the separation of individual enantiomers, e.g., diastereoisomeric salts separated by means of HPLC in the chiral phase or by means of crystallization with chiral acids, for example (+)-tartaric acid, (−)-tartaric acid, or (+)-10-camphorsulfonic acid. An enantiomer separated by chiral salt formation can readily be converted into an achiral or racemic pharmaceutically acceptable salt for use.

A compound of Series A, B, C-1 or C-2 or a pharmaceutically acceptable salt thereof is contemplated to be optionally used in a process of the invention in enantiomerically pure form; i.e., in (S) or (R) configuration or d and l forms, or in the form of a racemic mixture showing an (S,R) or (d,l) configuration, or as one or more diastereomers, and mixtures thereof.

Thus, a contemplated compound or its pharmaceutically acceptable salt can optionally be present in one or more forms. Illustratively, the compound or its salt can be in the form of an individual enantiomer or diastereoisomer. A contemplated compound or its salt can also be present in the form of a mixture of stereoisomers. A contemplated compound or salt can also be present in the form of a racemic mixture.

A compound useful as an active ingredient in a contemplated method can be readily synthesized. An illustrative synthetic scheme (Scheme 1) is shown below for the compounds of Series A. Similar schemes are set out thereafter for the preferred compound types.

Similar syntheses can be carried out for phenolic compounds, starting with phenol or a substituted phenol in place of D-menthol that is shown in Scheme 1. Another cyclohexanol or cyclohexenol can also be used in place of D-menthol. The alcohol formed by reaction of Compound 1 with an amine can be readily oxidized by known methods.

Scheme 1

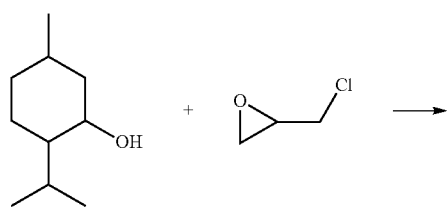

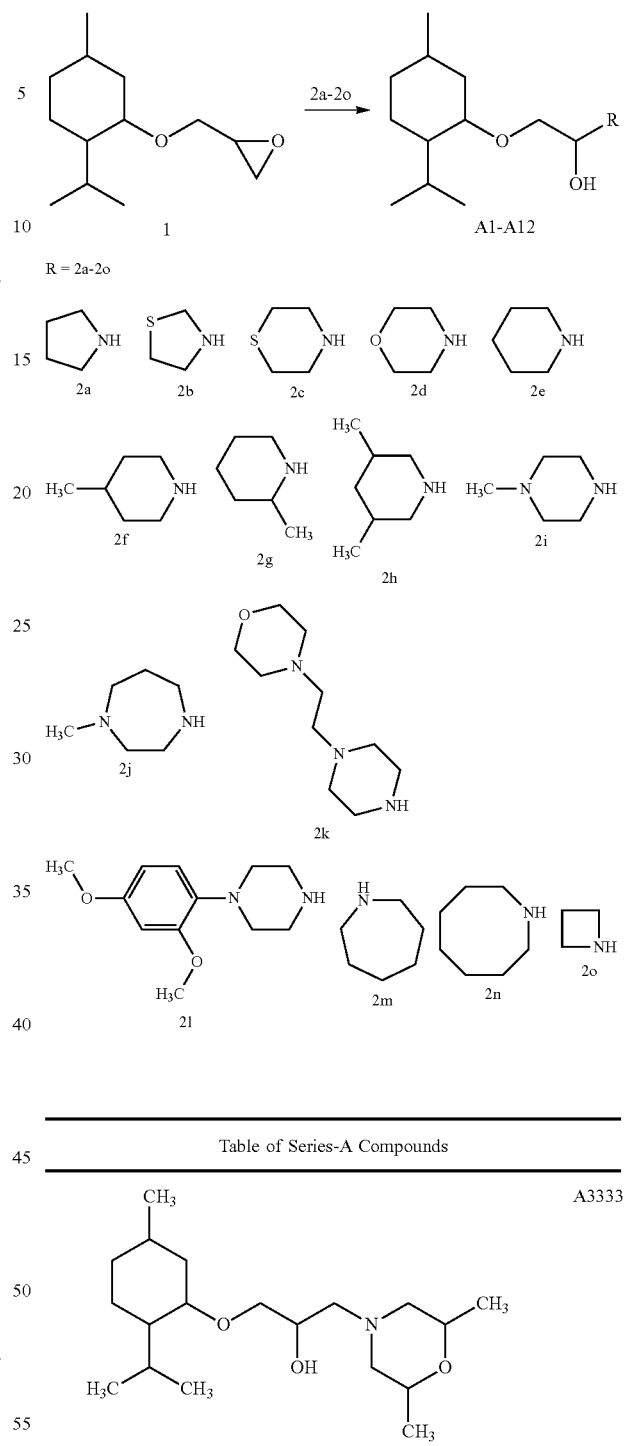

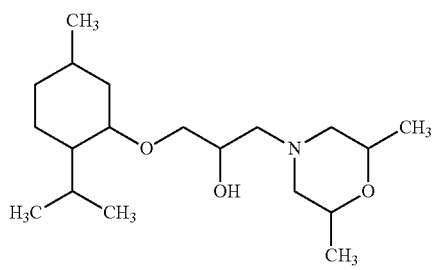 [SMILES: CC1CCC(C(C)C)C(OCC(O)CN2CC(C)OC(C)C2)C1]

A3333

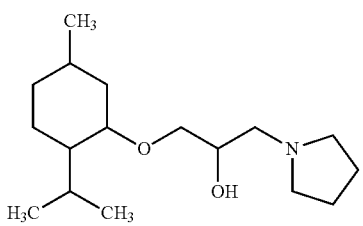

A0001

-continued
Table of Series-A Compounds
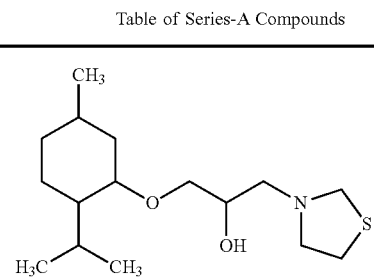
A0002
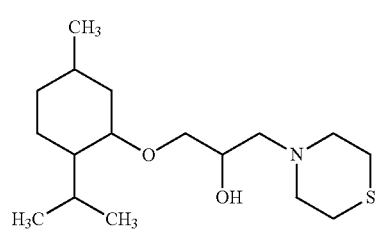
A0003
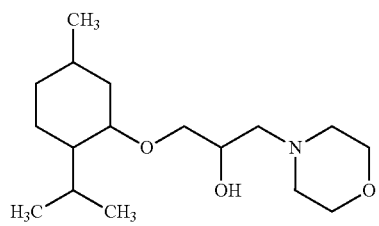 [SMILES: CC1CCC(C(C)C)C(OCC(O)CN2CCOCC2)C1]
A0004
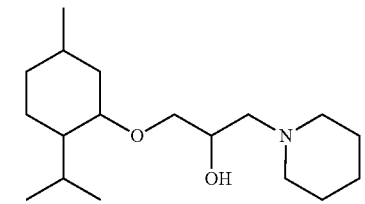 [SMILES: CC1CCC(C(C)C)C(OCC(O)CN2CCCCC2)C1]
A0005
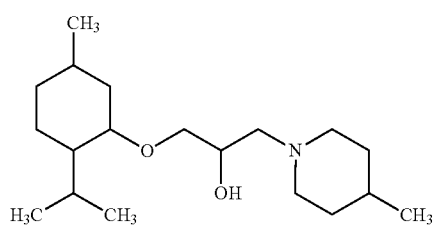
A0006
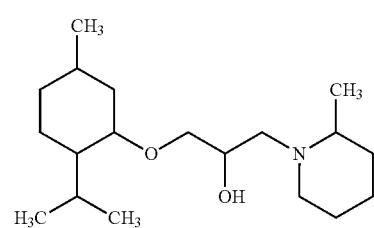
A0007
-continued
Table of Series-A Compounds
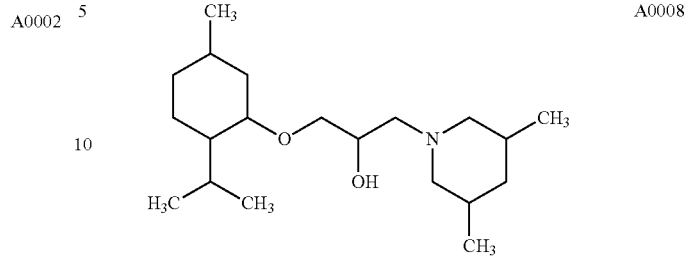
A0008
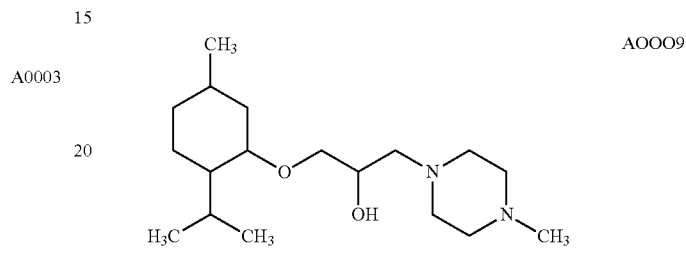
A0009
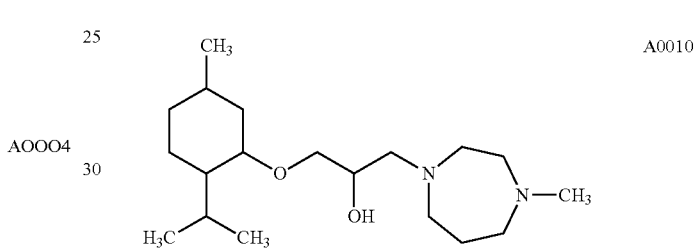
A0010
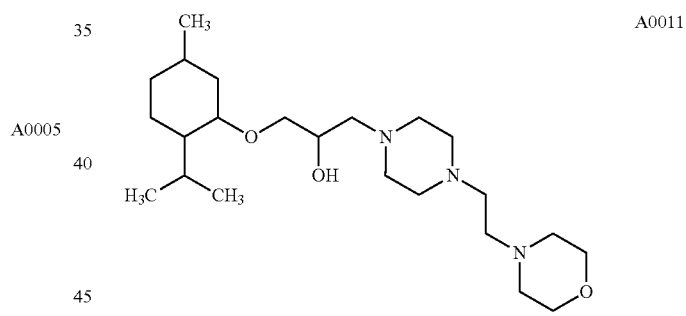
A0011
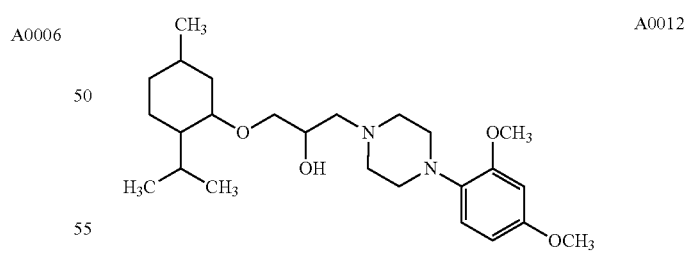
A0012
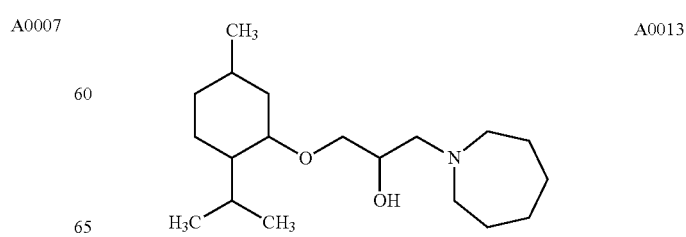
A0013

Table of Series-A Compounds
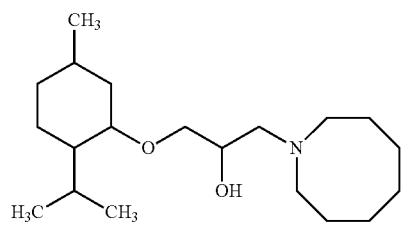 [SMILES: CC1CCC(C(C)C)C(OCC(O)CN2CCCCCCC2)C1]
A0014
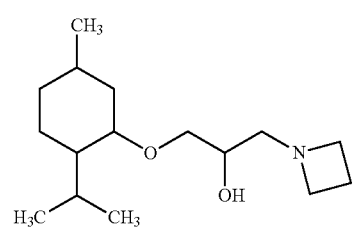 [SMILES: CC1CCC(C(C)C)C(OCC(O)CN2CCC2)C1]
A0015
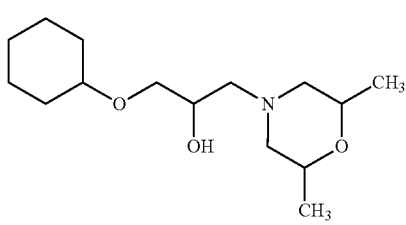 [SMILES: CC1CN(CC(O)COC2CCCCC2)CC(C)O1]
A0017
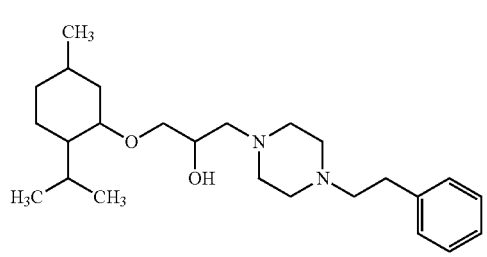 [SMILES: CC1CCC(C(C)C)C(OCC(O)CN2CCN(CCc3ccccc3)CC2)C1]
A0020
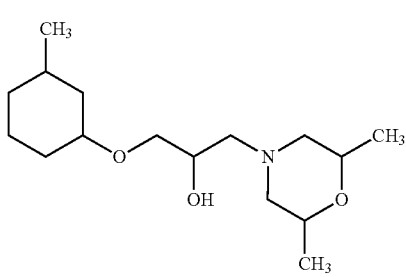 [SMILES: CC1CCCC(OCC(O)CN2CC(C)OC(C)C2)C1]
A0021
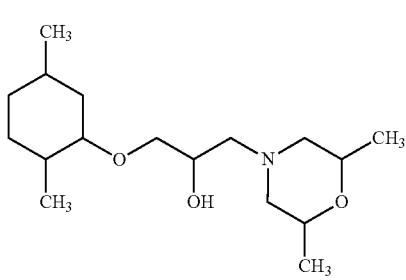 [SMILES: CC1CCC(C)C(OCC(O)CN2CC(C)OC(C)C2)C1]
A0022
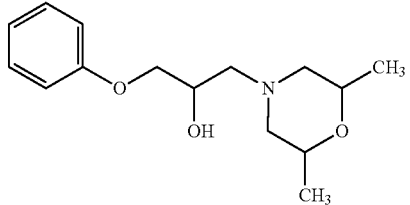 [SMILES: CC1CN(CC(O)COc2ccccc2)CC(C)O1]
A0025
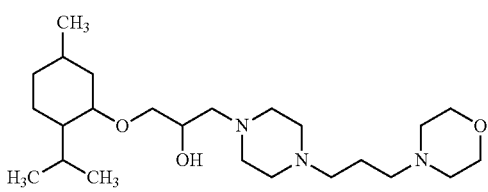 [SMILES: CC1CCC(C(C)C)C(OCC(O)CN2CCN(CCCN3CCOCC3)CC2)C1]
A0026
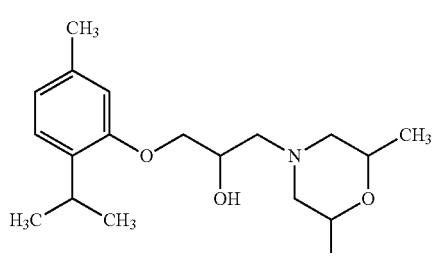
A0028
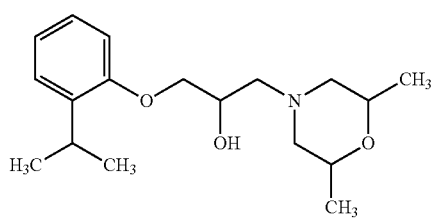 [SMILES: CC1CN(CC(O)COc2ccccc2C(C)C)CC(C)O1]
A0029
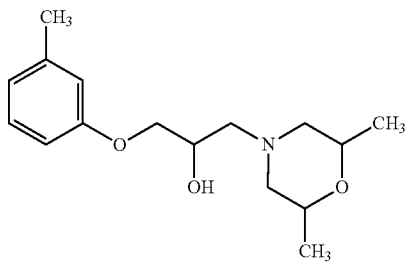 [SMILES: Cc1cccc(OCC(O)CN2CC(C)OC(C)C2)c1]
A0030
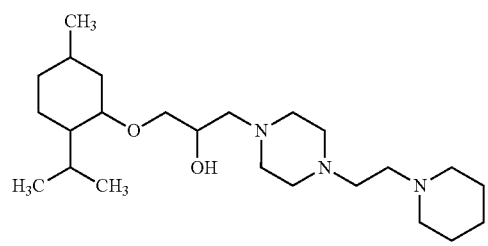 [SMILES: CC1CCC(C(C)C)C(OCC(O)CN2CCN(CCN3CCCCC3)CC2)C1]
A0031

Table of Series-A Compounds
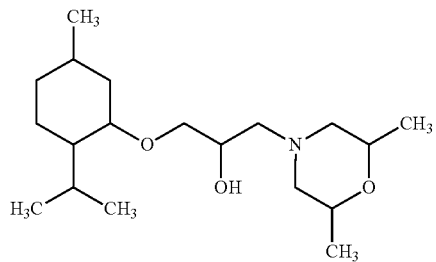 [SMILES: CC1CCC(C(C)C)C(OCC(O)CN2CC(C)OC(C)C2)C1]
A0032-1
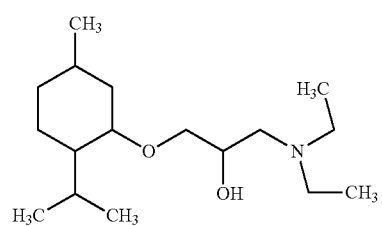 [SMILES: CCN(CC)CC(O)COC1CC(C)CCC1C(C)C]
A0032
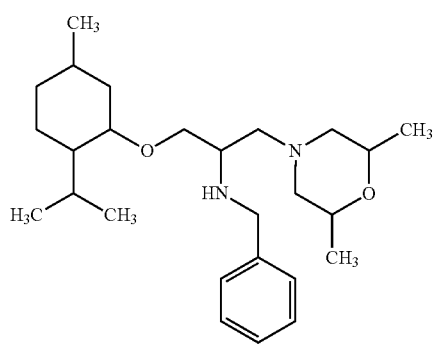 [SMILES: CC1CCC(C(C)C)C(OCC(CN2CC(C)OC(C)C2)NCc2ccccc2)C1]
A0033
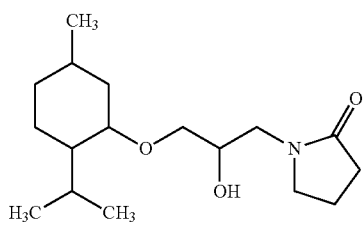 [SMILES: CC1CCC(C(C)C)C(OCC(O)CN2CCCC2=O)C1]
A0035
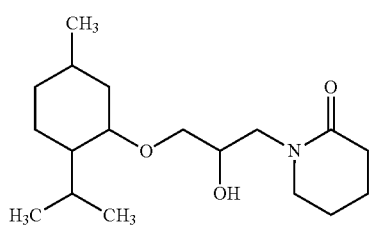 [SMILES: CC1CCC(C(C)C)C(OCC(O)CN2CCCCC2=O)C1]
A0036
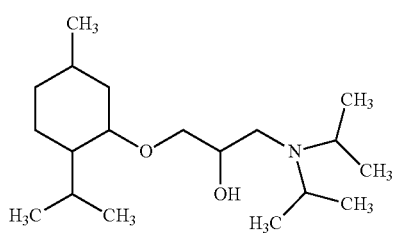 [SMILES: CC1CCC(C(C)C)C(OCC(O)CN(C(C)C)C(C)C)C1]
A0037
Table of Series-A Compounds
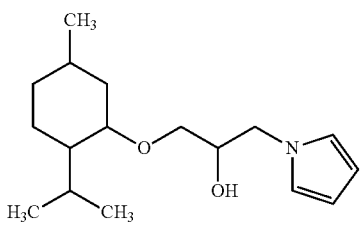
A0038
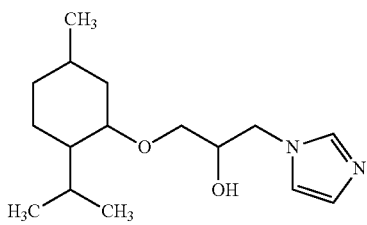 [SMILES: CC1CCC(C(C)C)C(OCC(O)Cn2ccnc2)C1]
A0039
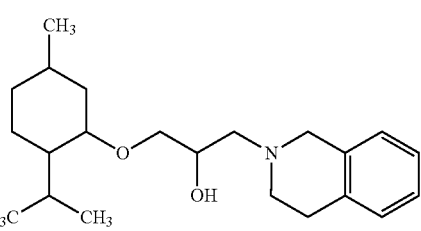
A0040
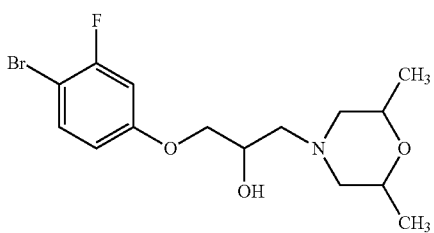 [SMILES: CC1CN(CC(O)COc2ccc(Br)c(F)c2)CC(C)O1]
A0041
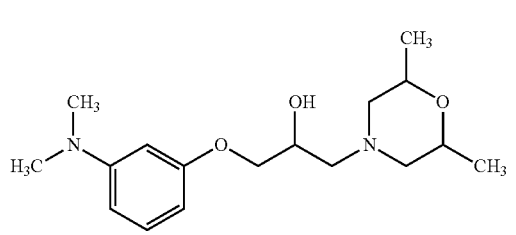
A0042
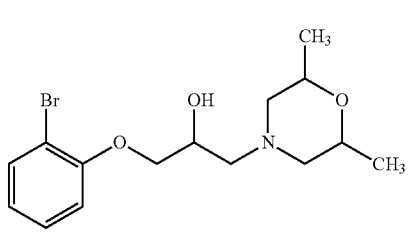 [SMILES: CC1CN(CC(O)COc2ccccc2Br)CC(C)O1]
A0043

Table of Series-A Compounds

A0044, A0045, A0046, A0047, A0048, A0049, A0050, A0051, A0053, A0054, A0055, A0056, A0057, A0058

Table of Series-A Compounds

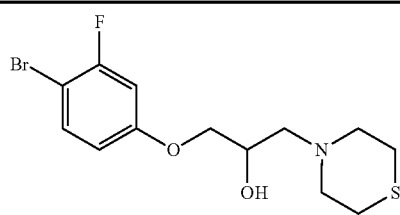
A0059

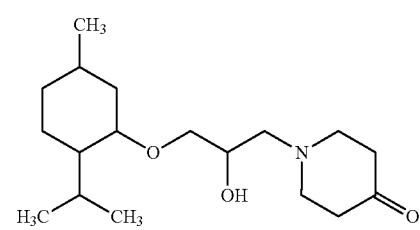
A0060

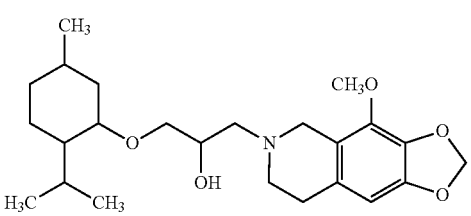
A0061

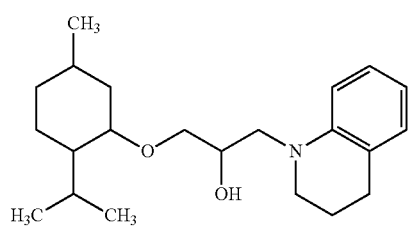
A0068

Table of Series-A Compounds

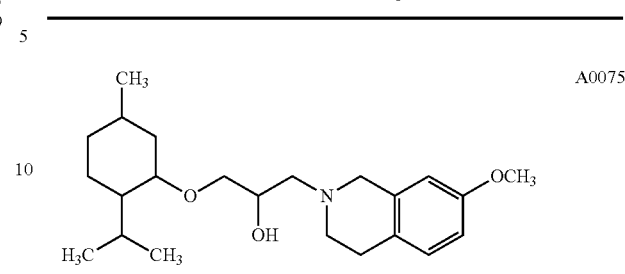
A0075

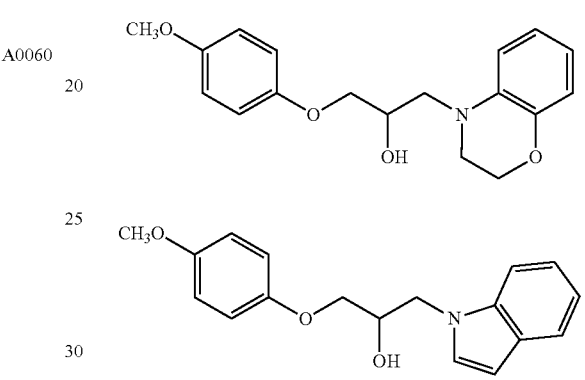
A0076

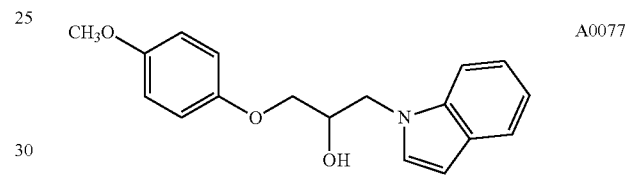
A0077

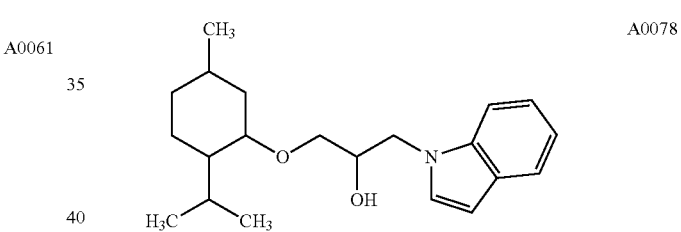
A0078

A compound of Series B can be prepared by following the synthetic route illustrated in Scheme 2, below. An illustrative synthetic scheme is shown below for the preparation of a first portion of a contemplated compound, with the second portion being added by a reaction with an appropriately substituted methylketone compound in the presence of a strong base such as sodium ethoxide. The resulting ketone can be converted into the corresponding alcohol by mild reduction as with sodium borohydride. A ketone or alcohol can be converted to the quaternary nitrogen atom-containing compound using an alkylating agent such as methyl iodide.

Scheme 2

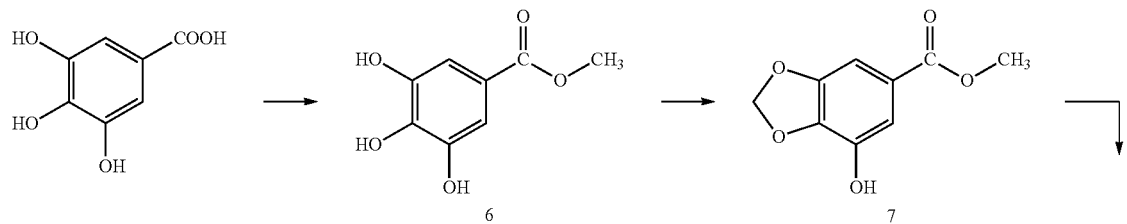

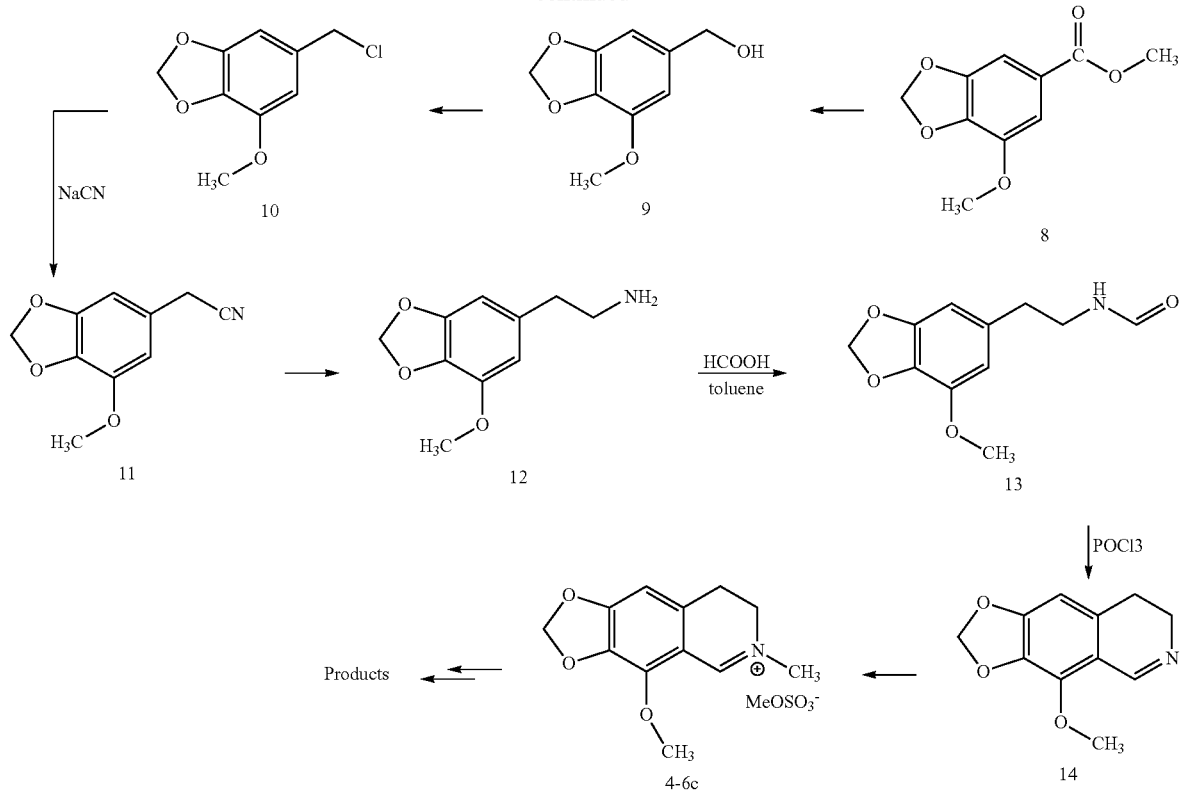
| Table of Series-B Compounds | |
|---|---|
| 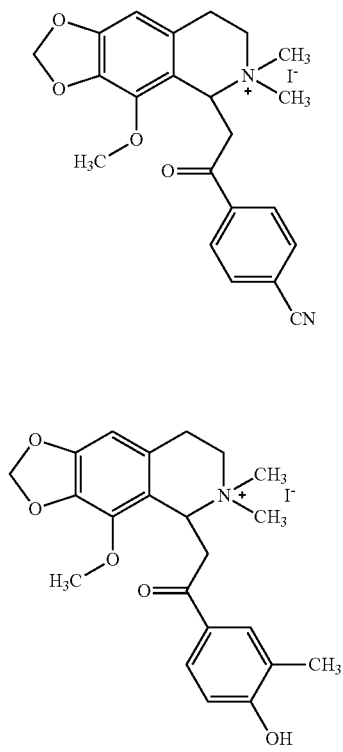 | B0001 |

Table of Series-B Compounds
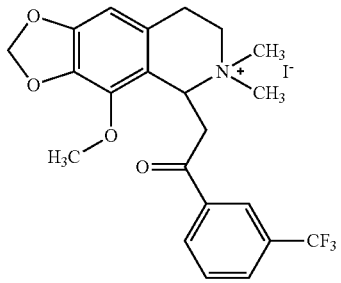 [SMILES: COc1c2c(cc3c1C(CC(=O)c1cccc(C(F)(F)F)c1)[N+](C)(C)CC3)OCO2 ; [I-]] B0006
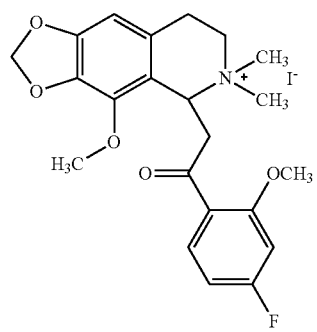 [SMILES: COc1cc(F)ccc1C(=O)CC1c2c(cc3c(c2OC)OCO3)CC[N+]1(C)C ; [I-]] B0007
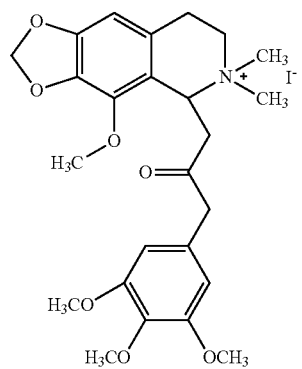 [SMILES: COc1cc(CC(=O)CC2c3c(cc4c(c3OC)OCO4)CC[N+]2(C)C)cc(OC)c1OC ; [I-]] B0008
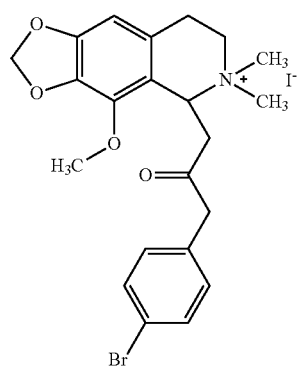 B0011
Table of Series-B Compounds
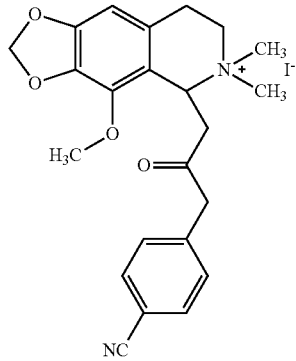 [SMILES: COc1c2c(cc3c1C(CC(=O)Cc1ccc(C#N)cc1)[N+](C)(C)CC3)OCO2 ; [I-]] B0012
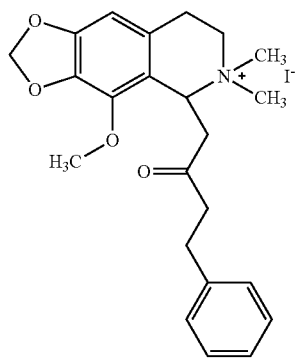 [SMILES: COc1c2c(cc3c1C(CC(=O)CCc1ccccc1)[N+](C)(C)CC3)OCO2 ; [I-]] B0015
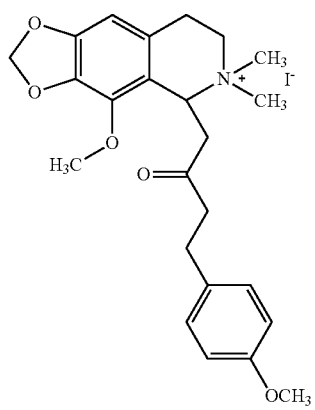 [SMILES: COc1ccc(CCC(=O)CC2c3c(cc4c(c3OC)OCO4)CC[N+]2(C)C)cc1 ; [I-]] B0016
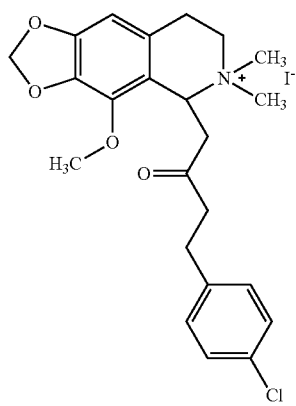 [SMILES: COc1c2c(cc3c1C(CC(=O)CCc1ccc(Cl)cc1)[N+](C)(C)CC3)OCO2 ; [I-]] B0017

Table of Series-B Compounds
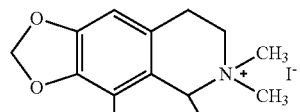
B0018
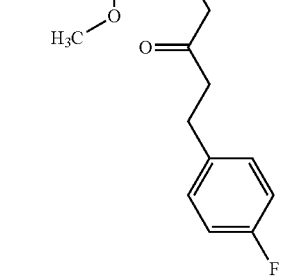
B0019
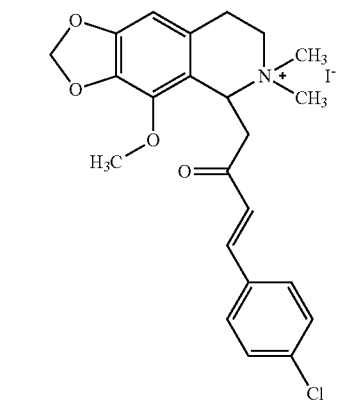 [SMILES: COc1c2c(cc3c1C(CC(=O)/C=C/c1ccc(Cl)cc1)[N+](C)(C)CC3)OCO2 ; [I-]]
B0020
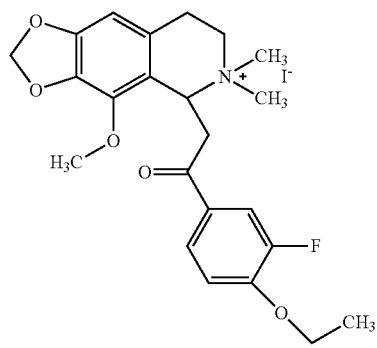 [SMILES: CCOc1ccc(C(=O)CC2c3c(cc4c(c3OC)OCO4)CC[N+]2(C)C)cc1F ; [I-]]
B0021
Table of Series-B Compounds
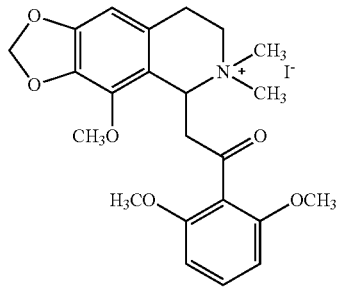
B0023
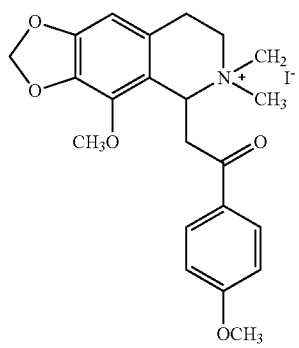
B0024
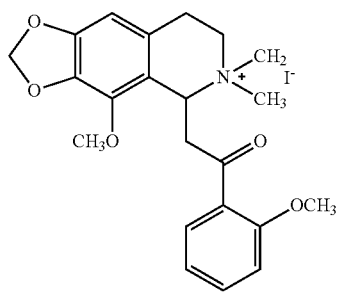
B0025
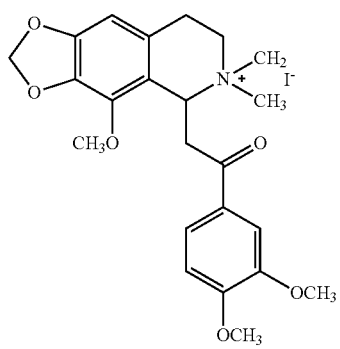
B0026

| Table of Series-B Compounds | |
|---|---|
| 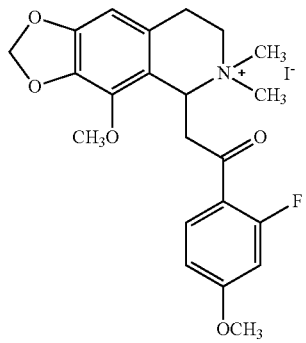 | B0027 |
| 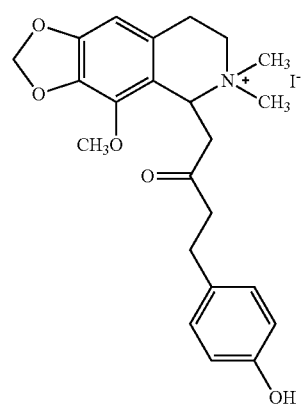 | B0028 |
| 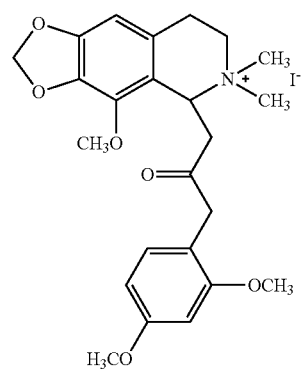 | B0029 |
| 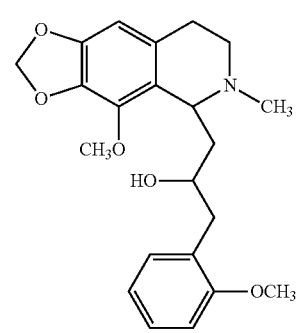 | B0030 |
| Table of Series-B Compounds | |
|---|---|
| 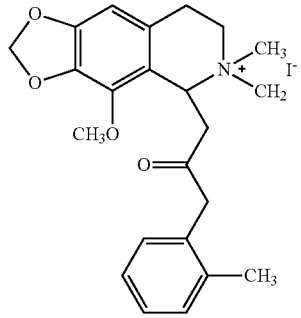 | B0031 |
| 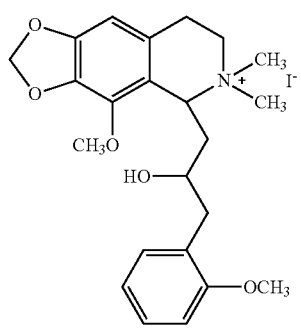 | B0032 |
| 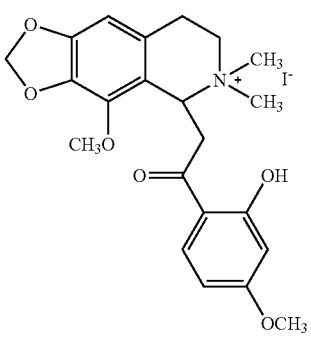 | B0033 |
| 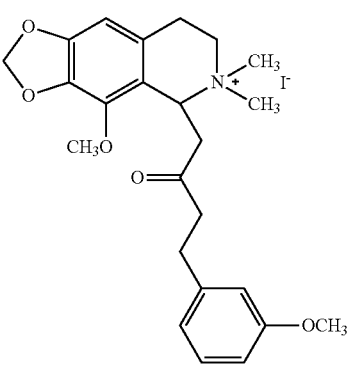 | B0034 |

| Table of Series-B Compounds | |
|---|---|
| 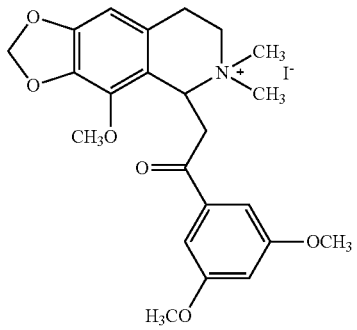 | B0035 |
| 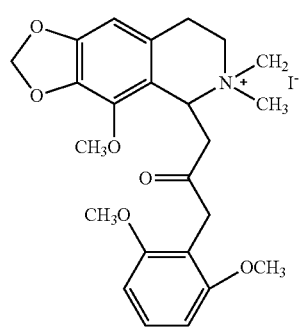 | B0036 |
| 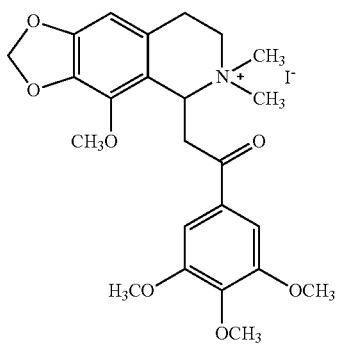 | B0037 |
| 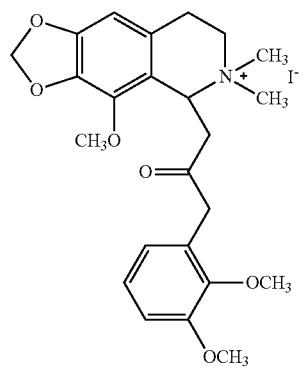 | B0038 |
| 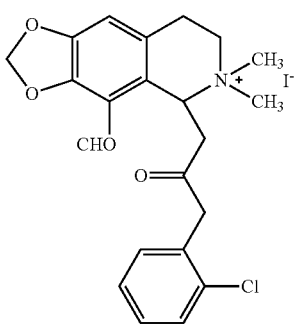 [SMILES: C[N+]1(C)CCc2cc3c(c(C=O)c2C1CC(=O)Cc1ccccc1Cl)OCO3 ; [I-]] | B0039 |
| 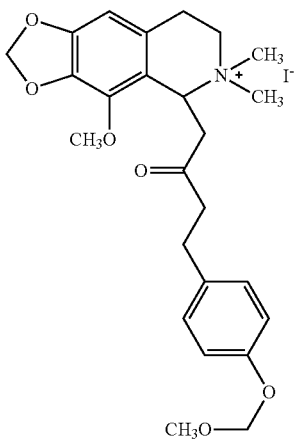 | B0040 |
| 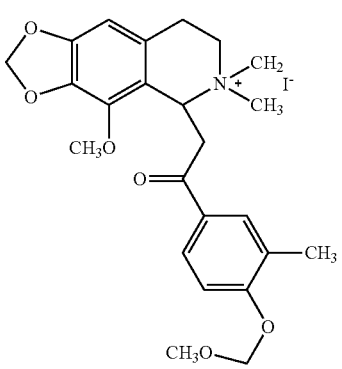 | B0041 |
| 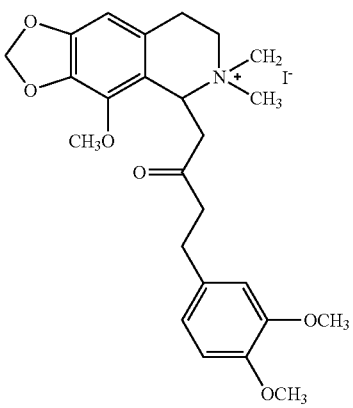 | B0042 |

Table of Series-B Compounds
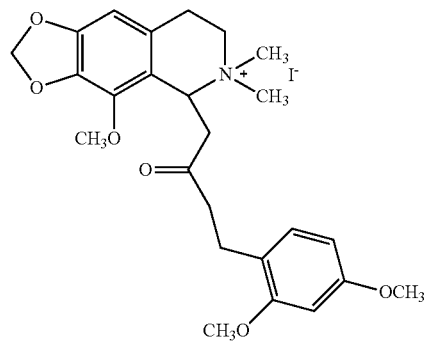
B0043
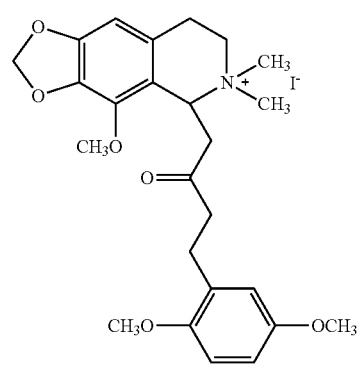
B0044
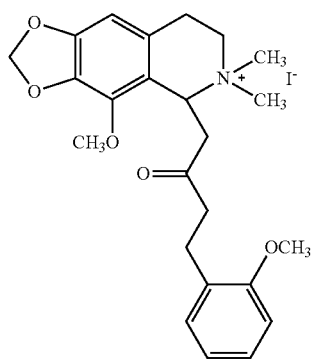
B0045
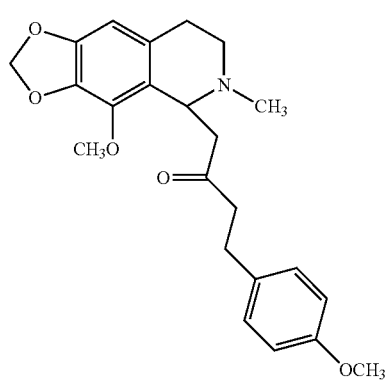
B0047
Table of Series-B Compounds
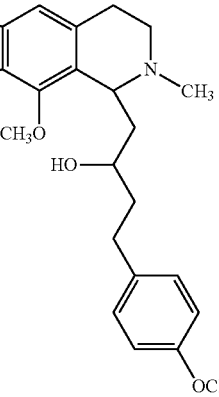
B0048
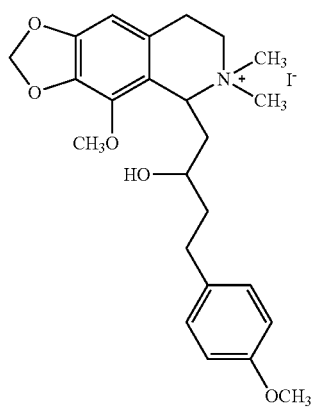
B0049
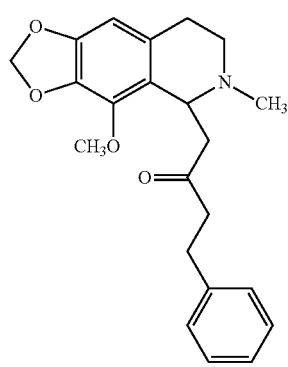
B0050
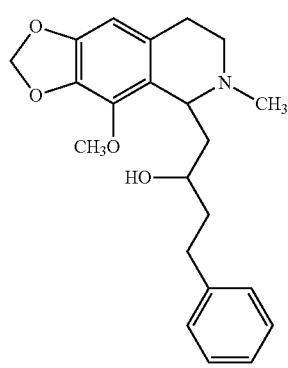
B0051

Table of Series-B Compounds
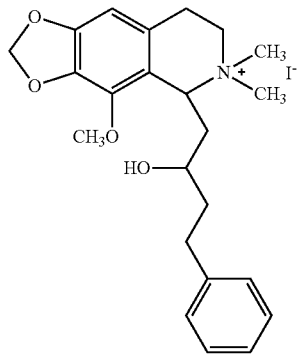
B0052
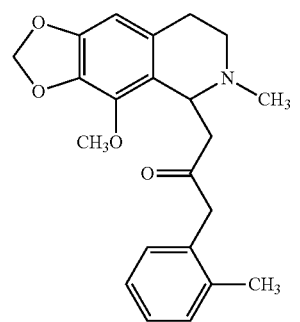
B0053
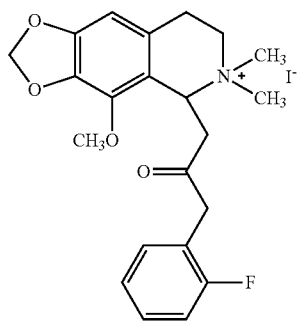
B0055
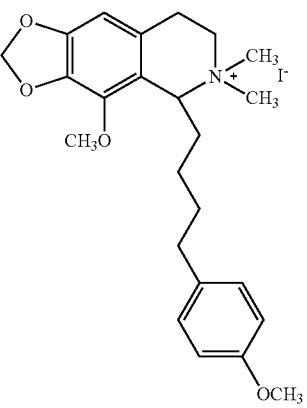
B0056
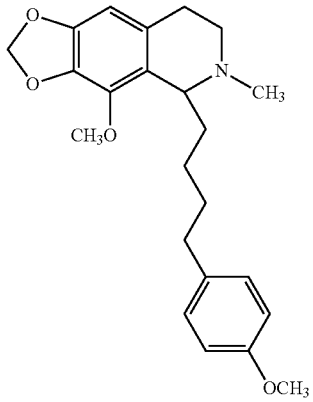
B0057
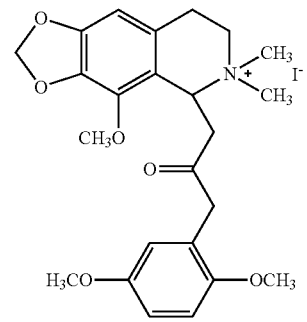
B0058
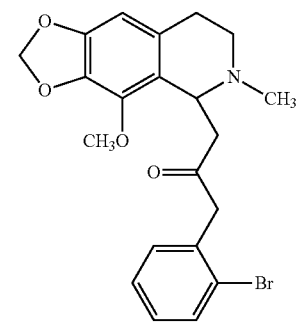
B0059
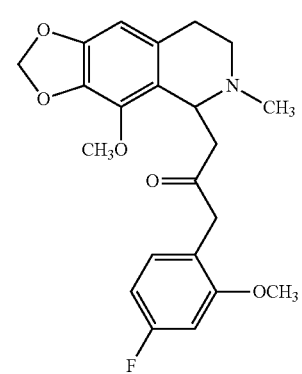
B0060

Table of Series-B Compounds
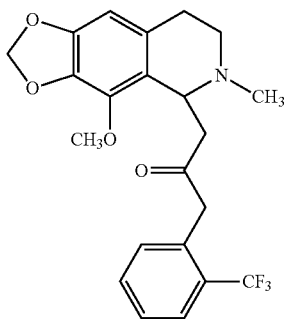 B0061
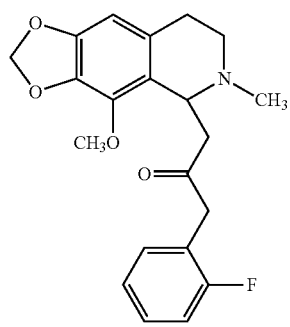 B0062
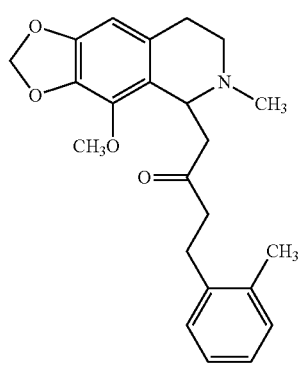 B0063
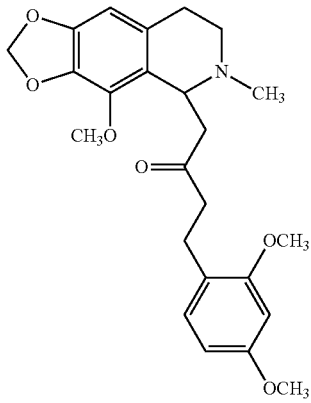 B0064
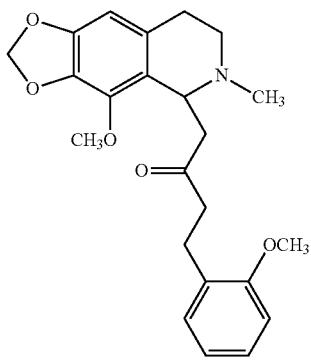 B0065
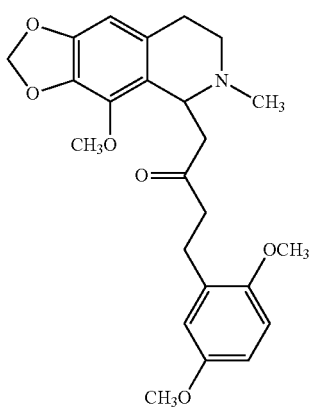 B0067

Table of Series-B Compounds

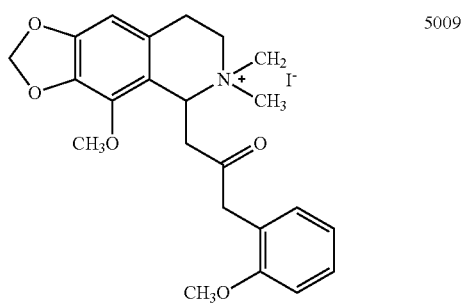

An illustrative synthetic scheme is shown below for preparation of Series-C (both C-1 and C-2) compounds that contain various substituents and ring atoms. That scheme can be readily adapted for the preparation of compounds containing two carbonyl linkages, and also one carbonyl and one sulfonyl linkage in the opposite configurations from those shown. Ethanolamine or thioethanolamine can be replaced by ethylenediamine or N-methylethylene-diamine to prepare the corresponding dinitrogen compounds. Similar replacement with 2-aminoacetamide or an N-substituted acetamide or propionamide provides the corresponding aminoamido-containing ring system.

Scheme 3

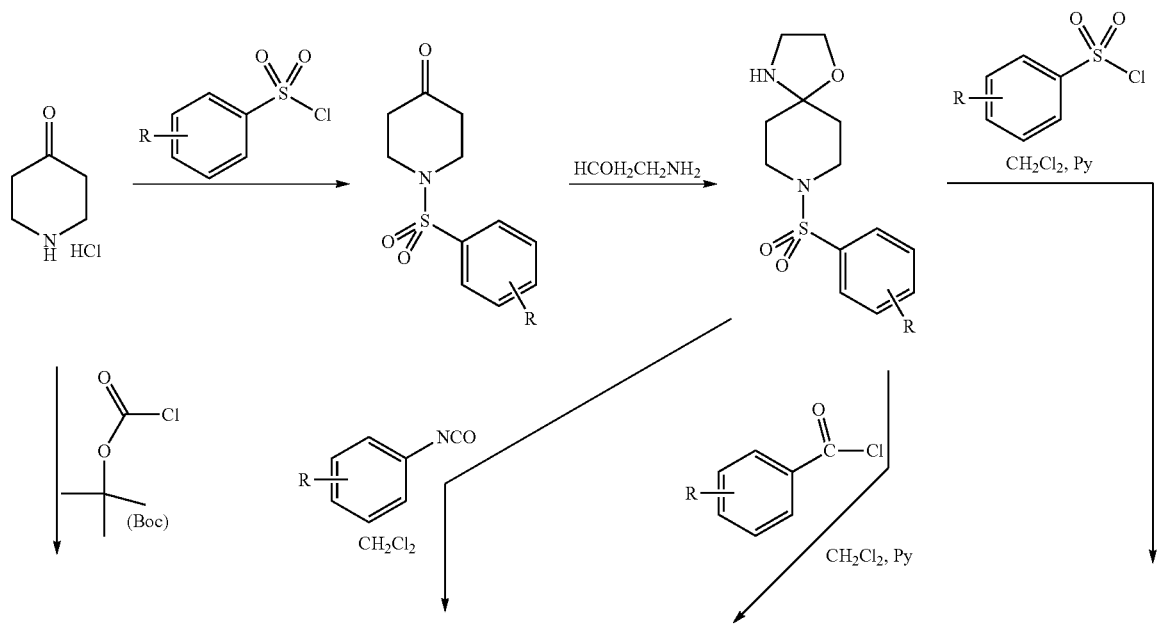

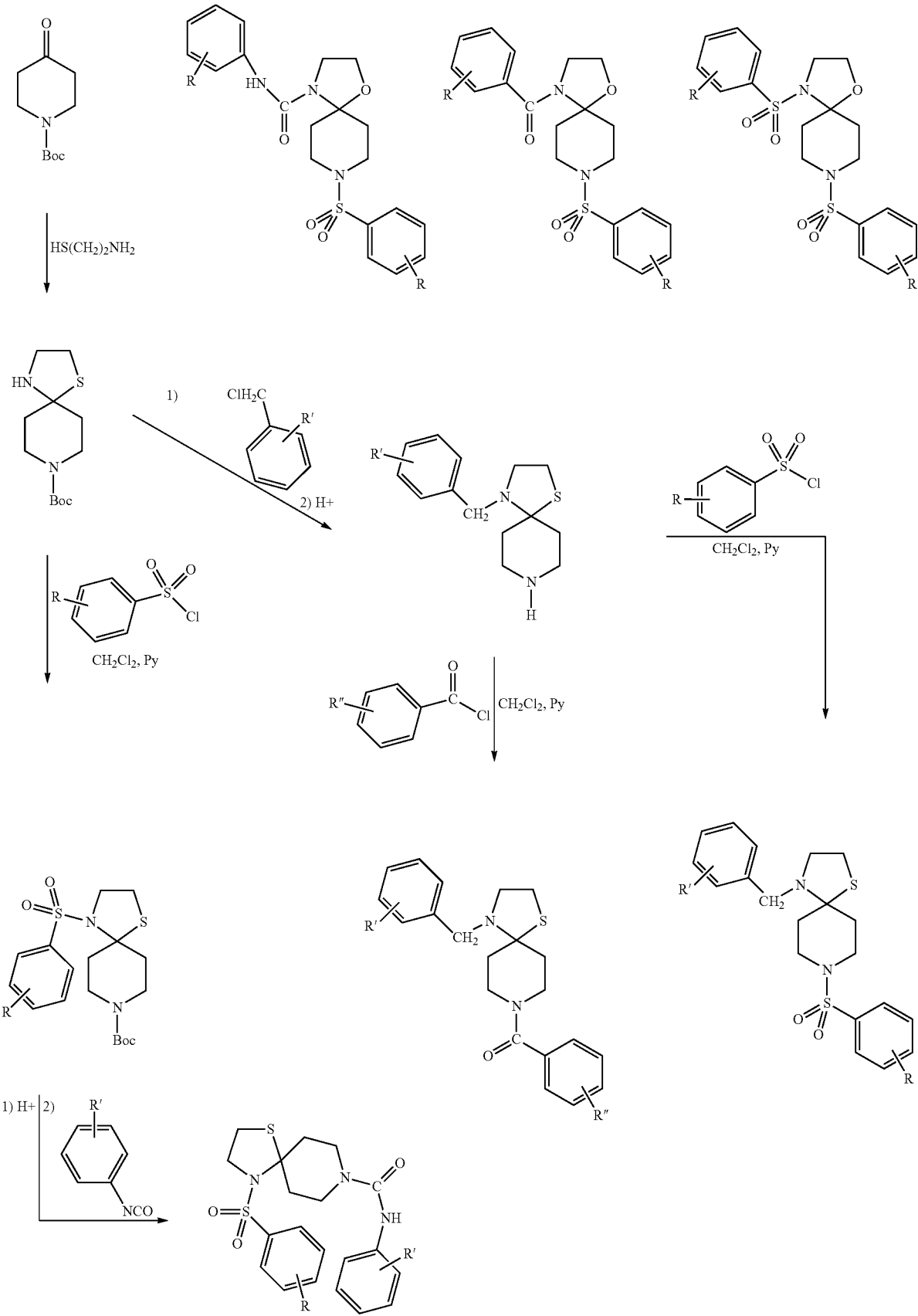

Table of Series-C-1 Compounds
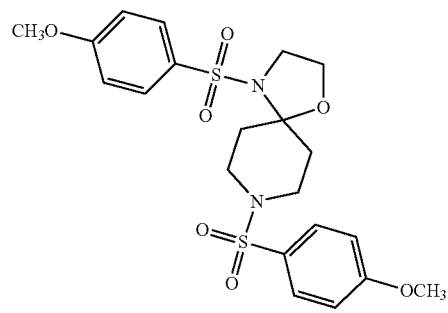
7866
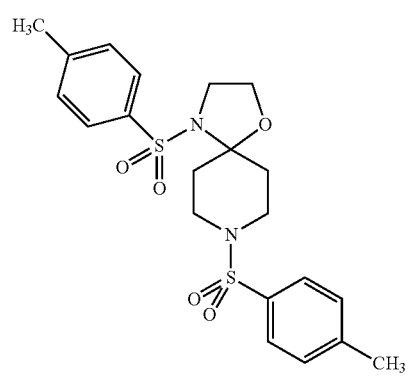
C0001
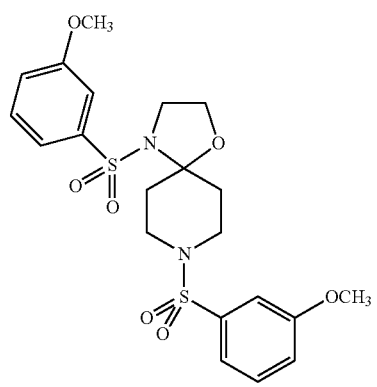 [SMILES: COc1cccc(S(=O)(=O)N2CCC3(CC2)OCCN3S(=O)(=O)c2cccc(OC)c2)c1]
C0002
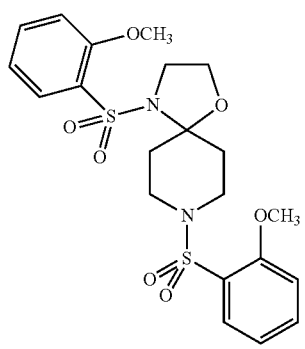 [SMILES: COc1ccccc1S(=O)(=O)N1CCC2(CC1)OCCN2S(=O)(=O)c1ccccc1OC]
C0003
Table of Series-C-1 Compounds
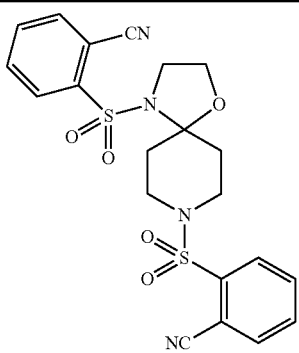
C0004
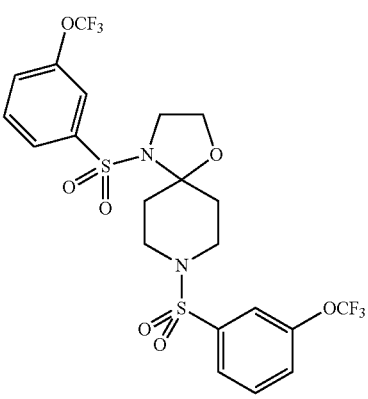 [SMILES: O=S(=O)(c1cccc(OC(F)(F)F)c1)N1CCC2(CC1)OCCN2S(=O)(=O)c1cccc(OC(F)(F)F)c1]
C0005
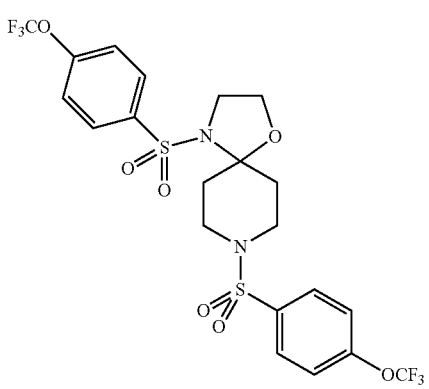 [SMILES: O=S(=O)(c1ccc(OC(F)(F)F)cc1)N1CCC2(CC1)OCCN2S(=O)(=O)c1ccc(OC(F)(F)F)cc1]
C0006
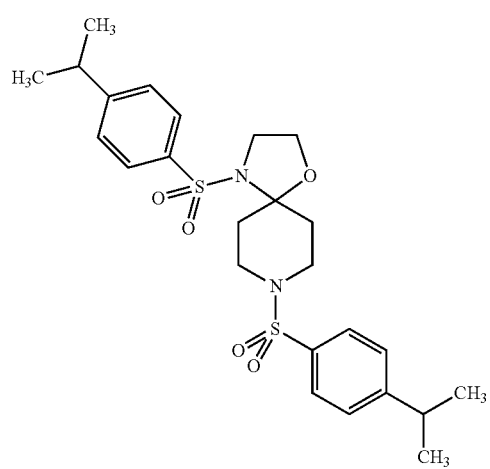 [SMILES: CC(C)c1ccc(S(=O)(=O)N2CCC3(CC2)OCCN3S(=O)(=O)c2ccc(C(C)C)cc2)cc1]
C0007

Table of Series-C-1 Compounds
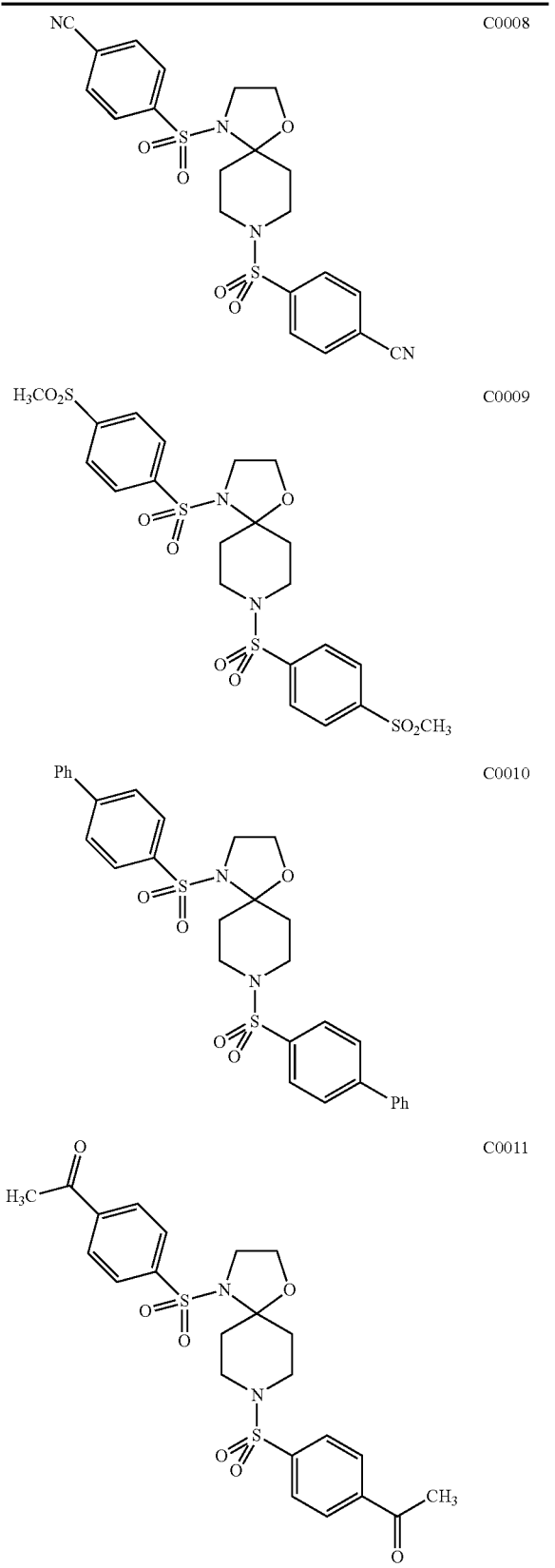
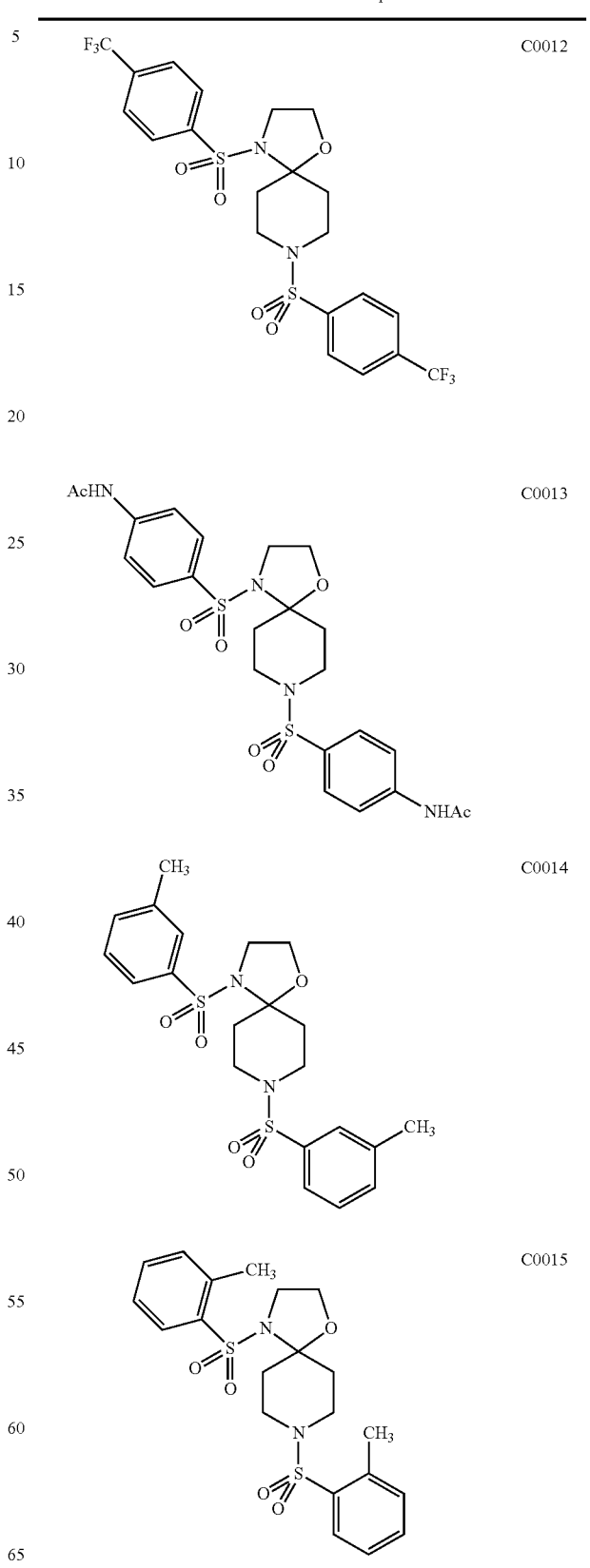

Table of Series-C-1 Compounds
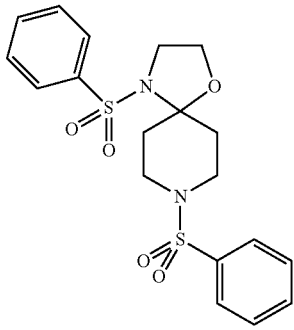 [SMILES: O=S(=O)(c1ccccc1)N1CCC2(CC1)OCCN2S(=O)(=O)c1ccccc1]
C0016
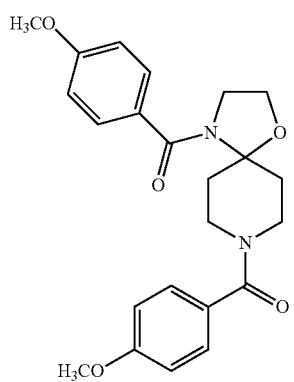
C0017
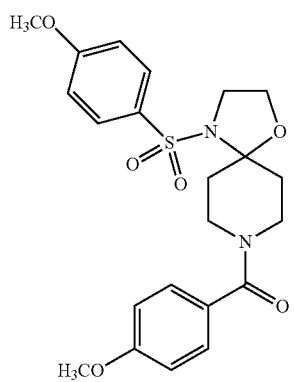
C0018
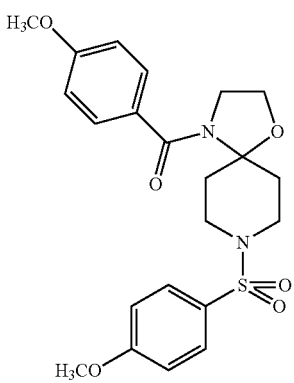 [SMILES: COc1ccc(C(=O)N2CCOC23CCN(S(=O)(=O)c2ccc(OC)cc2)CC3)cc1]
C0019
Table of Series-C-1 Compounds
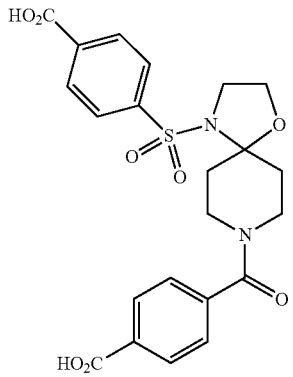 [SMILES: O=C(O)c1ccc(C(=O)N2CCC3(CC2)OCCN3S(=O)(=O)c2ccc(C(=O)O)cc2)cc1]
C0021
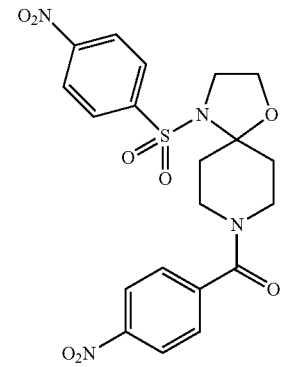 [SMILES: O=C(c1ccc([N+](=O)[O-])cc1)N1CCC2(CC1)OCCN2S(=O)(=O)c1ccc([N+](=O)[O-])cc1]
C0022
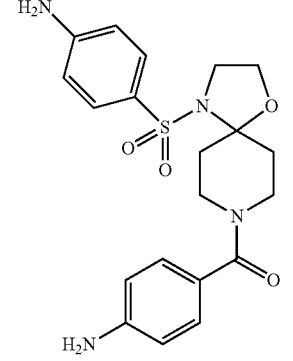
C0023
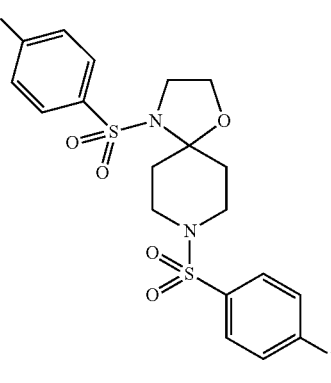
C0024

Table of Series-C-1 Compounds
C0025
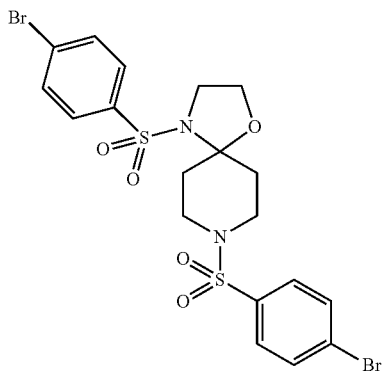 [SMILES: O=S(=O)(c1ccc(Br)cc1)N1CCC2(CC1)OCCN2S(=O)(=O)c1ccc(Br)cc1]
C0026
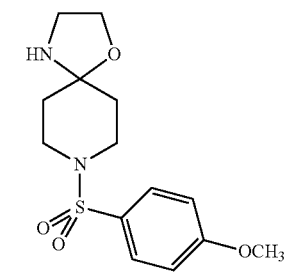
C0027-1
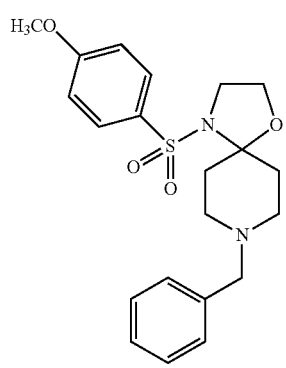 [SMILES: COc1ccc(S(=O)(=O)N2CCOC23CCN(Cc2ccccc2)CC3)cc1]
C0028
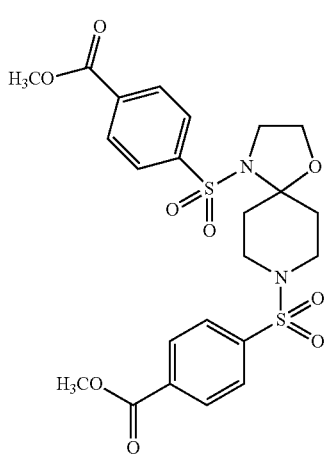 [SMILES: COC(=O)c1ccc(S(=O)(=O)N2CCC3(CC2)OCCN3S(=O)(=O)c2ccc(C(=O)OC)cc2)cc1]
Table of Series-C-1 Compounds
C0029
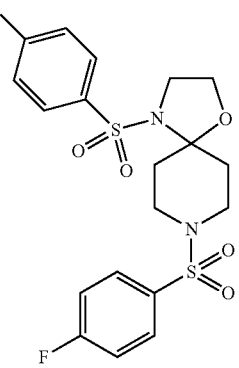
C0030
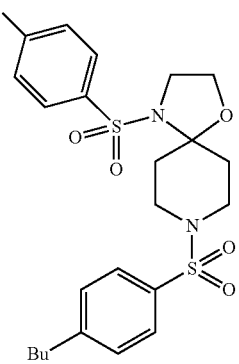
C0031
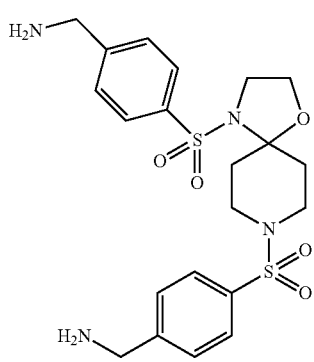 [SMILES: NCc1ccc(S(=O)(=O)N2CCC3(CC2)OCCN3S(=O)(=O)c2ccc(CN)cc2)cc1]
C0032
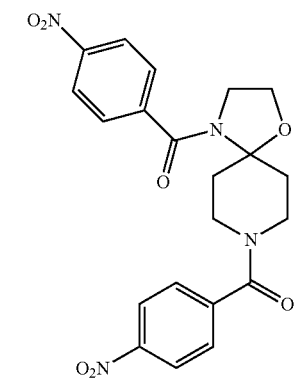 [SMILES: O=C(c1ccc([N+](=O)[O-])cc1)N1CCC2(CC1)OCCN2C(=O)c1ccc([N+](=O)[O-])cc1]

Table of Series-C-1 Compounds
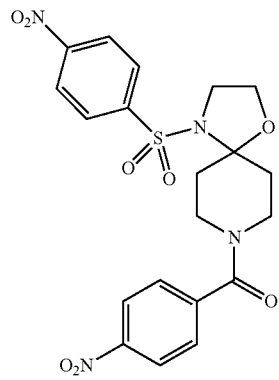 [SMILES: O=C(c1ccc([N+](=O)[O-])cc1)N1CCC2(CC1)OCCN2S(=O)(=O)c1ccc([N+](=O)[O-])cc1]
C0033
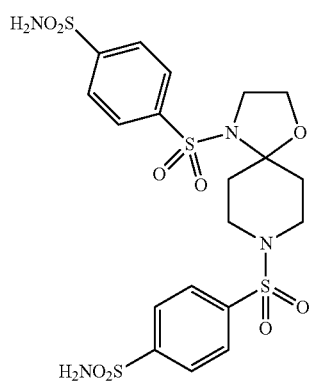 [SMILES: NS(=O)(=O)c1ccc(S(=O)(=O)N2CCC3(CC2)OCCN3S(=O)(=O)c2ccc(S(N)(=O)=O)cc2)cc1]
C0034
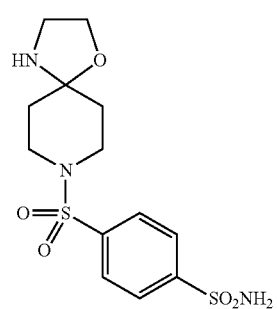 [SMILES: NS(=O)(=O)c1ccc(S(=O)(=O)N2CCC3(CC2)NCCO3)cc1]
C0034-3
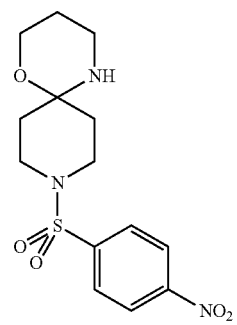 [SMILES: O=[N+]([O-])c1ccc(S(=O)(=O)N2CCC3(CC2)NCCCO3)cc1]
C0037-2
Table of Series-C-1 Compounds
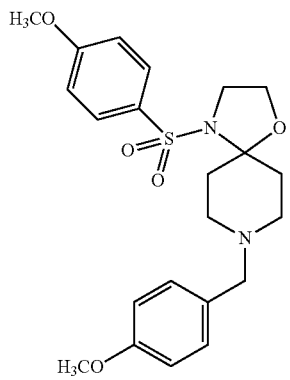 [SMILES: COc1ccc(CN2CCC3(CC2)OCCN3S(=O)(=O)c2ccc(OC)cc2)cc1]
C0038
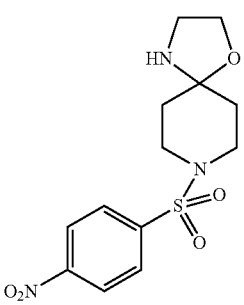 [SMILES: O=[N+]([O-])c1ccc(S(=O)(=O)N2CCC3(CC2)NCCO3)cc1]
C0040
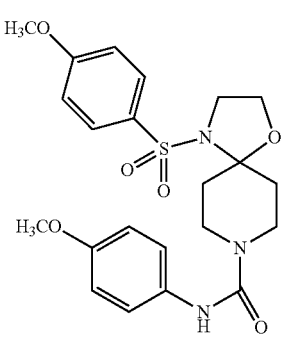 [SMILES: COc1ccc(NC(=O)N2CCC3(CC2)OCCN3S(=O)(=O)c2ccc(OC)cc2)cc1]
C0041
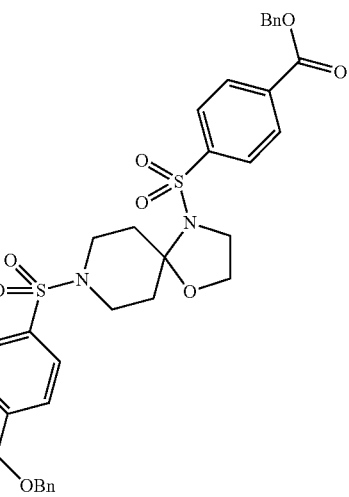
C0042

Table of Series-C-1 Compounds
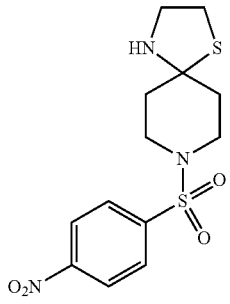 [SMILES: O=[N+]([O-])c1ccc(S(=O)(=O)N2CCC3(CC2)NCCS3)cc1]
C0044
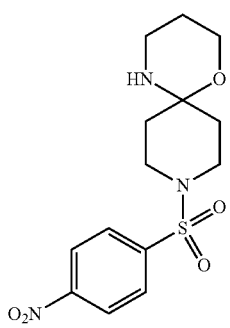
C0045
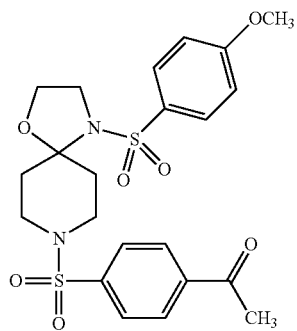 [SMILES: COc1ccc(S(=O)(=O)N2CCOC23CCN(S(=O)(=O)c2ccc(C(C)=O)cc2)CC3)cc1]
C0047
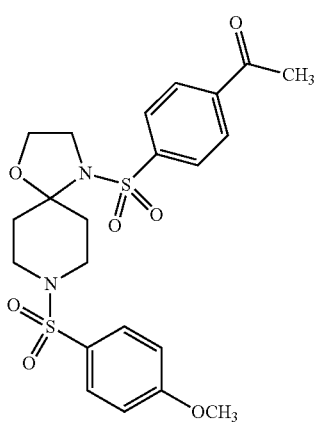 [SMILES: COc1ccc(S(=O)(=O)N2CCC3(CC2)OCCN3S(=O)(=O)c2ccc(C(C)=O)cc2)cc1]
C0048
Table of Series-C-1 Compounds
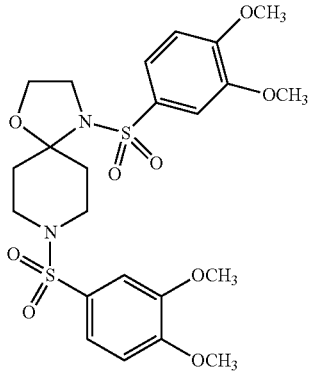 [SMILES: COc1ccc(S(=O)(=O)N2CCC3(CC2)OCCN3S(=O)(=O)c2ccc(OC)c(OC)c2)cc1OC]
C0049
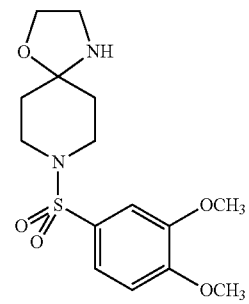 [SMILES: COc1ccc(S(=O)(=O)N2CCC3(CC2)NCCO3)cc1OC]
C0049-2
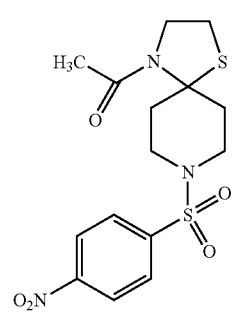 [SMILES: CC(=O)N1CCSC12CCN(S(=O)(=O)c1ccc([N+](=O)[O-])cc1)CC2]
C0050
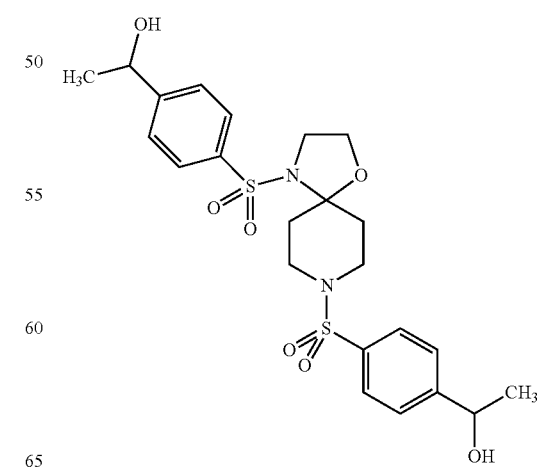
C0051

Table of Series-C-1 Compounds
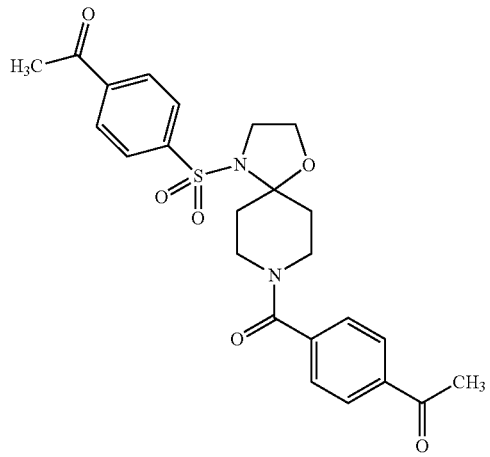 [SMILES: CC(=O)c1ccc(C(=O)N2CCC3(CC2)OCCN3S(=O)(=O)c2ccc(C(C)=O)cc2)cc1]
C0052
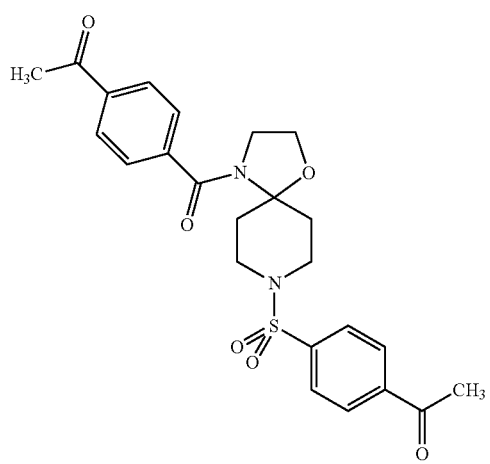 [SMILES: CC(=O)c1ccc(C(=O)N2CCOC23CCN(S(=O)(=O)c2ccc(C(C)=O)cc2)CC3)cc1]
C0053
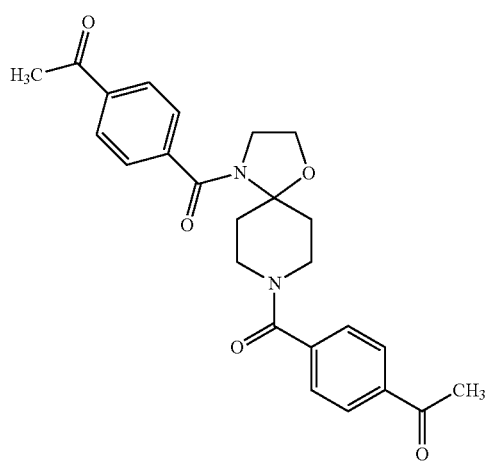 [SMILES: CC(=O)c1ccc(C(=O)N2CCC3(CC2)OCCN3C(=O)c2ccc(C(C)=O)cc2)cc1]
C0054
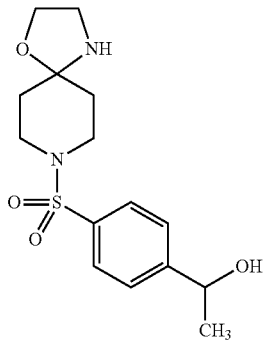 [SMILES: CC(O)c1ccc(S(=O)(=O)N2CCC3(CC2)NCCO3)cc1]
C0055-4
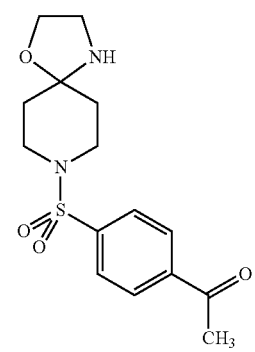
C0055
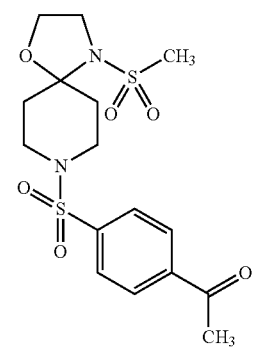 [SMILES: CC(=O)c1ccc(S(=O)(=O)N2CCC3(CC2)OCCN3S(C)(=O)=O)cc1]
C0056
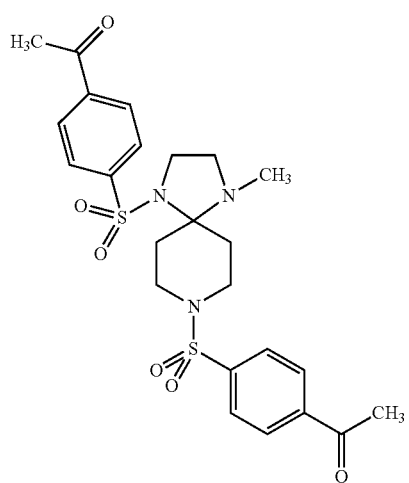 [SMILES: CC(=O)c1ccc(S(=O)(=O)N2CCC3(CC2)N(C)CCN3S(=O)(=O)c2ccc(C(C)=O)cc2)cc1]
C0057

| Table of Series-C-1 Compounds | |
|---|---|
| 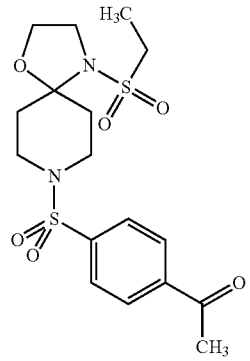 [SMILES: CCS(=O)(=O)N1CCOC12CCN(S(=O)(=O)c1ccc(C(C)=O)cc1)CC2] | C0058 |
| 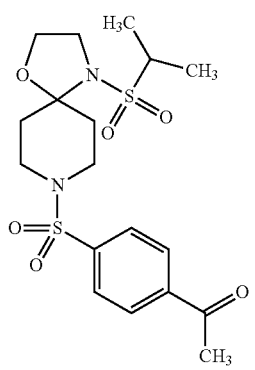 [SMILES: CC(=O)c1ccc(S(=O)(=O)N2CCC3(CC2)OCCN3S(=O)(=O)C(C)C)cc1] | C0059 |
| 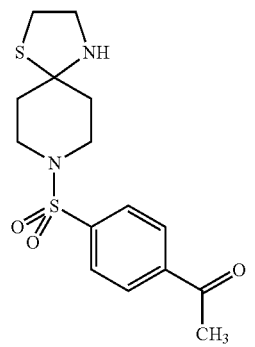 | C0060 |
| 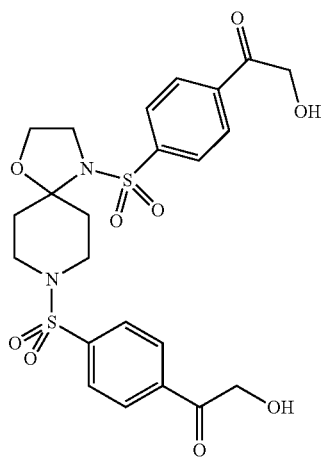 [SMILES: O=C(CO)c1ccc(S(=O)(=O)N2CCC3(CC2)OCCN3S(=O)(=O)c2ccc(C(=O)CO)cc2)cc1] | C0061 |
| Table of Series-C-1 Compounds | |
|---|---|
| 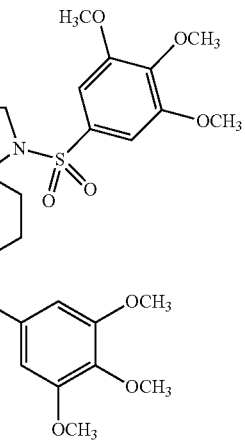 | C0062 |
| 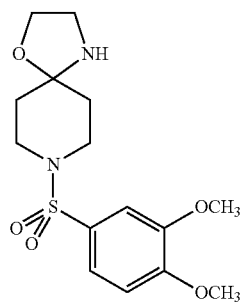 [SMILES: COc1ccc(S(=O)(=O)N2CCC3(CC2)NCCO3)cc1OC] | C0049-2 |
| 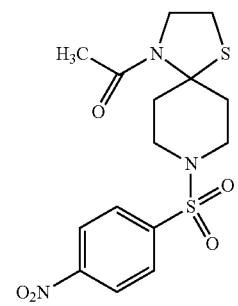 [SMILES: CC(=O)N1CCSC12CCN(S(=O)(=O)c1ccc([N+](=O)[O-])cc1)CC2] | C0050 |
| 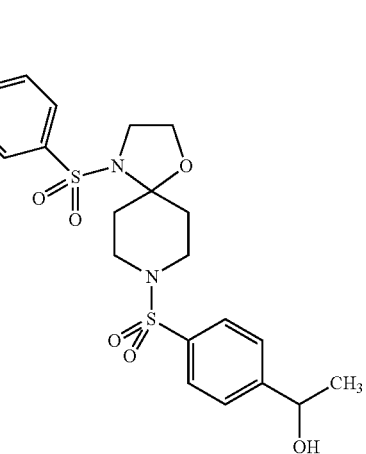 | C0051 |

| Table of Series-C-1 Compounds | Table of Series-C-1 Compounds |
|---|---|
| 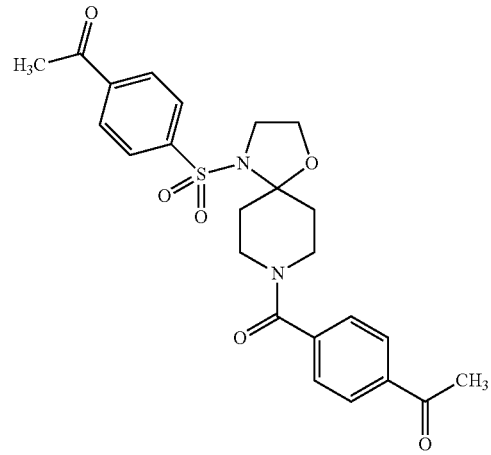 C0052 | 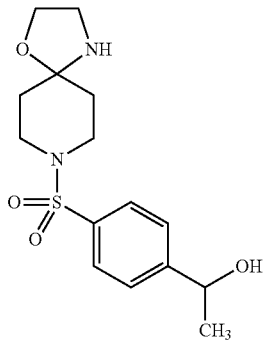 C0055-4 |
| 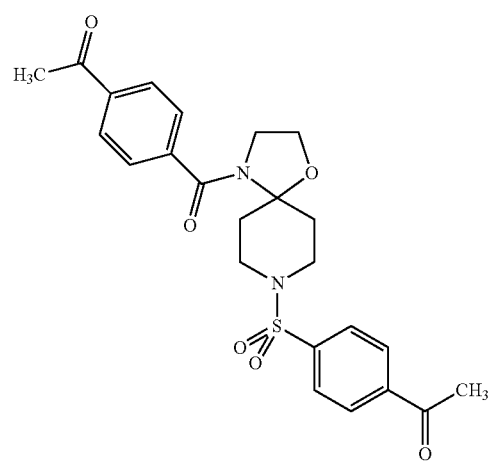 C0053 | 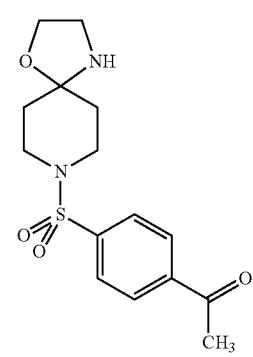 C0055 |
|  | 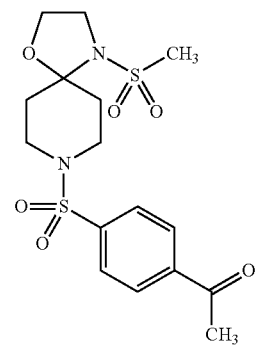 C0056 |
| 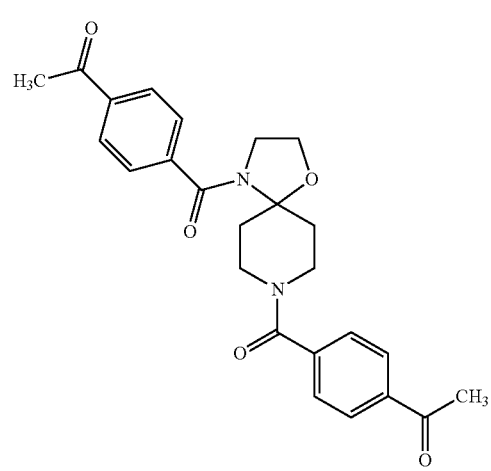 C0054 | 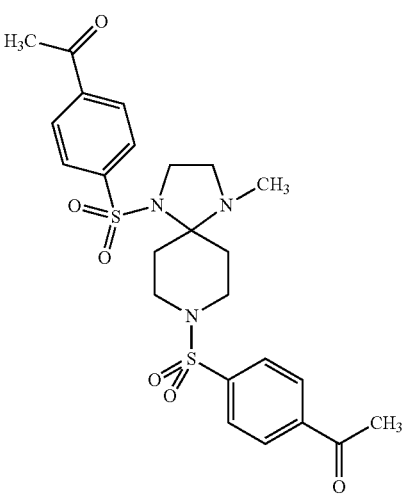 [SMILES: CC(=O)c1ccc(S(=O)(=O)N2CCC3(CC2)N(C)CCN3S(=O)(=O)c2ccc(C(C)=O)cc2)cc1] C0057 |

Table of Series-C-1 Compounds
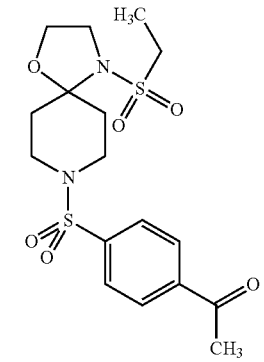 [SMILES: CCS(=O)(=O)N1CCOC12CCN(S(=O)(=O)c1ccc(C(C)=O)cc1)CC2] C0058
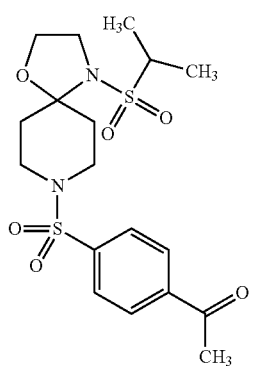 [SMILES: CC(=O)c1ccc(S(=O)(=O)N2CCC3(CC2)OCCN3S(=O)(=O)C(C)C)cc1] C0059
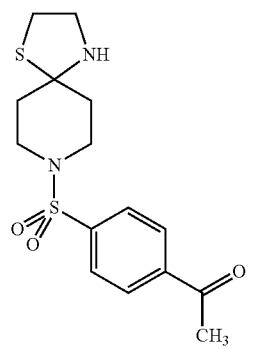 C0060
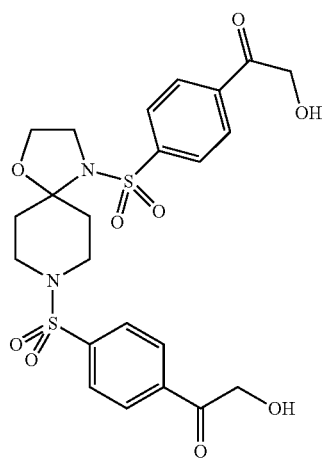 [SMILES: O=C(CO)c1ccc(S(=O)(=O)N2CCC3(CC2)OCCN3S(=O)(=O)c2ccc(C(=O)CO)cc2)cc1] C0061
Table of Series-C-1 Compounds
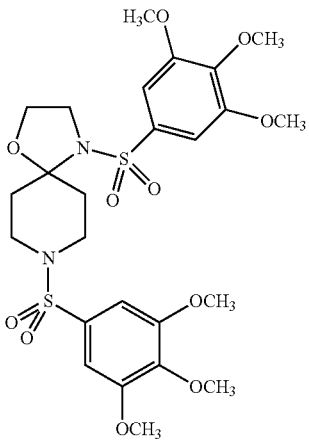 [SMILES: COc1cc(S(=O)(=O)N2CCC3(CC2)OCCN3S(=O)(=O)c2cc(OC)c(OC)c(OC)c2)cc(OC)c1OC] C0062
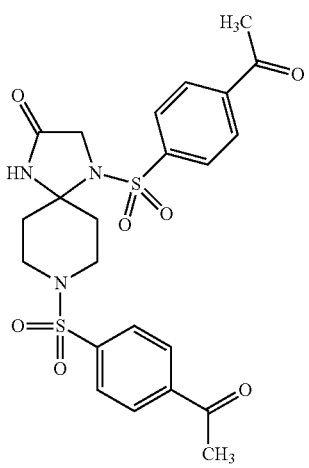 [SMILES: CC(=O)c1ccc(S(=O)(=O)N2CCC3(CC2)NC(=O)CN3S(=O)(=O)c2ccc(C(C)=O)cc2)cc1] C0064
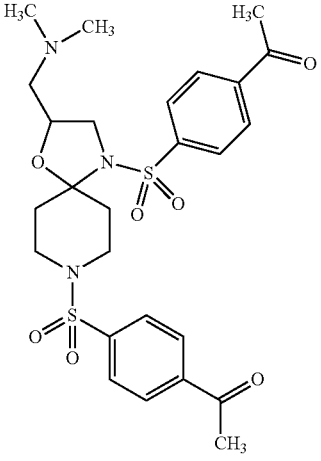 [SMILES: CC(=O)c1ccc(S(=O)(=O)N2CCC3(CC2)OC(CN(C)C)CN3S(=O)(=O)c2ccc(C(C)=O)cc2)cc1] C0065

Table of Series-C-1 Compounds
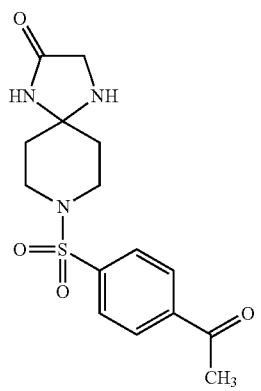 [SMILES: CC(=O)c1ccc(S(=O)(=O)N2CCC3(CC2)NCC(=O)N3)cc1] C0066
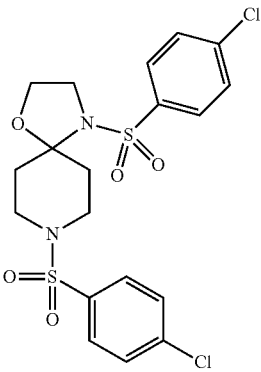 [SMILES: O=S(=O)(c1ccc(Cl)cc1)N1CCC2(CC1)OCCN2S(=O)(=O)c1ccc(Cl)cc1] C0067
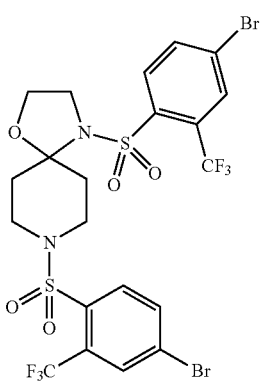 [SMILES: O=S(=O)(c1ccc(Br)cc1C(F)(F)F)N1CCC2(CC1)OCCN2S(=O)(=O)c1ccc(Br)cc1C(F)(F)F] C0068
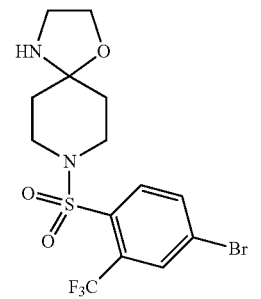 C0068-2
Table of Series-C-1 Compounds
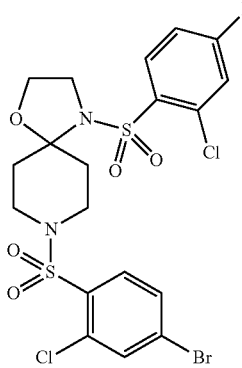 C0069
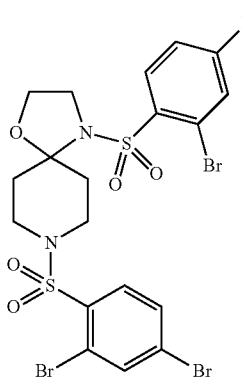 C0070
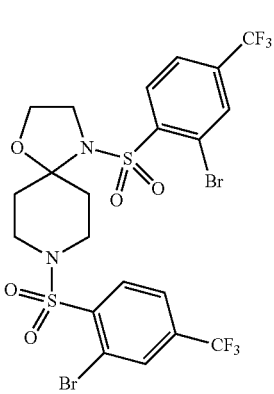 [SMILES: O=S(=O)(c1ccc(C(F)(F)F)cc1Br)N1CCC2(CC1)OCCN2S(=O)(=O)c1ccc(C(F)(F)F)cc1Br] C0071
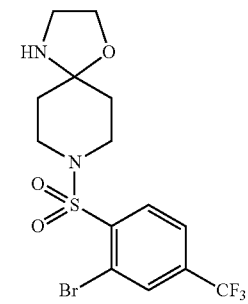 [SMILES: O=S(=O)(c1ccc(C(F)(F)F)cc1Br)N1CCC2(CC1)NCCO2] C0071-2

Table of Series-C-1 Compounds
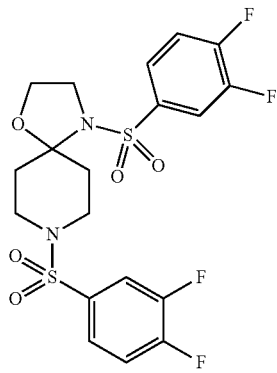 [SMILES: O=S(=O)(c1ccc(F)c(F)c1)N1CCC2(CC1)OCCN2S(=O)(=O)c1ccc(F)c(F)c1] C0072
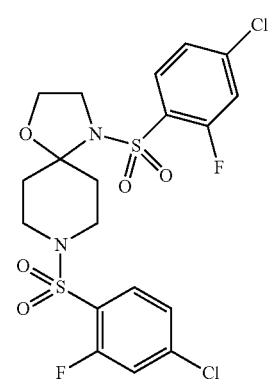 [SMILES: O=S(=O)(c1ccc(Cl)cc1F)N1CCC2(CC1)OCCN2S(=O)(=O)c1ccc(Cl)cc1F] C0073
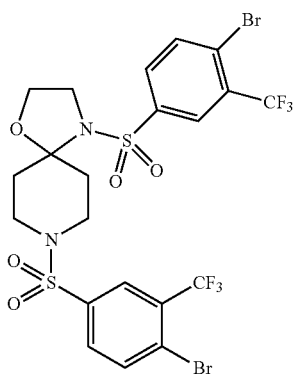 [SMILES: O=S(=O)(c1ccc(Br)c(C(F)(F)F)c1)N1CCC2(CC1)OCCN2S(=O)(=O)c1ccc(Br)c(C(F)(F)F)c1] C0077
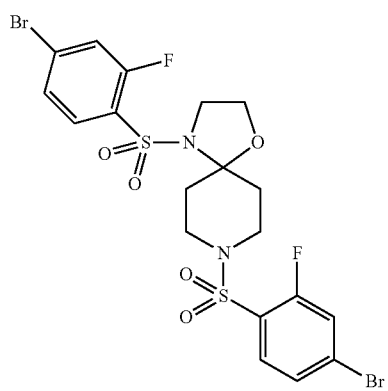 [SMILES: O=S(=O)(c1ccc(Br)cc1F)N1CCC2(CC1)OCCN2S(=O)(=O)c1ccc(Br)cc1F] C0078
Table of Series-C-1 Compounds
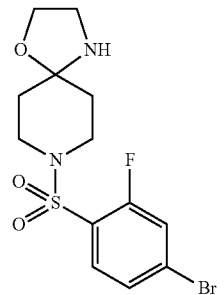 [SMILES: O=S(=O)(c1ccc(Br)cc1F)N1CCC2(CC1)NCCO2] C0078-2
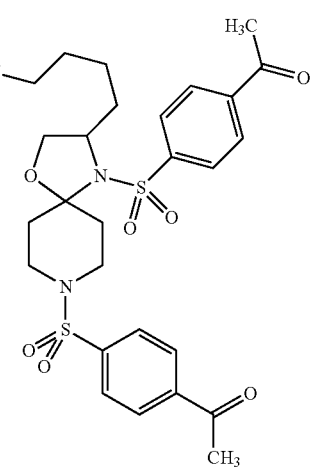 C0080
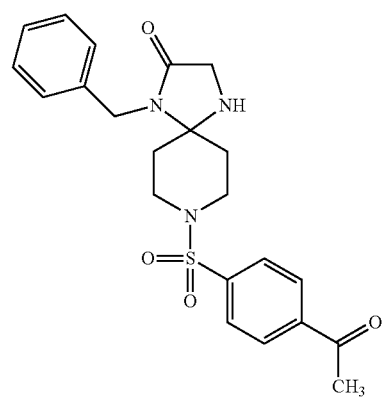 [SMILES: CC(=O)c1ccc(S(=O)(=O)N2CCC3(CC2)NCC(=O)N3Cc2ccccc2)cc1] C0082M
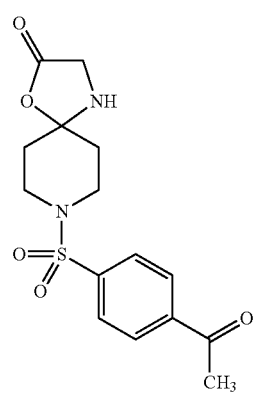 [SMILES: CC(=O)c1ccc(S(=O)(=O)N2CCC3(CC2)NCC(=O)O3)cc1] C0083M -continued
Table of Series-C-1 Compounds
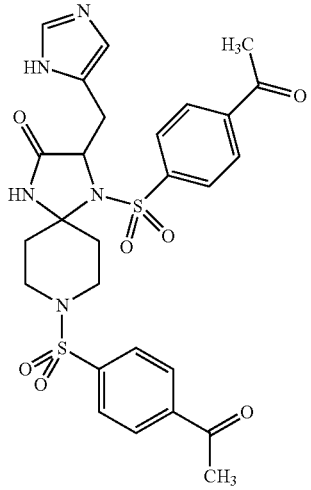 [SMILES: CC(=O)c1ccc(S(=O)(=O)N2CCC3(CC2)NC(=O)C(Cc2cnc[nH]2)N3S(=O)(=O)c2ccc(C(C)=O)cc2)cc1] C0084M
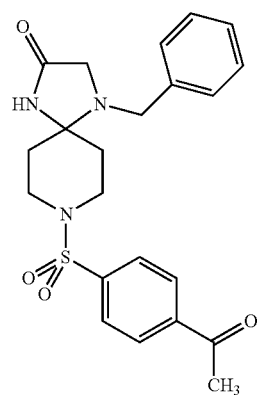 C0085M
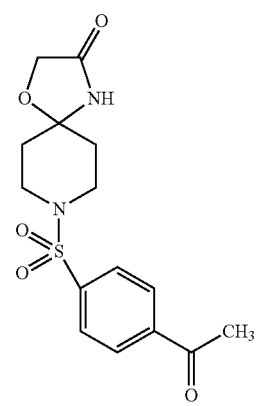 [SMILES: CC(=O)c1ccc(S(=O)(=O)N2CCC3(CC2)NC(=O)CO3)cc1] C0087M
-continued
Table of Series-C-1 Compounds
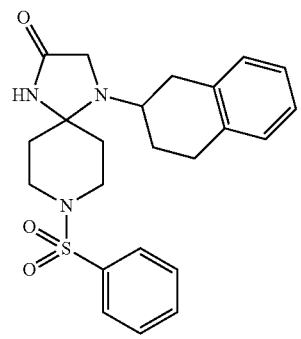 [SMILES: O=C1CN(C2CCc3ccccc3C2)C2(CCN(S(=O)(=O)c3ccccc3)CC2)N1] C0136M (P5)
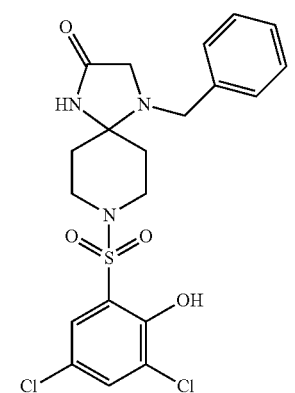 [SMILES: O=C1CN(Cc2ccccc2)C2(CCN(S(=O)(=O)c3cc(Cl)cc(Cl)c3O)CC2)N1] C0138M
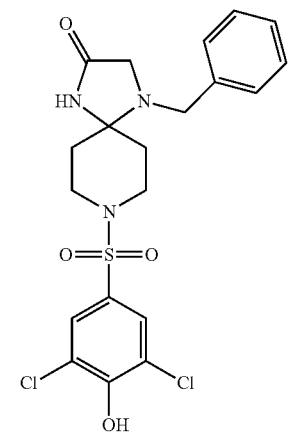 [SMILES: O=C1CN(Cc2ccccc2)C2(CCN(S(=O)(=O)c3cc(Cl)c(O)c(Cl)c3)CC2)N1] C0139M
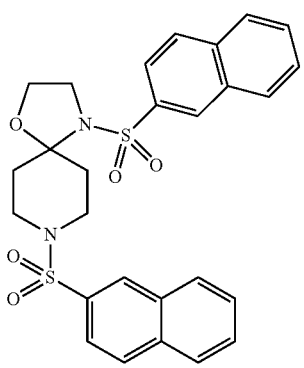 [SMILES: O=S(=O)(c1ccc2ccccc2c1)N1CCC2(CC1)OCCN2S(=O)(=O)c1ccc2ccccc2c1] C140M

Table of Series-C-1 Compounds
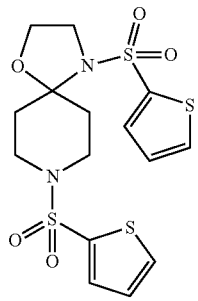 [SMILES: O=S(=O)(c1cccs1)N1CCC2(CC1)OCCN2S(=O)(=O)c1cccs1] C0141M
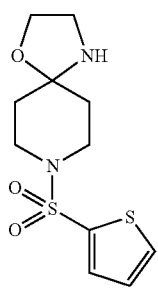 [SMILES: O=S(=O)(c1cccs1)N1CCC2(CC1)NCCO2] C0141M-2
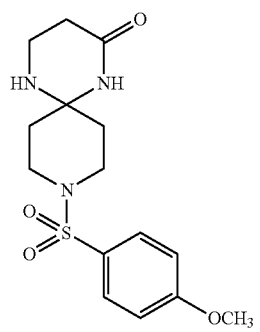 C0142M
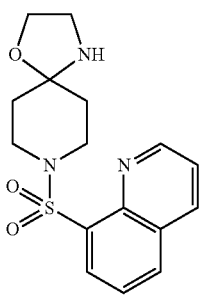 [SMILES: O=S(=O)(c1cccc2cccnc12)N1CCC2(CC1)NCCO2] C0143M-2
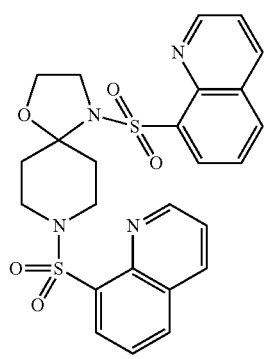 [SMILES: O=S(=O)(c1cccc2cccnc12)N1CCC2(CC1)OCCN2S(=O)(=O)c1cccc2cccnc12] C0143M
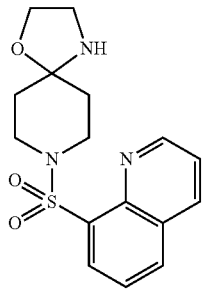 [SMILES: O=S(=O)(c1cccc2cccnc12)N1CCC2(CC1)NCCO2] C0143M-2
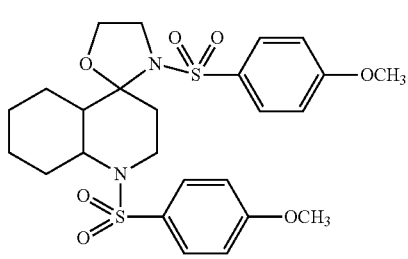 [SMILES: COc1ccc(S(=O)(=O)N2CCC3(OCCN3S(=O)(=O)c3ccc(OC)cc3)C3CCCCC32)cc1] C0144M
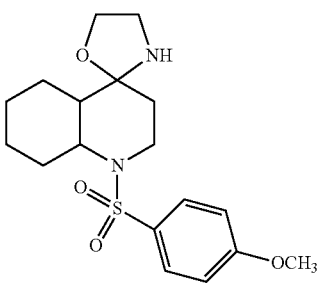 [SMILES: COc1ccc(S(=O)(=O)N2CCC3(NCCO3)C3CCCCC32)cc1] C0144M-2
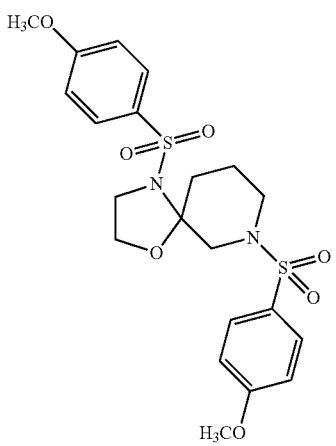 [SMILES: COc1ccc(S(=O)(=O)N2CCCC3(C2)OCCN3S(=O)(=O)c2ccc(OC)cc2)cc1] C0145M
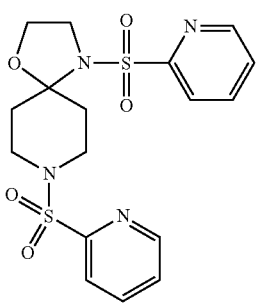 [SMILES: O=S(=O)(c1ccccn1)N1CCC2(CC1)OCCN2S(=O)(=O)c1ccccn1] C0146M Table of Series-C-1 Compounds
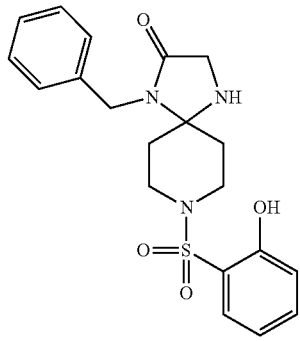 [SMILES: O=C1CNC2(CCN(S(=O)(=O)c3ccccc3O)CC2)N1Cc1ccccc1]
C0147M A2
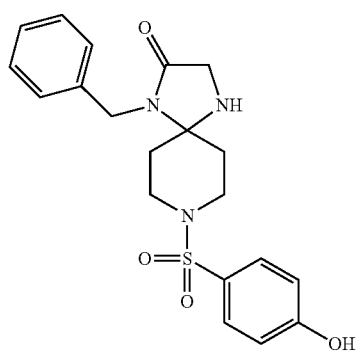 [SMILES: O=C1CNC2(CCN(S(=O)(=O)c3ccc(O)cc3)CC2)N1Cc1ccccc1]
C0148M
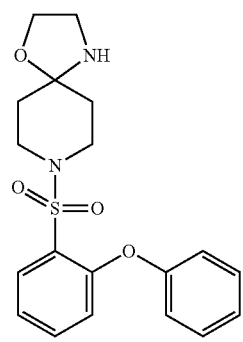 [SMILES: O=S(=O)(c1ccccc1Oc1ccccc1)N1CCC2(CC1)NCCO2]
C0149M-2
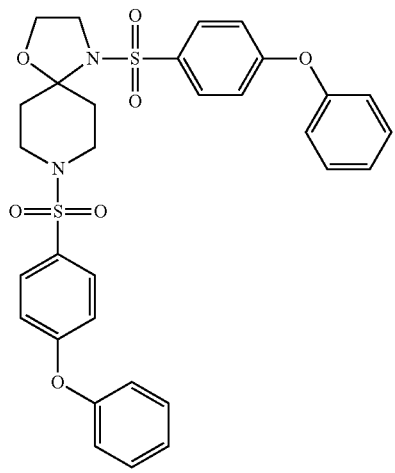 [SMILES: O=S(=O)(c1ccc(Oc2ccccc2)cc1)N1CCC2(CC1)OCCN2S(=O)(=O)c1ccc(Oc2ccccc2)cc1]
C0149M
Table of Series-C-1 Compounds
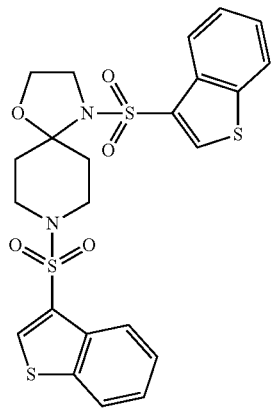 [SMILES: O=S(=O)(c1csc2ccccc12)N1CCC2(CC1)OCCN2S(=O)(=O)c1csc2ccccc12]
C0150M
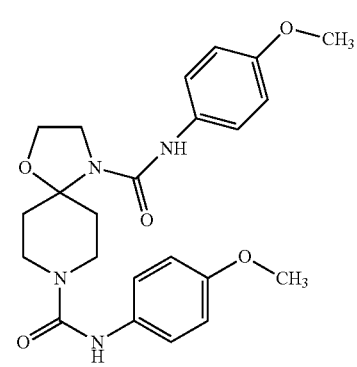 [SMILES: COc1ccc(NC(=O)N2CCC3(CC2)OCCN3C(=O)Nc2ccc(OC)cc2)cc1]
C0151M
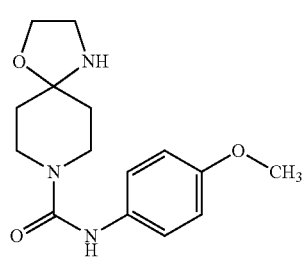 [SMILES: COc1ccc(NC(=O)N2CCC3(CC2)NCCO3)cc1]
C0151M-2
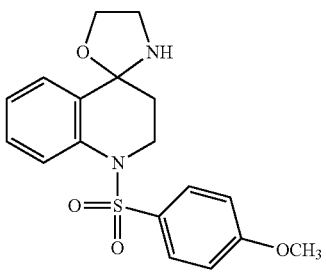 [SMILES: COc1ccc(S(=O)(=O)N2CCC3(NCCO3)c3ccccc32)cc1]
C0152M-4
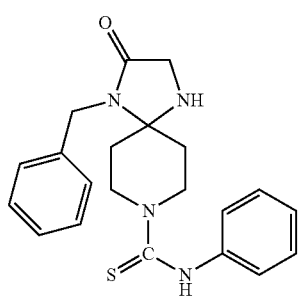 [SMILES: O=C1CNC2(CCN(C(=S)Nc3ccccc3)CC2)N1Cc1ccccc1]
Compound A

Table of Series-C-1 Compounds

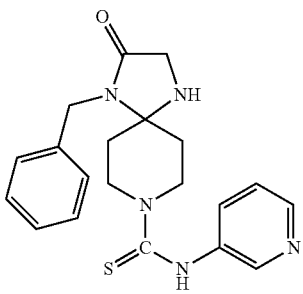 [SMILES: O=C1CNC2(CCN(C(=S)Nc3cccnc3)CC2)N1Cc1ccccc1]

Compound B

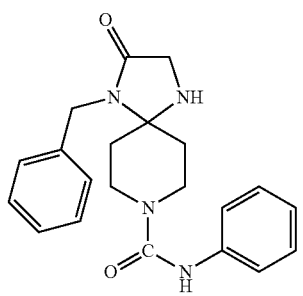 [SMILES: O=C(Nc1ccccc1)N1CCC2(CC1)NCC(=O)N2Cc1ccccc1]

Compound C

Preparation of Compounds A, B and C

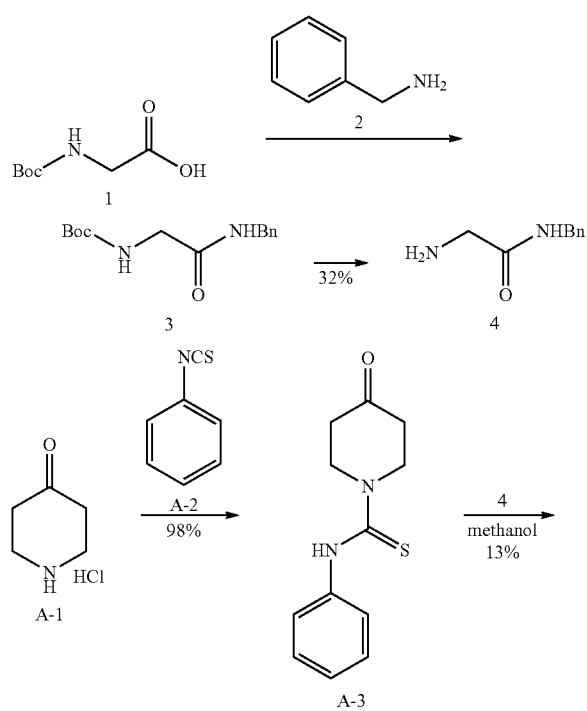

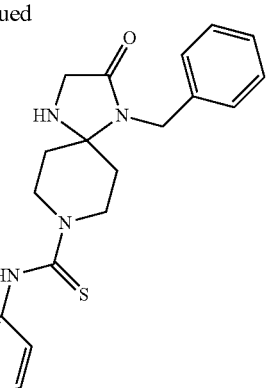

Compound A

Compound 4

To a solution of Compound 1 (10 g, 57 mmol) in THF (100 mL) was added 1,1'-carbonyldiimidazole (CDI) (11.1 g, 68.5 mmol) at room temperature, and the mixture was stirred for 30 minutes. Compound 2 (7.34 g, 68.5 mmol) was then added and stirred overnight (about 18 hours). The solvent was evaporated and the residue was dissolved in ethyl acetate (EA; 400 mL) to which was added 4M HCl/MeOH (50 mL), and the resulting admixture was stirred overnight (about 18 hours). The resulting white solid was filtered and suspended in EA, washed with aq.NaHCO$_3$ and concentrated to afford product as white solid (3.2 g, 34% yield, as confirmed by NMR).

1H-NMR (400 MHz, CDCl$_3$): 3.41 (s, 3H); 4.48 (d, J=6.0 Hz, 2H); 7.26~7.36 (m, 5H); 7.57 (br, s, 1H).

Compound A-3

A mixture of Compound A-1 (3.75 g, 24 mmol), A-2 (1.5 g, 11 mmol) and triethylamine (TEA) (4.5 g, 44.38 mmol) in dichloromethane (DCM) (50 mL) was stirred at room temperature overnight (about 18 hours). The reaction mixture was washed with water, dried over Na$_2$SO$_4$ and concentrated to afford product as white solid (2.55 g, 98% yield, confirmed by NMR).

1H-NMR (400 MHz, CDCl$_3$): 2.53 (t, J=6.4 Hz, 4H); 4.01 (t, J=6.4 Hz, 4H); 7.10~7.30 (m, 5H).

Compound A

A mixture of Compound A-3 (400 mg, 1.7 mmol) and Compound 4 (280 mg, 1.7 mmol) in methanol (60 mL) was heated to reflux overnight (about 18 hours) under argon. The mixture was concentrated and purified by pre-TLC to get product as pale white solid (84 mg, 13% yield, NMR and MS confirmed, 98% by HPLC).

1H-NMR (400 MHz, CDCl$_2$): 1.42 (d, J=12.4 Hz, 2H); 1.92 (dt, J=4.4, 13.2 Hz, 2H); 3.32 (dt, J=2.0, 12.8 Hz, 2H); 3.52 (s, 2H); 4.42 (s, 2H); 4.47 (s, 2H); 7.06 (t, J=7.6 Hz, 2H); 7.14 (t, J=7.6 Hz, 1H); 7.24~7.33 (m, 9H). MS (ESI) calcd for C$_{21}$H$_{24}$N$_4$OS (m/z): 380.17. found: 381.2 [M+1]$^+$.

Compound B

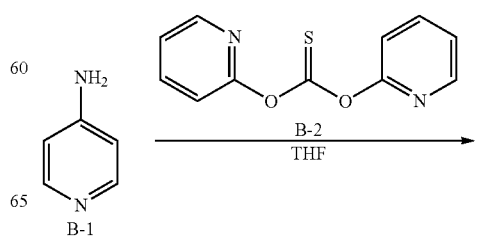

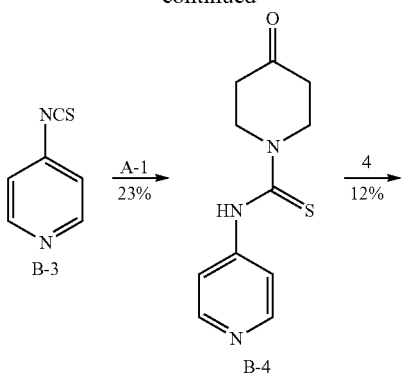

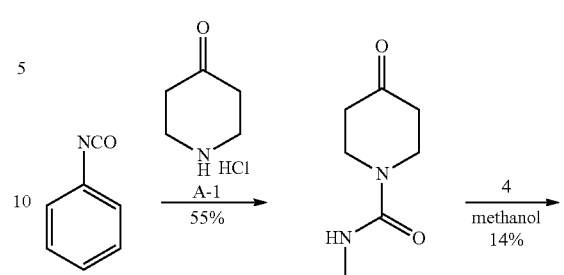

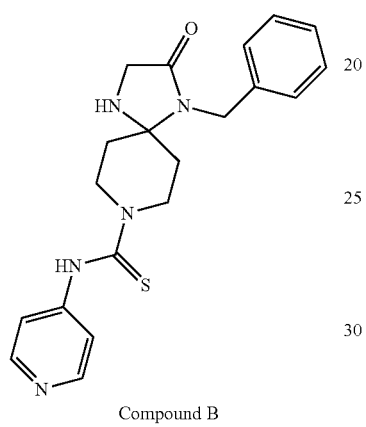

Compound B

Compound C

Compound B-4

To a solution of pyridin-4-amine (400 mg, 4.25 mmol) in THF (35 mL) was added 60% NaH (340 mg, 8.5 mmol) in an ice bath, and the mixture was stirred for 1 hour. Compound B-2 (0.99 g, 4.25 mmol) was added and the mixture was permitted to gradually to reach room temperature and stirred for 3 hours. Compound A-1 (0.78 g, 5.1 mmol) and N,N-diisopropyl-ethylamine (DIEA; 1 mL) was added and the mixture was stirred at room temperature overnight (about 18 hours). Water was added and the resulting composition was extracted with EA, washed with brine, dried over $Na_2SO_4$, concentrated and purified by column chromatography to afford oil (0.23 g, 23% yield, NMR was not pure but the major component was title compound).

1H-NMR (400 MHz, $CDCl_3$): 2.66 (t, J=6.4 Hz, 4H); 4.12 (t, J=6.4 Hz, 4H); 7.11~7.12 (d, J=4.8 Hz, 2H); 8.50~8.52 (d, J=5.6 Hz, 2H).

Compound B

A solution of Compound B-4 (230 mg, 1.7 mmol) and Compound 4 (225 mg, 1.37 mmol) in methanol (25 mL) was heated to reflux overnight (about 18 hours) under argon. The mixture was concentrated and purified by pre-TLC to get product as yellow solid (45 mg, 12% yield, NMR and MS confirmed, 96% by HPLC).

1H-NMR (400 MHz, $CDCl_3$): 1.47 (d, J=13.2 Hz, 2H); 1.92~1.98 (m, 2H); 3.41 (t, J=13.2 Hz, 2H); 3.54 (s, 2H); 4.44 (s, 4H); 6.95 (d, J=4.4 Hz, 2H); 7.26~7.31 (m, 5H); 8.45 (d, J=4.0 Hz, 2H). MS (ESI) calcd for $C_{20}H_{23}N_5OS$ (m/z): 381.16. found: 382.4 $[M+1]^+$.

Compound C-2

A mixture of Compound C-1 (1.0 g, 8.39 mmol), Compound A-1 (2.83 g, 18.45 mmol) and potassium carbonate (4.64 g, 33.6 mmol) in DCM (50 mL) was stirred at ambient temperature for 18 hours. The mixture was washed with water, 1N HCl (aqueous), dried over $Na_2SO_4$ and concentrated. The residue was purified by column chromatography (PE/EA=3:1) to afford product as white solid (1.0 g, 55% yield, NMR confirmed the title compound).

1H-NMR (400 MHz, $CDCl_3$): 2.56 (t, J=6.4 Hz, 4H); 3.81 (t, J=6.4 Hz, 4H); 6.50 (brs, 1H); 7.07 (t, J=7.2 Hz, 4H); 7.28~7.37 (m, 4H).

Compound C

A mixture of Compound C-2 (400 mg, 1.84 mmol) and Compound 4 (400 mg, 2.44 mmol) in methanol (40 mL) was heated to reflux overnight (about 18 hours) under argon. The mixture was concentrated and purified by pre-TLC to provide the product as white solid (96 mg, 14% yield, NMR and MS confirmed, 98% by HPLC).

1H-NMR (400 MHz, $CDCl_3$): 1.45 (d, J=12.0 Hz, 2H); 1.85 (dt, J=4.4, 13.2 Hz, 2H); 3.19 (dt, J=2.0, 13.2 Hz, 2H); 3.55 (s, 2H); 3.96 (dt, J=13.6, 2.0 Hz, 2H); 4.44 (s, 2H); 6.29 (s, 1H); 7.02~7.06 (m, 1H); 7.22~7.33 (m, 10H). MS (ESI) calcd for $C_{21}H_{24}N_4O_2$ (m/z): 364.19. found: 365.2 $[M+1]^+$.

Table of Series C-2 Compounds
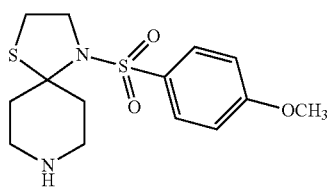 [SMILES: COc1ccc(S(=O)(=O)N2CCSC23CCNCC3)cc1] S-C0027
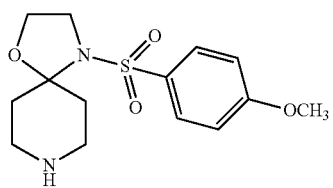 [SMILES: COc1ccc(S(=O)(=O)N2CCOC23CCNCC3)cc1] C0027
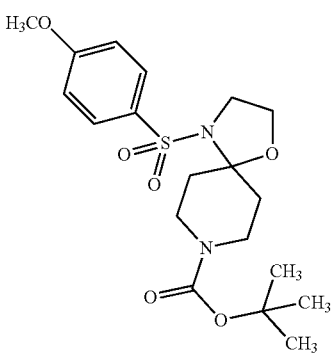 [SMILES: COc1ccc(S(=O)(=O)N2CCOC23CCN(C(=O)OC(C)(C)C)CC3)cc1] C0043
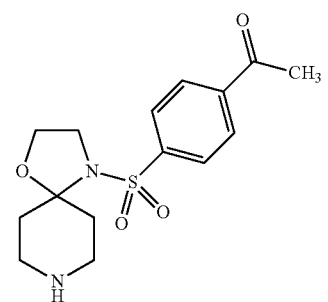 [SMILES: CC(=O)c1ccc(S(=O)(=O)N2CCOC23CCNCC3)cc1] C0046
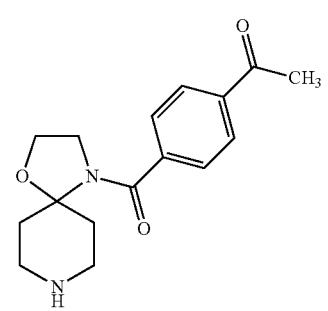 [SMILES: CC(=O)c1ccc(C(=O)N2CCOC23CCNCC3)cc1] C0053-3
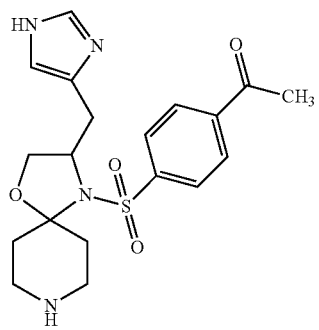 [SMILES: CC(=O)c1ccc(S(=O)(=O)N2C(Cc3c[nH]cn3)COC23CCNCC3)cc1] C0079M-7
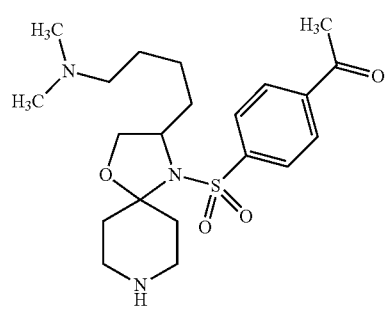 [SMILES: CC(=O)c1ccc(S(=O)(=O)N2C(CCCCN(C)C)COC23CCNCC3)cc1] C0080M-6
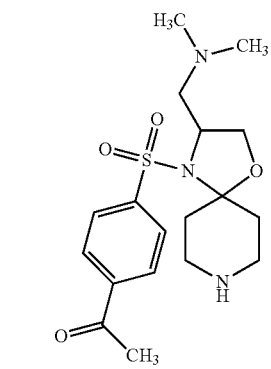 [SMILES: CC(=O)c1ccc(S(=O)(=O)N2C(CN(C)C)COC23CCNCC3)cc1] C0081M-7
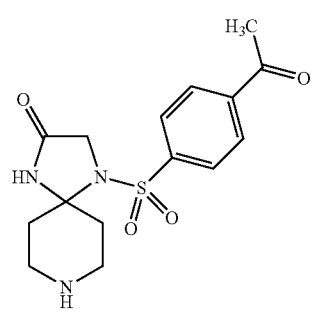 [SMILES: CC(=O)c1ccc(S(=O)(=O)N2CC(=O)NC23CCNCC3)cc1] C0086M
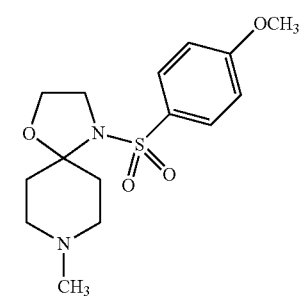 [SMILES: COc1ccc(S(=O)(=O)N2CCOC23CCN(C)CC3)cc1] C0088M -continued
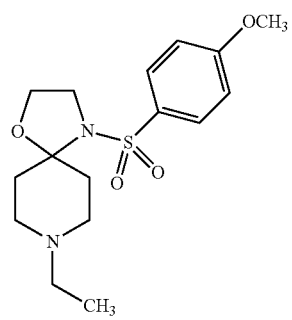 [SMILES: CCN1CCC2(CC1)OCCN2S(=O)(=O)c1ccc(OC)cc1] C0089M
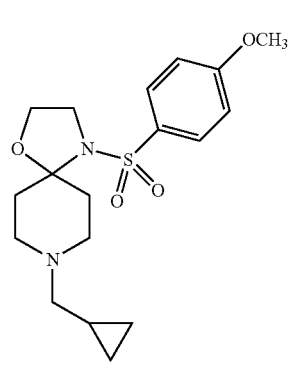 [SMILES: COc1ccc(S(=O)(=O)N2CCOC23CCN(CC2CC2)CC3)cc1] C0090M
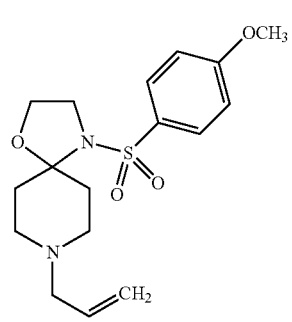 [SMILES: C=CCN1CCC2(CC1)OCCN2S(=O)(=O)c1ccc(OC)cc1] C0091M
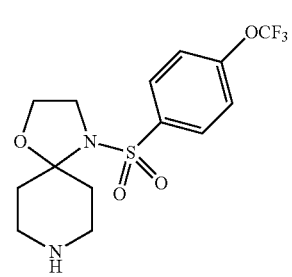 [SMILES: O=S(=O)(c1ccc(OC(F)(F)F)cc1)N1CCOC12CCNCC2] C0092M
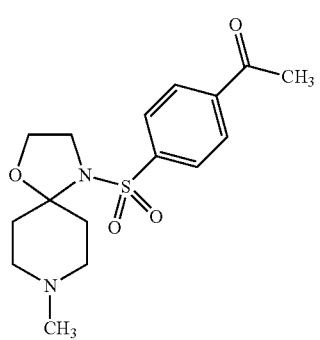 [SMILES: CC(=O)c1ccc(S(=O)(=O)N2CCOC23CCN(C)CC3)cc1] C0093M
-continued
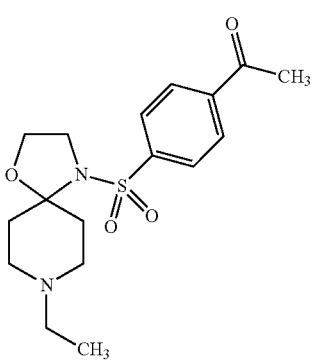 [SMILES: CCN1CCC2(CC1)OCCN2S(=O)(=O)c1ccc(C(C)=O)cc1] C0094M
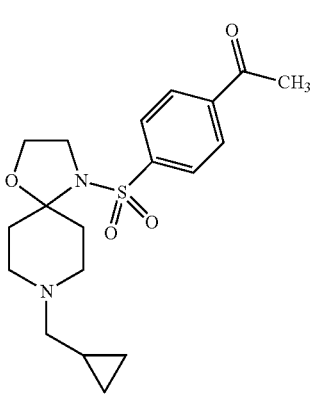 [SMILES: CC(=O)c1ccc(S(=O)(=O)N2CCOC23CCN(CC2CC2)CC3)cc1] C0095M
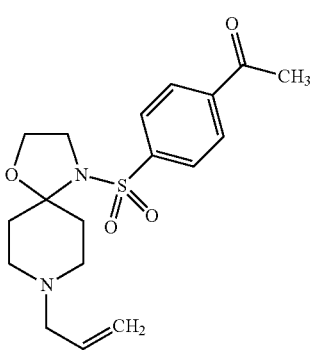 [SMILES: C=CCN1CCC2(CC1)OCCN2S(=O)(=O)c1ccc(C(C)=O)cc1] C0096M
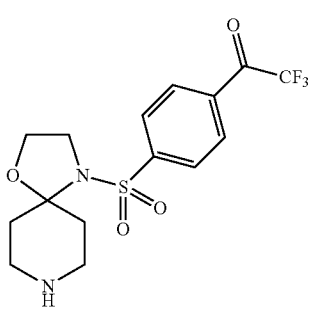 [SMILES: O=C(c1ccc(S(=O)(=O)N2CCOC23CCNCC3)cc1)C(F)(F)F] C0097M

| | |
|---|---|
| 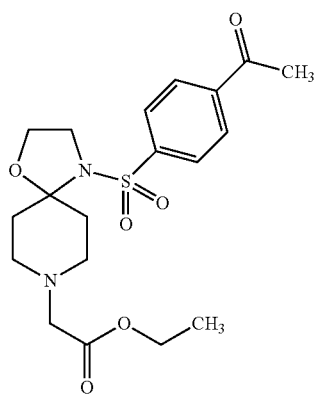 C0099M | 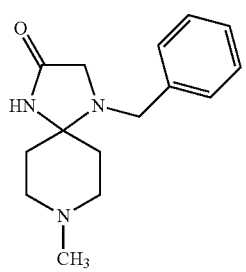 C0104M |
| 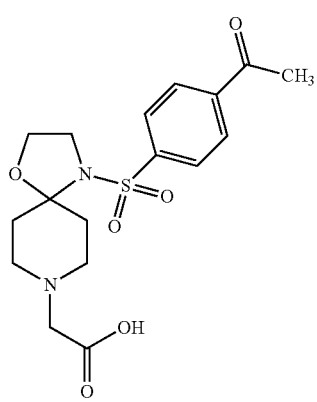 C0100M | 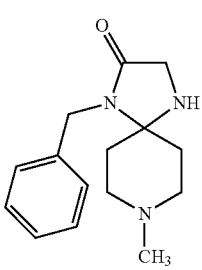 C0105M |
| | 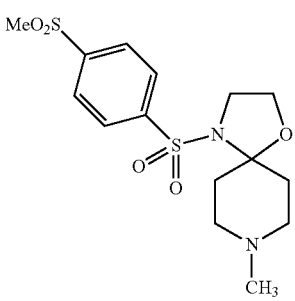 C0106M |
| 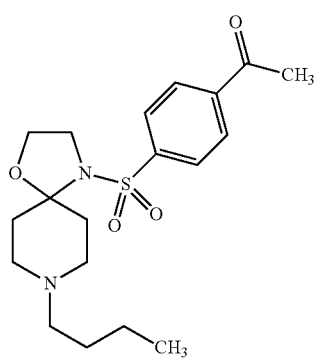 C0101M | 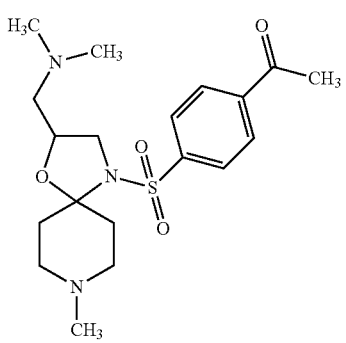 C0108M |
| 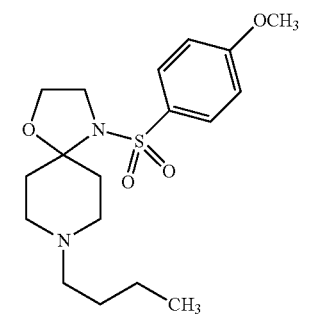 C0102M | 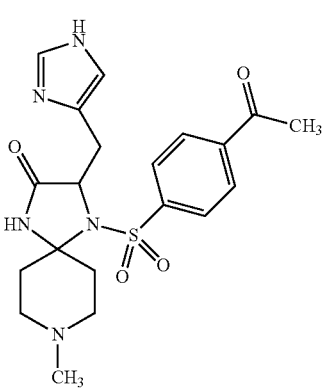 C0109M |

| | |
|---|---|
| 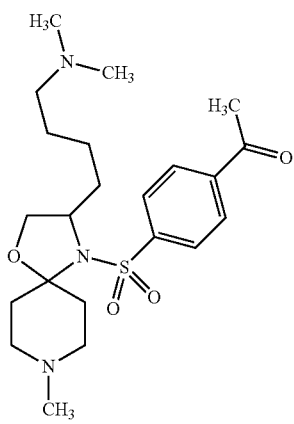 C0111M | 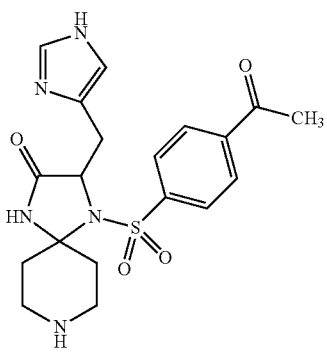 C0119M |
| 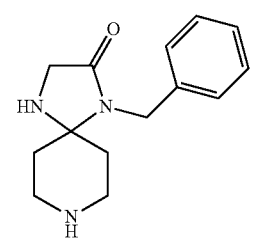 C0114M | 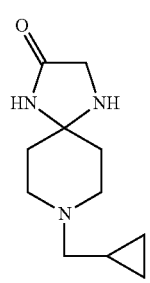 C0123M |
| 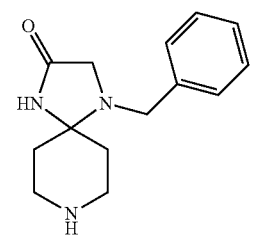 C0115M | 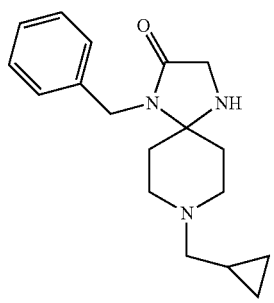 C0124M |
| 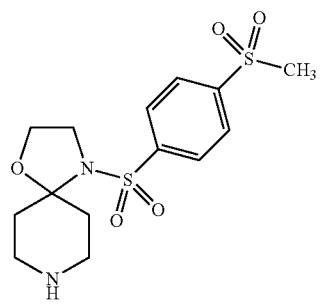 C0116M | 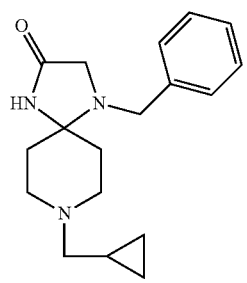 C0125M |
| 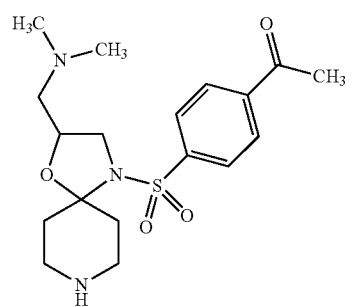 C0118M | 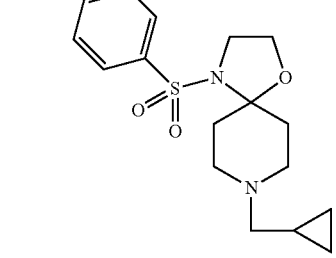 C0126M |

-continued
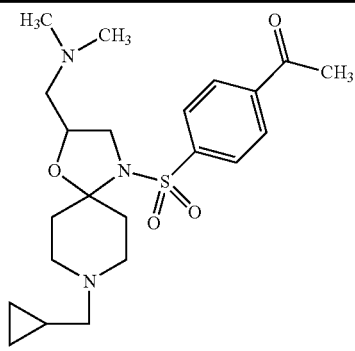 C0128M
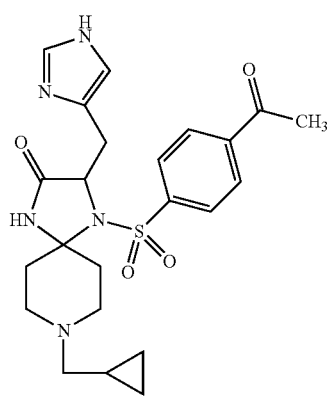 [SMILES: CC(=O)c1ccc(S(=O)(=O)N2C(Cc3c[nH]cn3)C(=O)NC23CCN(CC2CC2)CC3)cc1] C0129M
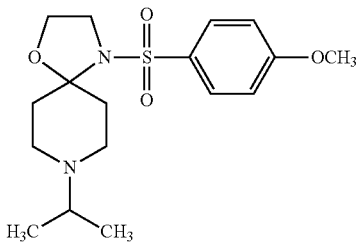 [SMILES: COc1ccc(S(=O)(=O)N2CCOC23CCN(C(C)C)CC3)cc1] C0133M
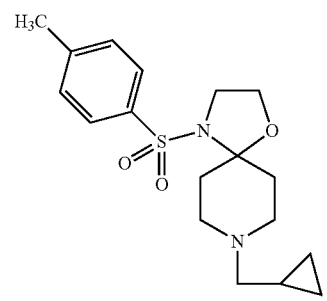 [SMILES: Cc1ccc(S(=O)(=O)N2CCOC23CCN(CC2CC2)CC3)cc1] C0134M
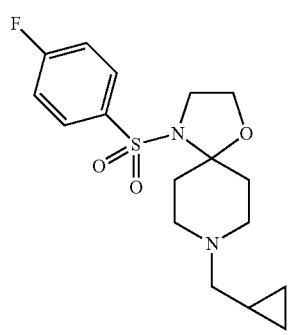 [SMILES: O=S(=O)(c1ccc(F)cc1)N1CCOC12CCN(CC1CC1)CC2] F-C0134
-continued
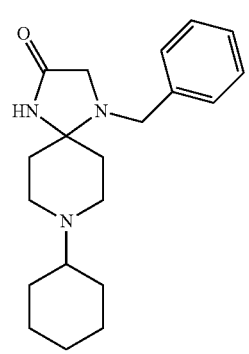 C0135M
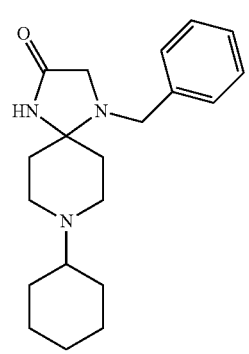 C0137M
P7
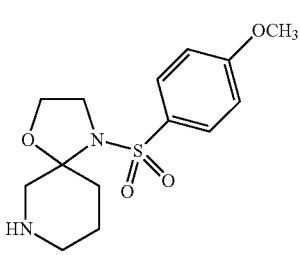 [SMILES: COc1ccc(S(=O)(=O)N2CCOC23CCCNC3)cc1] C0145M-3
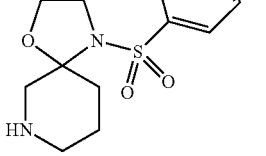 C0153M-3
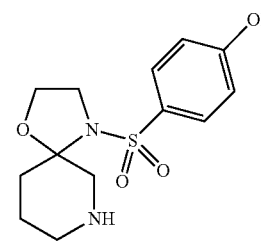 Compound 4

-continued

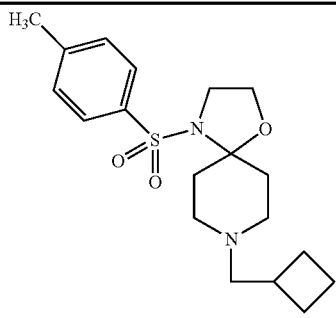
Compound 9

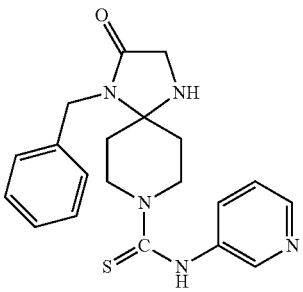
Compound B

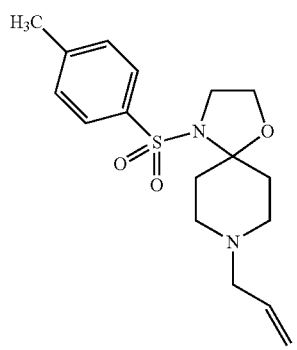 [SMILES: C=CCN1CCC2(CC1)OCCN2S(=O)(=O)c1ccc(C)cc1]
Compound 10

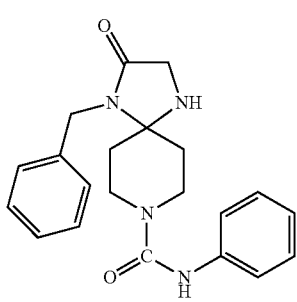 [SMILES: O=C1CNC2(CCN(C(=S)Nc3ccccc3)CC2)N1Cc1ccccc1]
Compound C

Table of Series D Compounds

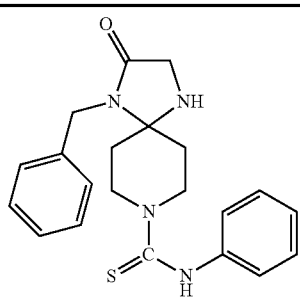
Compound A

Preparation of Series C-2 Compounds 4, 9 and 10

These compounds were prepared via a common intermediate designated 9-2 herein that was prepared during the synthesis of Compound C0116M in application Ser. No. 12/561,0091 (US Publication No. 20110105487 A1 dated May 5, 2011; WO 2010/051497), and referred to therein as Compound C0116M-1.

After preparation of Compound 9-2, the syntheses of Compounds 9 and 10 proceeded routinely by first adding the tosyl group in pyridine to the nitrogen of the five-membered ring, followed by removal of the t-BOC group with trifluoroacetic acid (TFA) in dichloromethane to form Compound 9-4 as shown below. Specifics of the syntheses are provided hereinafter.

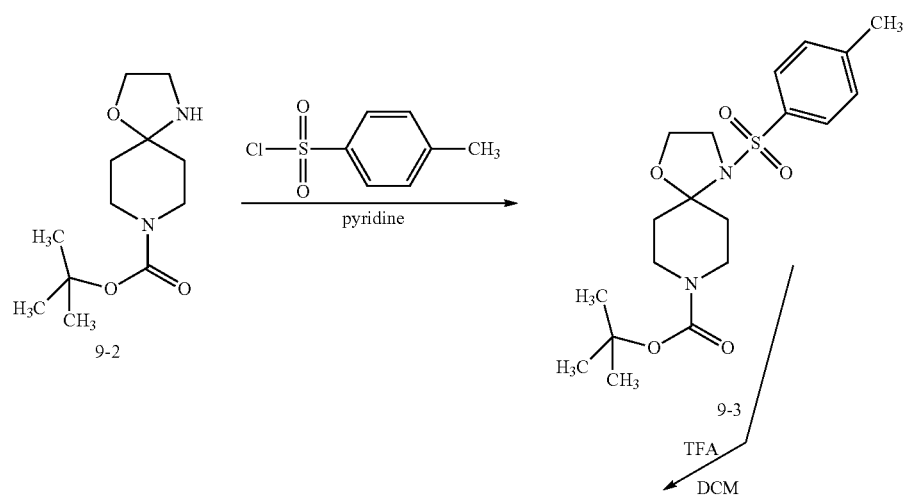

-continued

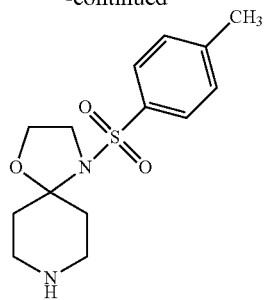

9-4

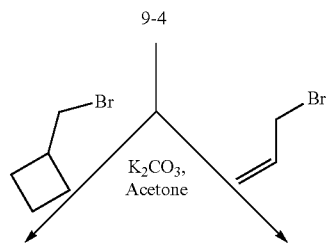

K₂CO₃,
Acetone

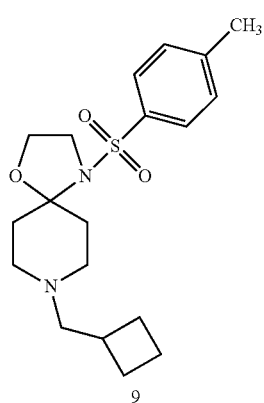

9

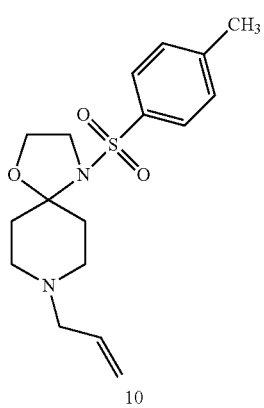

10

Compound 9-2 also served as the basis for preparation of Compound 4. Here, as shown below, 4-trifluoromethoxyphenyl sulfonylchloride was reacted in pyridine with the amine of the five-membered ring, and the t-BOC group removed in TFA/DCM as above to form Compound 4-1. The amine nitrogen of the six-membered ring of Compound 4-1 was then reacted with (bromomethyl)cyclopropane to form the N-alkylated product that is Compound 4.

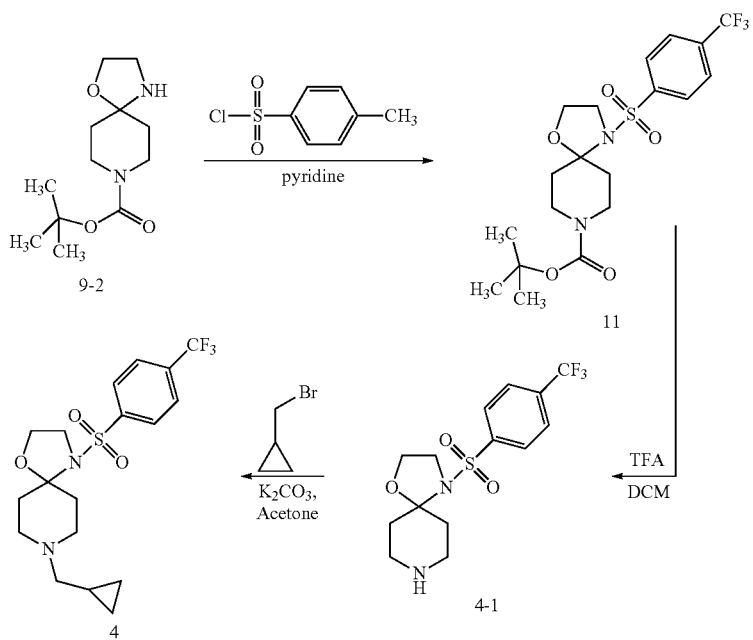 [SMILES: CC(C)(C)OC(=O)N1CCC2(CC1)NCCO2 ; Cc1ccc(S(=O)(=O)Cl)cc1 ; CC(C)(C)OC(=O)N1CCC2(CC1)OCCN2S(=O)(=O)c1ccc(C(F)(F)F)cc1 ; O=S(=O)(c1ccc(C(F)(F)F)cc1)N1CCOC12CCN(CC1CC1)CC2 ; BrCC1CC1 ; O=S(=O)(c1ccc(C(F)(F)F)cc1)N1CCOC12CCNCC2]

Preparation of Compound 9-2

To a solution of N-Boc-piperidin-4-one (50 g, 251 mmol) in ethanol (500 mL) was added 2-aminoethanol (46 g). The mixture was stirred at room temperature overnight (about 18 hours). Then the solvent was removed under reduced pressure. The residue was diluted with $CH_2Cl_2$ (DCM) and washed with saturated aqueous $Na_2CO_3$ (100 mL×6). The organic phase was dried over anhydrous $Na_2SO_4$, and concentrated to provide the product as a yellow oil (61 g, yield: 100%, confirmed by TLC).

Preparation of Compound 9-3

Toluenesulfonyl chloride (TsCl; 24.7 g, 130 mmol) was added to a solution of Compound 9-2 (31.2 g, 130 mmol) in pyridine (320 mL). The mixture was stirred overnight (about 18 hours) at room temperature. The reaction mixture was concentrated in vacuo to remove the pyridine and the residue was dissolved with DCM and washed with saturated $NaHCO_3$. The organic layer was dried over $Na_2SO_4$, concentrated and purified by column chromatography to provide the product as white solid (40 g, yield: 78%, confirmed by 1H NMR).

$^1$H NMR (400 MHz, $CDCl_3$): 7.74 (d, J=8.4 Hz, 2H); 7.31 (d, J=8.0 Hz, 2H); 4.13~4.03 (m, 4H); 3.56~3.50 (m, 2H); 2.89 (brs, 2H); 2.46 (s, 3H); 2.43~2.36 (m, 2H); 1.63 (brs, 2H); 1.47 (s, 9H).

Preparation of Compound 9-4

Trifluoroacetic acid ($CF_3COOH$; 60 mL) was added to a solution of Compound 9-3 (35.2 g, 88.7 mmol) in DCM (350 mL). The mixture was stirred at ice/water for 50 minutes. To the reaction mixture was added 200 mL of DCM, and the resulting composition washed with saturated $Na_2CO_3$. The organic layer was dried over $Na_2SO_4$, concentrated in vacuo to provide the crude product. The crude product was purified by column chromatography to provide the desired product as pale yellow oil (11.2 g, yield: 42%, confirmed by $^1$H NMR).

$^1$H NMR (400 MHz, $CDCl_3$): 7.75 (d, J=8.4 Hz, 2H); 7.29 (d, J=8.0 Hz, 2H); 3.95 (t, J=6.4 Hz, 2H); 3.75 (brs, 1H); 3.51~3.48 (t, J=5.6 Hz, 2H); 3.16~3.12 (dd, J=12.4, 4.0 Hz, 2H); 2.92~2.86 (td, J=12.8, 2.0 Hz, 2H); 2.48~2.44 (m, 2H); 2.41 (s, 3H); 1.65 (d, J=12.8 Hz, 2H).

Preparation of Compound 9

(Bromomethyl)cyclobutane (1.86 g, 12.5 mmol) was added to a mixture of Compound 9-4 (1.85 g, 6.25 mmol) and $K_2CO_3$ (3.39 g, 12.5 mmol) in acetone (40 mL), and the reaction mixture was stirred at reflux overnight (about 18 hours). After cooling, the mixture was filtered and concentrated, purified by chromatography with ethyl acetate (EA) to obtain crude product as pale yellow solid (1.6 g, yield: 70%, confirmed by LCMS, $^1$H NMR showed it was impure). The crude product was purified by further chromatography with EA to provide the desired product as white solid (1.15 g, yield: 50%, confirmed by LCMS and $^1$H NMR, HPLC: 99.3% @ 254 nm, 99.5 @ 214 nm).

$^1$H NMR (400 MHz, $CDCl_3$): 7.77 (d, J=8.0 Hz, 2H); 7.31 (d, J=8.0 Hz, 2H); 3.95 (t, J=6.0 Hz, 2H); 3.52 (t, J=6.4 Hz, 2H); 2.76~2.73 (d, J=10.0 Hz, 2H); 2.54~2.39 (m, 8H); 2.21~2.15 (t, J=11.6 Hz, 2H); 2.07~2.05 (m, 2H); 1.93~1.88 (m, 2H); 1.70~1.65 (m, 2H); 1.56~1.53 (d, J=12.4 Hz, 2H). MS (ESI) calcd for $C_{19}H_{28}N_2O_3S$ (m/z): 364.18. found: 365.1 [M+1]$^+$.

Preparation of Compound 10

To a mixture of Compound 9-4 (1.72 g, 5.8 mmol) and $K_2CO_3$ (1.6 g, 11.6 mmol) in acetone (30 mL) was added 3-bromoprop-1-ene (0.7 g, 5.8 mmol), and the reaction mixture was stirred at 40° C. for 2 hours. After cooling, the mixture was filtered and concentrated, purified by chromatography with EA to obtains the desired product as white solid (1.1 g, 56% yield, confirmed by LCMS and $^1$H NMR, HPLC: 98.8% @ 254 nm, 98.9 @ 214 nm).

$^1$H NMR (400 MHz, $CDCl_3$): 7.76~7.74 (d, J=8.0 Hz, 2H); 7.29~7.27 (d, J=8.0 Hz, 2H); 5.90~5.82 (m, 1H); 5.18~5.11 (m, 2H); 3.95~3.91 (t, J=6.0 Hz, 2H); 3.52~3.49 (t, J=6.0 Hz, 2H); 3.0~2.98 (d, J=6.4 Hz, 2H); 2.83~2.80 (dd, J=8.8, 2.4 Hz, 2H); 2.55~2.48 (td, J=13.2, 4.4 Hz, 2H); 2.41 (s, 3H); 2.19~2.14 (t, J=11.2 Hz, 2H); 1.58~1.55 (d, J=12.0 Hz, 2H). MS (ESI) calcd for $C_{17}H_{24}N_2O_3S$ (m/z): 336.45. found: 337.1 [M+1]$^+$.

Preparation of Compound 11

To a solution of Compound 9-2 (14.6 g, 60 mmol) in pyridine (150 mL) was added 4-(trifluoromethoxy)benzene-1-sulfonyl chloride (15.7 g, 60 mmol). The mixture was stirred overnight (about 18 hours) at room temperature. The reaction mixture was concentrated in vacuo to remove the pyridine and the residue was dissolved with DCM, washed with saturated NaHCO$_3$. The organic layer was dried over Na$_2$SO$_4$, concentrated and purified by column chromatography to give product as white solid (20 g, yield: 71%, confirmed by 1H NMR and LCMS).

$^1$H NMR (400 MHz, CDCl$_3$): 7.92~7.90 (d, J=8.4 Hz, 2H); 7.35~7.32 (d, J=8.4 Hz, 2H); 4.13~3.97 (m, 4H); 3.51 (brs, 2H); 2.90 (brs, 2H); 2.45~2.35 (m, 2H); 1.58 (brs, 2H); 1.47 (s, 9H). MS (ESI) calcd for C$_{19}$H$_{25}$F$_3$N$_2$O$_6$S (m/z): 466.14. found: 367.0 [M+1]$^+$.

Preparation of Compound 4-1

Trifluoroacetic acid (CF$_3$COOH; 20 mL) was added to a solution of Compound 11 (15 g, 32 mmol) in DCM (150 mL). The mixture was stirred at ice/water for 50 minutes. The reaction mixture was added to 200 mL of DCM, washed with saturated Na$_2$CO$_3$. The organic layer was dried over Na$_2$SO$_4$, concentrated in vacuo to provide the crude product. The crude product was purified by column chromatography to provide the desired product as pale yellow solid (5.9 g, yield: 50%, confirmed by $^1$H NMR).

$^1$H NMR (400 MHz, CDCl$_3$): 7.93~7.91 (d, J=8.4 Hz, 2H); 7.34~7.32 (d, J=8.0 Hz, 2H); 4.0~3.97 (t, J 5.6 Hz, 2H); 3.51~3.48 (t, J=6.0 Hz, 2H); 3.06~3.02 (dd, J=12.4, 4.0 Hz, 2H); 2.86~2.80 (t, J=13.2 Hz, 2H); 2.39~2.31 (td, J=12.8, 4.8 Hz, 2H); 2.48~2.44 (m, 2H); 1.64~1.62 (d, J=12.8 Hz, 2H).

Preparation of Compound 4

(Bromomethyl)cyclobutane (1.5 g, 4.1 mmol) was added to a mixture of Compound 4-1 (1.5 g, 4.1 mmol) and K$_2$CO$_3$ (1.13 g, 8.2 mmol) in acetone (15 mL), and the reaction mixture was stirred at reflux for 4 hours. After cooling, the mixture was filtered and concentrated, purified by chromatography with EA to provide the desired product as an off-white solid (1.05 g, yield: 61%, confirmed by LCMS and $^1$H NMR, HPLC: 96.9% @ 254 nm, 98.4 @ 214 nm).

$^1$H NMR (400 MHz, CDCl$_3$): 7.91~7.94 (d, J=8.8 Hz, 2H); 7.34~7.32 (d, J=8.0 Hz, 2H); 3.98~3.95 (t, J=6.0 Hz, 2H); 3.54~3.51 (t, J=6.4 Hz, 2H); 2.99~2.96 (dd, J=8.8, 2.0 Hz, 2H); 2.56~2.49 (td, J=12.8, 4.4 Hz, 2H); 2.26~2.17 (m, 4H); 1.60~1.57 (d, J=12.4 Hz, 2H); 0.87~0.84 (m, 1H); 0.52~0.48 (m, 2H); 0.10~0.07 (m, 2H). MS (ESI) calcd for C$_{18}$H$_{23}$F$_3$N$_2$O$_4$S (m/z): 420.13. found: 421.1 [M+1]$^+$.

Preparation of Series D Compounds A, B and C

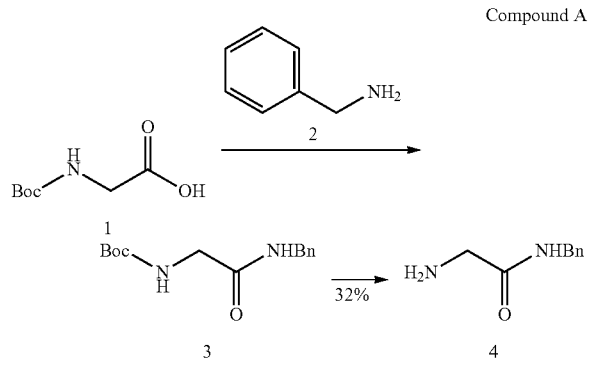

Compound A

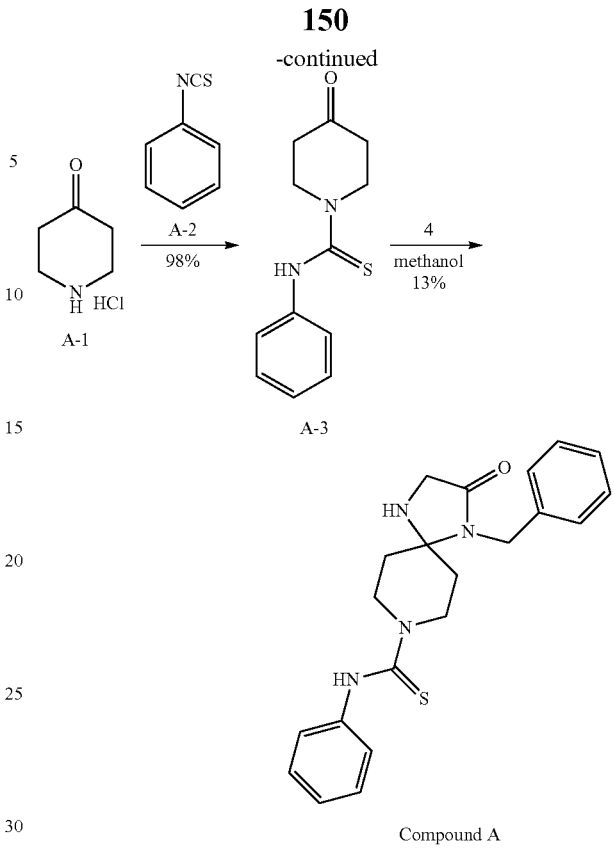

Compound A

Compound 4

To a solution of Compound 1 (10 g, 57 mmol) in THF (100 mL) was added 1,1'-carbonyldiimidazole (CDI) (11.1 g, 68.5 mmol) at room temperature, and the mixture was stirred for 30 minutes. Compound 2 (7.34 g, 68.5 mmol) was then added and stirred overnight (about 18 hours). The solvent was evaporated and the residue was dissolved in ethyl acetate (EA; 400 mL) to which was added 4M HCl/MeOH (50 mL), and the resulting admixture was stirred overnight (about 18 hours). The resulting white solid was filtered and suspended in EA, washed with aq.NaHCO$_3$ and concentrated to afford product as white solid (3.2 g, 34% yield, as confirmed by NMR).

1H-NMR (400 MHz, CDCl$_3$): 3.41 (s, 3H); 4.48 (d, J=6.0 Hz, 2H); 7.26~7.36 (m, 5H); 7.57 (br, s, 1H).

Compound A-3

A mixture of Compound A-1 (3.75 g, 24 mmol), A-2 (1.5 g, 11 mmol) and triethylamine (TEA) (4.5 g, 44.38 mmol) in dichloromethane (DCM) (50 mL) was stirred at room temperature overnight (about 18 hours). The reaction mixture was washed with water, dried over Na$_2$SO$_4$ and concentrated to afford product as white solid (2.55 g, 98% yield, confirmed by NMR).

1H-NMR (400 MHz, CDCl$_3$): 2.53 (t, J=6.4 Hz, 4H); 4.01 (t, J=6.4 Hz, 4H); 7.10~7.30 (m, 5H).

Compound A

A mixture of Compound A-3 (400 mg, 1.7 mmol) and Compound 4 (280 mg, 1.7 mmol) in methanol (60 mL) was heated to reflux overnight (about 18 hours) under argon. The mixture was concentrated and purified by pre-TLC to get product as pale white solid (84 mg, 13% yield, NMR and MS confirmed, 98% by HPLC).

1H-NMR (400 MHz, CDCl$_3$): 1.42 (d, J=12.4 Hz, 2H); 1.92 (dt, J=4.4, 13.2 Hz, 2H); 3.32 (dt, J=2.0, 12.8 Hz, 2H); 3.52 (s, 2H); 4.42 (s, 2H); 4.47 (s, 2H); 7.06 (t, J=7.6 Hz,

2H); 7.14 (t, J=7.6 Hz, 1H); 7.24~7.33 (m, 9H). MS (ESI) calcd for $C_{21}H_{24}N_4OS$ (m/z): 380.17. found: 381.2 $[M+1]^+$.

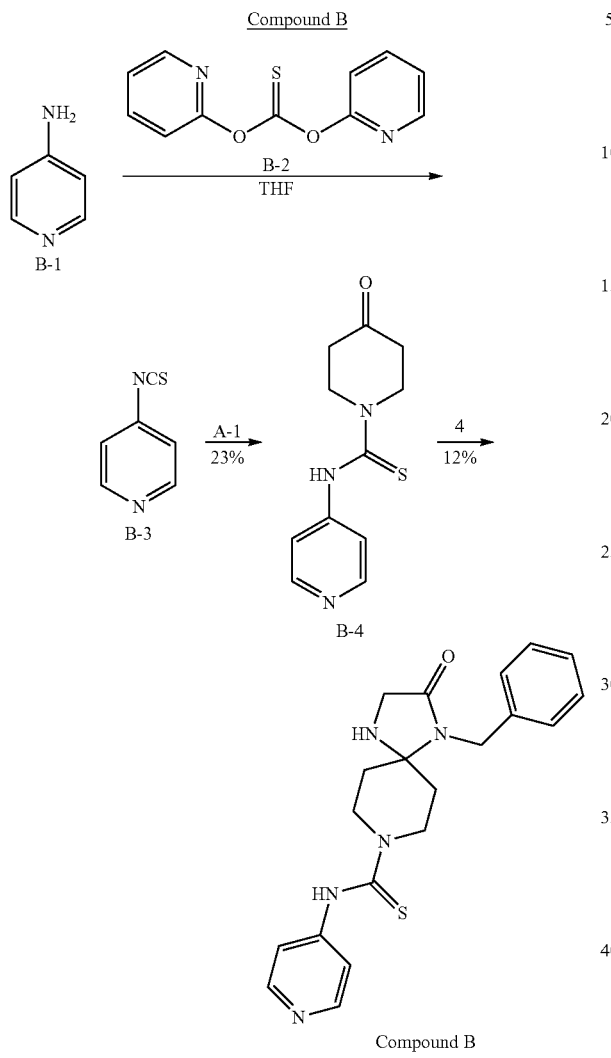

Compound B

Compound B-4

To a solution of pyridin-4-amine (400 mg, 4.25 mmol) in THF (35 mL) was added 60% NaH (340 mg, 8.5 mmol) in an ice bath, and the mixture was stirred for 1 hour. Compound B-2 (0.99 g, 4.25 mmol) was added and the mixture was permitted to gradually to reach room temperature and stirred for 3 hours. Compound A-1 (0.78 g, 5.1 mmol) and N,N-diisopropyl-ethylamine (DIEA; 1 mL) was added and the mixture was stirred at room temperature overnight (about 18 hours). Water was added and the resulting composition was extracted with EA, washed with brine, dried over $Na_2SO_4$, concentrated and purified by column chromatography to afford oil (0.23 g, 23% yield, NMR was not pure but the major component was title compound).

1H-NMR (400 MHz, $CDCl_3$): 2.66 (t, J=6.4 Hz, 4H); 4.12 (t, J=6.4 Hz, 4H); 7.11~7.12 (d, J=4.8 Hz, 2H); 8.50~8.52 (d, J=5.6 Hz, 2H).

Compound B

A solution of Compound B-4 (230 mg, 1.7 mmol) and Compound 4 (225 mg, 1.37 mmol) in methanol (25 mL) was heated to reflux overnight (about 18 hours) under argon. The mixture was concentrated and purified by pre-TLC to get product as yellow solid (45 mg, 12% yield, NMR and MS confirmed, 96% by HPLC).

1H-NMR (400 MHz, $CDCl_3$): 1.47 (d, J=13.2 Hz, 2H); 1.92~1.98 (m, 2H); 3.41 (t, J=13.2 Hz, 2H); 3.54 (s, 2H); 4.44 (s, 4H); 6.95 (d, J=4.4 Hz, 2H); 7.26~7.31 (m, 5H); 8.45 (d, J=4.0 Hz, 2H). MS (ESI) calcd for $C_{20}H_{23}N_5OS$ (m/z): 381.16. found: 382.4 $[M+1]^+$.

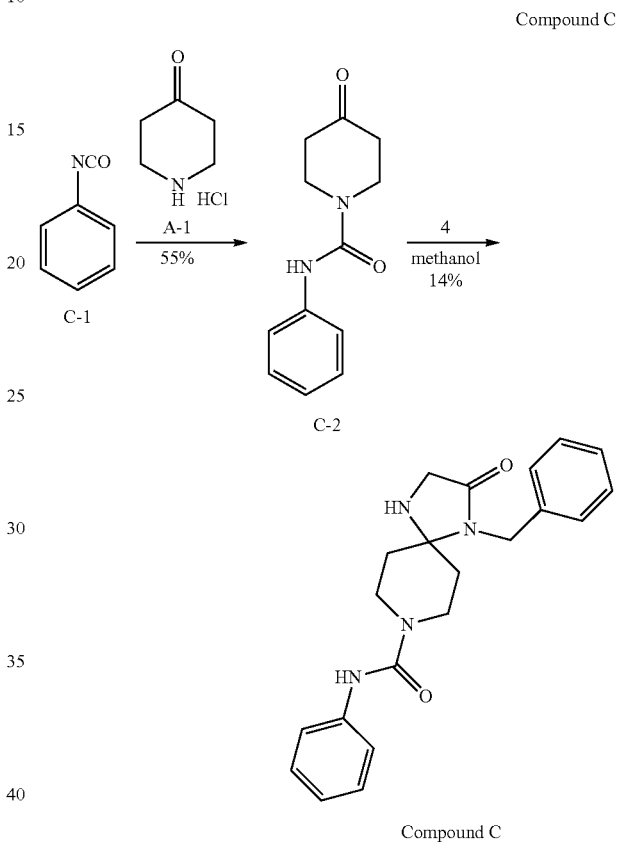

Compound C

Compound C-2

A mixture of Compound C-1 (1.0 g, 8.39 mmol), Compound A-1 (2.83 g, 18.45 mmol) and potassium carbonate (4.64 g, 33.6 mmol) in DCM (50 mL) was stirred at ambient temperature for 18 hours. The mixture was washed with water, 1N HCl (aqueous), dried over $Na_2SO_4$ and concentrated. The residue was purified by column chromatography (PE/EA=3:1) to afford product as white solid (1.0 g, 55% yield, NMR confirmed the title compound).

1H-NMR (400 MHz, $CDCl_3$): 2.56 (t, J=6.4 Hz, 4H); 3.81 (t, J=6.4 Hz, 4H); 6.50 (brs, 1H); 7.07 (t, J=7.2 Hz, 4H); 7.28~7.37 (m, 4H).

Compound C

A mixture of Compound C-2 (400 mg, 1.84 mmol) and Compound 4 (400 mg, 2.44 mmol) in methanol (40 mL) was heated to reflux overnight (about 18 hours) under argon. The mixture was concentrated and purified by pre-TLC to provide the product as white solid (96 mg, 14% yield, NMR and MS confirmed, 98% by HPLC).

1H-NMR (400 MHz, $CDCl_3$): 1.45 (d, J=12.0 Hz, 2H); 1.85 (dt, J=4.4, 13.2 Hz, 2H); 3.19 (dt, J=2.0, 13.2 Hz, 2H); 3.55 (s, 2H); 3.96 (dt, J=13.6, 2.0 Hz, 2H); 4.44 (s, 2H); 6.29 (s, 1H); 7.02~7.06 (m, 1H); 7.22~7.33 (m, 10H). MS (ESI) calcd for $C_{21}H_{24}N_4O_2$ (m/z): 364.19. found: 365.2 $[M+1]^+$.

EXAMPLE 1

FITC-NLX-based FLNA Screening Assay

A. Streptavidin-coated 96-well plates

Streptavidin-coated 96-well plates (Reacti-Bind™ NeutrAvidin™ High binding capacity coated 96-well plate, Pierce-ENDOGEN) are washed three times with 200 μl of 50 mM Tris HCl, pH 7.4 according to the manufacturer's recommendation.

B. N-biotinylated VAKGL Pentapeptide (Bn-VAKGL) (SEQ ID NO: 1)

Bn-VAKGL peptide (0.5 mg/plate) is dissolved in 50 μl DMSO and then added to 4450 μl of 50 mM Tris HCl, pH 7.4, containing 100 mM NaCl and protease inhibitors (binding medium) as well as 500 μl superblock in PBS (Pierce-ENDOGEN) [final concentration for DMSO: 1%].

C. Coupling of Bn-VAKGL Peptides to Streptavidin-Coated Plate

The washed streptavidin-coated plates are contacted with 5 μg/well of Bn-VAKGL (100 μl) for 1 hour (incubated) with constant shaking at 25° C. [50 μl of Bn-VAKGL peptide solution from B+50 μl binding medium, final concentration for DMSO: 0.5%]. At the end of the incubation, the plate is washed three times with 200 μl of ice-cold 50 mM Tris HCl, pH 7.4.

D. Binding of FITC-Tagged Naloxone [FITC-NLX] to VAKGL

Bn-VAKGL coated streptavidin plates are incubated with 10 nM fluorescein isothiocyanate-labeled naloxone (FITC-NLX; Invitrogen) in binding medium (50 mM Tris HCl, pH 7.4 containing 100 mM NaCl and protease inhibitors) for 30 minutes at 30° C. with constant shaking. The final assay volume is 100 μl. At the end of incubation, the plate is washed twice with 100 μl of ice-cold 50 mM Tris, pH 7.4. The signal, bound-FITC-NLX is detected using a DTX-880 multi-mode plate reader (Beckman).

E. Screening of Medicinal Chemistry Analogs

The compounds are first individually dissolved in 25% DMSO containing 50 mM Tris HCl, pH 7.4, to a final concentration of 1 mM (assisted by sonication when necessary) and then plated into 96-well compound plates. To screen the medicinal chemistry analogs (new compounds), each compound solution (1 μl) is added to the Bn-VAKGL coated streptavidin plate with 50 μl/well of binding medium followed immediately with addition of 50 μl of FITC-NLX (total assay volume/well is 100 μl). The final screening concentration for each compound is initially 10 μM.

Each screening plate includes vehicle control (total binding) as well as naloxone (NLX) and/or naltrexone (NTX) as positive controls. Compounds are tested in triplicate or quadruplicate. Percent inhibition of FITC-NLX binding for each compound is calculated [(Total FITC-NLX bound in vehicle−FITC-NLX bound in compound)/Total FITC-NLX bound in vehicle]×100%]. To assess the efficacies and potencies of the selected compounds, compounds that achieve approximately 60-70% inhibition at 10 μM are screened further at 1 and 0.1 μM concentrations.

The results of this screening assay are shown in the tables below.

FLNA Peptide Binding Assays

A-Series Compounds

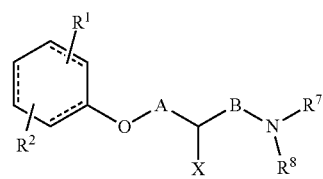

The $R^1$, $R^2$, $R^7$ and $R^8$, A, B and X groups are defined elsewhere herein.

| FLNA-binding Compound | Concentration of FLNA-binding Compound | | |
|---|---|---|---|
| | 0.01 μM | 0.1 μM | 1 μM |
| | Percent Binding Inhibition | | |
| Naloxone Control Average | 39.87% | 46.29% | 50.91% |
| 3333 | 40.4% | 48.5% | 54.2% |
| A0001 | 39.7% | 45.6% | 52.4% |
| A0002 | 38.7% | 43.7% | 49.9% |
| A0003 | 21.3% | 31.6% | 37.4% |
| A0004 | 40.0% | 43.7% | 47.6% |
| A0005 | 34.2% | 38.2% | 43.8% |
| A0006 | 37.9% | 43.5% | 47.5% |
| A0007 | 39.2% | 46.2% | 52.9% |
| A0008 | 34.5% | 33.5% | 39.8% |
| A0009 | 26.4% | 37.8% | 38.9% |
| A0010 | 36.0% | 36.5% | 39.0% |
| A0011 | 45.7% | 51.1% | 52.8% |
| A0012 | 39.7% | 49.6% | 54.4% |
| A0013 | 30.2% | 40.2% | 47.7% |
| A0014 | 33.8% | 39.7% | 44.7% |
| A0015 | 36.3% | 46.8% | 55.0% |
| A0017 | 29.8% | 38.6% | 44.0% |
| A0020 | 37.8% | 38.8% | 45.8% |
| A0021 | 36.8% | 43.4% | 49.5% |
| A0022 | 41.9% | 49.7% | 56.8% |
| A0025 | 39.0% | 49.8% | 53.2% |
| A0026 | 36.4% | 42.4% | 49.2% |
| A0028 | 39.5% | 43.8% | 50.5% |
| A0029 | 44.4% | 44.4% | 50.8% |
| A0030 | 35.6% | 44.4% | 48.9% |
| A0031 | 40.8% | 47.6% | 52.9% |
| A0032-1 | 35.6% | 43.9% | 50.0% |
| A0032 | 43.0% | 50.3% | 54.5% |
| A0033 | 46.4% | 51.8% | 56.5% |
| A0035 | 40.3% | 45.5% | 54.9% |
| A0036 | 45.6% | 50.1% | 54.4% |
| A0037 | 49.3% | 51.3% | 56.8% |
| A0038 | 46.4% | 52.3% | 56.6% |
| A0039 | 49.0% | 53.5% | 60.3% |
| A0040 | 45.0% | 50.4% | 56.3% |
| A0041 | 45.8% | 51.7% | 56.9% |
| A0042 | 47.2% | 48.3% | 55.8% |
| A0043 | 46.4% | 48.9% | 51.8% |
| A0044 | 32.4% | 36.9% | 39.6% |
| A0045 | 28.1% | 35.0% | 37.8% |
| A0046 | 34.3% | 38.4% | 40.9% |
| A0047 | 40.9% | 42.9% | 44.5% |
| A0048 | 38.5% | 44.0% | 46.9% |
| A0049 | 46.2% | 49.4% | 49.3% |
| A0050 | 42.9% | 49.8% | 52.1% |
| A0051 | 45.9% | 45.4% | 52.1% |
| A0053 | 34.8% | 40.0% | 46.9% |
| A0054 | 28.7% | 35.8% | 41.4% |
| A0055 | 28.1% | 32.4% | 41.8% |
| A0056 | 34.4% | 40.9% | 41.3% |

| FLNA-binding Compound | Concentration of FLNA-binding Compound | | |
|---|---|---|---|
| | 0.01 μM | 0.1 μM | 1 μM |
| | Percent Binding Inhibition | | |
| A0057 | 29.1% | 37.0% | 43.4% |
| A0058 | 28.9% | 36.6% | 42.1% |
| A0059 | 27.4% | 36.6% | 38.7% |
| A0060 | 32.4% | 39.0% | 42.0% |
| A0061 | 27.5% | 38.9% | 42.8% |
| A0062 | — | — | — |
| A0063 | 21.2% | 31.0% | 38.8% |
| A0064 | 41.8% | 46.2% | 53.6% |
| A0065 | 38.7% | 50.0% | 50.8% |
| A0066 | 36.7% | 45.4% | 53.7% |
| A0067 | 32.7% | 39.1% | 44.3% |
| A0068 | 51.9% | 54.2% | 58.3% |
| A0069 | 32.0% | 40.4% | 46.1% |
| A0070 | 32.9% | 39.1% | 41.7% |
| A0071 | 44.7% | 46.8% | 53.9% |
| A0072 | 45.5% | 52.2% | 59.4% |
| A0073 | 47.3% | 54.8% | 59.7% |
| A0074 | — | — | — |
| A0075 | — | — | — |
| A0076 | 36.1% | 40.0% | 44.9% |
| A0077 | 41.1% | 48.7% | 49.4% |
| A0078 | 50.1% | 55.8% | 57.6% |
| Naloxone Control Average | 39.87% | 46.29% | 50.91% |

B-Series Compounds

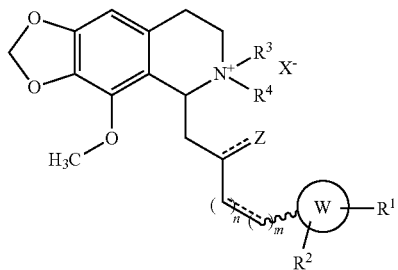

The $R^1$, $R^2$, $R^3$ and $R^4$, W, $X^-$ and Z groups, the dashed line, n and m are defined elsewhere herein.

| FLNA-binding Compound | Concentration of FLNA-binding Compound | | |
|---|---|---|---|
| | 0.01 μM | 0.1 μM | 1 μM |
| | Percent Binding Inhibition | | |
| Naloxone Control Average | 39.87% | 46.29% | 50.91% |
| 5009 | 42.5% | 47.3% | 54.3% |
| B0001 | 37.1% | 48.8% | 54.3% |
| B0002 | 40.2% | 46.4% | 55.0% |
| B0003 | 45.4% | 52.9% | 63.5% |
| B0004 | 38.9% | 50.0% | 54.8% |
| B0005 | 31.8% | 34.8% | 41.7% |
| B0006 | 45.1% | 53.5% | 61.3% |
| B0007 | 43.6% | 53.1% | 57.3% |
| B0008 | 35.5% | 40.3% | 52.8% |
| B0009 | 39.6% | 47.6% | 53.6% |
| B0010 | 39.4% | 43.4% | 50.3% |
| B0011 | 40.9% | 50.3% | 55.8% |
| B0012 | 39.4% | 46.9% | 51.7% |
| B0013 | 25.2% | 35.1% | 43.4% |
| B0014 | 25.7% | 30.9% | 37.8% |
| B0015 | 30.4% | 35.3% | 42.3% |
| B0016 | 27.1% | 33.7% | 41.9% |
| B0017 | 28.3% | 36.6% | 44.6% |
| B0018 | 37.2% | 43.7% | 47.6% |
| B0019 | 34.3% | 41.0% | 49.0% |
| B0020 | 38.1% | 45.5% | 50.6% |
| B0021 | 32.5% | 43.1% | 47.6% |
| B0022 | 34.3% | 40.4% | 45.6% |
| B0023 | 28.5% | 37.8% | 46.4% |
| B0024 | 34.8% | 43.4% | 47.7% |
| B0025 | 41.7% | 49.4% | 56.6% |
| B0026 | 41.1% | 43.3% | 48.2% |
| B0027 | 40.2% | 46.7% | 49.8% |
| B0028 | 38.2% | 42.8% | 49.1% |
| B0029 | 33.4% | 42.9% | 50.2% |
| B0030 | 47.0% | 50.5% | 57.6% |
| B0031 | 36.2% | 44.2% | 50.5% |
| B0032 | 45.1% | 51.3% | 48.9% |
| B0033 | 42.1% | 46.8% | 49.4% |
| B0034 | 49.1% | 54.2% | 59.1% |
| B0035 | 45.4% | 44.7% | 51.0% |
| B0036 | 46.6% | 52.8% | 62.1% |
| B0037 | 47.4% | 53.0% | 52.4% |
| B0038 | 41.2% | 50.1% | 57.0% |
| B0039 | 43.3% | 45.7% | 50.9% |
| B0040 | 40.0% | 53.1% | 57.1% |
| B0041 | 44.0% | 46.8% | 52.8% |
| B0042 | 40.8% | 46.4% | 51.6% |
| B0043 | 30.8% | 39.2% | 46.8% |
| B0044 | 35.2% | 39.5% | 44.4% |
| B0045 | 63.2% | 68.2% | 73.9% |
| B0046 | 42.2% | 50.2% | 55.4% |
| B0047 | 30.7% | 37.6% | 47.1% |
| B0048 | 34.7% | 41.9% | 43.9% |
| B0049 | 32.2% | 40.1% | 47.1% |
| B0050 | 29.2% | 34.5% | 39.8% |
| B0051 | 29.9% | 35.7% | 43.7% |
| B0052 | 30.2% | 39.1% | 44.3% |
| B0053 | 33.1% | 37.3% | 47.6% |
| B0054 | 25.6% | 32.6% | 43.3% |
| B0055 | 63.2% | 68.2% | 73.9% |
| Naloxone Control Average | 39.87% | 46.29% | 50.91% |

C-Series-1 Compounds

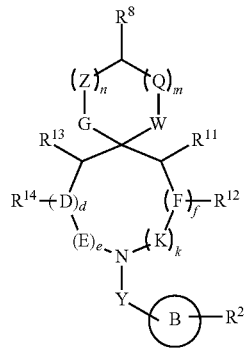

Each designation in the above formula is defined elsewhere herein.

| FLNA-binding Compound | Concentration of FLNA-binding Compound | | |
|---|---|---|---|
| | 0.01 μM | 0.1 μM | 1 μM |
| | Percent Binding Inhibition | | |
| Naloxone Control Average | 39.87% | 46.29% | 50.91% |
| 7866 | 38.5% | 47.9% | 53.4% |
| C0001 | 34.8% | 42.9% | 51.3% |
| C0002 | 38.4% | 45.6% | 42.8% |
| C0003 | 38.3% | 45.3% | 48.8% |
| C0004 | 37.6% | 42.3% | 44.7% |
| C0005 | 35.2% | 44.5% | 51.5% |
| C0006 | 41.6% | 46.8% | 51.8% |
| C0007 | 40.5% | 46.3% | 48.9% |
| C0008 | 42.2% | 52.3% | 54.4% |
| C0009 | 41.7% | 49.0% | 53.9% |
| C0010 | 39.8% | 42.7% | 47.1% |
| C0011 | 37.6% | 41.4% | 46.0% |
| C0012 | 26.3% | 39.5% | 46.4% |
| C0013 | 39.6% | 42.4% | 49.1% |
| C0014 | 29.5% | 38.8% | 40.0% |
| C0015 | 31.2% | 40.6% | 45.5% |
| C0016 | 38.3% | 43.8% | 49.1% |
| C0017 | 28.9% | 35.4% | 40.7% |
| C0018 | 42.3% | 45.9% | 53.4% |
| C0019 | 30.1% | 38.2% | 43.6% |
| C0021 | 34.0% | 38.4% | 40.6% |
| C0022 | 34.5% | 37.6% | 43.9% |
| C0023 | 35.9% | 41.7% | 47.2% |
| C0024 | 37.9% | 46.4% | 50.4% |
| C0025 | 37.2% | 41.4% | 45.1% |
| C0028 | 32.2% | 36.6% | 43.3% |
| C0029 | 38.6% | 43.2% | 50.5% |
| C0030 | 37.4% | 45.4% | 56.0% |
| C0032 | 41.5% | 50.5% | 55.3% |
| C0033 | 43.9% | 48.4% | 51.3% |
| C0034 | 29.6% | 38.3% | 44.8% |
| C0038 | 31.7% | 36.0% | 43.5% |
| C0041 | 38.3% | 47.0% | 51.2% |
| C0042 | 42.4% | 49.7% | 56.1% |
| C0047 | 30.8% | 35.2% | 41.4% |
| C0048 | 28.5% | 38.9% | 45.9% |
| C0049 | 25.3% | 27.9% | 30.3% |
| C0051 | 27.0% | 30.4% | 36.4% |
| C0052 | 28.0% | 35.6% | 40.8% |
| C0053 | 28.9% | 33.8% | 39.3% |
| C0054 | 32.9% | 39.4% | 43.3% |
| C0057 | ND* | ND | ND |
| C0060 | 60.3% | 64.0% | 68.0% |
| C0061 | ND | ND | ND |
| C0062 | 39.5% | 49.5% | 48.0% |
| C0064 | 37.3% | 44.4% | 49.2% |
| C0065 | 37.1% | 44.0% | 47.0% |
| C0067 | 31.3% | 39.7% | 45.0% |
| C0068 | 53.7% | 58.6% | 62.2% |
| C0069 | ND | ND | ND |
| C0070 | 42.6% | 50.6% | 53.6% |
| C0071 | 39.1% | 49.6% | 55.2% |
| C0072 | 28.4% | 37.4% | 44.0% |
| C0073 | ND | ND | ND |
| C0077 | 45.7% | 47.7% | 51.0% |
| C0078 | 46.6% | 48.0% | 50.5% |
| C0080M | 46.8% | 53.3% | 54.6% |
| C0084M | 47.2% | 53.7% | 55.9% |
| C0085M | 45.7% | 53.7% | 60.7% |
| C0138M | 53.0% | 52.0% | 59.5% |
| C0139M | 48.9% | 53.1% | 61.6% |
| C0140M | 42.3% | 49.2% | 54.4% |
| C0141M | 33.1% | 39.0% | 46.9% |
| C0143M | 45.3% | 48.4% | 57.8% |
| C0144M | 46.4% | 50.7% | 55.7% |
| C0145M | 45.1% | 53.7% | 58.3% |
| C0148M | 46.2% | 52.0% | 57.0% |
| C0149M | 48.5% | 52.3% | 62.0% |
| C0150M | 47.3% | 51.8% | 61.4% |
| C0151M | 48.3% | 51.7% | 58.7% |
| C0152M | ND | ND | ND |
| C0154M | ND | ND | ND |
| Naloxone Control Average | 39.87% | 46.29% | 50.91% |

*ND = Not Done.

C-Series-2 Compounds

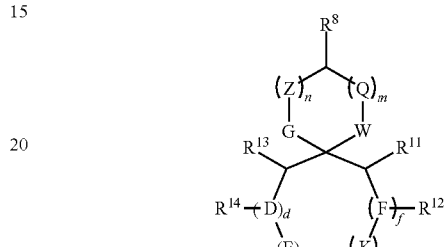

Each designation in the above formula is defined elsewhere herein.

| FLNA-binding Compound | Concentration of FLNA-binding Compound | | |
|---|---|---|---|
| | 0.01 μM | 0.1 μM | 1 μM |
| | Percent Binding Inhibition | | |
| Naloxone Control Average | 39.87 | 46.29% | 50.91 |
| C0011 | 37.6% | 41.4% | 46.0% |
| C0026 | 42.3% | 44.8% | 49.0% |
| C0027 | 50.8% | 61.2% | 63.8% |
| S-C0027 | 39.1% | 46.5% | 53.6% |
| C0034-3 | 29.6% | 38.3% | 44.8% |
| C0037-2 | ND* | ND | ND |
| C0040 | 38.4% | 46.3% | 55.9% |
| C0043 | 43.9% | 51.3% | 58.0% |
| C0044 | 37.3% | 43.9% | 50.6% |
| C0045 | 39.1% | 48.9% | 53.7% |
| C0046 | 30.8% | 35.7% | 42.2% |
| C0050 | 26.7% | 34.5% | 36.4% |
| C0055 | 29.0% | 34.9% | 39.5% |
| C0056 | 33.7% | 38.9% | 41.4% |
| C0060 | 60.3% | 64.0% | 68.0% |
| C0086M | 37.9% | 48.1% | 53.4% |
| C0087M | 51.6% | 57.9% | 61.5% |
| C0088M | 40.1% | 52.4% | 56.1% |
| C0089M | 40.7% | 46.1% | 51.2% |
| C0090M | 42.5% | 52.5% | 55.8% |
| C0091M | 38.1% | 39.8% | 46.3% |
| C0093M | 44.8% | 49.9% | 53.5% |
| C0094M | 43.0% | 52.8% | 57.5% |
| C0095M | 40.1% | 46.6% | 50.5% |
| C0096M | 43.0% | 48.3% | 55.0% |
| C0099M | 46.9% | 53.3% | 56.0% |
| C0100M | 52.2% | 58.2% | 64.5% |
| C0101M | 50.5% | 56.4% | 59.0% |
| C0102M | 52.3% | 53.1% | 56.6% |
| C0104M | 51.4% | 54.1% | 55.2% |
| C0105M | 55.7% | 62.0% | 68.8% |
| C0106M | 45.8% | 55.6% | 58.9% |
| C0108M | 54.6% | 61.4% | 68.7% |
| C0114M | 57.1% | 63.2% | 66.7% |
| C0115M | 47.8% | 57.8% | 59.9% |
| C0116M | 53.9% | 60.0% | 62.9% |
| C0118M | 56.6% | 61.4% | 62.4% |

-continued

| FLNA-binding Compound | Concentration of FLNA-binding Compound | | |
|---|---|---|---|
| | 0.01 µM | 0.1 µM | 1 µM |
| | Percent Binding Inhibition | | |
| C0119M | 41.6% | 55.5% | 60.0% |
| C0123M | 51.9% | 60.5% | 62.9% |
| C0124M | 47.7% | 52.2% | 58.7% |
| C0125M | 54.2% | 59.7% | 63.3% |
| C0126M | 50.7% | 55.4% | 67.3% |
| C0128M | 46.5% | 54.4% | 58.2% |
| C0133M | 47.8% | 54.9% | 58.5% |
| C0134M | 55.7% | 60.5% | 61.9% |
| F-C0134 | 37.4% | 45.7% | 53.1% |
| C0135M | 53.9% | 55.1% | 62.3% |
| C0136M(P5) | 46.7% | 55.2% | 58.2% |
| C0137M(P7) | 42.4% | 49.9% | 61.2% |
| C0142M | 35.1% | 39.4% | 56.0% |
| C0143M | 45.3% | 48.4% | 57.8% |
| C0148M | 46.2% | 52.0% | 57.0% |
| C0149M | 48.5% | 52.3% | 62.0% |
| C0150M | 47.3% | 51.8% | 61.4% |
| C0151M | 48.3% | 51.7% | 58.7% |
| C0152M-4 | ND | ND | ND |
| C0153M-3 | ND | ND | ND |
| Naloxone Control Average | 39.87% | 46.29% | 50.91% |

*ND = Not Done.

A preliminary study similar to that immediately above was carried out using Compounds 4, 9 and 10 and 100 nM of frozen-stored FITC-NLX rather than 10 nM FITC-NLX. The results of an average of two runs for this study are shown below.

| Compound | 0.1 nM | 1 nM | 10 nM | 100 nM | 1 µM |
|---|---|---|---|---|---|
| 4 | 18.8% | 21.3% | 17.9% | 28.8% | 42.9% |
| 9 | 22.5% | 24.8% | 27.7% | 35.3 | 49.6% |
| 10 | 27.5% | 27.3% | 26.6% | 27.3% | 34.5% |
| (+) NLX | 22.7% | 22.8% | 23.1% | 22.8% | 39.8% |

EXAMPLE 2

MOR Agonist Activity Using GTPγS Binding Assay

To assess the mu opiate receptor (MOR) agonist activity of positive compounds from the FLNA screening, compounds were tested in a [$^{35}$S]GTPγS binding assay using striatal membranes. A previous study has shown that in striatal membranes, activation of MOR leads to an increase in [$^{35}$S]GTPγS binding to Gαo (Wang et al., 2005 *Neuroscience* 135:247-261). This assay measures a functional consequence of receptor occupancy at one of the earliest receptor-mediated events. The assay permits for traditional pharmacological parameters of potency, efficacy and antagonist affinity, with the advantage that agonist measures are not subjected to amplification or other modulation that may occur when analyzing parameters further downstream of the receptor.

Thus, striatal tissue was homogenized in 10 volumes of ice cold 25 mM HEPES buffer, pH 7.4, which contained 1 mM EGTA, 100 mM sucrose, 50 µg/ml leupeptin, 0.04 mM PMSF, 2 µg/ml soybean trypsin inhibitor and 0.2% 2-mercaptoethanol. The homogenates were centrifuged at 800×g for 5 minutes and the supernatants were centrifuged at 49,000×g for 20 minutes. The resulting pellets were suspended in 10 volume of reaction buffer, which contained 25 mM HEPES, pH 7.5, 100 mM NaCl, 50 µg/ml leupeptin, 2 µg/ml soybean trypsin inhibitor, 0.04 mM PMSF and 0.02% 2-mercaptomethanol.

The resultant striatal membrane preparation (200 µg) was admixed and maintained (incubated) at 30° C. for 5 minutes in reaction buffer as above that additionally contained 1 mM MgCl$_2$ and 0.5 nM [$^{35}$S]GTPγS (0.1 µCi/assay, PerkinElmer Life and Analytical Sciences) in a total volume of 250 µl and continued for 5 minutes in the absence or presence of 0.1-10 µM of an assayed compound of interest. The reaction was terminated by dilution with 750 µl of ice-cold reaction buffer that contained 20 mM MgCl$_2$ and 1 mM EGTA and immediate centrifugation at 16,000×g for 5 minutes.

The resulting pellet was solubilized by sonicating for 10 seconds in 0.5 ml of immunoprecipitation buffer containing 0.5% digitonin, 0.2% sodium cholate and 0.5% NP-40. Normal rabbit serum (1 µl) was added to 1 ml of lysate and incubated at 25° C. for 30 minutes. Nonspecific immune complexes were removed by incubation with 25 µl of protein A/G-conjugated agarose beads at 25° C. for 30 minutes followed by centrifugation at 5,000×g at 4° C. for 5 minutes. The supernatant was divided and separately incubated at 25° C. for 30 minutes with antibodies raised against Gαo proteins (1:1,000 dilutions).

The immunocomplexes so formed were collected by incubation at 25° C. for 30 minutes with 40 µl of agarose-conjugated protein A/G beads and centrifugation at 5,000×g at 4° C. for 5 minutes. The pellet was washed and suspended in buffer containing 50 mM Tris-HCl, pH 8.0, and 1% NP-40. The radioactivity in the suspension was determined by liquid scintillation spectrometry. The specificity of MOR activation of [$^{35}$S]GTPγS binding to Gαo induced by a selective compound was defined by inclusion of 1 µM β-funaltrexamine (β-FNA; an alkylating derivative of naltrexone that is a selective MOR antagonist). DAMGO (1 or 10 µM) was used as a positive control.

The results of this study are shown in the Tables below.

| FLNA-Binding Compound MOR Agonist Activity | | | | | | |
|---|---|---|---|---|---|---|
| FLNA-Binding Compound | Concentration of FLNA-Binding Compound as Agonist | | | | | |
| | 0.1 µM | 1 µM | 1 µM + BFNA | % DAMGO (0.1 µM) | % DAMGO (1 µM) | % DAMGO + BFNA |
| A3333 | 170.7% | 328.3% | 65.9% | 88.9% | 101.0% | 136.7% |
| A0001 | 94.3% | 181.7% | 22.2% | 63.1% | 78.9% | 83.8% |
| A0002 | 155.6% | 199.4% | 6.5% | 104.1% | 86.6% | 24.5% |
| A0003 | 176.8% | 276.0% | 17.1% | 118.3% | 119.9% | 64.5% |
| A0004 | 97.4% | 144.2% | 86.0% | 55.2% | 55.6% | 130.9% |
| A0005 | 179.7% | 239.2% | 23.5% | 105.0% | 89.6% | 45.1% |
| A0006 | 170.0% | 190.9% | 18.2% | 113.8% | 82.9% | 68.7% |
| A0007 | 102.0% | 221.9% | 40.4% | 68.3% | 96.4% | 152.5% |
| A0008 | 163.8% | 235.0% | 133.9% | 109.6% | 102.1% | 505.3% |
| A0009 | 70.2% | 126.4% | 93.9% | 39.8% | 48.7% | 142.9% |
| A0010 | 277.2% | 319.0% | 190.3% | 161.9% | 119.5% | 365.3% |
| A0011 | 236.3% | 287.5% | 47.0% | 158.2% | 124.9% | 177.4% |
| A0012 | 149.3% | 185.7% | 122.4% | 99.9% | 80.7% | 461.9% |
| A0013 | 102.1% | 164.8% | 86.1% | 57.8% | 63.6% | 131.1% |
| A0014 | 147.0% | 174.9% | 140.8% | 83.2% | 67.5% | 214.3% |
| A0015 | 110.9% | 150.1% | 62.5% | 64.8% | 56.2% | 120.0% |
| A0017 | 161.9% | 246.0% | 65.2% | 96.9% | 100.4% | 187.9% |
| A0020 | 168.6% | 217.4% | 67.4% | 100.9% | 88.7% | 194.2% |
| A0021 | 133.3% | 275.3% | 12.1% | 79.8% | 112.4% | 34.9% |
| A0022 | 154.1% | 216.0% | 28.0% | 90.0% | 80.9% | 53.7% |
| A0025 | 58.6% | 138.7% | 52.2% | 33.2% | 54.5% | 198.5% |
| A0026 | 140.7% | 179.8% | 120.8% | 79.7% | 70.7% | 459.3% |
| A0028 | 143.6% | 187.7% | 116.7% | 81.3% | 73.8% | 443.7% |
| A0029 | 173.8% | 206.5% | 22.3% | 98.4% | 81.2% | 84.8% |

FLNA-Binding Compound MOR Agonist Activity

| FLNA-Binding Compound | Concentration of FLNA-Binding Compound as Agonist | | | | | |
|---|---|---|---|---|---|---|
| | 0.1 µM | 1 µM | 1 µM + BFNA | % DAMGO (0.1 µM) | % DAMGO (1 µM) | % DAMGO + BFNA |
| A0030 | 133.4% | 287.8% | 165.2% | 75.5% | 113.2% | 628.1% |
| A0031 | 178.2% | 297.0% | 150.9% | 100.9% | 116.8% | 573.8% |
| A0032-1 | 187.4% | 324.5% | 224.5% | 95.5% | 117.6% | 303.8% |
| A0032 | 226.9% | 257.8% | 133.0% | 115.6% | 93.4% | 180.0% |
| A0033 | 155.8% | 254.6% | 118.2% | 79.4% | 92.2% | 159.9% |
| A0035 | 120.6% | 158.8% | 88.6% | 61.5% | 57.5% | 119.9% |
| A0036 | 144.1% | 167.5% | 63.2% | 73.4% | 60.7% | 85.5% |
| A0037 | 177.9% | 236.2% | 104.6% | 90.7% | 85.6% | 141.5% |
| A0038 | 176.7% | 234.5% | 107.0% | 90.1% | 85.0% | 144.8% |
| A0039 | 267.8% | 339.6% | 173.5% | 136.5% | 123.0% | 234.8% |
| A0040 | 46.1% | 149.0% | 16.7% | 23.5% | 54.0% | 22.6% |
| A0041 | 212.7% | 283.6% | 50.6% | 108.4% | 102.8% | 68.5% |
| A0042 | 147.5% | 233.1% | 89.5% | 75.2% | 84.5% | 121.1% |
| A0043 | 183.3% | 223.8% | 89.1% | 93.4% | 81.1% | 120.6% |
| A0044 | 176.2% | 209.1% | 134.7% | 89.8% | 75.8% | 182.3% |
| A0045 | 143.9% | 274.2% | 99.2% | 73.3% | 99.3% | 134.2% |
| A0046 | 257.5% | 354.1% | 140.0% | 131.2% | 128.3% | 189.4% |
| A0047 | 233.0% | 255.0% | 116.5% | 118.8% | 92.4% | 157.6% |
| A0048 | 233.7% | 302.9% | 167.2% | 119.1% | 109.7% | 226.3% |
| A0049 | 232.3% | 370.3% | 107.1% | 118.4% | 134.2% | 144.9% |
| A0050 | 151.0% | 189.3% | 81.0% | 77.0% | 68.6% | 109.6% |
| A0051 | 290.4% | 386.6% | 211.6% | 148.0% | 140.1% | 286.3% |
| A0053 | 78.5% | 118.2% | 15.1% | 46.5% | 47.5% | 46.2% |
| A0054 | 74.9% | 159.2% | 114.1% | 44.4% | 63.9% | 348.9% |
| A0055 | 89.8% | 195.2% | 33.5% | 53.2% | 78.4% | 102.4% |
| A0056 | 115.6% | 129.6% | 17.4% | 74.1% | 56.2% | 43.6% |
| A0057 | 124.2% | 192.1% | 44.8% | 79.6% | 83.3% | 112.3% |
| A0058 | 70.7% | 244.3% | 59.9% | 45.3% | 106.0% | 150.1% |
| A0059 | 99.2% | 129.9% | 85.7% | 63.5% | 56.4% | 214.8% |
| A0060 | 99.7% | 158.2% | 14.3% | 63.9% | 68.6% | 35.8% |
| A0061 | 110.3% | 197.1% | 10.7% | 70.7% | 85.5% | 26.8% |
| A0062 | ND | ND | ND | ND | ND | ND |
| A0063 | 122.8% | 245.8% | 310% | 78.7% | 106.6% | 77.7% |
| A0064 | 219.2% | 262.9% | 43.7% | 127.4% | 119.7% | 126.7% |
| A0065 | 197.6% | 266.8% | 44.9% | 126.6% | 115.7% | 112.5% |
| A0066 | 151.9% | 195.6% | 59.2% | 88.3% | 89.0% | 171.6% |
| A0067 | 170.8% | 254.4% | 33.9% | 99.2% | 115.8% | 98.3% |
| A0068 | 73.9% | 110.4% | 98.1% | 36.8% | 35.2% | 182.0% |
| A0069 | 122.7% | 244.2% | 29.5% | 71.3% | 111.2% | 85.5% |
| A0070 | 128.6% | 195.3% | 80.3% | 74.7% | 88.9% | 232.8% |
| A0071 | 225.8% | 310.9% | 239.4% | 128.2% | 122.9% | 1088.2% |
| A0072 | 254.3% | 305.1% | 171.8% | 126.8% | 97.2% | 318.7% |
| A0073 | 201.7% | 325.7% | 185.8% | 100.5% | 103.7% | 344.7% |
| A0074 | ND | ND | ND | ND | ND | ND |
| A0075 | ND | ND | ND | ND | ND | ND |
| A0076 | 79.8% | 172.6% | 41.2% | 46.4% | 78.6% | 119.4% |
| A0077 | 300.1% | 334.7% | 103.5% | 170.5% | 132.3% | 470.5% |
| A0078 | 250.5% | 289.9% | 147.8% | 124.9% | 92.3% | 274.2% |

Series B FLNA-Binding Compound MOR Agonist Activity

| FLNA-Binding Compound | Concentration of FLNA-Binding Compound as Agonist | | | | | |
|---|---|---|---|---|---|---|
| | 0.1 µM | 1 µM | 1 µM + BFNA | % DAMGO (0.1 µM) | % DAMGO (1 µM) | % DAMGO + BFNA |
| 5009 | 128.5% | 270.4% | 87.5% | 66.9% | 83.2% | 181.5% |
| B0001 | 128.2% | 202.3% | 28.0% | 77.4% | 74.9% | 43.1% |
| B0002 | 165.7% | 219.0% | 101.4% | 100.0% | 81.1% | 156.0% |
| B0003 | 103.0% | 131.1% | 18.6% | 59.9% | 47.4% | 29.0% |
| B0004 | 170.3% | 231.7% | 72.0% | 102.8% | 85.8% | 110.8% |
| B0005 | 89.2% | 110.4% | 45.1% | 50.5% | 42.6% | 68.6% |
| B0006 | 77.0% | 131.3% | 18.6% | 44.8% | 47.5% | 29.0% |
| B0007 | 168.3% | 223.3% | 64.5% | 95.3% | 86.1% | 98.2% |
| B0008 | 148.3% | 264.1% | 46.0% | 84.0% | 101.9% | 70.0% |
| B0009 | 144.4% | 219.9% | 119.4% | 81.8% | 84.8% | 181.7% |
| B0010 | 132.9% | 184.4% | 152.0% | 75.3% | 71.1% | 231.4% |
| B0011 | 158.6% | 212.6% | 78.0% | 95.7% | 78.7% | 120.0% |
| B0012 | 167.4% | 212.0% | 145.1% | 97.8% | 79.4% | 278.5% |
| B0013 | 51.4% | 154.1% | 34.4% | 29.1% | 59.4% | 52.4% |
| B0014 | 166.6% | 250.5% | 44.3% | 98.5% | 93.7% | 67.1% |
| B0016 | 167.7% | 213.6% | 72.2% | 99.2% | 79.9% | 109.4% |
| B0017 | 99.6% | 122.0% | 49.6% | 58.9% | 45.6% | 75.2% |
| B0018 | 118.8% | 143.0% | 45.6% | 70.3% | 53.5% | 69.1% |
| B0019 | 101.0% | 256.5% | 81.4% | 59.7% | 96.0% | 123.3% |
| B0020 | 51.6% | 181.6% | 24.9% | 30.1% | 68.0% | 47.8% |
| B0021 | 126.9% | 256.4% | 42.9% | 75.9% | 104.7% | 123.6% |
| B0022 | 131.9% | 182.7% | 45.8% | 78.9% | 74.6% | 132.0% |
| B0023 | 166.1% | 245.3% | 28.4% | 99.4% | 100.1% | 81.8% |
| B0024 | 155.8% | 285.9% | 20.2% | 93.2% | 116.7% | 58.2% |
| B0025 | 159.6% | 234.6% | 137.7% | 96.3% | 86.8% | 211.8% |
| B0026 | 152.0% | 233.3% | 28.8% | 88.8% | 87.4% | 55.3% |
| B0027 | 140.9% | 266.9% | 21.6% | 82.3% | 100.0% | 41.5% |
| B0028 | 199.1% | 357.7% | 55.0% | 103.5% | 131.0% | 125.3% |
| B0029 | 171.9% | 210.3% | 17.6% | 89.4% | 77.0% | 40.1% |
| B0030 | 107.2% | 276.1% | 90.1% | 62.6% | 103.4% | 172.9% |
| B0031 | 210.8% | 272.0% | 28.8% | 109.6% | 99.6% | 65.6% |
| B0032 | 221.1% | 297.7% | 15.6% | 115.0% | 109.0% | 35.5% |
| B0033 | 149.3% | 188.9% | 41.9% | 77.6% | 69.2% | 95.4% |
| B0034 | 122.5% | 235.2% | 41.8% | 71.6% | 88.1% | 80.2% |
| B0035 | 188.0% | 248.7% | 74.2% | 109.8% | 93.2% | 142.4% |
| B0036 | 61.4% | 120.6% | 65.1% | 39.2% | 52.1% | 199.7% |
| B0037 | 119.8% | 186.0% | 106.2% | 76.5% | 80.4% | 325.8% |
| B0038 | 147.5% | 205.3% | 117.1% | 94.2% | 88.7% | 359.2% |
| B0039 | 171.8% | 290.5% | 78.3% | 100.4% | 108.8% | 150.3% |
| B0040 | 146.0% | 243.3% | 55.3% | 93.2% | 105.1% | 169.6% |
| B0041 | 61.6% | 109.3% | 41.9% | 39.3% | 47.2% | 128.5% |
| B0042 | 69.9% | 107.5% | 43.1% | 39.6% | 42.3% | 163.9% |
| B0043 | 74.8% | 248.1% | 166.4% | 42.4% | 97.6% | 632.7% |
| B0044 | 87.3% | 170.0% | 134.6% | 49.4% | 66.9% | 511.8% |
| B0045 | 129.3% | 193.1% | 83.8% | 82.6% | 83.4% | 257.1% |
| B0046 | 99.9% | 141.9% | 90.5% | 63.8% | 61.3% | 277.6% |
| B0047 | 187.8% | 235.6% | 68.4% | 106.3% | 92.6% | 260.1% |
| B0048 | 185.1% | 223.4% | 78.5% | 104.8% | 87.8% | 298.5% |
| B0049 | 181.6% | 364.0% | 133.2% | 102.8% | 143.1% | 506.5% |
| B0050 | 98.2% | 211.0% | 48.8% | 58.1% | 96.4% | 294.0% |
| B0051 | 115.6% | 167.9% | 43.8% | 68.4% | 76.7% | 263.9% |
| B0052 | 98.2% | 151.7% | 40.9% | 58.1% | 69.3% | 246.4% |
| B0053 | 160.2% | 299.8% | 134.3% | 94.8% | 137.0% | 809.0% |
| B0054 | 157.8% | 186.7% | 111.0% | 93.4% | 85.3% | 668.7% |
| B0055 | 162.1% | 338.5% | 117.5% | 91.8% | 133.1% | 446.8% |
| B0056 | 174.7% | 288.8% | 41.8% | 98.9% | 113.6% | 158.9% |

Series C-1 FLNA-Binding Compound MOR Agonist Activity

| FLNA-Binding Compound | Concentration of FLNA-Binding Compound as Agonist | | | | | |
|---|---|---|---|---|---|---|
| | 0.1 µM | 1 µM | 1 µM + BFNA | % DAMGO (0.1 µM) | % DAMGO (1 µM) | % DAMGO + BFNA |
| 7866 | 152.3% | 308.2% | 62.4% | 79.3% | 94.8% | 129.5% |
| C0001 | 129.3% | 184.3% | 33.9% | 75.2% | 66.6% | 52.9% |
| C0002 | 88.4% | 93.8% | 3.9% | 51.4% | 33.9% | 6.1% |
| C0003 | 162.3% | 215.9% | 107.7% | 91.9% | 83.3% | 163.9% |

-continued

| | Series C-1 FLNA-Binding Compound MOR Agonist Activity | | | | | |
|---|---|---|---|---|---|---|
| FLNA- | Concentration of FLNA-Binding Compound as Agonist | | | | | |
| Binding Compound | 0.1 μM | 1 μM | 1 μM + BFNA | % DAMGO (0.1 μM) | % DAMGO (1 μM) | % DAMGO + BFNA |
| C0004 | 122.0% | 228.4% | 65.8% | 72.1% | 85.4% | 99.7% |
| C0005 | 180.4% | 227.2% | 166.4% | 105.4% | 85.1% | 319.4% |
| C0006 | 121.5% | 204.0% | 4.6% | 70.6% | 73.8% | 7.2% |
| C0007 | 79.1% | 195.0% | 10.9% | 46.0% | 70.5% | 17.0% |
| C0008 | 71.2% | 201.6% | 2.8% | 41.4% | 72.9% | 4.4% |
| C0009 | 146.3% | 256.2% | 26.4% | 85.1% | 92.6% | 41.2% |
| C0010 | 136.5% | 307.0% | 89.1% | 80.7% | 114.9% | 135.0% |
| C0011 | 217.0% | 305.0% | 19.0% | 126.8% | 114.3% | 36.5% |
| C0012 | 96.8% | 224.8% | 184.4% | 54.8% | 86.7% | 280.7% |
| C0013 | 156.6% | 301.2% | 39.6% | 91.0% | 108.9% | 61.8% |
| C0014 | 144.9% | 153.5% | 76.3% | 82.0% | 59.2% | 116.1% |
| C0015 | 138.7% | 204.7% | 126.8% | 78.5% | 78.9% | 193.0% |
| C0016 | 172.7% | 230.5% | 96.7% | 100.4% | 83.3% | 150.9% |
| C0017 | 153.8% | 284.5% | 94.1% | 87.1% | 109.7% | 143.2% |
| C0018 | 195.5% | 247.7% | 106.5% | 110.7% | 95.5% | 162.1% |
| C0019 | 104.4% | 176.6% | 52.8% | 59.1% | 68.1% | 80.4% |
| C0021 | 159.7% | 192.0% | 90.7% | 94.5% | 87.8% | 546.4% |
| C0022 | 194.3% | 328.7% | 13.4% | 113.5% | 123.2% | 25.7% |
| C0023 | 153.2% | 233.7% | 23.2% | 89.5% | 87.6% | 44.5% |
| C0024 | 178.4% | 229.6% | 59.3% | 92.8% | 84.1% | 135.1% |
| C0025 | 235.7% | 320.7% | 80.2% | 122.6% | 117.5% | 182.7% |
| C0028 | 93.9% | 132.4% | 78.4% | 55.6% | 60.5% | 472.3% |
| C0029 | 175.4% | 308.8% | 16.6% | 91.2% | 113.1% | 37.8% |
| C0030 | 150.3% | 226.8% | 95.0% | 96.0% | 98.0% | 291.4% |
| C0032 | 145.4% | 202.0% | 80.9% | 92.8% | 87.3% | 248.2% |
| C0033 | 134.5% | 186.4% | 76.6% | 85.9% | 80.6% | 235.0% |
| C0034 | 103.6% | 167.9% | 80.1% | 61.3% | 76.7% | 482.5% |
| C0041 | 186.1% | 244.4% | 95.5% | 110.1% | 111.7% | 575.3% |
| C0042 | 167.1% | 260.9% | 110.6% | 98.9% | 119.2% | 666.3% |
| C0047 | 142.2% | 206.1% | 80.1% | 98.1% | 88.5% | 182.0% |
| C0048 | 209.1% | 245.3% | 89.9% | 144.2% | 105.3% | 204.3% |
| C0049 | 106.6% | 210.0% | 81.0% | 73.5% | 90.1% | 184.1% |
| C0051 | 94.4% | 170.4% | 55.9% | 65.1% | 73.1% | 127.0% |
| C0052 | 108.4% | 162.8% | 42.7% | 74.8% | 69.9% | 97.0% |
| C0053 | 104.0% | 157.2% | 93.1% | 71.7% | 67.5% | 211.6% |
| C0054 | 68.2% | 127.0% | 43.5% | 47.0% | 54.5% | 98.9% |
| C0057 | ND* | ND | ND | ND | ND | ND |
| C0061 | ND | ND | ND | ND | ND | ND |
| C0062 | 127.8% | 310.5% | 59.8% | 81.9% | 134.7% | 149.9% |
| C0064 | 213.8% | 349.6% | 38.1% | 124.2% | 159.1% | 110.4% |
| C0065 | 198.3% | 279.5% | 47.7% | 127.0% | 121.3% | 119.5% |
| C0067 | 142.7% | 179.0% | 33.5% | 82.9% | 81.5% | 97.1% |
| C0068 | 107.2% | 263.1% | 165.9% | 53.4% | 83.8% | 307.8% |
| C0069 | ND | ND | ND | ND | ND | ND |
| C0070 | 165.6% | 210.8% | 114.2% | 96.2% | 95.9% | 331.0% |
| C0071 | 276.3% | 355.3% | 177.1% | 160.5% | 161.7% | 513.3% |
| C0072 | 172.7% | 259.1% | 67.1% | 100.3% | 117.9% | 194.5% |
| C0073 | ND | ND | ND | ND | ND | ND |
| C0077 | 192.7% | 265.4% | 136.7% | 109.5% | 104.9% | 621.4% |
| C0078 | 138.1% | 236.6% | 170.7% | 82.4% | 106.4% | 359.4% |
| C0080M | 187.9% | 205.4% | 167.1% | 112.1% | 92.4% | 351.8% |
| C0082M | 228.1% | 338.4% | 97.6% | 113.7% | 107.8% | 181.1% |
| C0084M | 163.1% | 255.5% | 133.2% | 97.3% | 114.9% | 280.4% |
| C0085M | 211.6% | 246.2% | 43.7% | 105.5% | 78.4% | 112.6% |
| C0138M | 126.9% | 183.9% | 51.5% | 86.3% | 90.9% | 131.0% |
| C0139M | 156.1% | 206.6% | 51.0% | 106.2% | 102.2% | 129.8% |
| C0140M | 126.1% | 215.4% | 83.0% | 85.8% | 106.5% | 211.2% |
| C0141M | 161.5% | 213.9% | 47.9% | 109.9% | 105.8% | 121.9% |
| C0143M | 81.0 | 193.3 | 86.5 | 47.1% | 59.3% | 94.7% |
| C0144M | 186.3 | 295.9 | 125.9 | 108.3% | 90.8% | 137.9% |
| C0145M | 193.0 | 289.2 | 87.0 | 112.2% | 88.7% | 95.3% |
| C0146M | ND | ND | ND | ND | ND | ND |
| C0147M A2 | ND | ND | ND | ND | ND | ND |
| C0148M A2 | 181.3 | 360.6 | 87.6 | 105.4% | 110.6% | 95.9% |
| C0149M | 209.8 | 406.7 | 93.4 | 122.0% | 124.8% | 102.3% |
| C0150M | 167.1 | 423.1 | 93.4 | 97.2% | 129.8% | 173.2% |
| C0151M | 346.8 | 397.6 | 212.8 | 201.6% | 122.0% | 233.1% |

| Series C-1 FLNA-Binding Compound MOR Agonist Activity ||||||
|---|---|---|---|---|---|
| FLNA-Binding Compound | Concentration of FLNA-Binding Compound as Agonist |||||
| | 0.1 µM | 1 µM | 1 µM + BFNA | % DAMGO (0.1 µM) | % DAMGO (1 µM) | % DAMGO + BFNA |
| C0152M | ND | ND | ND | ND | ND | ND |
| DAMGO Average | 168.5% | 266.1% | 53.2% | ND | ND | ND |

*DN = Not Done.

| Series C-2 FLNA-Binding Compound MOR Agonist Activity ||||||
|---|---|---|---|---|---|
| FLNA-Binding Compound | Concentration of FLNA-Binding Compound as Agonist |||||
| | 0.1 µM | 1 µM | 1 µM + BFNA | % DAMGO (0.1 µM) | % DAMGO (1 µM) | % DAMGO + BFNA |
| C0011 | 217.0% | 305.0% | 19.0% | 126.8% | 114.3% | 36.5% |
| C0026 | 207.2% | 288.4% | 21.2% | 107.7% | 105.6% | 48.3% |
| C0027 | 233.2% | 313.9% | 72.2% | 121.3% | 115.0% | 164.5% |
| S-00027 | 156.2% | 286.8% | 56.2% | 74.2% | 84.4% | 98.1% |
| C0034-3 | ND* | ND | ND | ND | ND | ND |
| C0037-2 | ND | ND | ND | ND | ND | ND |
| C0040 | 145.8% | 308.3% | 90.4% | 93.1% | 133.2% | 277.3% |
| C0043 | 175.4% | 242.6% | 83.3% | 103.8% | 110.9% | 501.8% |
| C0044 | 173.7% | 280.1% | 59.1% | 102.8% | 128.0% | 356.0% |
| C0045 | 149.2% | 238.8% | 105.3% | 88.3% | 109.1% | 634.5% |
| C0046 | 286.2% | 492.9% | 156.8% | 197.4% | 211.5% | 356.4% |
| C0050 | 110.3% | 127.6% | 59.0% | 76.1% | 54.8% | 134.1% |
| C0055 | ND | ND | ND | ND | ND | ND |
| C0056 | 98.6% | 193.4% | 86.3% | 68.0% | 83.0% | 196.1% |
| C0060 | 166.5% | 218.9% | 143.9% | 114.8% | 93.9% | 327.0% |
| C0086M | 206.8% | 265.3% | 152.3% | 117.5% | 104.9% | 692.3% |
| C0087M | 262.8% | 329.6% | 142.5% | 138.9% | 132.8% | 293.8% |
| C0088M | 276.3% | 355.3% | 177.1% | 160.5% | 161.7% | 513.3% |
| C0089M | 234.5% | 295.3% | 81.9% | 136.3% | 134.4% | 237.4% |
| C0090M | 237.0% | 341.0% | 41.0% | 137.7% | 155.2% | 118.8% |
| C0091M | 207.9% | 274.4% | 80.8% | 118.1% | 108.5% | 367.3% |
| C0093M | 140.0% | 211.8% | 44.0% | 81.3% | 96.4% | 127.5% |
| C0094M | 172.5% | 263.5% | 115.3% | 100.2% | 119.9% | 334.2% |
| C0095M | 189.1% | 224.6% | 107.7% | 107.4% | 88.8% | 489.5% |
| C0096M | 186.4% | 328.9% | 127.1% | 105.9% | 130.0% | 577.7% |
| C0099M | 157.2% | 195.7% | 114.7% | 93.8% | 88.0% | 241.5% |
| C0100M | 173.6% | 245.9% | 195.6% | 103.6% | 110.6% | 411.8% |
| C0101M | 138.2% | 274.3% | 174.8% | 82.5% | 123.4% | 368.0% |
| C0102M | 131.8% | 272.0% | 150.4% | 78.6% | 122.4% | 316.6% |
| C0104M | 188.2% | 238.9% | 143.8% | 99.5% | 96.3% | 296.5% |
| C0105M | 198.1% | 220.3% | 73.1% | 104.7% | 88.8% | 150.7% |
| C0106M | 171.8% | 240.7% | 117.2% | 102.5% | 108.3% | 246.7% |
| C0108M | 205.6% | 258.5% | 76.9% | 108.7% | 104.1% | 158.6% |
| C0114M | 114.0% | 144.3% | 35.9% | 77.6% | 71.4% | 91.3% |
| C0115M | 177.2% | 226.8% | 118.4% | 105.7% | 102.0% | 249.3% |
| C0116M | 258.4% | 302.8% | 152.0% | 136.6% | 122.0% | 313.4% |
| C0118M | 166.2% | 261.5% | 79.2% | 87.8% | 105.4% | 163.3% |
| C0119M | 105.7% | 167.8% | 35.1% | 71.9% | 83.0% | 89.3% |
| C0124M | 252.0% | 305.1% | 61.4% | 133.2% | 122.9% | 126.6% |
| C0125M | 168.6% | 195.2% | 159.7% | 89.1% | 78.6% | 329.3% |
| C0126M | 181.8% | 265.3% | 108.5% | 108.5% | 119.3% | 228.4% |
| C0128M | 197.8% | 286.0% | 63.9% | 104.5% | 115.2% | 131.8% |
| C0133M | 139.4% | 214.8% | 72.4% | 83.2% | 96.6% | 152.4% |
| C0134M | 158.5% | 207.3% | 46.6% | 94.6% | 93.3% | 98.1% |
| F-00134 | 290.6% | 378.9% | 66.6% | 138.1% | 111.4% | 116.2% |
| C0135M | 161.3% | 310.1% | 113.3% | 85.3% | 124.9% | 233.6% |
| C0136M (P5) | 176.8% | 237.3% | 74.5% | 93.4% | 95.6% | 153.6% |
| 0137M (P7) | 180.8% | 193.8% | 55.8% | 95.6% | 78.1% | 115.1% |
| C0142M | 143.7% | 192.5% | 98.7% | 97.8% | 95.2% | 251.1% |
| C0143M | 81.0% | 193.3% | 86.5% | 47.1% | 59.3% | 94.7 |
| C0144M-2 | 186.3% | 295.9% | 125.9% | 108.3% | 90.8% | 137.9% |
| C0145M-3 | 193.0% | 289.2% | 87.0% | 112.2% | 88.7% | 95.3% |
| C0149M-2 | 209.8% | 406.7% | 93.4% | 122.0% | 124.8% | 102.3% |
| C0150M-2 | 167.1% | 423.1% | 158.1% | 97.2% | 129.8% | 173.2% |

Series C-2 FLNA-Binding Compound MOR Agonist Activity

| FLNA-Binding Compound | Concentration of FLNA-Binding Compound as Agonist | | | | | |
|---|---|---|---|---|---|---|
| | 0.1 µM | 1 µM | 1 µM + BFNA | % DAMGO (0.1 µM) | % DAMGO (1 µM) | % DAMGO + BFNA |
| C0151M-2 | 346.8% | 397.6% | 212.8% | 201.6% | 122.0% | 233.1% |
| C0152M-2 | ND | ND | ND | ND | ND | ND |
| C0153M-3 | ND | ND | ND | ND | ND | ND |
| DAMGO Average | 168.5% | 266.1% | 53.2% | ND | ND | ND |

*ND = Not Done.

A preliminary study similar to that immediately above was carried out using Compounds 4, 9 and 10 and resynthesized Compound C0134M and DAMGO. The results of an average of two runs for this study are shown below.

| Compound | Concentration of FLNA-Binding Compound as Agonist | | |
|---|---|---|---|
| | 0.1 µM | 1 µM | 1 µM + βNFA |
| 4 | 133.9% | 165.2% | 49.5% |
| 9 | 156.6% | 197.2% | 56.6% |
| 10 | 163.1% | 191.8% | 60.4% |
| C0134M | 150.7% | 224.0% | 53.2% |
| DAMGO | 144.7% | 233.4% | 56.8% |

The above results indicate that Compounds 9 and 10 not only bind well to FLNA, but are also MOR agonists, whereas Compound 4 bound well to FLNA, but was not as potent a MOR agonist as were the other two compounds. The newly synthesized Compound C0134M exhibited similar MOR agonist activity to that shown previously.

EXAMPLE 3A

Pilot Study: Western Blot Assay Assessment of FLNA-α7nAChR/TLR4 and Aβ$_{42}$-α7nAChR Associations by Co-Immunoprecipitation To prepare lymphocytes, 7 ml of venous blood was collected into an EDTA-containing collecting tube or S-monovette (Sarstedt, Newton, N.C.). Collected blood (6 ml) was layered onto 6 ml HISTOPAQUE-1077 (Sigma, St Louis, Mo.) at 25° C. and the entire anti-coagulated blood was centrifuged at 400×g for 30 minutes (25° C.) to yield plasma (top layer) and lymphocytes (opaque interface). The lymphocytes were washed twice by mixing with 6 ml oxygenated Kreb's-Ringer followed by centrifugation at 250×g for 10 minutes and re-suspension. The final pellet was resuspended in 250 µl oxygenated Kreb's-Ringer prior to protein content determination by the Bradford method and assessment of the levels of FLNA-α7nAChR, FLNA-TLR4 and α7nAChR-Aβ$_{42}$ complexes. To store lymphocytes, the lymphocyte pellet was resuspended in 250 µl ice-cold oxygenated Kreb's-Ringer containing 10% glycerol, and stored at −20° C. for 1 hour before storage at −80° C.

To determine the levels of FLNA-α7nAChR, FLNA-TLR4 and α7nAChR-Aβ$_{42}$ complexes in the lymphocytes, lymphocytes (50 µg) from control subjects were incubated for 30 minutes at 37° C. in 0.25 ml Kreb's-Ringer without or with 100 nM Aβ 42, and lymphocytes (50 µg) from AD subjects were incubated for 30 minutes at 37° C. in 0.25 ml Kreb's-Ringer. Lymphocytes from control and AD subjects were also simultaneously incubated with or without Compound C0105 (1 nM). The incubation mixtures were aerated with 95% $O_2$/5% $CO_2$ every 10 minutes for 1 minute during the incubation. In the case that frozen lymphocyte samples were used, a lymphocyte suspension was gradually thawed by storing at −20° C. for 1 hour after removal from −80° C. and then at thawed at 4° C.

The incubation was terminated by adding 1 ml ice-cold $Ca^{2+}$-free Kreb's-Ringer containing 0.5 mM EGTA/0.1 mM EDTA, protease and phosphatase inhibitors followed by centrifugation. The resultant lymphocyte pellet was homogenized in 0.25 ml ice-cold immunoprecipitation buffer. The homogenates were centrifuged at 1000×g for 5 minutes (4° C.) and the supernatant (post-mitochondrial fraction) was sonicated for 10 seconds on ice and solubilized in 0.5% digitonin/0.2% sodium cholate/0.5% polyoxyethylene (40) nonyl phenyl ether (NP-40) for 60 minutes (4° C.) with end-to-end rotation. The resultant lysates were cleared by centrifugation at 50,000×g for 5 minutes and diluted with 0.75 ml immunoprecipitation buffer before co-immunoprecipitation to assess FLNA-α7nAChR, FLNA-TLR4, and α7nAChR-Aβ$_2$ complexes.

The FLNA-α7nAChR, FLNA-TLR4 and Aβ$_2$-α7nAChR complexes in the lysate were isolated by immunoprecipitation with 16-hour incubation at 4° C. with respective rabbit anti-FLNA (1 µg) or anti-Aβ$_{42}$ antibodies (1 µg) immobilized on protein A-conjugated agarose beads. The resultant immunocomplexes were pelleted by centrifugation at 4° C. After three washes with 1 ml ice-cold phosphate-buffered saline (PBS, pH 7.2) and centrifugation, the isolated FLNA-α7nAChR, FLNA-TLR4 and Aβ$_{42}$-α7nAChR complexes were separately solubilized by boiling for 5 minutes in 100 µl SDS-PAGE sample preparation buffer (62.5 mM Tris-HCl, pH 6.8; 10% glycerol, 2% SDS; 5% 2-mercaptoethanol, 0.1% bromophenol blue).

The content of α7nAChRs and TLR4s in 50% of the anti-FLNA and the content α7nAChRs in 50% of the anti-Aβ$_{42}$ immunoprecipitate was determined by Western blotting with monoclonal anti-α7nAChR or anti-TLR4 antibodies and quantified by densitometry. The FLNA-α7nAChR/TLR4 complex blots were stripped and re-probed with monoclonal anti-FLNA to assess immunoprecipitation efficiency and loading. The results are shown in FIG. 1A and quantified in FIG. 1C.

The amount of α7nAChR associated with FLNA is higher in AD lymphocytes compared to Control lymphocytes (compare AD K-R lanes and Control K-R lanes). The addition of Aβ$_{42}$ to Control lymphocytes increases the α7nAChR-FLNA association (compare Control K-R and Aβ$_{42}$ lanes). This treatment of Control lymphocytes with Aβ$_{42}$ mimics the level of α7nAChR-FLNA association of untreated AD lymphocytes (compare Control $A\beta_{42}$-treated lanes to AD1 and AD2 K-R lanes) and, as such, could serve as an AD surrogate standard. The addition of C0105 to $A\beta_{42}$-treated Control lymphocytes decreases the amount of α7nAChR-FLNA complexes compared to non-treatment (compare Control K-R and $A\beta_{42}$+C0105 treated lanes). This is decrease is also the case for the addition of C0105 to untreated AD lymphocytes (compare AD KR and C0105 lanes.

The amount of TLR4 associated with FLNA is higher in AD lymphocytes compared to Control lymphocytes (compare AD K-R lanes and Control K-R lanes). The addition of $A\beta_{42}$ to Control lymphocytes increases the TLR4-FLNA association (compare Control K-R and $A\beta_{42}$ lanes). This treatment of Control lymphocytes with $A\beta_{42}$ mimics the level of TLR4-FLNA association of untreated AD lymphocytes (compare Control $A\beta_{42}$-treated lanes to AD1 and AD2 K-R lanes). The addition of C0105 to $A\beta_{42}$-treated Control lymphocytes decreases the amount of TLR4-FLNA complexes compared to non-treatment (compare Control K-R and $A\beta_{42}$+C0105 treated lanes). This decrease is also seen for the addition of C0105 to untreated AD lymphocytes (compare AD KR and C0105 lanes.

The $A\beta_{42}$-α7nAChR complexes in the lysate were isolated by immunoprecipitation with 16-hour incubation at 4° C. with rabbit anti-$A\beta_{42}$ antibodies (1 µg) immobilized on protein A-conjugated agarose beads. The resultant immunocomplexes were pelleted by centrifugation at 4° C. After three washes with 1 ml ice-cold phosphate-buffered saline (PBS, pH 7.2) and centrifugation, the isolated $A\beta_{42}$-α7nAChR complexes were solubilized by boiling for 5 minutes in 100 µl SDS-PAGE sample preparation buffer (62.5 mM Tris-HCl, pH6.8; 10% glycerol, 2% SDS; 5% 2-mercaptoethanol, 0.1% bromophenol blue). The content of α7nAChRs in 50% of the anti-$A\beta_{42}$ immunoprecipitate was determined by Western blotting with monoclonal anti-α7nAChR, and quantified by densitometry as discussed in the first portion of Example 3B, below.

Figure 1B:
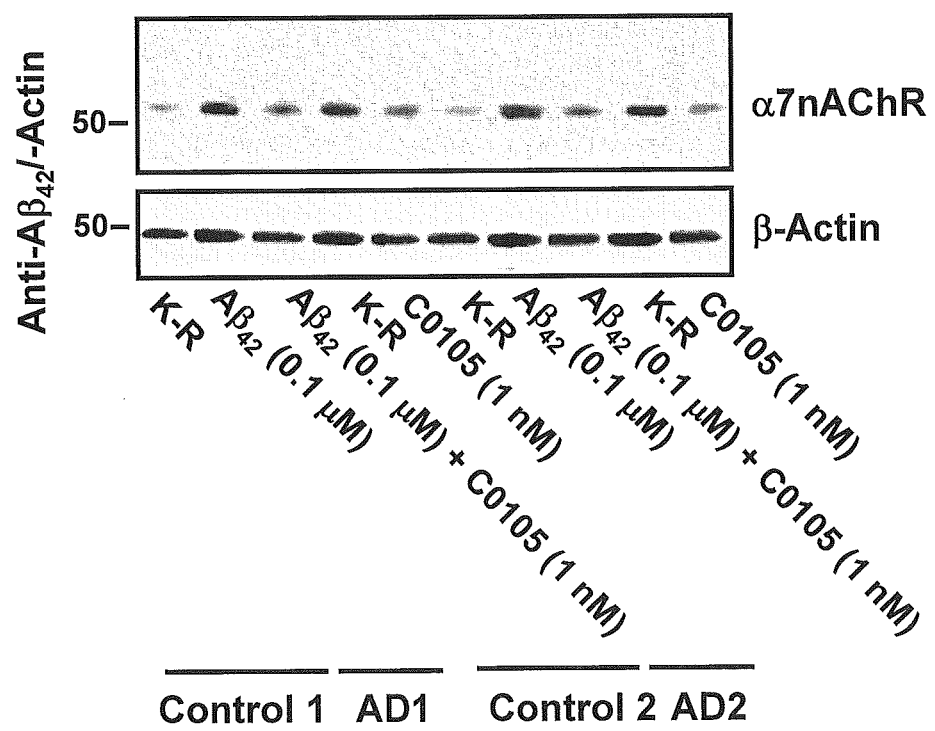
Figure 1C:
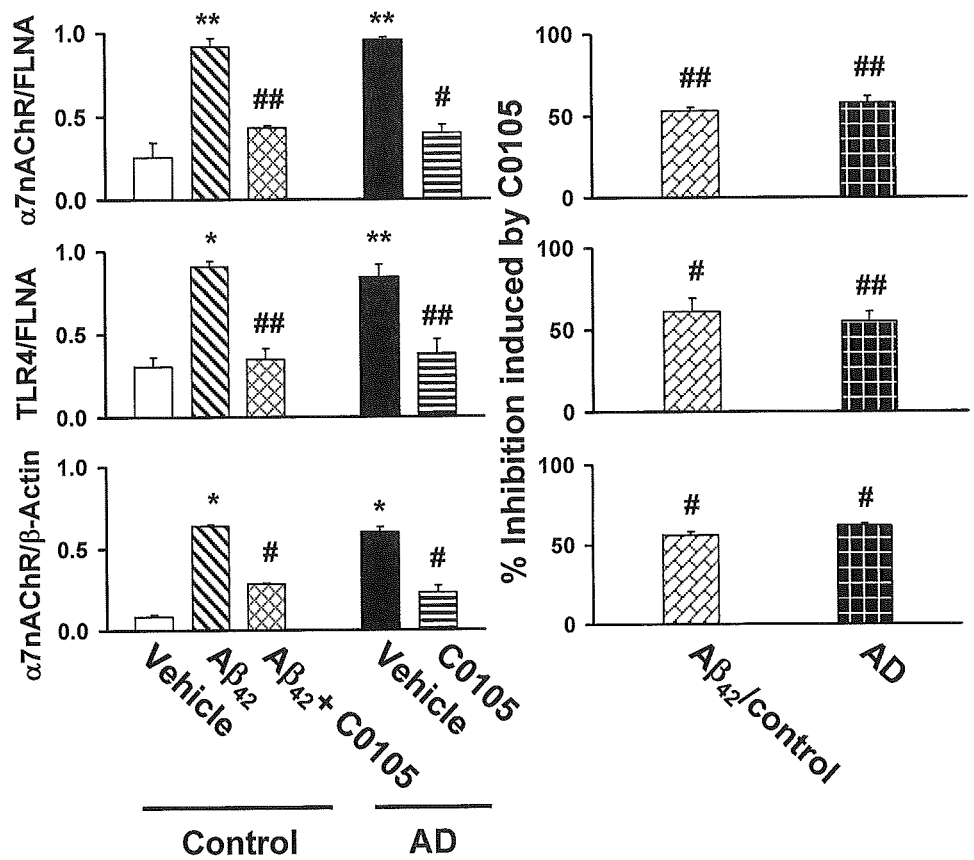

To determine $A\beta_{42}$-α7nAChR complex levels, immobilized rabbit anti-actin (0.5 µg)-protein A-conjugated agarose was added together with anti-$A\beta_{42}$ in the co-immunoprecipitation process. The content of β-actin in resultant immunoprecipitates was analyzed by immunoblotting using monoclonal anti-β-actin to illustrate even immunoprecipitation efficiency and loading. The results are shown in FIG. 1B and quantified in FIG. 1C. The amount of $A\beta_{42}$ associated with α7nAChR is higher in AD lymphocytes compared to Control lymphocytes. The addition of $A\beta_{42}$ to Control lymphocytes increases the $A\beta_{42}$-α7nAChR complexes (compare Control K-R and $A\beta_{42}$ lanes). The addition of C0105 to AD lymphocytes decreases the amount of $A\beta_{42}$-α7nAChR complexes compared to non-treatment (compare AD K-R and C0105 lanes).

EXAMPLE 3B

Clinical Studies

Western Blot Assay Assessment of FLNA-α7nAChR/TLR4 and $A\beta_{42}$-α7nAChR Association by Co-Immunoprecipitation Expanded studies were carried out following the procedures discussed below that involved the use of lymphocyte preparations from treatment-naïve (untreated), clinically diagnosed AD patients, Age Matched Control (AMC) subjects and from Young Cognitively Intact (YCI) subjects. The results of those studies are set out individually below for each of the three protein ratios discussed above (α7nAChR/FLNA, TLR4/FLNA and $A\beta_{42}$/α7nAChR).

A. The Association of α7nAChR with FLNA in Alzheimer's Patients and Comparison of the α7nAChR/FLNA Amounts from Patients and Normal Subjects' Lymphocyte Body Sample Preparations after Excess $A\beta_{42}$ Treatment In untreated lymphocyte body sample preparation portions (no addition of exogenous $A\beta_{42}$) the average ratio α7nAChR to FLNA is about 0.6 in Alzheimer's patients (n=20), about 0.2 in Young Cognitively Intact subjects (n=11) and 0.3 in Age-Matched Control Normal subjects (n=24), values consistent with the concept that FLNA is recruited to associate with α7nAChR in AD patients as a consequence of the binding of $A\beta_{42}$ to the α7nAChR. The range of values of association in Alzheimer's patients is about 0.3 to about 1.4, in Young Cognitively Intact subjects about 0.1 to about 0.4 and in Age-Matched Control normal subjects about 0.1 to about 0.8.

In $A\beta_{42}$-treated samples, the average ratio of α7nAChR to FLNA is approximately 0.8 in the Alzheimer's patients (AD), is approximately 0.9 in Young Cognitively Intact (YCI) subjects and is approximately 0.9 in Age-Matched Control (AMC) normal subjects, consistent with the concept of nearly complete occupancy of the α7nAChR in all of these populations, as a consequence of disease (in the case of an AD patient) or the added $A\beta_{42}$ (in the case of the excess $A\beta_{42}$ added to the Young Cognitively Intact and Age-Matched Control Normal Subjects' lymphocyte preparations). The range of values in 20 tested AD patients was about 0.5 to about 1.6, in 11 tested young cognitively intact subjects was about 0.5 to 1.3 and in 24 tested Age-Matched Control Normal subjects was about 0.5 to about 1.8.

Although, AD patients have a greater association of α7nAChR with FLNA, the range of values in both untreated and $A\beta_{42}$-treated test samples was effective, but was not optimal to discriminate between AD patients and normal subjects (YCI and AMC subjects). A more preferred result is obtained by comparing the differences between the values obtained from untreated lymphocytes to those treated with excess $A\beta_{42}$.

In AD patients, the average increase in the association of FLNA with α7nAChR after the addition of $A\beta_{42}$ was about 45 percent. That value compares to an about 290 percent increase in the association of FLNA with α7nAChR after treatment with $A\beta_{42}$ in Young Cognitively Intact subjects and about a 220 percent increase in the association of FLNA with α7nAChR in Age Matched Control subjects.

Importantly, there was no overlap in the range of values obtained with AD patients and Young Cognitively Intact Subjects. The range of values in AD patients was about 5 to about 130 percent, and in Young Cognitively Intact subjects the range was about 180 to about 470 percent. The range of values in Age-Matched Control subjects was about 6 to about 700. All AD patients had values less than about 130 percent and all Young Cognitively Intact patients had values greater than 180 percent. Of the Age-Matched Control Normal subjects, 15 of 24 (63 percent) had association values in excess of about 130 percent. The overlap in values between the AD patients Age-Matched Control Normals is to be expected. Although there is statistical separation between the AD and Age Matched Control Normals (p<0.001), approximately 35 percent of the Age-Matched Control Normals had values in the AD range, which is consistent with the number of older cognitively normal people (between ages 70-85) that upon autopsy after death had evidence of amyloid plaques similar to those in AD patients [Savva et al., *N Engl J Med* 360:2302-2309 (May 28, 2009)]. For these reasons, for the purposes of establishing ranges of values consistent with subjects having AD pathology and values consistent with no AD pathology, values obtained from AD patient are used to establish AD pathology ranges and values obtained from YCI subjects are to be used to establish ranges inconsistent with AD pathology.

With few exceptions, the absolute values of the ratios from an Alzheimer's patient can be used by themselves as indicative of a patient having AD. However, a more preferred result is obtained by comparing the difference between the first determination of the ratio (in the absence of $A\beta_{42}$) and the second determination in the presence of $A\beta_{42}$. Therefore, an increase of less than about 130 percent in the α7nAChR/FLNA ratio before and after the addition of excess $A\beta_{42}$ indicates that AD pathology is present. Values greater than about 180 percent indicate the absence of underlying AD pathology.

Because the overlap in the range of values obtained from AD patients and Age-Matched Normal subjects, other tests can be beneficial in confirming the presence or absence of AD pathology. These tests include, but are not limited to, the FLNA/TLR4 ratio as described, the $A\beta_{42}$/α7AChR ratio as described, levels of tau protein in the CSF, levels of phosphorylated tau in the CSF, PET imaging using Amyvid® (Lilly) or $^{18}$FDG or PIB-45, MRI, and the presence of auto-antibodies to CNS proteins.

B. Alzheimer's Patient Association of TLR4 with FLNA and TLR4/FLNA Ratio Comparisons from Subjects' Lymphocyte Preparations after Treatment with Excess $A\beta_{42}$ The ratio of TLR4 to FLNA in untreated lymphocyte preparations from AD patients averages about 0.5 (n=20), with a range of approximately 0.2 to about 0.8. In Young Cognitively Intact subjects, the TLR4/FLNA ratio in untreated lymphocyte preparations averages about 0.1 (n=11) with a range of about 0.1 to about 0.2 and in Age-Matched Control normal subjects, the TLR4/FLNA ratio in untreated lymphocyte preparations averages about 0.4 (n=24), with a range of approximately 0.1 to about 0.9

The ratio of TLR4 to FLNA in $A\beta_{42}$-treated lymphocyte body sample preparations from AD patients averages about 0.6 (n=20), with a range of approximately 0.4 to about 1.0. In Young Cognitively Intact Control normal subjects, the TLR4/FLNA ratio in treated lymphocyte preparations averaged about 0.1 (n=11), with a range of approximately 0.1 to about 0.2 and the TLR4/FLNA ratio in treated lymphocyte preparations from Age-Matched Control normal subject averaged about 0.4 (n=24) with a range of approximately 0.1 to about 0.9.

Although, examination of the absolute values of TLR4/FLNA ratio's indicates that AD patients have, on the average, a higher association of TLR4 with FLNA than is the case with Young Cognitively Intact subjects and similar values to Age-Matched Control Normal subjects, with extensive overlap of values, comparing association levels before and after treatment with excess $A\beta_{42}$ provides an enhanced differentiation of the three populations, and is preferred.

After treatment with excess $A\beta_{42}$, modest increases in lymphocyte preparation TLR4/FLNA ratios are exhibited from AD patients, the increase averaging approximately 40%. All AD patient lymphocyte preparations treated with excess $A\beta_{42}$ exhibited increases in their TLR4/FLNA ratios no greater than about 200 percent compared to their untreated lymphocytes. An increase of less than about 200 percent in the TLR4/FLNA ratio after treatment of lymphocyte body sample preparations with 442, therefore indicates an underlying AD pathology is present.

Lymphocyte body sample preparations from Age-matched Control Normal subjects after treatment with excess $A\beta_{42}$, on the other hand, demonstrate marked increase in the association of TLR4 with FLNA, averaging about 150 percent. Young Cognitively Intact subjects demonstrated increase in the association of TLR4 with FLNA, averaging about 300 percent. All Young Cognitively Intact Subjects (n=11) exhibited increases in their TLR4/FLNA ratios greater than about 180 percent. An increase of greater than 200 percent in the TLR4/FLNA ratio after treatment of lymphocyte body sample preparations with $A\beta_{42}$, therefore, indicates the absence of any AD pathology.

Because of the overlap in the range of values obtained from AD patients and Young Cognitively Intact subjects and the greater than expected overlap in the range of values obtained from AD patients and Age-Matched Control Normal subjects other tests as discussed above can be beneficial in confirming the presence or absence of AD pathology.

C. Alzheimer Patient Association of $A\beta_{42}$ α7AChR, and α7nAChR/$A\beta_{42}$ Comparison Ratios from Subjects' Lymphocyte Body Sample Preparations after Excess $A\beta_{42}$ Treatment The ratio of α7AChR to $A\beta_{42}$ in untreated lymphocyte preparations from AD patients averages about 0.5 (n=20), with a range of approximately 0.1 to about 1.0. In Young Cognitively Intact subjects the α7AChR/$A\beta_{42}$ ratio in untreated lymphocyte preparations averages about 0.3 (n=11), with a range of approximately 0.2 to about 0.5. The ratio of α7AChR to $A\beta_{42}$ in untreated lymphocyte preparations from Age-Matched Control Normal subjects averages about 0.4 (n=24), with a range of approximately 0.1 to about 1.1.

The ratio of α7AChR to $A\beta_{42}$ in $A\beta_{42}$-treated lymphocyte body sample preparations from AD patients averages about 0.6 (n=20), with a range of approximately 0.2 to about 1.1. In Young Cognitively Intact Normal subjects, the α7AChR to $A\beta_{42}$ ratio in treated lymphocyte preparations averaged about 0.9 (n=11), with a range of approximately 0.6 to about 1.4. In Age-Matched Control Normal subjects, the α7AChR to $A\beta_{42}$ ratio in treated lymphocyte preparations averaged about 0.9 (n=24), with a range of approximately 0.4 to about 1.2.

Although, examination of the absolute values of α7AChR/$A\beta_{42}$ ratios indicates that AD patients have, on the average, a higher association of $A\beta_{42}$ with α7ChR than is the case with either Young Cognitively Intact Normal subjects or Age-Matched Normal subjects, comparing association levels before and after treatment with excess $A\beta_{42}$ again provides an enhanced differentiation of the three populations, and is preferred.

After treatment with excess $A\beta_{42}$ (a saturating amount of $A\beta_{42}$), lymphocyte body sample preparations from AD patients exhibit modest increases in α7AChR/$A\beta_{42}$ ratios, the increase averaging approximately 60 percent. That value compares to an about 270 percent increase in α7AChR/$A\beta_{42}$ ratios after treatment with $A\beta_{42}$ in Young Cognitively Intact subjects and about a 150 percent increase α7AChR/Aβ$_{42}$ ratios in Age-Matched Control Normal subjects.

The range of values in AD patients was about 1.7 to about 230 percent, and in Young Cognitively Intact subjects the range was about 160 to about 380 percent. The range of values in Age-Matched Control Normal subjects was about 0 (zero) to about 430. All AD patient lymphocyte preparations treated with Aβ$_{42}$ showed increases in their α7AChR/Aβ$_{42}$ ratios no greater than about 230 percent compared to their untreated lymphocytes. Due to the overlap in value ranges between AD patients and Normal subjects an increase of less than about 100 percent in the α7AChR/Aβ$_{42}$ ratio after treatment of lymphocyte preparations with Aβ$_{42}$, therefore, indicates an underlying AD pathology to be present.

Lymphocyte preparations from Young Cognitively Intact Normal subjects after treatment with excess Aβ$_{42}$, on the other hand, demonstrate marked increases in the association of Aβ$_{42}$ with α7AChR, averaging about 270 percent. In Young Cognitively Intact Normal Subjects, 9 of 11 had increases in their α7AChR/Aβ$_{42}$ ratios greater than about 220 percent. An increase of greater than about 250 percent in the α7AChR/Aβ$_{42}$ ratio after treatment of lymphocyte preparations with Aβ$_{42}$, therefore, indicates the absence of AD pathology.

Because of the overlap in the range of values obtained from AD patients and Young Cognitively Intact and Age-Matched Control Normal subjects other tests as described previously can be beneficial in confirming the presence or absence of AD pathology.

Further clinical studies were carried out with a slightly modified procedure that is set out below.

Ex Vivo Incubation of Lymphocytes

1. Lymphocytes (50 μg) from test subjects were incubated with vehicle (0.1% DMSO containing Kreb's Ringer), 100 nM Aβ$_{42}$, 1 nM Compound C0105 or 100 nM Aβ$_{42}$+1 nM Compound C0105 (control only). Lymphocytes from AD subjects were incubated with vehicle or 1 nM Compound C0105.

2. Incubation was carried out at 37° C. for 30 minutes in 250 μl Kreb's-Ringer [25 mM HEPES, pH 7.4; 118 mM NaCl, 4.8 mM KCl, 25 mM NaHCO$_3$, 1.3 mM CaCl$_2$, 1.2 mM MgSO$_4$, 1.2 mM KH$_2$PO$_4$, 10 mM glucose, 100 μM ascorbic acid, protease inhibitor cocktail tablet (1 tablet/10 ml, Roche) that was aerated with 95% O$_2$/5% CO$_2$ for 10 minutes.

3. The incubation mixtures were aerated every 10 minutes for 1 minute during the incubation.

4. Lymphocytes were collected by centrifugation, sonicated on ice for 10 sec (50% output, Fisher Scientific) in 150 μl of protease and protein phosphatase-containing immunoprecipitation [IP] buffer (25 mM HEPES, pH 7.5; 200 mM NaCl, protease inhibitor tablet (1 tablet/10 ml), 2 μg/ml soybean trypsin inhibitor, 5 mM NaF, 1 mM sodium vanadate, 0.5 mM β-glycerophosphate and 0.1% 2-mercaptoethanol) and solubilized with 0.5% digitonin/0.2% sodium cholate/0.5% NP-40 for 1 hour at 4° C., adjust to total volume of 200 μl with end-over-end shacking. Following addition of 900 μl IP buffer, the entire content was centrifuged at 4° C. (13,000 g for 5 minutes) to remove insoluble debris.

Immunoprecipitation of FLNA-Associated Complexes

1. To assess the levels of FLNA-α7nAChR, FLNA-TLR4 complexes in the lymphocytes, the obtained lymphocyte lysate (0.5 ml) was added with 0.5 ml IP buffer, mixed and then immunoprecipitated with 1 μg of anti-FLNA (SC-7565, goat pAb, or SC-28284, rabbit pAb) for FLNA-α7nAChR, FLNA-TLR4 complexes).

2. To measure the level Aβ$_{42}$-α7nAChR complexes, the remained lymphocyte lysate (0.5 ml) was added with 0.5 ml IP buffer, mixed and then immunoprecipitated with anti-Aβ$_{42}$ (AB5078p-Chemicon rabbit pAb)/-actin (SC-1616-R, rabbit pAb).

3. Incubation takes place at 4° C. with end-over-end shaking for 30 minutes.

4. Suspension of the protein A/G-conjugated agarose beads (30 μl) were added, mixed and incubation continued for 2 hours at 4° C. with end-over-end shaking. It is noted that incubation can be about 16 hours (overnight) without affecting the quality of the results.

5. The immunocomplexes were isolated by centrifugation (13,000 g for 5 minutes).

6. The obtained immunoprecipitates were washed three times with 1 ml of ice-cold phosphate-buffered saline, pH 7.2 (PBS) and centrifugation.

7. The isolated anti-FLNA and anti-Aβ$_{42}$/-actin immunoprecipitates were solubilized by boiling for 5 minutes in 100 μl of SDS-PAGE sample preparation buffer (62.5 mM Tris-HCl, pH 6.8; 10% glycerol, 2% SDS; 5% 2-mercaptoethanol, 0.1% bromophenol blue).

8. After cooling down at room temperature, the solubilized immunoprecipitates were stored in −80° C. until use.

Western Blotting

1. Frozen immunoprecipitate solutions were removed from −80° C. freezer and placed on the bench until they were completely thawed. These immunoprecipitates were again boiled for 5 minutes and then permitted to cool down to room temperature and centrifuged at 13,000 g for 1 minute before loading.

2. Fifty μl of the each immunoprecipitate solution (50%) was loaded onto 7.5% SDS-PAGE (for FLNA-α7nAChR/-TLR4 complexes) or 10% SDS-PAGE (for Aβ$_{42}$-α7nAChR complexes and actin) along with molecular weight markers (5 μl, protein ladder from Fermentas-Thermo) usually in 1$^{st}$ left-hand lane. To ensure FLNA moves down the gel, 7.5% SDS-PAGE is run until the 55 KDa molecular weight marker is about 1.5 cm above the bottom. Pre-cast gradient gels can be used as well.

3. The protein samples were then size-fractionated under denaturing conditions according to manufacturer's specifics.

4. The well-separated proteins were transferred to 0.2 μm nitrocellulose membrane (Bio-Rad). Wet transfer is preferred (transfer condition: 300 mA, 2 hours for 7.5%, 1.5 hour for 10%) because high molecular weight proteins such as FLNA usually are not effectively transferred using semi-dry transfer.

5. The resultant nitrocellulose membranes were then washed three times (2 minutes each) with 0.1% Tween®-20 containing phosphate-buffered saline (PBS, pH 7.2) and then blocked at room temperature for 1 hour with 10% non-fat milk in 0.1% Tween®-20-containing PBS.

6. After being washed three times (2 minutes each) with 0.1% Tween®-20-containing PBS, the levels of α7nAChRs and TLR4s were detected using Western blotting with anti-α7nAChR (SC-58607, rat mAb) and anti-TLR4 (SC-13593, mouse mAb—if IP with rabbit pAb anti-FLNA; SC-30002, rabbit pAb if IP with goat anti-FLNA) for 2 hours at room temperature or preferably for overnight (about 16 hours) at 4° C. The levels of α7nAChRs in the solubilized anti-Aβ$_{42}$ immunoprecipitates were detected using Western blotting with anti-α7nAChR (SC-58607, rat mAb).

7. The membranes were then washed 3 times (2 minutes each) with 0.1% Tween®-20-containing PBS, then incubated with 1:7500 HRP-conjugated anti-species (rat, rabbit or mouse) IgG (pre-adsorbed, from Santa Cruz biotechnology) for 1 hour at room temperature. The dilution of secondary antibodies is adjusted if different sources of secondary antibodies are used.

8. The membranes were then washed 3 times (1 minutes each) with 0.1% Tween-20 containing PBS and then once with distilled water for 1 minutes. The immunoreactivity was detected by a chemiluminutesescent method (Supersignal chemiluminutesescent reagents–Pierce/Thermo), and visualized by immediate exposure to X-ray film for 10-30 seconds (depending on the intensity of the signal). Specific protein bands were quantified by densitometric scanning (GS-800 calibrated densitometer, Bio-Rad Laboratories).

9. The blots were then washed with distilled water, stripped by incubating with 10 ml of stripping buffer (Restore Western blot stripping buffer, Thermo #21063) for 5 minutes, washed 5 times with 0.1% Tween®-20-containing PBS and then blocked by incubating with 10% fat-free milk in 0.1% Tween®-20-containing PBS for 1 hour.

10. The blots were washed three times (2 minutes each) with 0.1% Tween®-20-containing PBS, the level of FLNA was determined by contacting with anti-FLNA (SC-58764, mouse mAb if IP with rabbit anti-FLNA pAb; SC-28284 rabbit pAb if IP with goat anti-FLNA) for 2 hours at room temperature. The level of β-actin was determined by contacting with anti-β-Actin (SC-4778 mouse mAb).

11. The membranes were then washed 3 times (2 minutes each) with 0.1% Tween®-20-containing PBS, then incubated with 1:7500 HRP-conjugated anti-species (rabbit or mouse) IgG (pre-adsorbed, from Santa Cruz biotechnology) for 1 hour at room temperature. The dilution of secondary antibodies is adjusted if different sources of secondary antibodies are used.

12. The membranes were then washed 3 times (1 minutes each) with 0.1% Tween®-20-containing PBS and then once with distilled water for 1 minute. The immunoreactivity was detected by a chemiluminutesescent method (Supersignal chemiluminutesescent reagents—Pierce/Thermo), and visualized by immediate exposure to X-ray film for 10-30 seconds (depending on the intensity of the signal). Specific protein bands were quantified by densitometric scanning (GS-800 calibrated densitometer, Bio-Rad Laboratories). The data are expressed as the ratio of α7nAChR/FLNA, TLR4/FLNA or α7nAChR/β-Actin optical intensities (in arbitrary units).

Composition of Buffers (L):
1. Running Buffer (5×):
   Tris (base): 15 g
   Glycine: 72 g
   SDS: 5 g
   Dilute to 1× before use.
2. Transfer Buffer:
   Tris (base): 14.5 g
   Glycine: 72.5 g
   SDS: 5 g
   in 800 ml of DD $H_2O$. Add 200 ml of Methanol (HPLC grade) before transfer. Tris and glycine in the transfer buffer are doubled to increase transfer efficiency.

Cumulative data from the clinical studies are set out in Tables 1-6. Those data are expressed as a as a percentage of increase over a basal ratio that was observed after admixture of excess exogenously supplied $Aβ_{42}$ to a lymphocyte preparation

TABLE 1

Alzheimer's Patients

| Patient Sample # | Aβ42/Basal % increase | Basal α7 OD | FLNA OD | α7/FLNA | Aβ42 α7 OD | FLNA OD | α7/FLNA |
|---|---|---|---|---|---|---|---|
| 78 | 5.03% | 1210 | 1285 | 0.94 | 1618 | 1636 | 0.99 |
| 67 | 8.66% | 754 | 1543 | 0.49 | 969 | 1825 | 0.53 |
| 10 | 7.64% | 1214 | 1267 | 0.96 | 1447 | 1403 | 1.03 |
| 1 | 15.70% | 1074 | 1102 | 0.97 | 1458 | 1293 | 1.13 |
| 43 | 11.40% | 738 | 1786 | 0.41 | 789 | 1714 | 0.46 |
| 79 | 12.32% | 1710 | 1718 | 1.00 | 1943 | 1738 | 1.12 |
| 80U | 12.90% | 845 | 1215 | 0.70 | 932 | 1187 | 0.79 |
| 31 | 13.00% | 1703 | 1197 | 1.42 | 1889 | 1175 | 1.61 |
| 47 | 20.31% | 893 | 1763 | 0.51 | 1092 | 1792 | 0.61 |
| 77 | 21.69% | 1042 | 1598 | 0.65 | 1299 | 1637 | 0.79 |
| 60 | 27.77% | 793 | 1361 | 0.58 | 1046 | 1405 | 0.74 |
| 70 | 34.14% | 1014 | 1583 | 0.64 | 1398 | 1627 | 0.86 |
| 69 | 38.38% | 1029 | 1688 | 0.61 | 1467 | 1739 | 0.84 |
| 62 | 96.05% | 425 | 1631 | 0.26 | 1011 | 1979 | 0.51 |
| 61 | 41.35% | 715 | 1358 | 0.53 | 995 | 1337 | 0.74 |
| 75 | 66.99% | 788 | 1636 | 0.48 | 1369 | 1702 | 0.80 |
| 76 | 98.73% | 672 | 1624 | 0.41 | 1407 | 1711 | 0.82 |
| 74 | 109.12% | 659 | 1854 | 0.36 | 1309 | 1761 | 0.74 |
| 72 | 129.91% | 587 | 1679 | 0.35 | 1356 | 1687 | 0.80 |
| 71 | 131.60% | 468 | 1362 | 0.34 | 1255 | 1577 | 0.80 |
| Average | 45.13% | 916.65 | 1512.50 | 0.63 | 1302.45 | 1596.25 | 0.84 |

TABLE 2

Young Cognitively Intact

| Sample # | Aβ42/Basal % increase | Basal α7 OD | FLNA OD | α7/FLNA | Aβ42 α7 OD | FLNA OD | α7/FLNA |
|---|---|---|---|---|---|---|---|
| YC8 | 179.05% | 661 | 1765 | 0.37 | 1786 | 1709 | 1.05 |
| YC1 | 196.08% | 611 | 1816 | 0.34 | 1828 | 1835 | 1.00 |

TABLE 2-continued

| | Young Cognitively Intact | | | | | | |
|---|---|---|---|---|---|---|---|
| Sample # | Aβ42/Basal % increase | Basal α7 OD | FLNA OD | α7/ FLNA | Aβ42 α7 OD | FLNA OD | α7/ FLNA |
| YC9 | 200.08% | 582 | 1775 | 0.33 | 1714 | 1742 | 0.98 |
| YC3 | 231.84% | 432 | 1922 | 0.22 | 1535 | 2058 | 0.75 |
| YC7 | 267.72% | 529 | 1721 | 0.31 | 1917 | 1696 | 1.13 |
| 81U | 268.23% | 187 | 1317 | 0.14 | 698 | 1335 | 0.52 |
| YC10 | 302.51% | 523 | 1668 | 0.31 | 2119 | 1679 | 1.26 |
| YC6 | 330.16% | 330 | 1648 | 0.20 | 1429 | 1659 | 0.86 |
| YC2 | 390.61% | 257 | 1653 | 0.16 | 1299 | 1703 | 0.76 |
| YC5 | 399.10% | 323 | 1628 | 0.20 | 1623 | 1639 | 0.99 |
| YC4 | 467.74% | 182 | 1947 | 0.09 | 1158 | 2182 | 0.53 |
| Average | 293.92% | 419.73 | 1714.55 | 0.24 | 1555.09 | 1748.82 | 0.89 |

TABLE 3

| | Alzheimer's Patients | | | | | | |
|---|---|---|---|---|---|---|---|
| Sample # | TLR4/Basal % increase | Basal TLR4 OD | FLNA OD | TLR4/ FLNA | Aβ42 TLR4 OD | FLNA OD | TLR4/ FLNA |
| 78 | 33.28% | 409 | 1285 | 0.32 | 694 | 1636 | 0.42 |
| 67 | 27.31% | 522 | 1543 | 0.34 | 786 | 1825 | 0.43 |
| 10 | 42.65% | 754 | 1267 | 0.60 | 1191 | 1403 | 0.85 |
| 1 | 1.17% | 759 | 1102 | 0.69 | 901 | 1293 | 0.70 |
| 43 | 1.12% | 982 | 1786 | 0.55 | 953 | 1714 | 0.56 |
| 79 | 10.68% | 802 | 1718 | 0.47 | 898 | 1738 | 0.52 |
| 80 | 5.42% | 467 | 1215 | 0.38 | 483 | 1192 | 0.41 |
| 31 | 26.82% | 988 | 1197 | 0.83 | 1230 | 1175 | 1.05 |
| 47 | 0.19% | 1032 | 1763 | 0.59 | 1051 | 1792 | 0.59 |
| 77 | 21.27% | 1201 | 1598 | 0.75 | 1492 | 1637 | 0.91 |
| 60 | 13.18% | 689 | 1361 | 0.51 | 805 | 1405 | 0.57 |
| 70 | −4.22% | 711 | 1583 | 0.45 | 829 | 1927 | 0.43 |
| 69 | 1.47% | 903 | 1688 | 0.53 | 944 | 1739 | 0.54 |
| 62 | 94.42% | 528 | 1631 | 0.323728 | 1238 | 1967 | 0.629385 |
| 61 | 12.19% | 966 | 1358 | 0.71 | 1067 | 1337 | 0.80 |
| 75 | 66.29% | 611 | 1636 | 0.37 | 1057 | 1702 | 0.62 |
| 76 | 44.41% | 813 | 1624 | 0.50 | 1422 | 1967 | 0.72 |
| 74 | 120.70% | 509 | 1854 | 0.27 | 1067 | 1761 | 0.61 |
| 72 | 213.35% | 384 | 1679 | 0.23 | 1209 | 1687 | 0.72 |
| 71 | 60.49% | 656 | 1362 | 0.48 | 1219 | 1577 | 0.77 |
| Average | 39.61% | 734.3 | 1512.5 | 0.494409 | 1026.8 | 1623.7 | 0.641809 |

TABLE 4

| | Young Cognitively Intact | | | | | | |
|---|---|---|---|---|---|---|---|
| Patient Sample # | TLR4/Basal % increase | Basal TLR4 OD | FLNA OD | TLR4/ FLNA | AB42 TLR4 OD | FLNA OD | TLR4/ FLNA |
| YC8 | 328.04% | 249 | 1765 | 0.14 | 1032 | 1709 | 0.60 |
| YC1 | 186.00% | 327 | 1816 | 0.18 | 945 | 1835 | 0.51 |
| YC9 | 284.86% | 287 | 1775 | 0.16 | 1084 | 1742 | 0.62 |
| YC3 | 184.93% | 314 | 1922 | 0.16 | 958 | 2058 | 0.47 |
| YC7 | 355.87% | 199 | 1721 | 0.12 | 894 | 1696 | 0.53 |
| 81U | 202.28% | 265 | 1317 | 0.20 | 812 | 1335 | 0.61 |
| YC10 | 305.30% | 276 | 1668 | 0.17 | 1126 | 1679 | 0.67 |
| YC6 | 391.37% | 187 | 1648 | 0.11 | 925 | 1659 | 0.56 |
| YC2 | 316.57% | 168 | 1653 | 0.10 | 721 | 1703 | 0.42 |
| YC5 | 482.21% | 166 | 1628 | 0.10 | 973 | 1639 | 0.59 |
| YC4 | 294.22% | 189 | 1947 | 0.10 | 835 | 2182 | 0.38 |
| Average | 302.88% | 238.82 | 1714.55 | 0.14 | 936.82 | 1748.82 | 0.54 |

TABLE 5

Alzheimer's Patients

| Sample # | Aβ42/Basal % increase | Basal α7 OD | Aβ42 OD | α7/Aβ42 | Aβ42 α7 OD | Aβ42 OD | α7/Aβ42 |
|---|---|---|---|---|---|---|---|
| 78 | 2.08% | 936 | 1363 | 0.69 | 1273 | 1816 | 0.70 |
| 67 | 19.31% | 741 | 1875 | 0.40 | 853 | 1809 | 0.47 |
| 10 | 1.68% | 1017 | 1719 | 0.59 | 1226 | 2038 | 0.60 |
| 1 | 6.72% | 608 | 1157 | 0.53 | 844 | 1505 | 0.56 |
| 43 | 16.88% | 981 | 1171 | 0.84 | 1128 | 1152 | 0.98 |
| 79 | 13.65% | 1226 | 1489 | 0.82 | 1354 | 1447 | 0.94 |
| 80 | 16.64% | 1180 | 1491 | 0.79 | 1344 | 1456 | 0.92 |
| 31 | 15.39% | 945 | 1269 | 0.74 | 1276 | 1485 | 0.86 |
| 47 | 6.51% | 1146 | 1080 | 1.06 | 1163 | 1029 | 1.13 |
| 77 | 58.82% | 311 | 1670 | 0.19 | 517 | 1748 | 0.30 |
| 60 | 25.84% | 291 | 1490 | 0.20 | 392 | 1595 | 0.25 |
| 70 | 58.77% | 481 | 1793 | 0.27 | 759 | 1782 | 0.43 |
| 69 | 18.56% | 842 | 1829 | 0.46 | 965 | 1768 | 0.55 |
| 62 | 56.83% | 483 | 1859 | 0.26 | 852 | 2091 | 0.41 |
| 61 | 14.37% | 466 | 1517 | 0.31 | 579 | 1648 | 0.35 |
| 75 | 134.20% | 195 | 1788 | 0.11 | 483 | 1891 | 0.26 |
| 76 | 125.27% | 167 | 1682 | 0.10 | 431 | 1927 | 0.22 |
| 74 | 101.21% | 563 | 1681 | 0.33 | 1275 | 1892 | 0.67 |
| 72 | 208.48% | 337 | 1641 | 0.21 | 1089 | 1719 | 0.63 |
| 71 | 226.82% | 362 | 1639 | 0.22 | 1134 | 1571 | 0.72 |
| Average | 56.40% | 663.9 | 1560.15 | 0.46 | 946.85 | 1668.45 | 0.60 |

TABLE 6

Young Cognitively Intact

| Patient Sample # | Aβ42/Basal % increase | Basal α7 OD | Aβ42 OD | α7/Aβ42 | Aβ42 α7 OD | Aβ42 OD | α7/Aβ42 |
|---|---|---|---|---|---|---|---|
| YC8 | 262.57% | 387 | 1967 | 0.20 | 1834 | 2571 | 0.71 |
| YC1 | 215.23% | 755 | 1660 | 0.45 | 2704 | 1886 | 1.43 |
| YC9 | 327.09% | 339 | 1950 | 0.17 | 2050 | 2761 | 0.74 |
| YC3 | 163.22% | 769 | 2177 | 0.35 | 2145 | 2307 | 0.93 |
| YC7 | 262.73% | 478 | 1958 | 0.24 | 2050 | 2315 | 0.89 |
| 81U | 195.12% | 356 | 1721 | 0.21 | 1014 | 1661 | 0.61 |
| YC10 | 382.30% | 301 | 2068 | 0.15 | 1861 | 2651 | 0.70 |
| YC6 | 259.94% | 446 | 2029 | 0.22 | 1834 | 2318 | 0.79 |
| YC2 | 379.63% | 274 | 1225 | 0.22 | 1547 | 1442 | 1.07 |
| YC5 | 260.41% | 421 | 1952 | 0.22 | 1721 | 2214 | 0.78 |
| YC4 | 222.76% | 484 | 1517 | 0.32 | 1798 | 1746 | 1.03 |
| Average | 70.92% | 455.45 | 1838.55 | 0.25 | 1868.91 | 2170.18 | 0.88 |

EXAMPLE 4

96-Well FITC-Solid Phase Method for Determining α7nAChR-FLNA, TLR4-FLNA and α7nAChR-Aβ$_{42}$ Complex Levels in Lymphocytes To prepare lymphocytes, 7 ml of venous blood was collected into an EDTA-containing collecting tube or S-monovette (Sarstedt). Collected blood (6 ml) was layered onto 6 ml of Histopaque®-1077 (Sigma) at 25° C., and the anticoagulated blood was centrifuged at 400×g for 30 minutes (25° C.) to yield plasma (top layer) and lymphocytes (opaque interface). The lymphocytes were washed twice by mixing with 6 ml of oxygenated K-R followed by centrifugation at 250×g for 10 minutes and resuspension.

The final pellet was resuspended in 250 µl of oxygenated K-R before protein content determination by the Bradford method and assessment of the levels of FLNA-α7nAChR/TLR4 and Aβ$_{42}$-α7nAChR complexes. To store lymphocytes, the lymphocyte pellet was resuspended in 250 µl of ice-cold oxygenated K-R containing 10% glycerol and was stored at −20° C. for 1 hour before storage at −80° C.

Figure 2:
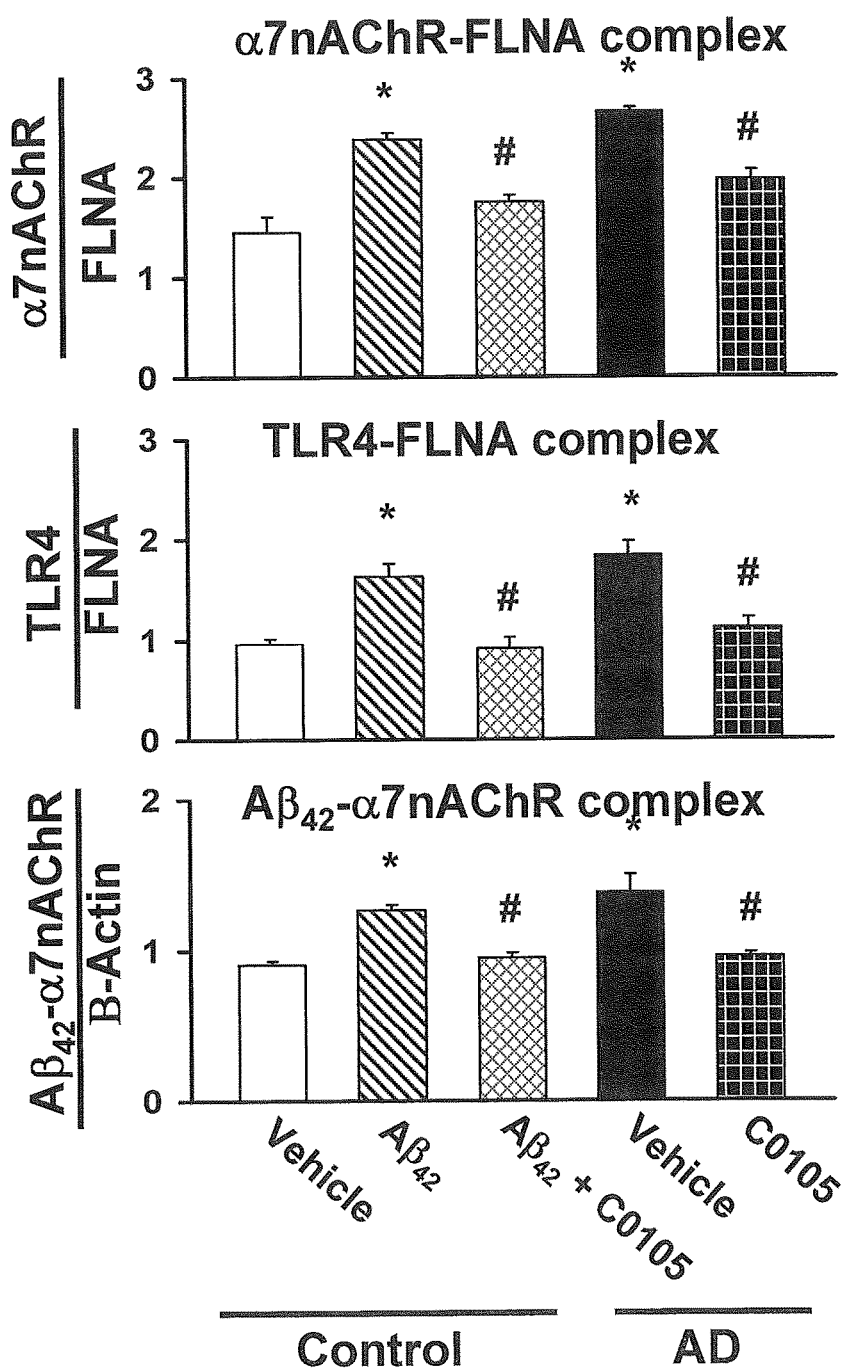
FIG. 2 illustrates the utility of a 96-well FITC-solid phase assay method to assess, in lymphocytes from AD patients and control subjects, levels of 1) the FLNA-α7nAChR association 2) the FLNA-TLR4 association and 3) α7nAChR-Aβ$_{42}$ complexes. The top two panels show α7nAChR and TLR4 levels detected using respective FITC-anti-α7nAChR or FITC-anti-TLR4 antibodies after capturing FLNA coupled to α7nAChR and TLR4, respectively, with an anti-FLNA antibody coated on the microtiter solid phase plate. The bottom panel shows α7nAChR-Aβ$_{42}$ complexes detected by a FITC-α7nAChR antibody binding α7nAChR coupled to Aβ$_{42}$ captured by an anti-Aβ$_{42}$ antibody coated on the microtiter solid phase plate.
Figure 3A:
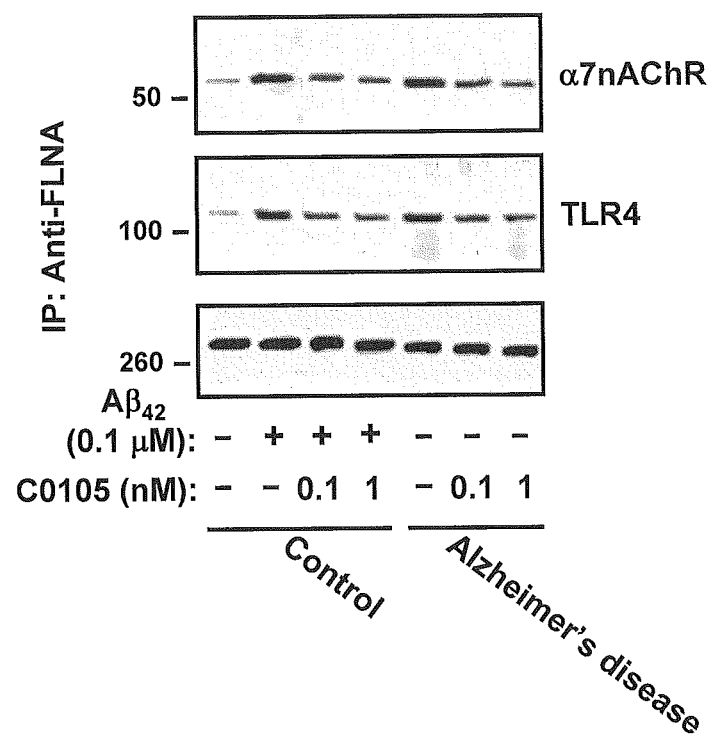
FIG. 3 in five panels illustrates that Compound C0105 decreased Aβ$_{42}$-induced FLNA association with both α7nAChR and TLR4 in human postmortem AD and control brain tissue. AD and age-matched control brain slices were treated with 0.1 or 1 nM concentrations of Compound C0105, and control brain slices were simultaneously treated with Aβ$_{42}$. The extent of FLNA association with α7nAChR or TLR4 was assessed in the solubilized synaptosomes by immunoprecipitating with immobilized anti-FLNA and Western blot detection (FIG. 3A) using antibodies specific to each of the second proteins of the complexes. Blots were analyzed by densitometric quantitation (FIG. 3B and FIG. 3D). AD tissue and Aβ$_{42}$-treated control tissue showed a markedly increased association of α7nAChR and TLR4 with FLNA, and Compound C0105 reduced these associations. Percent inhibition is depicted in FIG. 3C and FIG. 3E. n=11. Data are means±SEM. *p<0.01 vs. vehicle-treated control, #p<0.01 vs. Aβ$_{42}$-treated control or vehicle-treated AD.
Figure 3B:
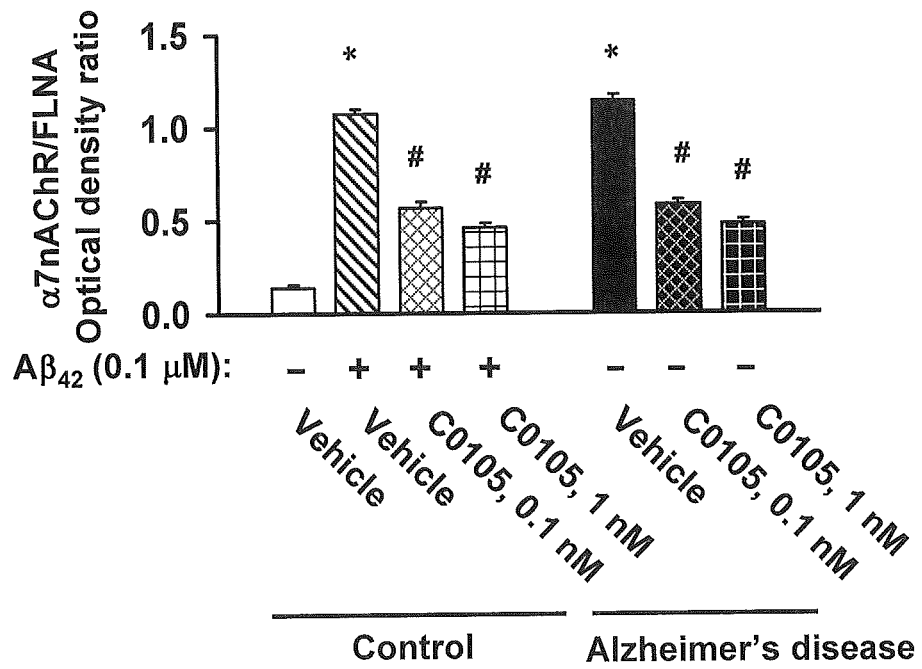
Figure 3C:
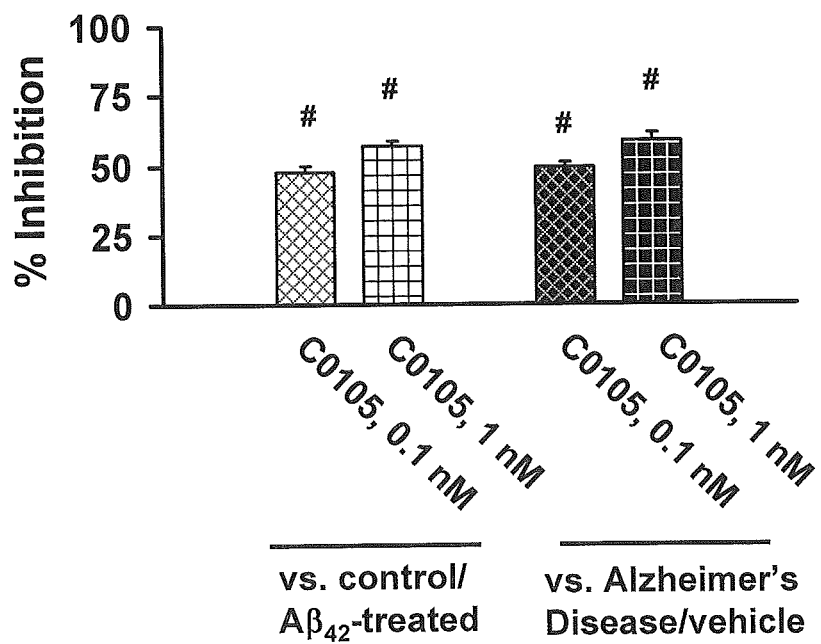
Figure 3D:
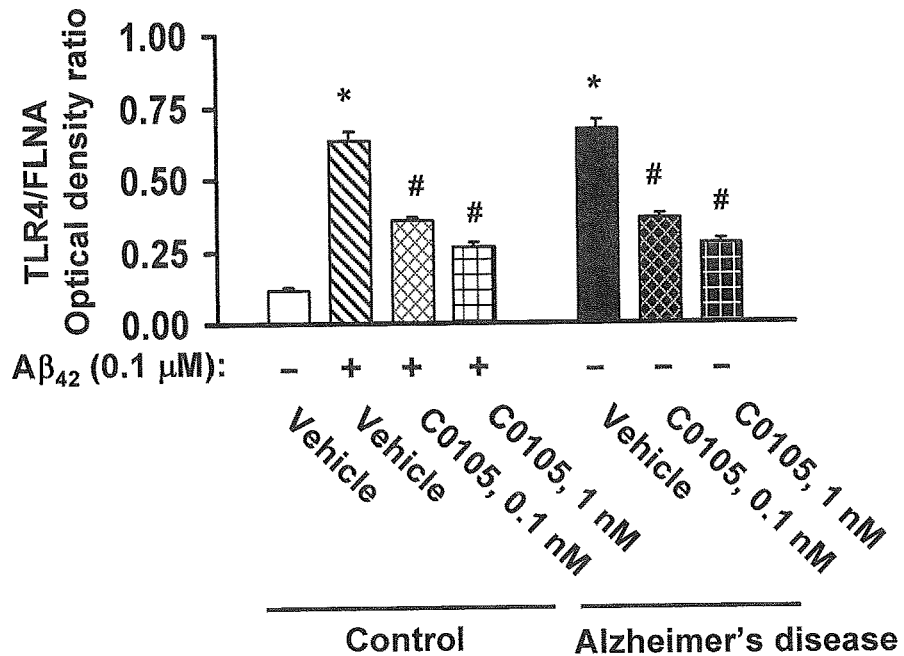
Figure 3E:
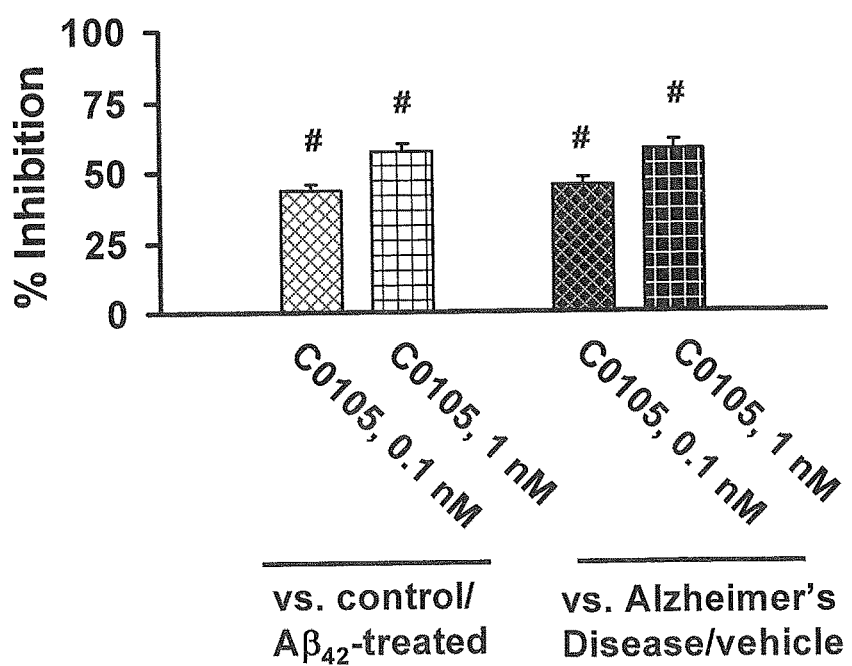

An objective of this study was to use lymphocyte α7nAChR-FLNA, TLR4-FLNA and Aβ$_{42}$-α7nAChR complex levels as individual biomarkers for tracking AD progression and the efficacy of AD treatments. These results are illustrated in FIG. 2.

Thus, FLNA associations with α7nAChR and with TLR4 are dramatically increased in AD and Aβ$_{42}$-treated control lymphocytes and 30 minute incubation with C0105 reduced these associations. Additionally, the level of Aβ$_{42}$-α7nAChR complexes was elevated in AD or Aβ$_{42}$-treated control lymphocytes. Incubation with 1 nM Compound C0105 for 30 minutes significantly reduced the increased associations with FLNA and the level of Aβ$_{42}$-treated control lymphocytes.

Anti-FLNA (rabbit polyclonal), anti-Aβ$_{42}$ (rabbit polyclonal) and anti-actin (rabbit polyclonal) antibodies were biotinylated using a biotinylation kit (Thermo Scientific, Pittsburgh, Pa.) according to manufacturer's recommendation. The free biotin was removed using a 10-KDa cut-off filter and centrifugation.

Lymphocytes (50 µg) from control subjects were incubated with vehicle (0.1% DMSO containing Kreb's Ringer), 100 nM Aβ$_{42}$ or 100 nM Aβ$_{42}$+1 nM Compound C0105. Lymphocytes from AD subjects were incubated with vehicle or 1 nM Compound C0105. Incubation was carried out at 37° C. for 30 minutes in 250 µl Kreb's-Ringer that was aerated with 95% O$_2$/5% CO$_2$ every 10 minutes for 1 minute during the incubation. Lymphocytes were collected by centrifugation, sonicated briefly and solubilized with 0.5% digitonin/0.2% sodium cholate/0.5% polyoxyethylene (40) nonyl phenyl ether (NP-40) in 100 µl of protease and protein phosphatase-containing PBS for 1 hour at 4° C. Following addition of 300 µl PBS, the entire content was centrifuged to remove insoluble debris.

To determine the levels of α7nAChR-FLNA and TLR4-FLNA complexes, 0.5 µg/well biotinylated rabbit polyclonal anti-FLNA were coated onto streptavidin-coated plates (Reacti-Bind™ NeutrAvidin™ High binding capacity coated 96-well plate). To measure the levels of Aβ$_{42}$-α7nAChR complexes, biotinylated rabbit polyclonal anti-Aβ$_{42}$ and anti-actin (0.25 µg each/well) were loaded onto streptavidin-coated plates (Reacti-Bind™ NeutrAvidin™ High binding capacity coated 96-well plate).

Plates were first washed 3 times with ice-cold 50 mM Tris HCl (pH 7.4) and incubated at 25° C. with above-mentioned biotinylated antibodies in 100 µl of 0.1% Tween®)-20 and 0.5% superblock (Thermo) containing phosphate-buffered saline, pH 7.2. The wells were washed twice with 200 µl of 0.1% Tween®-20 containing PBS. Plates were incubated with 150 µl of lymphocyte lysate derived from each of the above mentioned conditions for 1 hour at 25° C. for 1 hour (in duplicate). Plates were washed 3 times with ice-cold 50 mM Tris HCl (pH 7.4) and incubated at 30° C. with 0.5 µg/well un-conjugated mouse anti-α7nAChR (for α7nAChR-FLNA complexes), anti-α7nAChR or anti-β-actin (Aβ$_{42}$-α7nAChR complexes) or anti-TLR4 (for TLR4-FLNA complexes) for 1 hour.

After two 1-minute washes with 50 mM Tris HCl (pH 7.4), each well was incubated in 0.5 µg/well FITC-conjugated anti-mouse IgG (human and mouse absorbed) for 1 hour at 25° C. Plates were washed twice with 200 µl ice-cold Tris HCl, pH 7.4 and the residual FITC-Aβ$_{42}$ signals were determined by multimode plate reader, DTX880 (Beckman).

For the preliminary plate assay, β-actin was used for normalizing in the Aβ$_{42}$-α7nAChR complex assessment. Because exogenous Aβ$_{42}$ was added to the control samples (to assess effect of Compound C0105), an anti-β-actin antibody was used as well as the anti-Aβ$_{42}$ antibody on the plates that assess Aβ$_{42}$-α7nAChR complexes. The protein levels were normalized against the β-actin signal to be sure the same amount of protein was present in each well. The α7nAChR (α7nAChR that is stuck to Aβ$_{42}$, and is trapped by the anti-Aβ$_{42}$ antibody on the plate) is detected with a FITC-labeled anti-α7nAChR antibody. The anti-actin is not usually used.

EXAMPLE 5

Postmortem Human Brain Tissue Studies

This study protocol conformed to the Declaration of Helsinki: Ethical Principles for Biomedical Research Involving Human Beings (the 4$^{th}$ amendment) as reflected in a prior approval by the City College of New York and City University of New York Medical School human research committee. The participants had a uniform clinical evaluation that included a medical history, complete neurological examination, cognitive testing including Mini-Mental state examination and other cognitive tests on episodic memory, semantic memory and language, working memory, perceptual speed, and visuospatial ability as well as psychiatric rating. Based on this information, subjects received AD diagnoses based on NINCDS-ADRDA criteria. [McKhann et al., *Neurology* 34, 939-944 (1984).]

Postmortem brain tissues FCX from patients with clinically diagnosed sporadic AD and control tissues from normal, age-matched, neurologically normal individuals were obtained from the Harvard Brain Tissue Resource Center (HBTRC, Belmont, Mass.) and UCLA Brain Tissue Resource Center (UBTRC, Los Angeles, Calif.). Both HBTRC and UBTRC are supported in part by the National Institute of Health. The postmortem time intervals for collecting these brains were ≤13 hour (mean postmortem intervals for collection of AD and control brain samples were 6.0±0.9 hour and 5.8±0.8 hour, respectively). Diagnostic neuropathological examination was conducted on fixed sections stained with hematoxylin and eosin stain and with modified Bielschowsky silver staining [Yamamoto et al., *Neuropathol Appl Neurobiol* 12, 3-9 (1986)] to establish any disease diagnosis according to defined criteria [Hyman et al., *J Neuropathol Exp Neurol* 56, 1095-1097 (1997)] and brain tissue from age-matched controls was similarly screened.

The presence of both neuritic (amyloid) plaques and neurofibrillary tangles in all AD brains was confirmed by Nissl and Bielschowsky staining and characterized immunohistochemically with anti-Aβ$_{42}$ and -NFT staining in frontal and entorhinal cortex as well as hippocampus as described previously [Wang et al., *J Neurochem* 75, 1155-1161 (2000)]. Control tissues exhibited only minimal, localized microscopic neuropathology of AD (0-3 neuritic plaques/10× field and 0-6 NFTs/10× field in hippocampus). One gram blocks from Brodmann areas 10 and/or 46 of FCX were dissected using a band saw from fresh frozen coronal brain sections maintained at −80° C. All postmortem tissues were identified by an anonymous identification number, and experiments were performed as a best matched pair without knowledge of clinical information.

For in vitro assessments, postmortem tissues were gradually thawed (from −80° C. to −20° C.), sliced using a chilled McIlwain tissue chopper (200 µm×200 µm×3 mm) and suspended in ice-cold oxygenated Kreb's-Ringer solution (K-R), containing 25 mM HEPES, pH7.4, 118 mM NaCl, 4.8 mM KCl, 1.3 mM CaCl$_2$, 1.2 mM KH$_2$PO$_4$, 1.2 mM MgSO$_4$, 25 mM NaHCO$_3$, 10 mM glucose, 100 µM ascorbic acid, 50 µg/ml leupeptin, 0.2 mM PMSF, 25 µg/ml pepstatin A, and 0.01 U/ml soybean trypsin inhibitor (approximately 20 mg/1 ml K-R). Following centrifugation and two additional washes with 1 ml ice-cold K-R, brain slices were suspended in 1 ml K-R.

To examine effects of exogenous Aβ$_{42}$, approximately 20 mg of FCX from control subjects were incubated with 0.1 µM of Aβ$_{42}$ at 37° C. for 70 minutes. To test the effects of Compound C0105 on Aβ$_{42}$-incubated control and native AD tissues, Compound C0105 (0.1 and 1 nM) was added 10 minutes following 0.1 µM Aβ$_{42}$. Incubation continued for 1 hour in the dark. The incubation mixture in a total incubation volume of 0.5 ml was aerated for 1 minute every 15 minutes with 95% O$_2$/5% CO$_2$. Reaction was terminated by the addition of 1.5 ml of ice-cold Ca$^{2+}$-free K-R, and slices were collected by a brief centrifugation.

Western blot detection of α7nAChR or TLR4 in anti-FLNA immunoprecipitates demonstrate that FLNA association with α7nAChR and TLR4 are elevated in postmortem AD compared with control tissue. The addition of exogenous Aβ$_{42}$ to control tissue elevated these associations, and Compound C0105 incubation for 1 hour reduced these associations in both AD and $A\beta_{42}$-treated control tissue in this ex vivo setting (FIG. 3, A-E).

EXAMPLE 6

$A\beta_{42}$ Infusion in an ICV $A\beta_{42}$ Infusion Mouse Model Increases the Association of FLNA with α7nAChR and TLR4

Eight-week-old male and female E129 mice (30-35 g), progeny of the breeding pairs from Taconic (Germantown, N.Y.) were used in the intracerebroventricular (ICV) $A\beta_{42}$ study. Mice were maintained on a 12-hour light/dark cycle with food and water. All animal procedures comply with the National Institutes of Health Guide for Care Use of Laboratory Animals and were approved by the City College of New York Animal Care and Use Committee.

Intracerebroventricular $A\beta_{42}$ Administration and Compound Treatment

Mice anesthetized with 30 mg/kg sodium pentobarbital intraperitoneally were placed in a mouse stereotaxic surgery apparatus as described by Wang et al., *Biol Psychiatry* 67:522-530 (2010). Mice receiving 7-day continuous ICV $A\beta_{42}$ infusion were implanted with a minipump for mice (Alzet) that delivers 0.1 µl/hour through a surgical glue-secured cannula placed in the left ventricle at the following coordinates: [anterior-posterior from bregma, 3.0 mm; lateral, 1.0 mm; horizontal, 3.0 mm]. The $A\beta_{42}$ (0.2 nmol/µl) was dissolved in 10% DMSO containing 50 mM Tris, pH 9.0, to prevent aggregation. Each mouse received 4.8 nmol $A\beta_{42}$ daily for 7 days. Control mice received 7-day ICV infusion of vehicle.

To assess the effect of in vivo Compound C0105 on $A\beta_{42}$-elicited effects, mice received 10 mg/kg of C0105 by intraperitoneal (i.p.) injection daily for 2 weeks starting on the day of surgery (day 1: 2 hr after recovery from surgery, day 2-14 twice daily: between 10-11 a.m. and 3-4 p.m.). Twenty-four hr after the last injection, frontal cortex (FCX) and hippocampus from one half brain was solubilized for assessment of α7nAChR-filamin A (FLNA) complex level using published methods (Wang et al., above).

Brain synaptosomes (P2 fraction) were prepared from prefrontal cortex and hippocampus of treated mice sacrificed by rapid decapitation. Following methods described previously (Wang et al., *J Biol Chem* 278:31547-31553 (2003)) tissue was solubilized immediately after harvesting to obtain synaptosomes. The synaptosomes were washed twice and suspended in 2 ml of ice-cold Kreb's-Ringer (K-R): 25 mM HEPES, pH 7.4; 118 mM NaCl, 4.8 mM KCl, 25 mM NaHCO$_3$, 1.3 mM CaCl$_2$, 1.2 mM MgSO$_4$, 1.2 mM KH$_2$PO$_4$, 10 mM glucose, 100 µM ascorbic acid, mixture of protease and protein phosphatase inhibitors (Roche Diagnostics) that had been aerated for 10 min with 95% O$_2$/5% CO$_2$. The protein concentration was determined using the Bradford method (Bio-Rad).

These assessments used previously described co-immunoprecipitation methods. [Wang et al., *J Neurosci* 35, 10961-10973 (2009).] Two-hundred µg of synaptosomes from either postmortem brain slices or prefrontal cortex or hippocampus of treated mice were pelleted by centrifugation, solubilized by brief sonication in 250 µl of immunoprecipitation buffer (25 mM HEPES, pH7.5; 200 mM NaCl, 1 mM EDTA, 50 µg/ml leupeptin, 10 µg/ml aprotinin, 2 µg/ml soybean trypsin inhibitor, 0.04 mM PMSF, 5 mM NaF, 1 mM sodium vanadate, 0.5 mM β-glycerophosphate and 0.1% 2-mercaptoethanol containing 0.5% digitonin, 0.2% sodium cholate and 0.5% NP-40) and incubated at 4° C. with end-to-end shaking for 1 hour.

Following dilution with 750 µl of ice-cold immunoprecipitation buffer and centrifugation (4° C.) to remove insoluble debris, the α7nAChR-/LR4-FLNA and $A\beta_{42}$-α7nAChR complexes in the lysate were separately isolated by immunoprecipitation with 16-hour incubation at 4° C. with respective rabbit anti-FLNA (1 µg) and anti-$A\beta_{42}$ antibodies (1 µg) immobilized on protein A-conjugated agarose beads. The resultant immunocomplexes were pelleted by centrifugation at 4° C.

After three washes with 1 ml of ice-cold phosphate-buffered saline (PBS) (pH 7.2) and centrifugation, the isolated α7nAChR/TLR4, α7nAChR/FLNA and $A\beta_{42}$/α7nAChR complexes were solubilized by boiling for 5 minutes in 100 µl of SDS-PAGE sample preparation buffer (62.5 mM Tris-HCl, pH6.8; 10% glycerol, 2% SDS; 5% 2-mercaptoethanol, 0.1% bromophenol blue). The content of α7nAChRs/TLR4s in 50% of the anti-FLNA and α7nAChRs in 50% of the anti-$A\beta_{42}$ immunoprecipitate was determined by Western blotting with monoclonal anti-α7nAChR or -TLR4 antibodies.

The α7nAChR-/TLR4-FLNA complex blots were stripped and re-probed with monoclonal anti-FLNA to assess immunoprecipitation efficiency and loading. To determine $A\beta_{42}$-α7nAChR complex levels, immobilized rabbit anti-actin (0.5 µg)-protein A-conjugated agarose was added together with anti-$A\beta_{42}$ in the co-immunoprecipitation process. The content of β-actin in resultant immunoprecipitates was analyzed by immunoblotting using monoclonal anti-β-actin to illustrate even immunoprecipitation efficiency and loading.

In the ICV $A\beta_{42}$ infusion mouse model of Alzheimer's disease, $A\beta_{42}$ dramatically increased FLNA association with both α7nAChR and TLR4. Twice daily treatment with 10 mg/kg Compound C0105 markedly reduced the effects of the $A\beta_{42}$ infusion.

Figure 4:
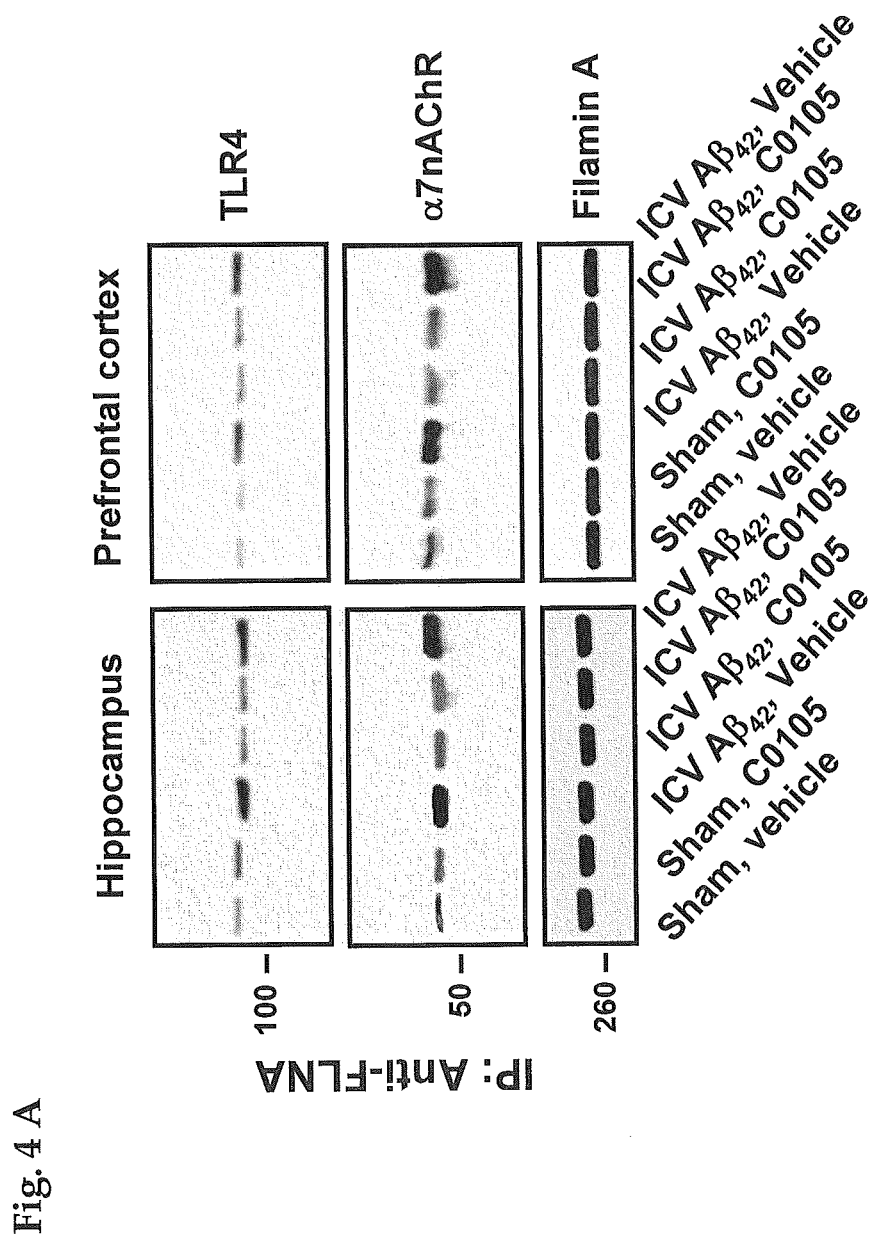
FIG. 4 in three parts illustrates that the systemic administration of Compound C0105 to mice decreased Aβ$_{42}$-induced FLNA association with both α7nAChR and toll-like receptor 4 (TLR4). Thus, synaptosomes prepared from pre-frontal cortex and hippocampus of mice receiving continuous intracerebroventricular (ICV) infusion of Aβ$_{42}$ or vehicle and twice daily injections of Compound C0105 or vehicle were analyzed for their FLNA-α7nAChR and FLNA-TLR4 interactions. The extent of FLNA association with α7nAChR or TLR4 was assessed in the solubilized synaptosomes by immunoprecipitation with immobilized anti-FLNA and Western blot detection (FIG. 4A) using antibodies specific to each receptor. Blots were analyzed by densitometric quantitation (FIG. 4B). $A\beta_{42}$ greatly increased association of α7nAChR and TLR4 with FLNA, and Compound C0105 decreased these $A\beta_{42}$-induced increases. Percent inhibition is depicted in FIG. 4C. n=3. Data are means±SEM. *p<0.01 vs. sham, vehicle; #p<0.01 vs. $A\beta_{42}$, vehicle.
Figure 4B:
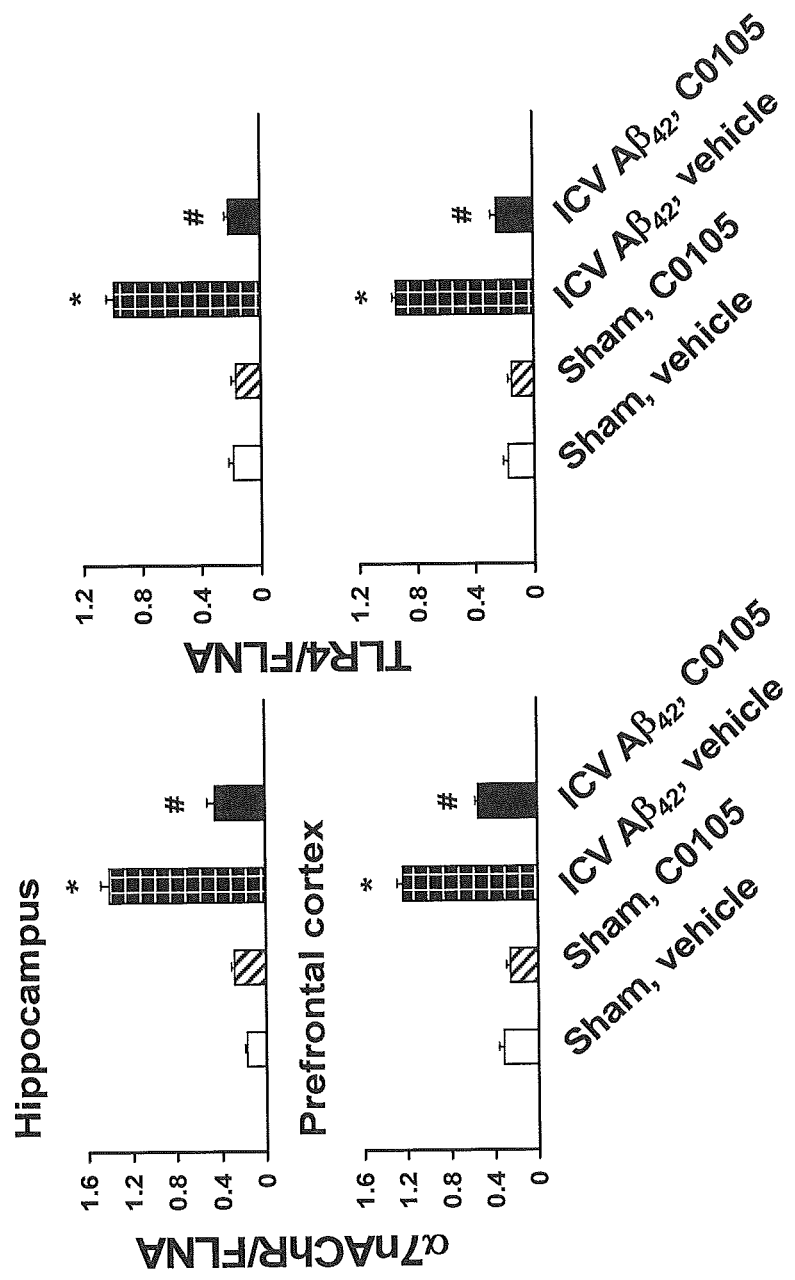
FIG. 4C illustrates similar results to those of FIGS. 14A and 14B from a separate, but similar study. Data are means±SEM. **p<0.05, *p<0.01 vs. $A\beta_{42}$ alone. The letter designation "M" that accompanies many of the "C-series" compounds is omitted from FIG. 14, the remaining figures and most discussions of the figures and compounds hereinafter for ease in expression. Structural formulas of the compounds used in this and the other figures are provided hereinafter.
Figure 4C:
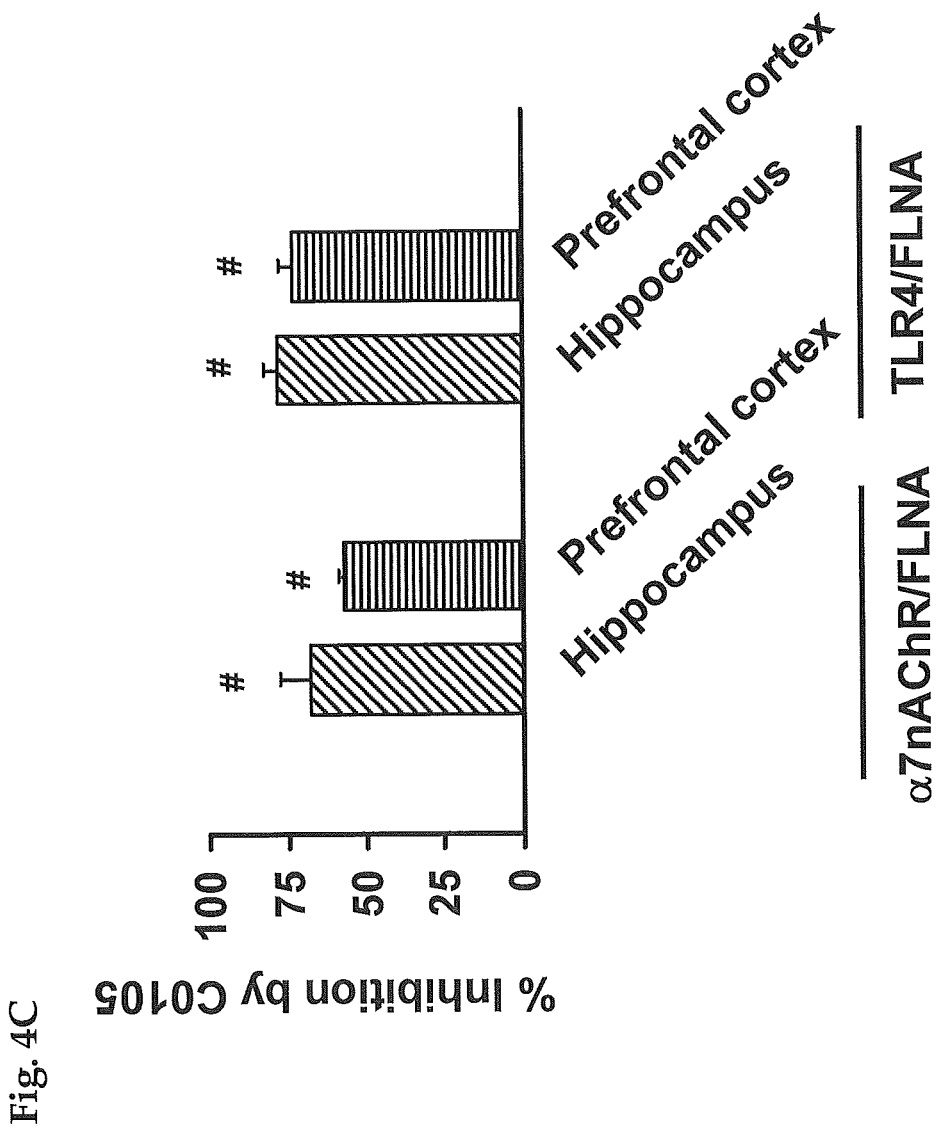
Figure 5A:
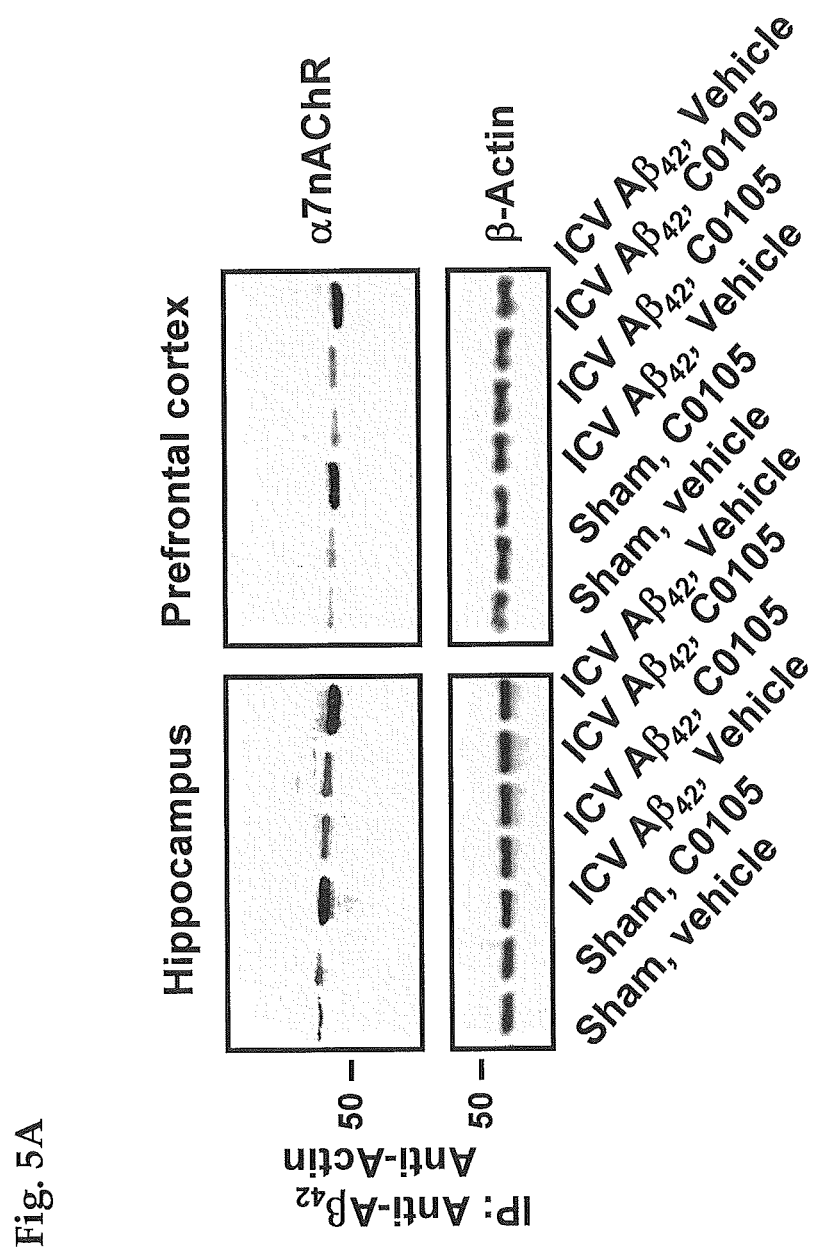
FIG. 5 in three parts illustrates that administration of Compound C0105 to mice reduces $A\beta_{42}$-α7nAChR complexes. Twice daily treatment of mice with Compound C0105 greatly reduced the level of $A\beta_{42}$-α7nAChR complexes in both prefrontal cortex and hippocampus in ICV $A\beta_{42}$-infused mice; n=7 or n=8. Western blots (FIG. 5A) were analyzed by densitometric quantitation (FIG. 5B). Percent inhibition is depicted in FIG. 5C. Data are means±SEM. *p<0.01 vs. sham, vehicle; #p<0.01 vs. $A\beta_{42}$, vehicle.

Compound C0105 reduced $A\beta_{42}$-induced increases in FLNA associations with both α7nAChR and TLR4 (FIG. 4), suggesting a reduction in $A\beta_{42}$-mediated signaling of both these receptors. The high-affinity binding of C0105 to FLNA appears to reduce $A\beta_{42}$ signaling via α7nAChR by reducing $A\beta_{42}$ binding to α7nAChR: the level of these $A\beta_{42}$-α7nAChR complexes is reduced in C0105-treated animals (FIG. 5).

Importantly, because FLNA association with TLR4 is increased by $A\beta_{42}$ and normalized by Compound C0105, whether the inflammatory cytokine release after ICV $A\beta_{42}$ infusion would be suppressed by Compound C0105 treatment was assessed. ICV $A\beta_{42}$ infusion did increase IL-6, TNF-α and IL-1β production. Compound C0105 treatment completely abolished the $A\beta_{42}$-induced IL-6 production and suppressed TNF-α and IL-1β levels by 86 and 80%, respectively (FIG. 6).

EXAMPLE 7

α7nAChR/FLNA ELISA

A further set of ELISA assays was conducted using lymphocyte lysates and determining only the α7nAChR/FLNA protein amount, rather than all three ratios or amounts. Experimental conditions were optimized for highest signal-to-noise ratio and linear detection range established.

Materials and Methods

The capture antibody was the mouse anti-human Filamin A SC-17749 (Santa Cruz Biotechnology), and rabbit anti-human α7nAChR SC-5544 (Santa Cruz Biotechnology Santa Cruz Biotechnology) as the detection antibody. The assays were carried out in Santa Cruz Flat Bottom Plates.

Lysis buffer was PBS with 0.5% digitonin+0.2% sodium cholate+0.5% NP-40+1× Proteinase inhibitor cocktail (no EDTA; Thermo Scientific). PBS buffer used was 1×PBS (Mg-, and Ca-free) from Thermo Scientific, whereas PBST was 1×PBS+0.05% Tween®-20.

Coating buffer was prepared by dissolving 1.59 g of $Na_2CO_3$ in 0.9 L distilled $H_2O$, to which was added 0.1 g $NaN_3$ and 3.93 g of $NaHCO_3$. The pH value was adjusted to 9.6, and the volume adjusted to 1 L with additional distilled $H_2O$. Santa Cruz BSA blocking buffer supplemented with 1% BSA (sc-293965).

The HRP Detection Reagent (TMB) was prepared using 1-Step Ultra TMB-ELISA, (Cat#34028; Thermo Scientific). Standard protocol using 100 µl of the TMB substrate solution per each microplate well, followed by 10-15 minute incubation (or until color develops) and stopping reaction by adding 100 µl of 2 M sulfuric acid to each well. Absorbance ($OD_{450}$) measured at 450 nm. Santa Cruz BSA blocking buffer was used supplemented with 1% BSA (SC-293965), and assays were carried out using a Molecular Devices Spectramax™ PLUS ELISA plate reader at 450 nm.

Lymphocyte Isolation and Cell Lysis

AD patient samples: 20 microtubes (labeled #1-#20; 100 ul volume each) with AD patients lymphocytes were received frozen on dry ice. Samples were kept at −20° C. freezer for 1 hour, following thawing at 4° C. Lymphocytes were collected by centrifugation, sonicated for 10 seconds on ice and solubilized in 0.5% digitonin/0.2% sodium cholate/0.5% NP-40 supplemented with 1× Proteinase inhibitor cocktail (Thermo) for 60 minutes (4° C.) with tube rotation. Ice-cold PBS (300 µl) was added and entire contents were centrifuged to remove insoluble debris.

Normal patient sample was prepared by following procedure: 8 mL of venous blood was collected into cat#362761 BD Vacutainer™ CPT tube (cell preparation tube with sodium citrate) and following manufacturer's recommended protocol for white blood cells isolation (including two centrifugation/PBS wash steps). Resulting white blood cells were collected by centrifugation, sonicated at 50 W for 10 seconds on ice and solubilized in 0.5% digitonin/0.2% sodium cholate/0.5% NP-40 (final concentration) supplemented with 1× Proteinase inhibitor cocktail (Thermo) for 60 minutes (4° C.) with tube rotation. Ice-cold PBS (300 µl) was added and entire content was centrifuged to remove insoluble debris, resulting in "NP sample".

The AD samples #1-4 were combined and assayed by Bradford assay to establish total protein concentration:AD sample #1-4=1.92 µg/µl.

The AD sample was split into two (+/−C0105 treatment) and diluted in 1×PBS for further analysis.

C0105 Treatment

Compound C0105 treatment was performed using AD patient white blood cells resuspended in 1×PBS and treated with: a) 10 µM Compound C0105 (final concentration), and b) control (PBS only) for 60 minutes at 37° C. (total volume is 400 µl of each sample).

Indirect ELISA Study

Anti-Filamin A antibody (SC-17749) was diluted in Coating Buffer (at dilution ratio of 1:30) and 100 µl sample loaded per well and incubated 2.5 hours at room temperature (RT). The plate was covered with adhesive cover to prevent evaporation. Followed by washing of the microtiter plate with 150 µl of Blocking Buffer (supplemented with 1% BSA) and added 100 µl of Blocking Buffer to the wells for 30 minutes at RT.

AD samples (AD patients lymphocytes, as described above) were used to generate serial dilution series samples (dilution performed in PBS) and 100 µl sample loaded per well and incubated 1 hour at RT (total protein concentration is indicated as established by Bradford assay, as described above). The plate was covered with adhesive cover to prevent evaporation, followed by washing each well two times with 160 µl PBST Buffer.

After washing of the microtiter plate with washing buffer, 100 µl of α7nAChR primary antibody (SC-5544) were added per well (1:50 dilution ratio) in 1×PBS and incubated for 1 hour at RT.

The plate was washed two times with PBST buffer, and 100 ml of HRP-conjugated secondary antibody diluted in 1×PBS was added to each well and incubated at RT for 1 hour. The plate was washed three times with PBST buffer, and TMB reagent substrate for detection of horseradish peroxidase (HRP) enzyme was added (100 ml of the TMB substrate solution per each microplate well, followed by 10-15 minute incubation (or until color developed) and stopping reaction by adding 100 ml of 2 M sulfuric acid to each well. Absorbance ($OD_{450}$) measured at 450 nm).

A curve was generated using the data produced by serial dilutions and with concentrations indicated on the X axis vs absorbance value indicated on the Y axis to provide quantitative measures.

Figure 17A:
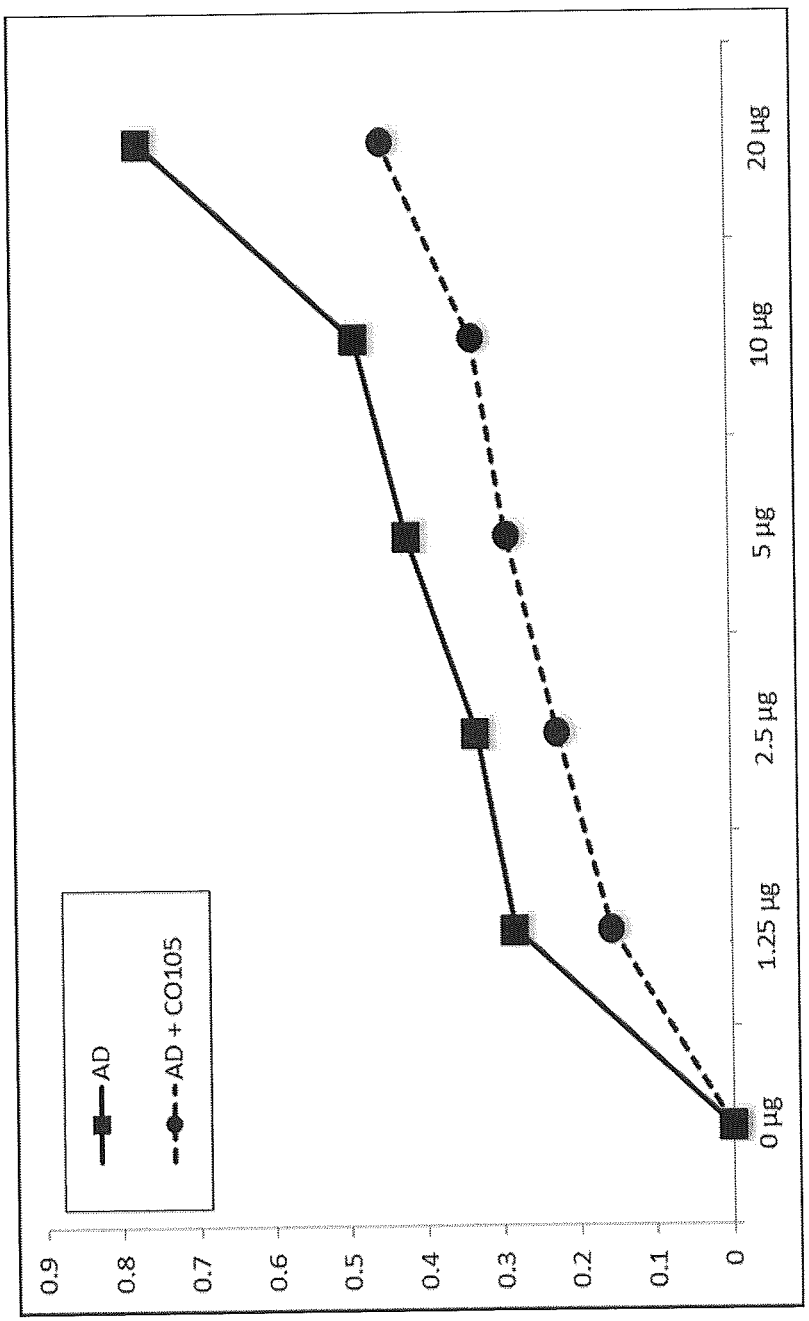
FIG. 17A is a graph of data from a lysate from an AD patient (filled squares) and that same lymphocyte lysate to which sufficient Compound C0105 (filled circles) was added to provide a 10 μM concentration.

Summary data from four replicate studies are shown in the Table below (and FIG. 17A) with data obtained after subtraction of background.

| Analyzed Sample | Optical Density α7nAChR/FLNA Weight of Lysate Per Well (mg) | | | | | |
|---|---|---|---|---|---|---|
| | 0 | 1.25 | 2.5 | 5 | 10 | 20 |
| AD Average | 0 | 0.283725 | 0.332475 | 0.420325 | 0.487425 | 0.769825 |
| AD StDv | 0 | 0.030384 | 0.021754 | 0.05033 | 0.02996 | 0.086486 |
| AD + C0105 Average | 0 | 0.15715 | 0.226125 | 0.291025 | 0.3349 | 0.4504 |
| AD + C0105 StDv | 0 | 0.050422 | 0.070406 | 0.062596 | 0.025613 | 0.045808 |

Preincubation of AD lymphocytes with Compound C0105 resulted in a significant reduction in the amount of α7nAChR associated with FLNA. The amount of α7nAChR associated with FLNA increased with the amount of lysate added to the wells of the microtiter plate.

Figure 17B:
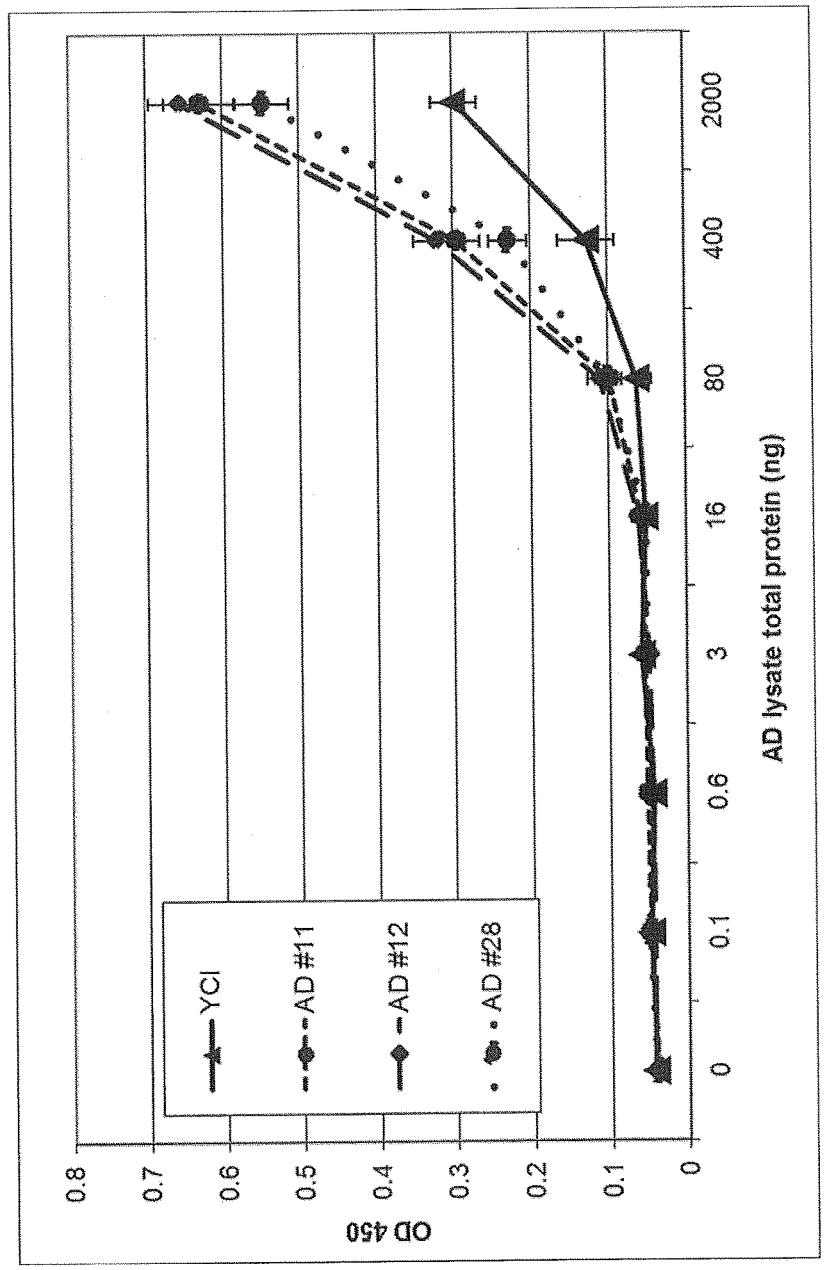
FIG. 17B is a graph showing data from lysates from patients with Alzheimer's Disease (AD) and young cognitively intact individuals (YCI) to which no additions were made.

A similar series of studies were conducted using lymphocytes obtained from patients clinically determined to have AD and from pooled lymphocytes obtained from young cognitively intact (YCI) subjects. Here, the capture monoclonal was SC-28284 H300 anti-FLNA and the anti-α7nAChR SC-37428 84 monoclonal was used as the detection antibody, followed by use a HRP-linked antibody to the detection antibodies. The results of detection of 0 (zero) to 2000 ng of lysate added to the wells are shown in FIG. 17B along with data from YCI lymphocyte lysates. Consistent with data obtained from Western blot analysis of AD and YCI lymphocyte lysates, there is a significant increase in the amount of α7nAChR associated with FLNA in AD patients compared to that from YCI subjects.

Figure 18A:
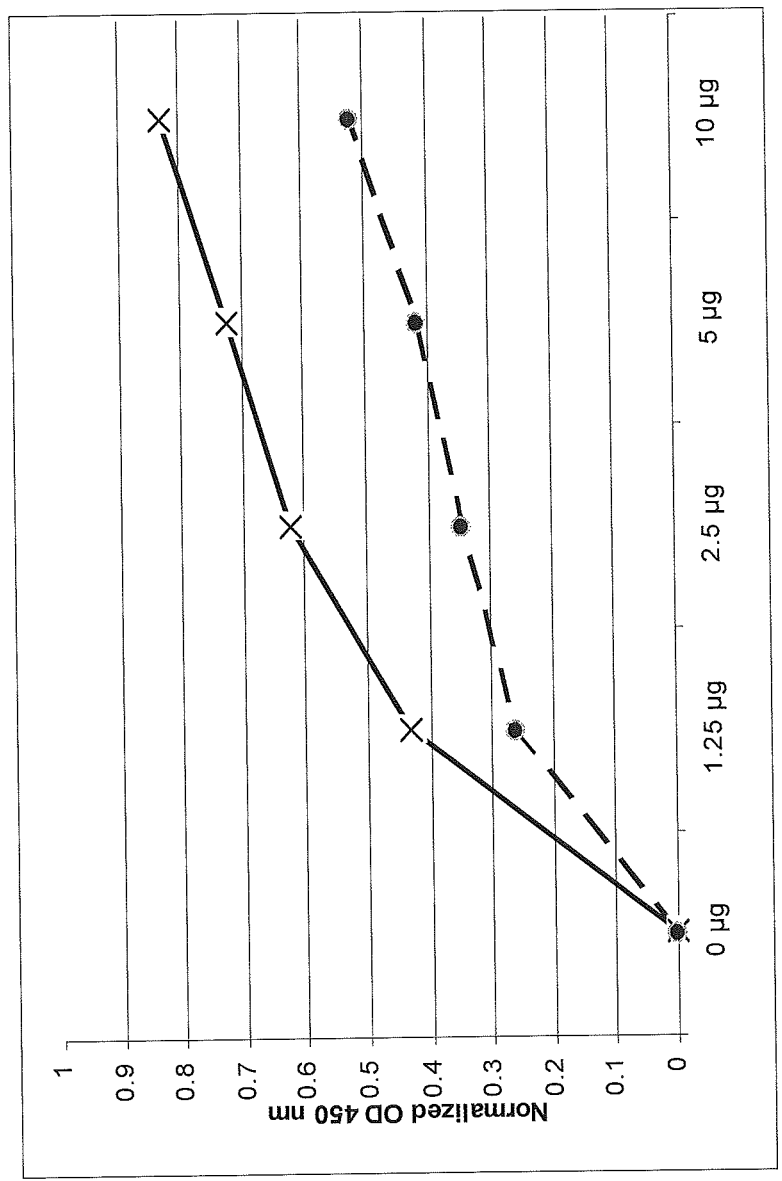
Figure 18B:
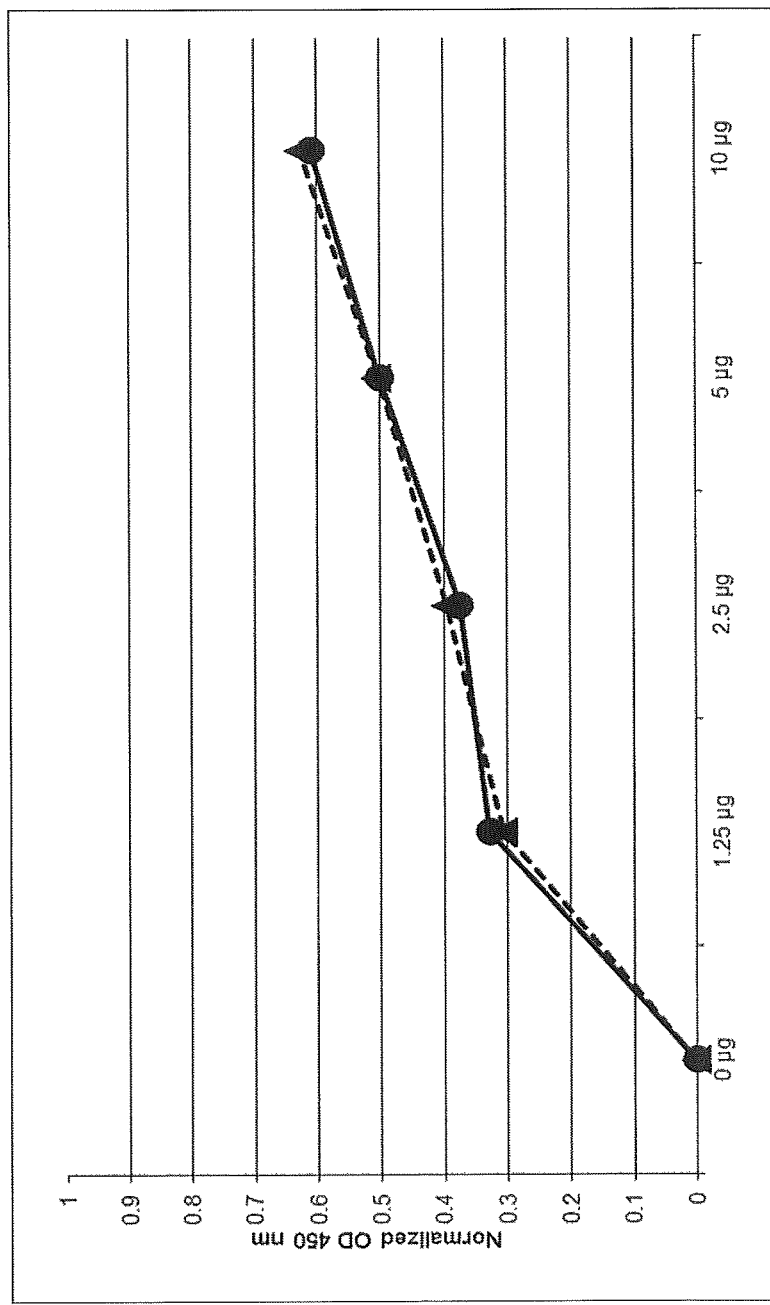
FIG. 18B shows a similar study using lysate from the lymphocytes of a young cognitively intact (YCI) subject with Compound C0105 added to provide a 10 µM concentration to the lysate (filled circles) and lysate without added compound (filled triangles).

A plot of the α7nAChR/FLNA amounts present in lysates from an AD patient (AD) and the amounts found after addition of 10 μM Compound C0105 (AD+C0105) to each lysate prior to performing the assay to provide a concentration of 10 μM (FIG. 18A). A similar study with (YCI+C0105) and without (YCI) Compound C0105 added to 10 μM using lymphocytes from YCI is shown in FIG. 18B, going to 10 μg rather than to 20 μg of lysate loading per well.

As is seen in FIG. 18A, the addition of Compound CO105 to AD lymphocyte preparations results in a significant reduction in the amount of α7nAChR/FLNA complex. As is seen from FIG. 18B, there is substantially no difference between the presence and absence of Compound C0105 for the YCI lymphocyte preparation.

Figure 18C:
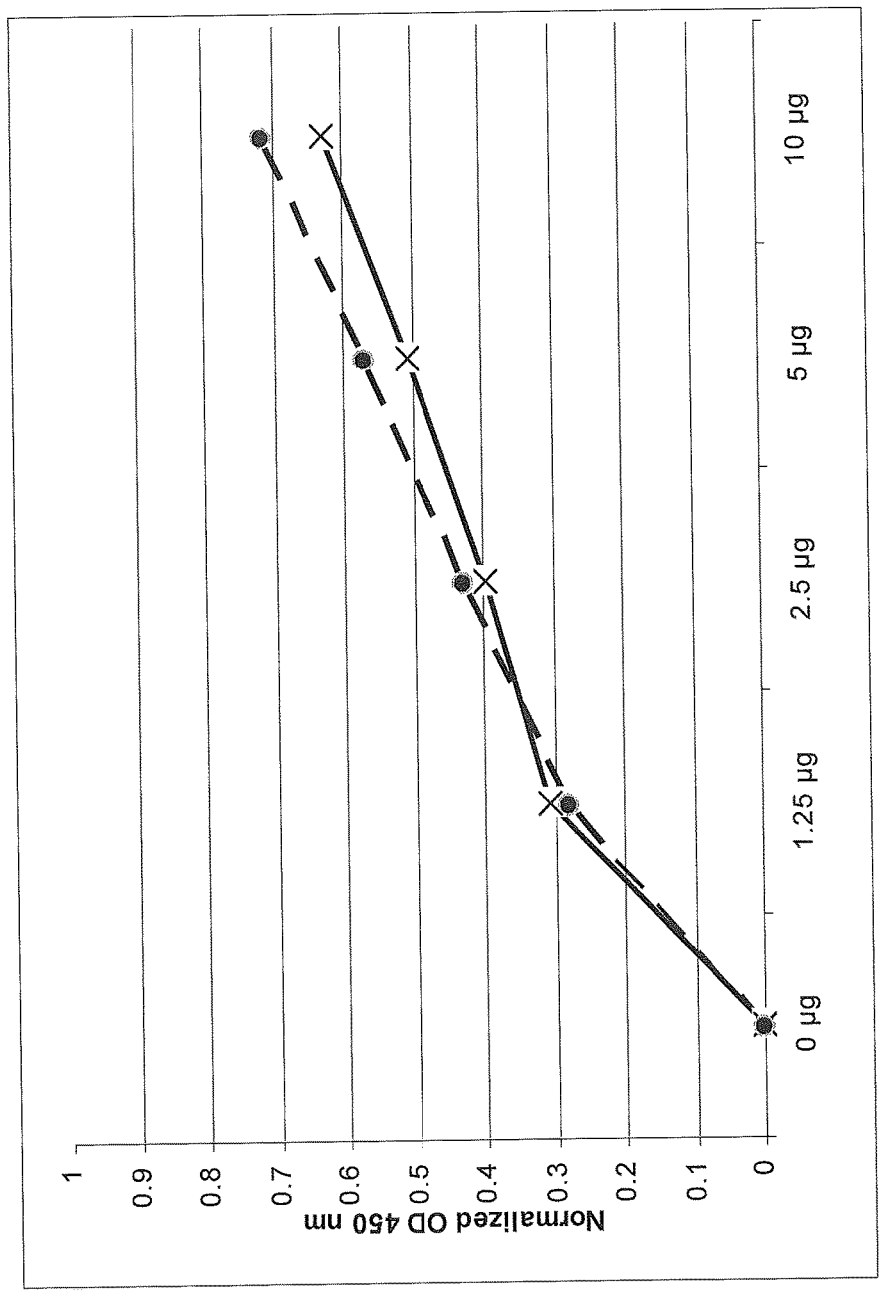
Figure 18D:
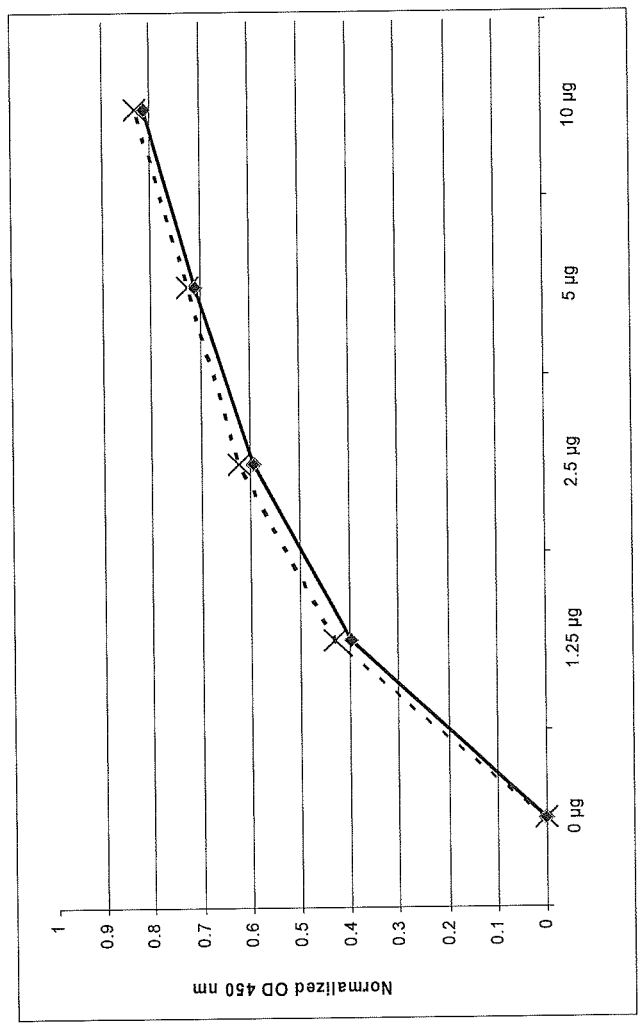
FIG. 18D shows similar results using a lymphocyte lysate from an AD patient (X's) and that preparation further containing a saturating amount of A$\beta_{42}$ (filled circles).
Figure 19A:
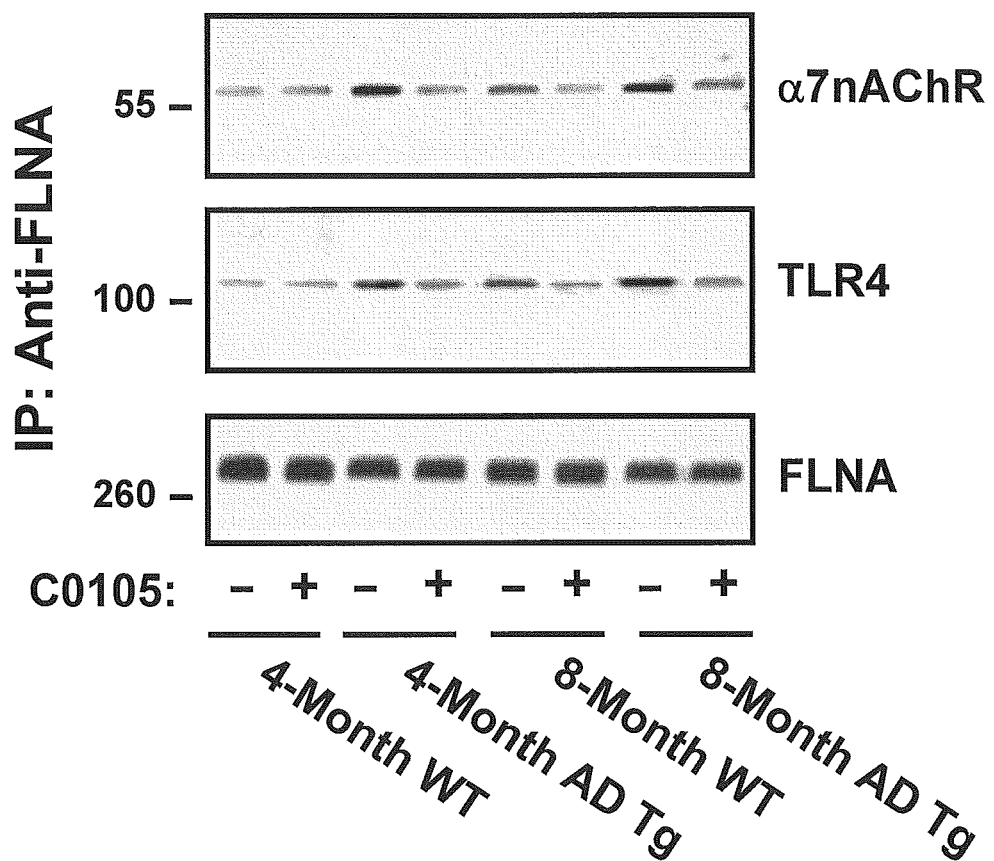
FIG. 19, in five panels as FIG. 19A and FIG. 19B, FIG. 19C, FIG. 19D and FIG. 19E, illustrate the effects of oral administration of 30 mg/kg of Compound C0105 for a period of two months to E129 mice and AD transgenic (tau/APP695sw(-9E0/PS1) mice beginning at the ages of 4 and 8 months. Mice were sacrificed, and their brains extracted/dissected to confirm pathologies. Trunk blood was collected and lymphocyte lysate preparations were analyzed for levels of α7nAChR and FLNA as well as TLR4 and FLNA by measuring α7nAChR and TLR4 contents in anti-FLNA immunoprecipitates by Western blotting and visualization with FITC. Data are expressed as the ratios of optical intensities of α7nAChR to FLNA (FIGS. 19B and 19C) and TLR4 to FLNA (FIGS. 19D and 19E). n=5. Data are means±SEM. *p<0.01 compared to vehicle-treated 4-month-old wild type (WT) group and #p<0.01 compared to Compound C0105 to vehicle treated in each group using the Newman-Keuls test for multiple comparisons.
Figure 19B:
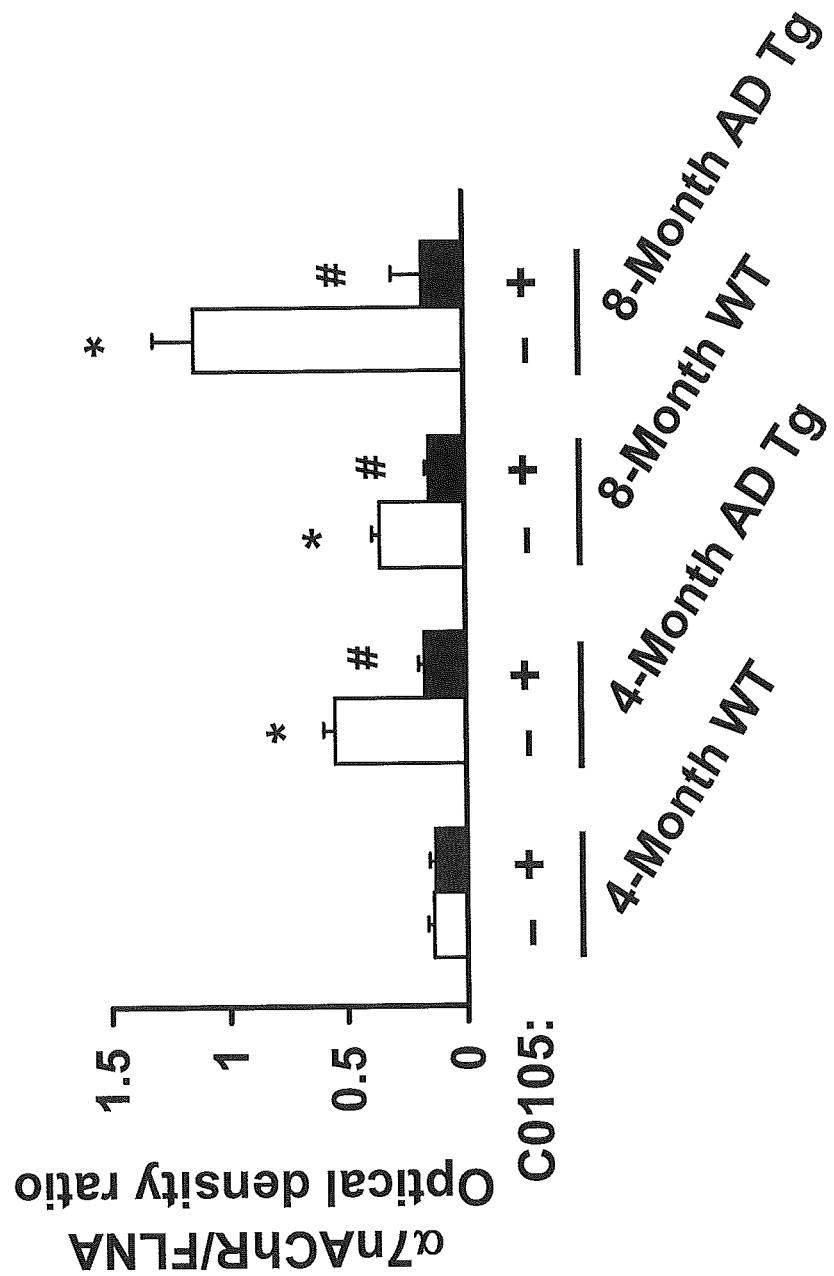
Figure 19C:
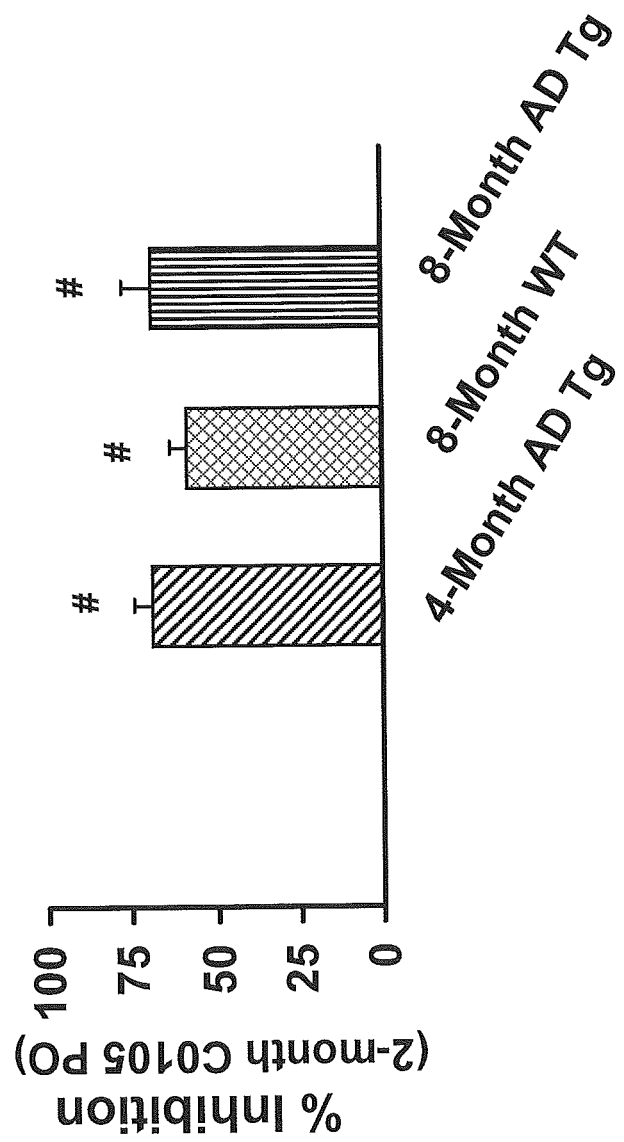
Figure 19D:
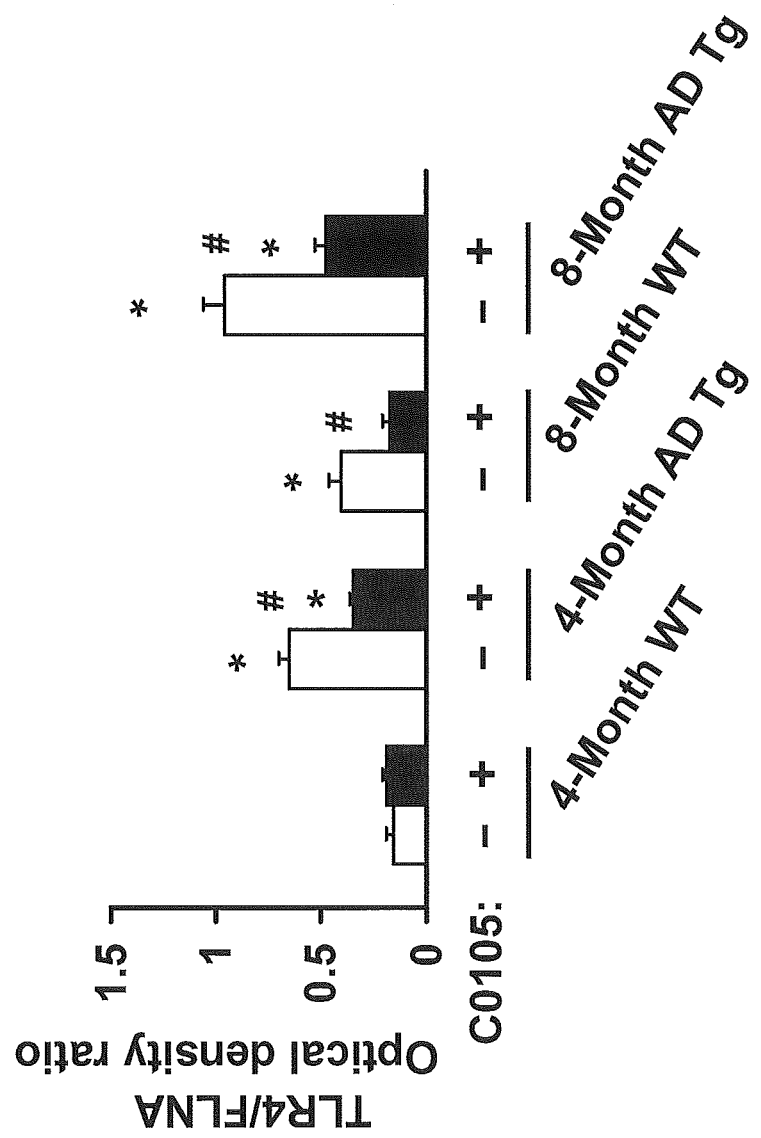
Figure 19E:
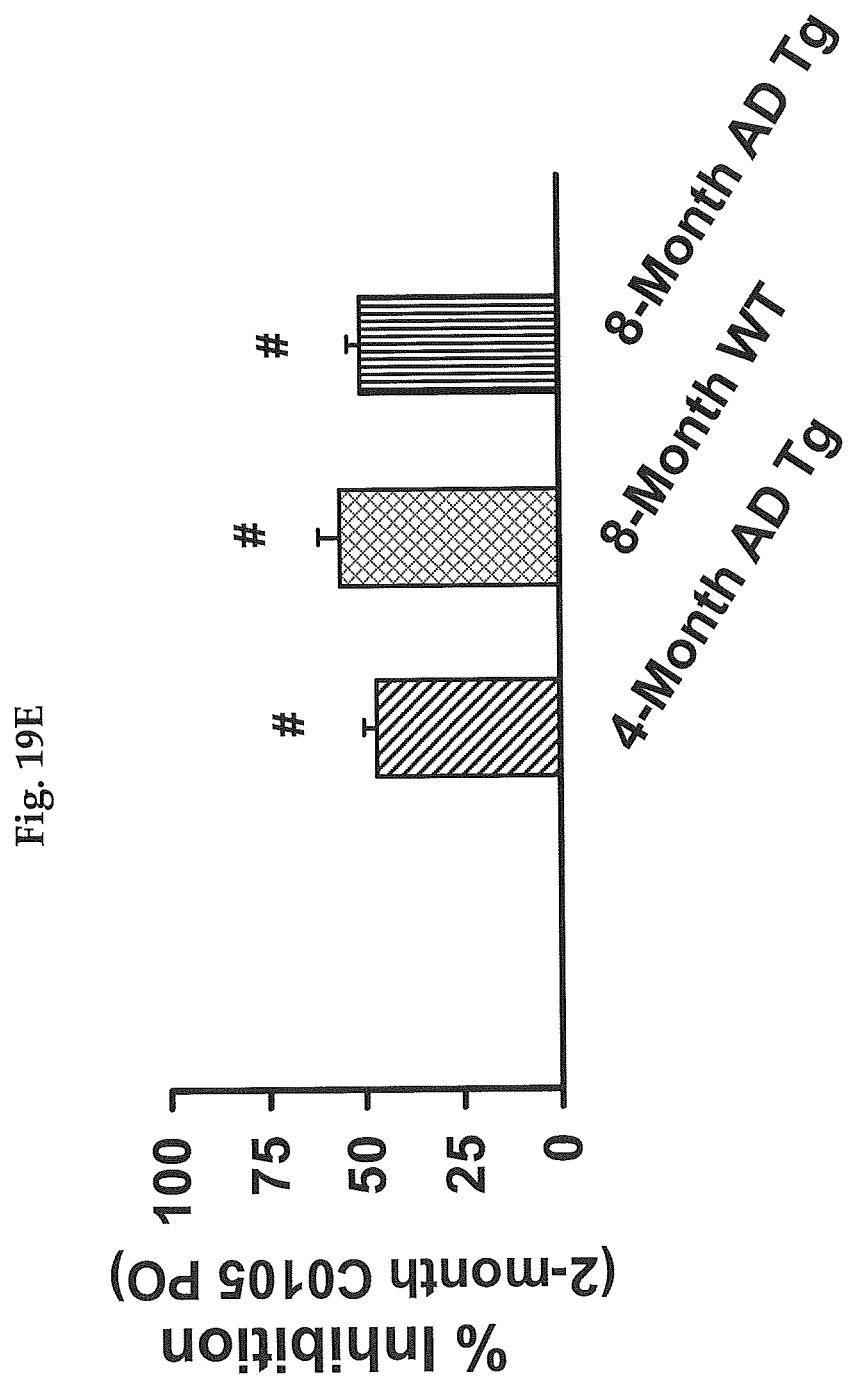

FIG. 18C illustrates that there was a minor change when $A\beta_{42}$ at a 100 nM final concentration was added to the lymphocyte lysate of a YCI subject and maintained for 30 minutes at 37° C. prior to the assay. As seen from FIG. 18D, there was substantially no change when the same amount of $A\beta_{42}$ was added to the lymphocyte lysate of an AD patient and maintained as above.

EXAMPLE 8

Supplemental ELISA Protocol

The following study was carried out to assist in development of a protocol for an ELISA assay method for quantitative detection of human FLNA-α7nAChR/TLR4 complex. The following ELISA method activities were carried out to quantify FLNA-α7nAChR complex: specificity; accuracy; precision/repeatability; linearity and range; and, detection limit.
Specificity:
To assure ELISA assay uniquely identifies human FLNA-α7nAChR complex, the cross reactivity to human FLNA-α7nAChR complex, unrelated human proteins human leptin and human chorionic gonadotropin (hLeptin and hCG) were added to the lymphocyte lysate preparations and the ELISA assay performed.
Accuracy:
To assure the ELISA assay returns a value that is representative of the "true" value, a range of concentrations of recombinant human leptin was spiked into lysate sample with FLNA-α7nAChR complex. Recovery percent concentrations were measured and accuracy calculated.
Precision: Repeatability
To assure that three measurements of a single lysate sample (e.g., sample AD#63) made in the same assay provide the same result, three samples were measured using the ELISA assay, three times on the same day using the same methods (repeatability). Within-day RSD was calculated.
Linearity and Range
To assure that the response is linear over the range of expected sample values, OD 450 of different concentrations of human FLNA-α7nAChR complex were detected using the ELISA assay.
Detection Limit
The limit of detection (LOD), which is the smallest amount of total protein (lysate) that must be loaded per well to enable ELISA-based differentiation of AD vs NP sample responses, was determined to thereby establish the lowest response that is detectable.
Materials and Methods
Antibodies:
Capture Ab: Rabbit pAb anti-human Filamin A antibody, cat# SC-28284, Santa Cruz Biotechnology.

Detection Ab: Rat mAb anti-human AChR7 antibody, cat# SC-58607, Santa Cruz Biotechnology.

Detection Ab: Mouse mAb anti-human Filamin A antibody, cat# SC-58764, Santa Cruz Biotechnology.

Ab Biotinylation: Capture Antibody Biotinylation Kit: EZ-Link Sulfo-NHS-Biotinylation Kit, Thermo cat#21425 (Thermo Scientific, Pittsburgh, Pa.).

Amyloid Beta: Amyloid-beta peptide cat#03111, 500 μg (Invitrogen). Because this peptide is a TFA salt, it should be dissolved in 50 mM Tris HCl, pH 9.0 containing 10% DMSO. The dissolved peptide is at pH 8, and should be stored in −80° C. Any lower pH value or higher temperature substantially increases aggregation, rendering the peptide less effective.

Lysis buffer: PBS with 0.5% digitonin+0.2% sodium cholate+0.5% NP-40+1× Proteinase inhibitor cocktail (no EDTA, Thermo Scientific, 100× solution)

PBS and PEST: PBS: 1×PBS (Mg- and Ca-free) from Thermo Scientific; PEST: 1×PBS+0.05% Tween®-20

ELISA microplates (coated): Pierce Streptavidin High Binding Capacity Coated 96-Well Plates (Pierce cat #15500)

Blocking buffer: 10% SuperBlock® Blocking Buffer (Pierce)

HRP Detection Reagent (TMB): 1-Step™ Ultra TMB-ELISA, cat#34028 (Thermo Scientific). Standard protocol using 100 μl of the TMB substrate solution per each microplate well, followed by 10-15 minute incubation (or until color develops) and stopping reaction by adding 100 μl of 2 M sulfuric acid to each well. Absorbance ($OD_{450}$) measured at 450 nm.

ELISA plate reader: Molecular Devices Spectramax® PLUS, assay at 450 nm Lymphocyte Isolation, Cell Lysis, $A\beta_{42}$ and C0105 Treatment:

AD patient samples: Sample tubes labeled #63 and #80 (100 μl volume per each tube) that contained Alzheimer's disease (AD) patients' lymphocytes were received frozen on dry ice from Dr. Hoau-Yan Wang, City University of New York. Samples were stored at −80° C. and at the time of study were thawed at 4° C., and then kept at −20° C. for 1 hour thereafter.

Lymphocytes were collected by centrifugation, sonicated for 10 seconds on ice and solubilized in 0.5% digitonin/0.2% sodium cholate/0.5% NP-40 supplemented with 1× Proteinase inhibitor cocktail (Thermo Scientific) for 60 minutes (4° C.) with tube rotation. Ice-cold PBS (300 μl) was added, and entire contents centrifuged to remove insoluble debris.

NP patient sample: Sample tubes labeled #81 (100 μl volume per each tube) with Normal patient (NP) lymphocytes were also received frozen on dry ice from Dr. Hoau-Yan Wang. Samples were stored at −80° C. and at the time of a study were thawed at 4° C., and then kept at −20° C. for 1 hour thereafter. Lymphocytes were collected by centrifugation, sonicated for 10 seconds on ice and solubilized in 0.5% digitonin/0.2% sodium cholate/0.5% NP-40 supplemented with 1× Proteinase inhibitor cocktail (Thermo Scientific) for 60 minutes (4° C.) with tube rotation. Ice-cold PBS (300 μl) was added and entire contents centrifuged to remove insoluble debris.

Total Protein Concentration:
AD Samples:
  #63 (2.21 mg/ml)
  #80 (2.25 mg/ml)

NP Sample:
81 (3.38 mg/ml)

NP sample (#81) and two AD samples (#63 and #80) were split into three samples each (no treatment, +C0105 treatment, +A$\beta_{42}$ treatment) and diluted in 1×PBS for further analysis.

C0105 Treatment:

Compound C0105 (Pain Therapeutics) treatment was performed using NP and AD patient white blood, cells resuspended in 1×PBS and treated with: a) 100 nM C0105 (final concentration), and b) control (PBS only) for 30 minutes at 37° C. (total volume is 400 µl of each sample).

A$\beta_{42}$ Treatment:

A$\beta_{42}$ (Invitrogen) treatment was performed using AD and normal patient white blood cells resuspended in 1×PBS as a final step of the protocol and treated with: a) 10 µM A$\beta_{42}$ (final concentration), and b) control (PBS only) for 30 minutes at 37° C.

Results

Indirect ELISA Studies

Anti-filamin A antibody (rabbit polyclonal) was biotinylated using a biotinylation kit (Thermo Scientific) according to manufacturer's protocol. The free biotin was removed using a 10-KDa cut-off filter and centrifugation.

Lymphocyte lysate (5 µg) from two AD patients and one normal, healthy volunteer (NP) were split into 3 samples each and incubated with: one or the other of a) vehicle (1×PBS), b) 10 µM A$\beta_{42}$, c) 100 nM C0105. Incubation was carried out at 37° C. for 30 minutes in 250 µl of 1×PBS and aerated with 95% O$_2$ every 10 minutes for 1 minute during the incubation.

Lymphocytes were collected by centrifugation, sonicated briefly and solubilized with 0.5% digitonin/0.2% sodium cholate/0.5% NP-40 in 100 µl of protease and protein phosphatase-containing PBS for 1 hour at 4° C. Following addition of 300 µl PBS, the entire contents were centrifuged to remove insoluble debris.

NP and AD samples (AD patients' lymphocytes, as described above) were used to prepare serial dilution series samples (dilution performed in 1×PBS) and 150 µl samples were loaded per well as described above. The plate was covered with adhesive cover to prevent evaporation.

To determine the levels of α7nAChR-FLNA complexes, 0.5 µg/well of biotinylated rabbit polyclonal anti-FLNA antibody were loaded onto streptavidin-coated plates (Pierce). Plates were washed 3 times with 50 mM Tris-HCl (pH 7.4) and incubated at 25° C. with above-mentioned biotinylated antibodies. After incubation and washing, plates were blocked with 10% SuperBlock® (Thermo Scientific) for 1 hour at room temperature. The wells were then washed three times with 50 mM Tris-HCl (pH 7.4).

The washed plates were incubated with 150 µl of lymphocyte lysate obtained from each of the above-mentioned treatment conditions for 1 hour at 25° C. for 1 hour (in duplicate). Plates were washed 3 times with ice-cold 50 mM Tris-HCl (pH 7.4) and contacted (incubated) at 30° C. with 0.5 µg/well of un-conjugated mouse anti-FLNA (for Filamin A) and un-conjugated rat anti-α7nAChR for 1 hour.

After two 1 minute washes with 50 mM Tris-HCl (pH 7.4), each well was incubated with HRP-conjugated anti-mouse IgG or anti-rat IgG as appropriate for 30 minutes at 25° C. Plates were washed three times with 200 µl Tris-HCl, pH 7.4 and TMB reagent substrate for detection of horseradish peroxidase (HRP) enzyme was added (75 µl of the TMB substrate solution per each microplate well, followed by 10-15 minute incubation (or until color developed) and stopping reaction by adding 75 µl of 2M sulfuric acid to each well. Absorbance (OD$_{450}$) measured at 450 nm).

The curve was prepared using the data produced by serial dilutions.

Specificity

To assure that the ELISA assay uniquely identifies the human FLNA-α7nAChR complex, cross reactivity to human FLNA-α7nAChR complex of unrelated human proteins (hLeptin and hCG) was examined. The standard ELISA was performed using 5 µg of total lymphocyte lysate per well. Human recombinant leptin (5 µg) and human recombinant CG (5 µg) were loaded per well instead of 5 µg of total lymphocyte lysate and the ELISA assay was performed using standard conditions. The table below shows that the cross-reactivity is 4.3% to hLeptin and 3.1% to hCG. These data indicate that ELISA assay is specific for FLNA-α7nAChR complex.

TABLE

| | Human lymphocyte lysate, AD#63 (5 µg) | 5 µg hLeptin | 5 µg hCG |
|---|---|---|---|
| Normalized OD, Replicate 1-3 | 0.52/0.57/ 0.53 | 0.02/0.01/ 0.04 | 0.01/0.01/ 0.03 |
| Normalized OD, Average | 0.54 | 0.02 | 0.01 |
| % Cross reactivity | — | 4.3 | 3.1 |

Accuracy

To assure the ELISA assay returns a value that is representative of the "true" value, a range of concentrations of recombinant human leptin was spiked into lysate samples that contained the FLNA-α7nAChR complex. Recovery percent concentrations were measured and accuracy calculated. These results are shown in the table below.

TABLE

| | Human lymphocyte lysate, AD#63 (5 µg) | hLeptin added (µg) | Accuracy (recovery percent) |
|---|---|---|---|
| Normalized OD, Mean (n = 6) | 0.528 | zero | 100.00 |
| | 0.532 | 1 | 100.75 |
| | 0.524 | 2 | 99.24 |
| | 0.525 | 3 | 99.43 |
| | 0.516 | 4 | 97.72 |
| | 0.516 | 5 | 97.72 |
| | 0.518 | 6 | 98.1 |
| | 0.507 | 7 | 96.02 |
| | 0.509 | 8 | 96.40 |
| | 0.498 | 9 | 94.31 |
| | 0.497 | 10 | 94.12 |

Precision: Repeatability

Three measurements of a single lysate sample (sample AD#63) were made in the same assay to determine if they would provide the same result. Three samples were measured using the ELISA assay, three times on the same day using the same methods (repeatability).

To assure that isolation procedure does not interfere with assay results, three isolations of the same sample #63 were performed and ELISA assay run for these three same sample lysates. Lysate isolations were performed on three different days.

A total of six assays were carried out for each sample on each day. Of those six, two samples were not treated, two were admixed with Aβ$_{42}$ to provide 100 μM Aβ$_{42}$, and two were admixed with Compound C0105 to provide a concentration of 100 nM. Levels of α7nAChR are shown (with background subtracted).

The assay results were substantially identical for each of the three days on which the assays were run. In each case, the two untreated samples and the two Aβ$_{42}$-treated samples exhibited little if any difference from each other, whereas the two samples assayed with admixture of Compound C0105 were almost identical to each other on each day as well as across all three days as well as being substantially different from the other four sample results each day.

Three different isolations were performed on three different days using the same lymphocyte sample (AD #63). Indirect ELISA study using AD patient sample #63 treated (+/− Compound C0105, +/− Aβ$_{42}$).

Here, the no treatment and the Aβ$_{42}$ treatment results were substantially identical to each other for each lysate, but differed slightly between the lysates. The Compound C0105 treatment results for each lysate were clearly different from the no treatment or Aβ$_{42}$ treatment, but differed from each other between the three lysates.

Linearity and Range

To assure that the response is linear over the range of expected sample values, OD$_{450}$ of different concentrations of human FLNA-α7nAChR complex were detected using the ELISA assay.

Indirect ELISA study with two AD patient samples and two YC controls (+/− Compound C0105, +/− Aβ$_{42}$) at 5 μg total protein per well and 14 μg total protein per well. The data indicate that the binding results were not a function of the amount of total protein used, as was expected.

Detection Limit

The limit of detection (LOD) was determined, which is the smallest amount of total protein (lysate) that must be loaded per well to enable ELISA-based differentiation of AD vs NP sample response to establish the lowest response that is detectable.

The obtained data indicate that appropriate results could be obtained using loadings of 1 or 5 μg of total protein along with 10 μM AB$_{42}$ and with 100 nM Compound C0105.

EXAMPLE 9

FLNA Affinity Binding Studies

A series of binding studies using various compounds as ligand and FLNA or the FLNA pentamer of SEQ ID NO:1 as the receptor. These studies were carried out in a generally similar manner using a competition (displacement) curve for the inhibition of [$^3$H]NLX binding by in the presence of the ligand, and the results are shown in FIG. 16. Specifics of each study are set out below.

The competition (displacement) curve (FIG. 16A) for the inhibition of [$^3$H]NLX binding by naltrexone to membranes from FLNA-expressing A7 A curve was generated using (human melanocytic; ATCC CRL-2500) cells that are free of most receptors and particularly mu shows two affinity states with IC$_{50-H}$ (high) of 3.94 picomolar and IC$_{50-L}$ (low) of 834 picomolar. A nonlinear curve-fit analysis was performed using a competition equation that assumed two saturable sites for the naltrexone curve comprising of 16 concentrations ranging from 0.1 pM to 1 μM. Data are derived from six studies each using a different set of A7 cells.

Figure 16A:
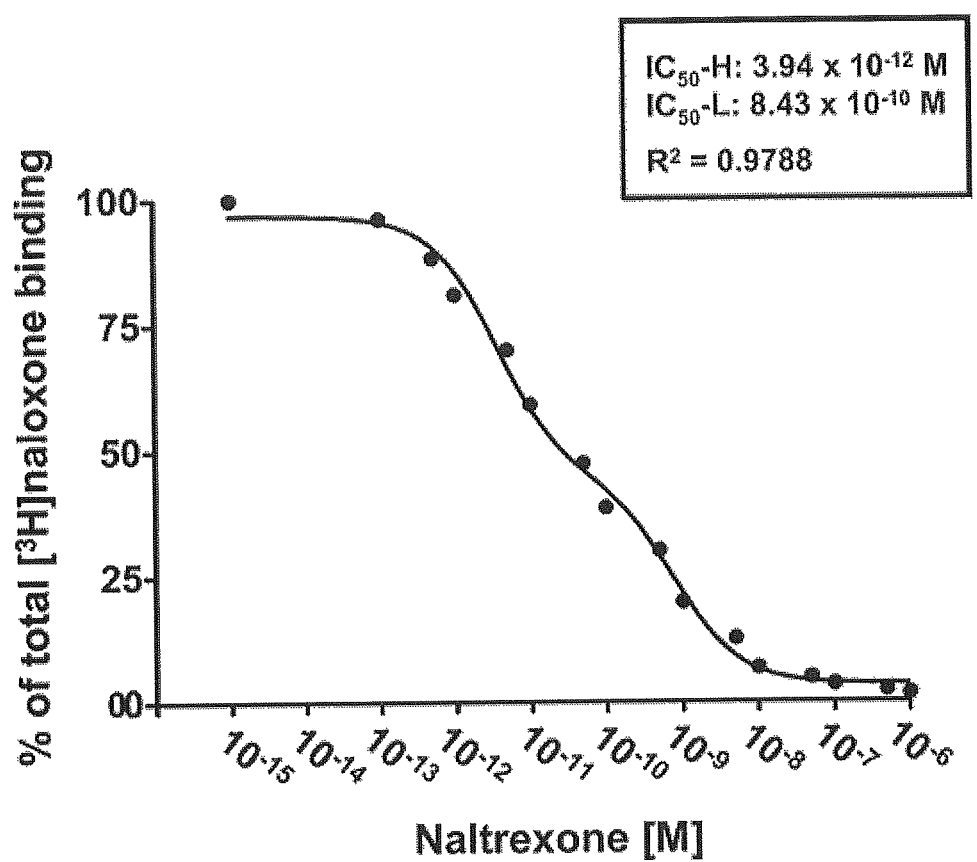
FIG. 16A illustrates binding to FLNA present in the membranes of A7 cells in the presence of indicated amounts of naltrexone (NTX) and is taken from Wang et al., *PLoS One.* 3(2):e1554 (2008), FIG. 3.
Figure 16B:
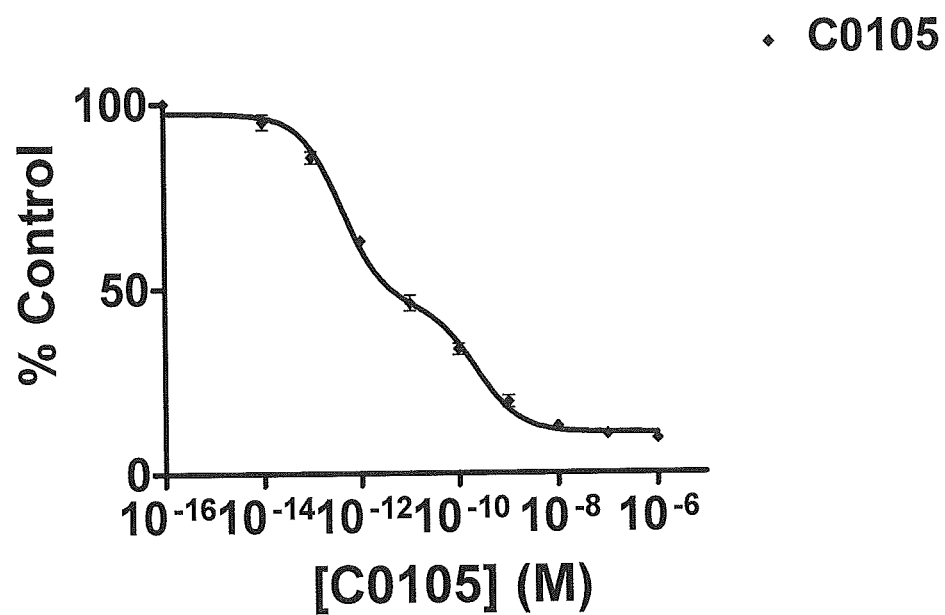
FIG. 16B illustrates binding of [$^3$H]NLX in the presence of Compound C0105 to FLNA in the membranes of A7 cells in the presence of indicated amounts of Compound C0105.

The binding affinity of Compound C0105 for FLNA was similarly determined (FIG. 16B). Briefly, 100 μg of A7 cell membranes were incubated with 0.5 nM [$^3$H]NLX in the presence of 0.01 nM-1 μM Compound C0105 at 30° C. for 60 minutes in 250 ml of the binding medium (50 mM Tris-HCl, pH 7.5; 100 mM NaCl; and protease and protein phosphatase inhibitors). Nonspecific binding was defined by 1 μM NTX. Reactions were terminated by rapid filtration through 3% BSA-treated glass microfiber binder free grade B (GF/B) membranes under vacuum. Filters were washed twice with 5 ml ice-cold binding medium, and [$^3$H]NLX retained on the filters was measured by liquid scintillation spectrometry. The data obtained were analyzed using the GraphPad Software, Inc. (San Diego, Calif.) Prism program. Here, an IC$_{50-H}$ of 0.43 picomolar and IC$_{50-L}$ of 226 picomolar were determined. N=4.

Figure 16C:
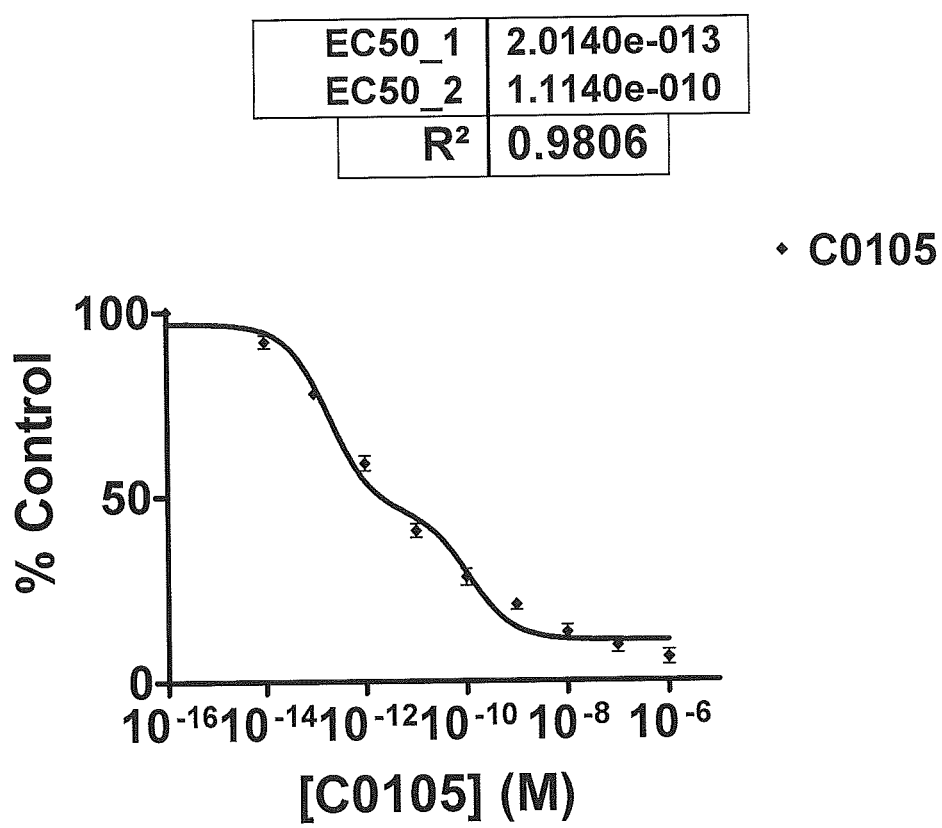
FIG. 16C illustrates binding of [$^3$H]NLX to FLNA in the membranes of SK-N-MC cells in the presence of indicated amounts of Compound C0105.

The binding affinity of Compound C0105 for FLNA in SK-N-MC membranes was similarly determined (FIG. 16C). Briefly, 200 μg of SK-N-MC (human neuroepithelioma; ATCC HTB-10) cell membranes that contain with both α7nAChR and mu-opioid receptors were incubated with 0.5 nM [$^3$H]NLX in the presence of 1 μM DAMGO and 0.01 nM-1 μM Compound C0105 at 30° C. for 60 minutes in 250 ml of the binding medium (50 mM Tris-HCl, pH 7.5; 100 mM NaCl; and protease and protein phosphatase inhibitors). Nonspecific binding was defined by 1 μM NTX. Reactions were terminated by rapid filtration through 3% BSA-treated GF/B membranes under vacuum. Filters were washed twice with 5 ml ice-cold binding medium, and [$^3$H]NLX retained on the filters was measured by liquid scintillation spectrometry. The data obtained were analyzed using the GraphPad Software, Inc. (San Diego, Calif.) Prism program. Here, an IC$_{50-H}$ of 0.201 picomolar and IC$_{50-L}$ of 111 picomolar were determined. N=4.

Figure 16D:
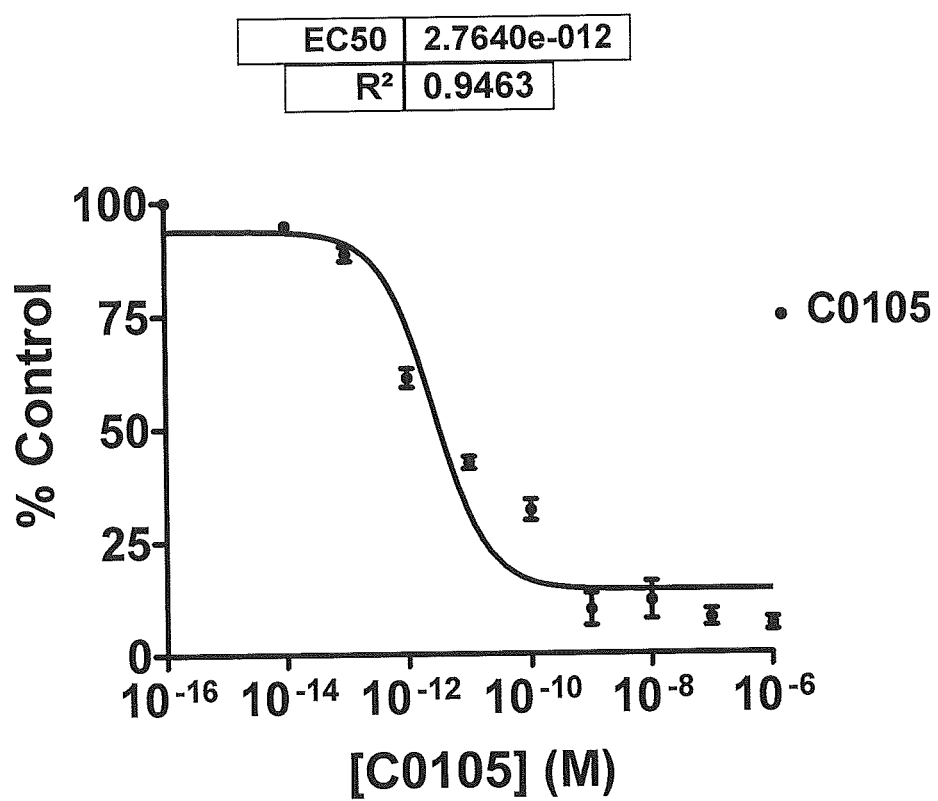
FIG. 16D illustrates binding of [$^3$H]NLX to the FLNA pentamer of SEQ ID NO. 1 in the presence of indicated amounts of Compound C0105.

The binding affinity of Compound C0105 for the VAKGL peptide of SEQ ID NO:1 was also determined by a displacement assay (FIG. 16D). Briefly, 10 mg of N-terminal biotinylated VAKGL (SEQ ID NO:1) peptide (Bn-VAKGL) was incubated with 0.5 nM [$^3$H]NLX in the presence of 0.01 nM-1 μM Compound C0105 at 30° C. for 60 minutes in 250 ml of the binding medium (50 mM Tris-HCl, pH 7.5; 100 mM NaCl; and protease and protein phosphatase inhibitors). Nonspecific binding was defined by 1 μM NTX. The reaction was terminated by addition of 1 ml of ice-cold binding medium. The [$^3$H]NLX-bound Bn-VAKGL was trapped by incubation with 20 ml NeutrAvidin®-agarose (Thermo), followed by centrifugation. Following two 1.5 ml washes with PBS, the bound [$^3$H]NLX was determined using scintillation spectrometry. The data obtained were analyzed using the GraphPad Software, Inc. (San Diego, Calif.) Prism program. Here, a single IC$_{50}$ value was obtained, as was expected for the 5-mer peptide of SEQ ID NO:1, and its value was 2.76 picomolar. N=4.

The data obtained in these studies illustrate the similar affinities exhibited between naloxone and illustrative Compound C0105 for FLNA. These data also illustrate the similarity in binding activity as a receptor shown between the intact FLNA molecule and the 5-mer FLNA peptide of SEQ ID NO:1, and thereby validate the use of that 5-mer peptide as a surrogate for the complete molecule in the assays carried out herein.

EXAMPLE 10

Compound C0105 AD Mouse Treatment

To assess the C0105's AD treatment efficacy, E129 mice and AD transgenic (tau/APP695sw(-9E)/PS1) mice at age of 4-months (minimal plaque pathologies) and 8-months (established plaque pathologies) were treated orally with 30 mg/kg of C0105 for 2 months. Mice were sacrificed after completion of treatment, brains were extracted/dissected and trunk blood was collected into EDTA containing tubes. Lymphocytes were isolated and solubilized, the levels of α7nAChR and FLNA as well as TLR4 and FLNA complexes were purified by immunoprecipitation with anti-FLNA followed by measuring α7nAChR and TLR4 contents in anti-FLNA immunoprecipitate by Western blotting. The protein bands were detected using a chemiluminescent method, visualized by exposure to x-ray film and quantified by densitometric scan.

The data were expressed as the ratios of optical intensities of α7nAChR to FLNA and TLR4 to FLNA. Each data point is the mean±SEM from 5 mice.

The data summarized indicate that α7nAChR-FLNA and TLR4-FLNA complexes in lymphocytes are elevated in AD transgenic mice in an age-dependent, pathology-related manner. This AD-related change is robustly normalized by 2-month oral administration of Compound C0105. Altogether, these data suggest that Compound C0105 is an effective AD treatment and the magnitude of reduction in α7nAChR-FLNA and TLR4-FLNA complexes in lymphocytes can be used as a biomarker to confirm AD diagnosis, assess the severity of AD and determine the treatment efficacy of AD therapeutic agents.

EXAMPLE 11

Protein a and Protein G Capture Methods

Exemplary assays were carried out using lymphocyte preparations prepared from lymphocytes from two AD patients (#63 and #80) and from one YCI subject (#81) using commercially available 96-well microtiter plates coated with either Protein A or Protein G as the capturing entity for antibody-bound α7nAChR/FLNA, TLR4/FLNA and α7nAChR/Aβ protein-protein complexes as discussed below.

Lymphocytes (25 µg) from subjects to be assayed were incubated with vehicle (0.1% DMSO containing Kreb's Ringer), 100 nM $A\beta_{42}$, 1 nM Compound C0105. Incubation was carried out at 37° C. for 30 minutes in 250 µl Kreb's Ringer [25 mM HEPES, pH 7.4, 118 mM NaCl, 4.8 mM KCl, 25 mM $NaHCO_3$, 1.3 mM $CaCl_2$, 1.2 mM $MgSO_4$, 1.2 mM $KH_2PO_4$, 10 mM glucose, 100 mM ascorbic acid, Protease inhibitor cocktail that was aerated with 95% $CO_2O_2$/5% $CO_2$ for 10 minutes. The incubation mixtures were aerated every 10 minutes for 1 minute during the incubation. Lymphocytes were collected by centrifugation, sonicated on ice for 10 seconds in 150 µl of immunoprecipitation [IP] buffer (25 mM HEPES, pH 7.5; 200 mM NaCl, protease inhibitors tablet (1 tablet/10 ml), 2 µg/ml soybean trypsin inhibitor, 5 mM NaF, 1 mM sodium vanadate, 0.5 mM β-glycerophosphate and 0.1% 2-mercaptoethanol) and solubilized with 0.5% digitonin/0.2% sodium cholate/0.5% NP-40 for 1 hour at 4° C. (adjust to total volume of 200 µl) with end-over-end shaking. Following centrifugation to remove the insoluble debris, the resultant lymphocyte lysate was diluted to 1 ml with ice-cold IP buffer and 1 µg of anti-FLNA (Santa Cruz) or 1 µg anti-$A\beta_{42}$ 1 µg anti-actin was then added. The antibody-antigen (lymphocyte lysate) mixture was then incubated for 1 hour at 4° C. with end-over-end shaking.

Protein A- or Protein G-coated 96-well plates (Pierce/Thermo) were washed with phosphate-buffered saline, pH 7.2 (PBS) containing 0.05% Tween-20 (0.05% PBST) three times and the plates were then blocked with 10% superblock (Pierce/Thermo) at 25° C. for 30 minutes. After three washes with 0.05% PBST, 100 µl of anti-FLNA or anti-$A\beta_{42}$/anti-actin immunocomplex suspension was then added to each well and incubation continued at 4° C. for 1 hour. Each sample was assessed in duplicate.

The plates were decanted, washed three times with 0.05% PEST and nonspecific binding was blocked by 200 µl of 1 µg/ml normal human IgG and 1% superblock containing 0.05% PBST for 30 min. The plates were then washed three times with 0.05% PEST. The contents of α7nAChRs, TLR4s, FLNA and β-actin were assessed by incubating with 0.2 µg of their respective antibodies at 4° C. for 1 hour. Following three washes with 0.05% PBST, the plates were then incubated with FITC-conjugated anti-species IgG (1:25000) for 1 hour. Following one wash with 0.1% PEST, two washes with 0.05% PBST and one with PBS, the residual FITC signals were measured using a multimode plate reader (DTX880, Beckman).

Figure 20A:
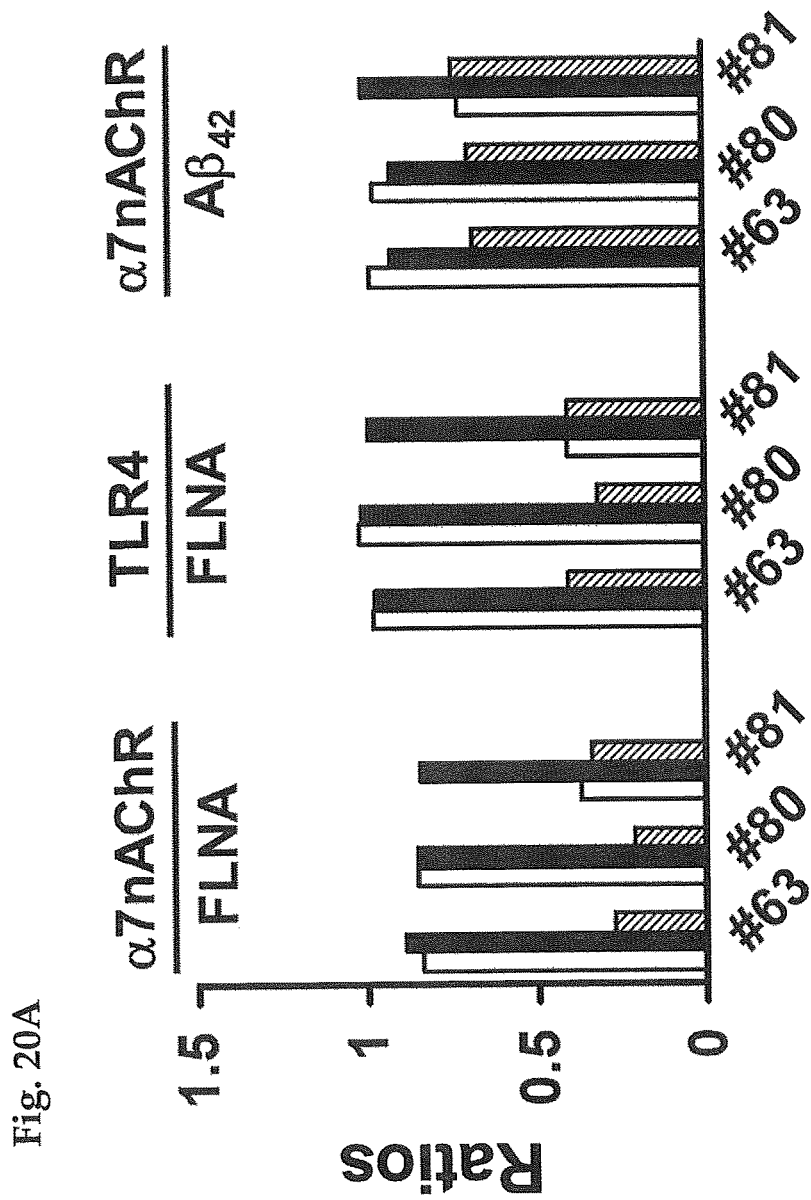
FIG. 20 in two panels, as FIG. 20A and FIG. 20B, show the results of assays for the presence of each of antibody-bound protein-protein complexes α7nAChR/FLNA, TLR4/FLNA and α7nAChR/Aβ protein using commercially available Protein A- and Protein G-coated 96-well microtiter plates. The amount of each complex assayed was determined after incubation of each lymphocyte lysate with 1 nM Compound C0105 (hatched bars), 100 µM Aβ42 (black bars) and Kreb's Ringer solution (open bars). Protein amounts were determined by immunoreaction with anti-protein antibodies and then with FITC-conjugated species-specific antibodies.
Figure 20B:
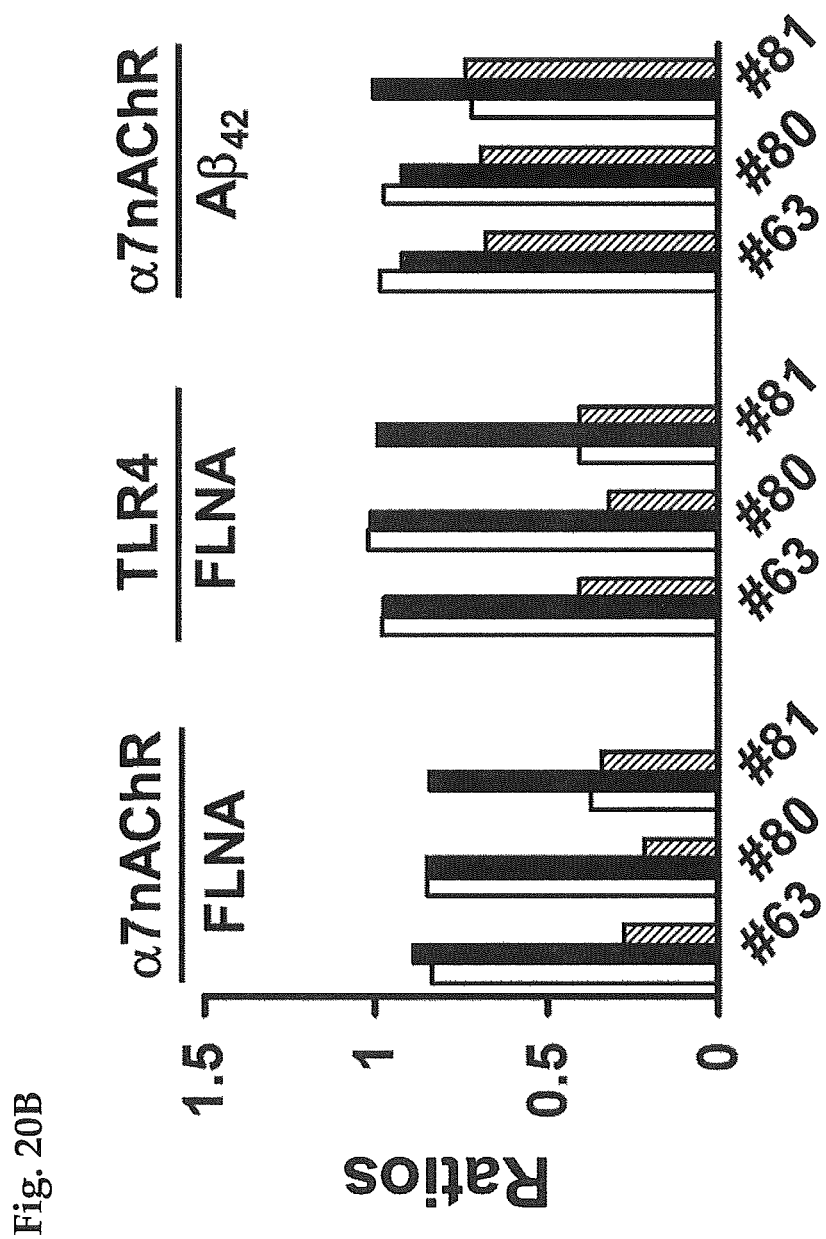
Figure 21A:
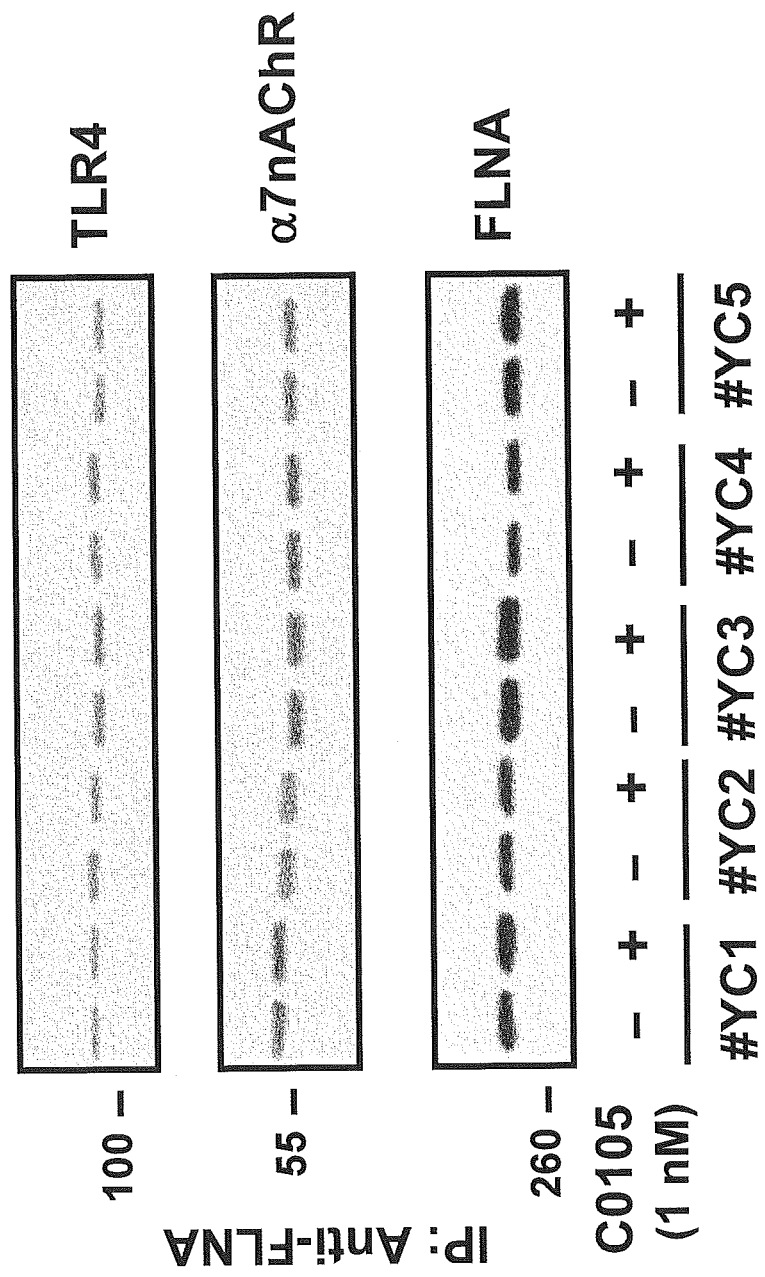
FIG. 21A and FIG. 21B show data from five representative YCI subjects of the ten YCI subjects whose lymphocytes were studied.
Figure 21B:
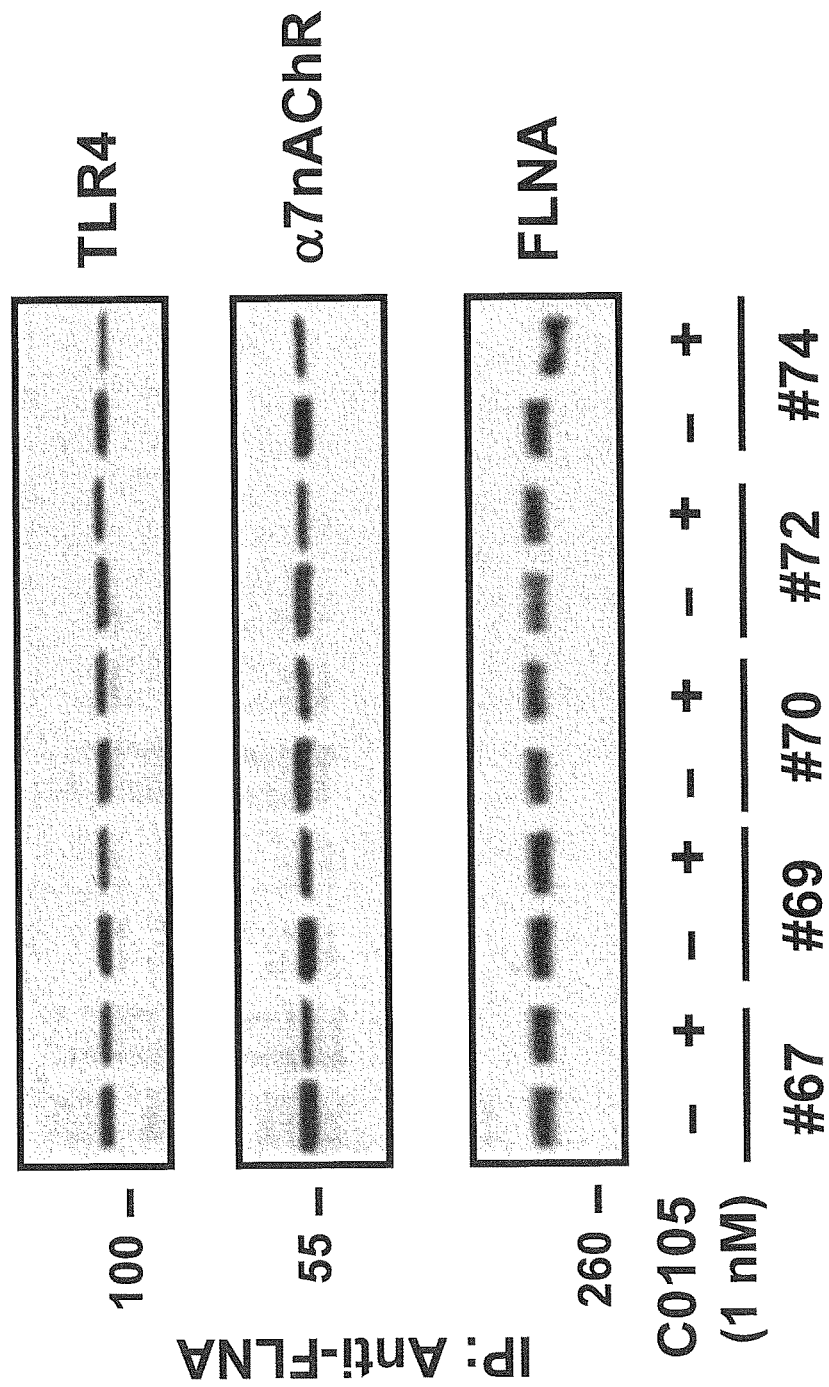
Figure 21C:
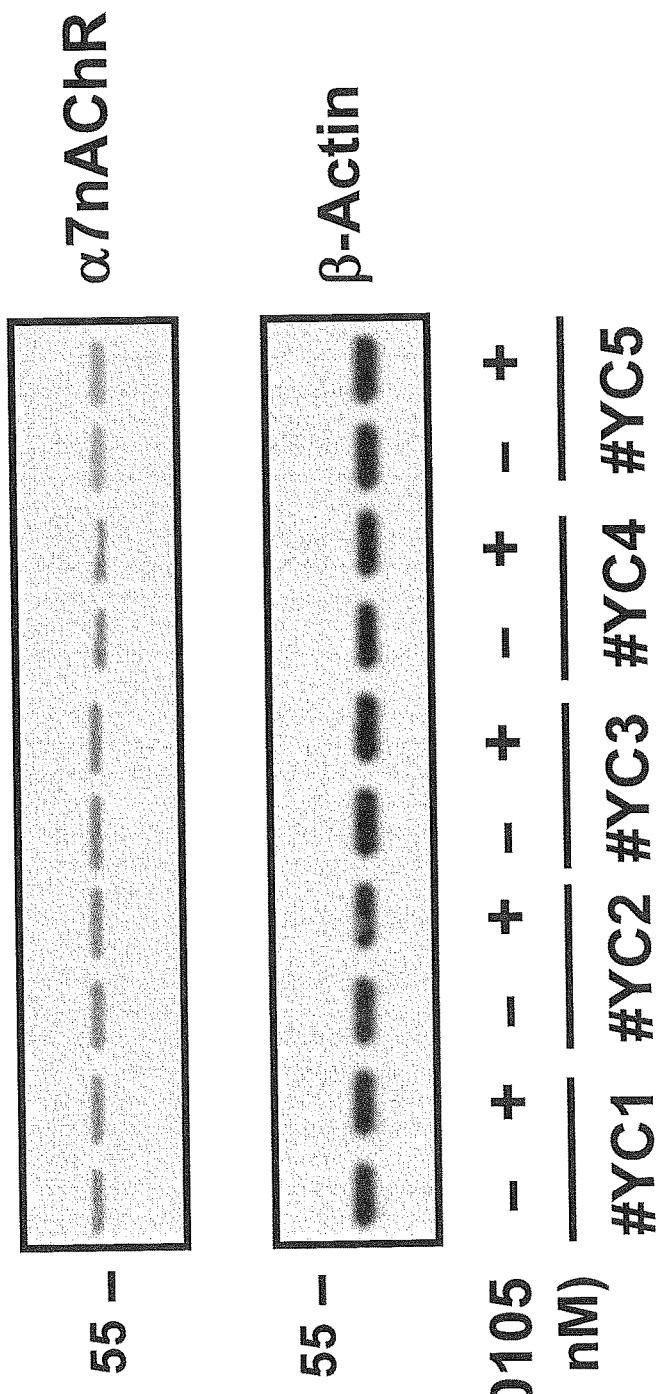
FIG. 21C and FIG. 21D show data from lymphocytes of five representative patients of the 20 AD patients studied.
Figure 21D:
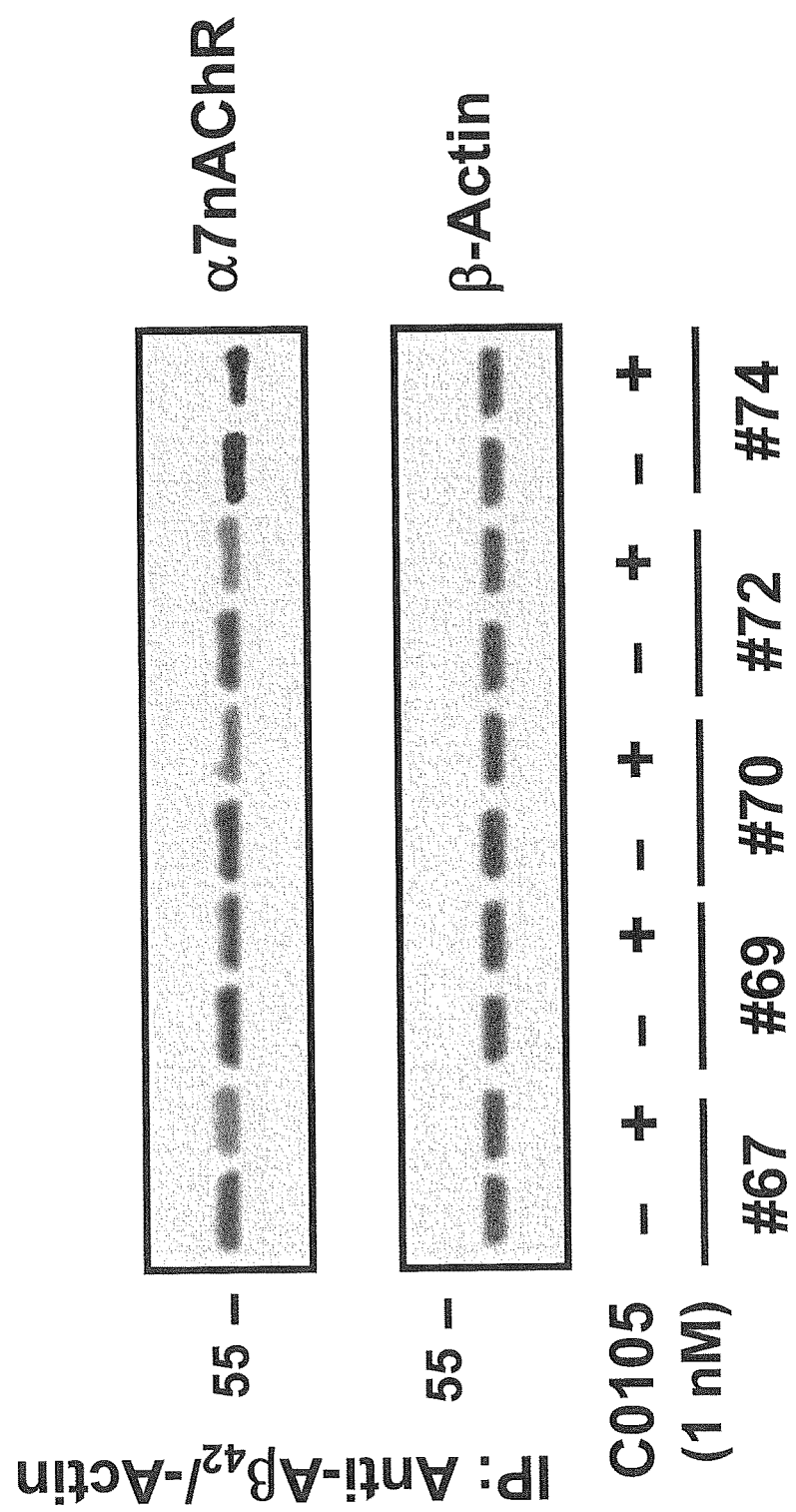
Figure 21E:
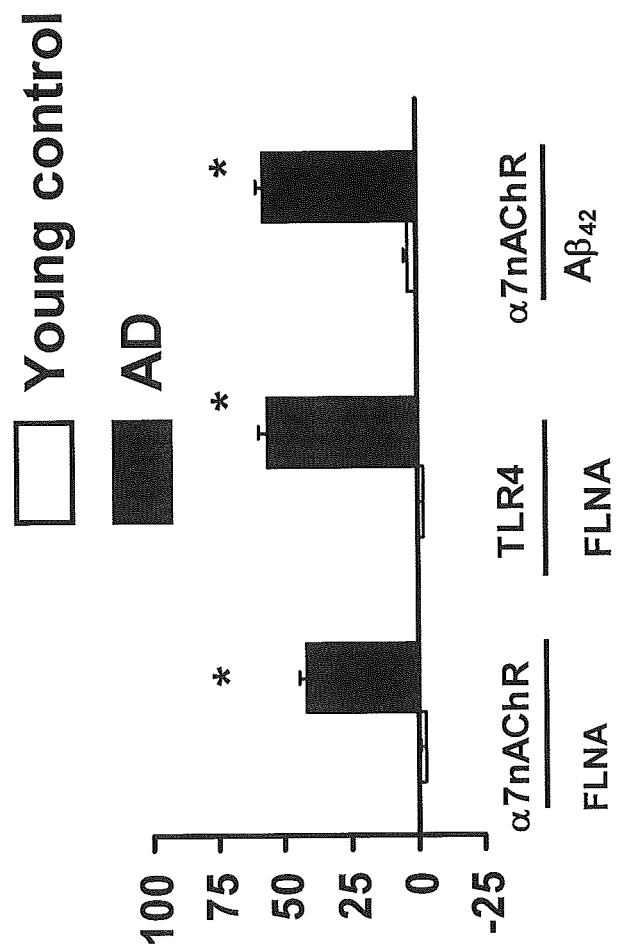
FIG. 21E shows composite data from all of the patients of each group. *p<0.00001.

The background was defined by the residual FITC signals derived from wells without added antibody-antigen (lymphocyte lysate) mixture and subtracted from each well. The data illustrated in FIG. 20A and FIG. 20B are expressed as the ratios of α7nAChR to FLNA (α7nAChR/FLNA complexes), TLR4 to FLNA (TLR4/FLNA complexes) or α7nAChR to β-actin (α7nAChR/$A\beta_{42}$ complexes).

These data dramatically demonstrate the use of exogenously added Compound C0105 or A-beta to differentially perturb α7nAChR/FLNA, TLR4/FLNA and α7nAChR/$A\beta_{42}$ complexes from AD and YCI lymphocytes. AD lymphocytes are essentially non-responsive to the addition of $A\beta_{42}$ whereas YCI lymphocytes (having $A\beta_{42}$ unsaturated α7nACh receptors)undergo a significant shift (increase) in the amount of α7nAChR and TLR4 FLNA complexes. The addition of $A\beta_{42}$ also increases the amount of α7nAChR/$A\beta_{42}$ complexes in YCI lymphocytes. The addition of Compound CO105 to AD lymphocytes results in significant decreases (approximately 50%) in the amount of α7nAChR and TLR4 FLNA complexes, as well as α7nAChR/$A\beta_{42}$ complexes.

In stark contrast to the response of AD lymphocytes to Compound CO105, YCI lymphocytes are essentially non-responsive. These results are quite consistent with those obtained by Western blot, ELISA and FITC-based multi-well microtiter plates assays. These results demonstrate the utility of using a protein A or protein G antibody capture microtiter plate to capture α7nAChR and TLR4 FLNA complexes, as well as α7nAChR/$A\beta_{42}$ complexes, in order to assess amounts of FLNA associated α7nACh and TLR4 receptors and α7nAChR/$A\beta_{42}$ complexes to assess the presence of AD pathology in, but not limited to, cognitively impaired patients.

EXAMPLE 12

Effect of Compound C0105 on Protein Complexes in YCI and AD Patient Lymphocytes

Lymphocytes (25 µg) from test subjects were incubated with vehicle (0.1% DMSO containing Kreb's Ringer) or 1 nM C0105. Incubation was carried out at 37° C. for 30 minutes in 250 µl Kreb's Ringer [25 mM HEPES, pH 7.4, 118 mM NaCl, 4.8 mM KCl, 25 mM $NaHCO_3$ 1.3 mM $CaCl_2$, 1.2 mM $MgSO_4$, 1.2 mM $KH_2PO_4$, 10 mM glucose, 100 mM ascorbic acid, Protease inhibitor cocktail that was aerated with 95% $O_2$/5% $CO_2$ for 10 minutes. The incubation mixtures were aerated every 10 minutes for 1 minute during the incubation. Lymphocytes were collected by centrifugation, sonicated on ice for 10 sec in 150 μl of immunoprecipitation [IP] buffer (25 mM HEPES, pH7.5; 200 mM NaCl, protease inhibitors cocktail, 2 μg/ml soybean trypsin inhibitor, 5 mM NaF, 1 mM sodium vanadate, 0.5 mM β-glycerophosphate and 0.1% 2-mercaptoethanol) and solubilized with 0.5% digitonin/0.2% sodium cholate/0.5% NP-40 for 1 hour at 4° C. (adjust to total volume of 200 μl) with end-over-end shaking.

Following centrifugation to remove the insoluble debris, the resultant lymphocyte lysate was diluted to 1 ml with ice-cold IP buffer and 1 μg of anti-FLNA or 1 μg anti-Aβ$_{42}$+1 μg anti-actin was then added. The antibody-antigen (lymphocyte lysate) mixture was then incubated for 30 min at 4° C. with end-over-end shaking and 30 μl of 10% protein A/G conjugated agarose beads were then added and incubation continued for 2 hours. The immunocomplexes were then pelleted by centrifugation, washed twice with PBS and then solubilized by boiling in sample preparation buffer for 5 minutes. The solubilized anti-FLNA and anti-Aβ$_{42}$/actin immunoprecipitates were sized-fractionated respectively on 7.5% and 10% SDS-PAGE, electrophoretically transferred to nitrocellulose membranes and the levels of α7nAChR, TLR4 and β-actin were determined by Western blotting. The immunoreactive protein bands were detected using a chemiluminescent method and visualized by exposure to x-ray film. The protein bands were quantified by densitometry.

The results of this study are shown in FIG. 21, with data being expressed as the ratios of optical densities of α7nAChR to FLNA (α7nAChR/FLNA complexes), TLR4 to FLNA (TLR4/FLNA complexes) or α7nAChR to β-actin (α7nAChR/Aβ$_{42}$ complexes). The effect of C0105 is realized by comparing the levels of α7nAChR/FLNA, TLR4/FLNA, α7nAChR/Aβ$_{42}$ complex in C0105- and Kreb's-Ringer-treated samples from each test subject and expressed as % inhibition.

The quantitative figure (FIG. 21E) summarized the data from 10 YCI controls and 20 AD subjects. Whereas C0105 robustly and significantly reduces the levels of all three complexes from AD patients by approximately 50% (p<0.00001), Compound C0105 has no discernible effect on YCI controls. These data again illustrate that Compound C0105 is an efficacious AD therapeutic agent and importantly, the effect of Compound C0105 on these three protein-protein complexes in lymphocytes can be used as biomarkers for AD pathology diagnosis and tracking AD treatment efficacy.

The foregoing description and the examples are intended as illustrative and are not to be taken as limiting. Still other variations within the spirit and scope of this invention are possible and will readily present themselves to those skilled in the art.

The invention claimed is:
1. A method of therapeutic treatment of a living patient believed to have Alzheimer's disease (AD) comprising the steps of:
   a) treating the patient with a therapeutic composition containing a FLNA-binding effective amount of a compound of Series C-2 that binds to the FLNA peptide of SEQ ID NO: 1, or a pharmaceutically acceptable salt of that compound, wherein said compound of Series C-2 corresponds in structure to the Formula A below:

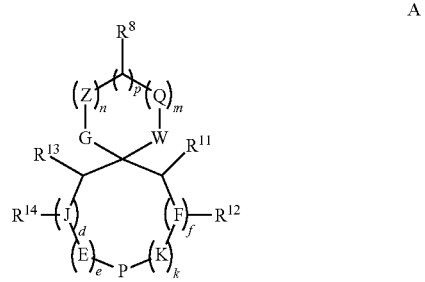

A wherein
   Q is CHR$^9$ or C(O), Z is CHR$^{10}$ or C(O), and only one of Q and Z is C(O);
   each of m and n and p is zero or one and the sum of m+n+p is 2 or 3;
   each of G, P and W is selected from the group consisting of NR$^{20}$, NR$^2$, NR$^7$, S and O, where R$^7$ and R$^2$ are the same or different and are H, C(H)$_v$(D)$_h$ where each of v and h is 0, 1, 2 or 3 and v+h =3, C(H)$_q$(D)$_r$-aliphatic C$_1$-C$_{11}$ hydrocarbyl where each of q and r is 0, 1, or 2 and q+r =0, 1 or 2, and R$^{20}$ is X-circle A-R$^1$ as defined hereinafter;
   each of d, e, f and k is either zero or one and the sum of (d+e+f+k)=2;
   D and F are the same or different and are CH or CD;
   E and K are the same or different and are CH$_2$, CHD or CD$_2$;
   X is SO$_2$, C(O), CH$_2$, CD$_2$, OC(O), NHC(NH), NHC(S) or NHC(O);
   circle A is an aromatic or heteroaromatic ring system that contains a single ring or two fused rings;
   R$^1$ is H or represents up to three substituents, R$^{1a}$, R$^{1b}$, and R$^{1c}$, that themselves can be the same or different, wherein each of those three groups, R$^{1a\text{-}c}$, is separately selected from the group consisting of H, C$_1$-C$_6$ hydrocarbyl, C$_1$-C$_6$hydrocarbyloxy, C$_1$-C$_6$ hydrocarbyloxy-

SEQUENCE LISTING

<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: synthetic sequence

<400> SEQUENCE: 1

Val Ala Lys Gly Leu
1               5 carbonyl, trifluoromethyl, trifluoromethoxy, $C_1$-$C_7$ hydrocarboyl, hydroxy-, trifluoromethyl- or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate, carboxamide or sulfonamide, wherein the amido nitrogen in either amide group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl or heteroaryl group and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms;

$R^{11}$, $R^{12}$, $R^{13}$ and $R^{14}$ are all H or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D; and b) comparing the amount of one or more of a protein-protein complex of i) α7nAChR/FLNA, ii) TLR4/FLNA or iii) α7nAChR/Aβ present in a lymphocyte preparation from the blood of said living patient obtained before and after said treatment, wherein a later determined amount that is significantly less than an earlier determined amount indicates that the therapeutic treatment is effective in providing an improvement in the patient's disease state.

2. The method according to claim 1, wherein each of G and W is selected from the group consisting of $NR^{20}$, $NR^7$, S and O.

3. The method according to claim 1, wherein $R^2$ of the depicted $NR^2$ is other than —$S(O)_2C_1$-$C_3$-hydrocarbyl when (a) the sum of m+n+p is 2 and the Q or Z present is $CH_2$, (b) the G or W that is not $NR^{20}$ is O, and (c) $R^{20}$ is —$S(O)_2$phenyl-$R^1$, where $R^1$ is H, $C_1$-$C_3$-hydrocarbyl or halogen.

4. The method according to claim 1, wherein said compound has a structure selected from the group consisting of one or more of

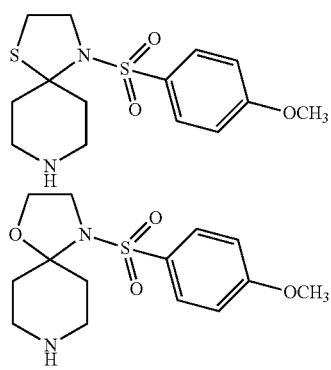

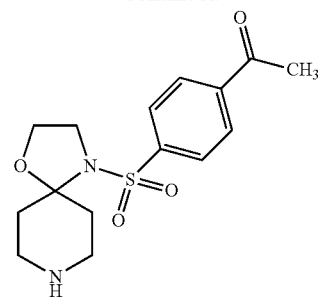

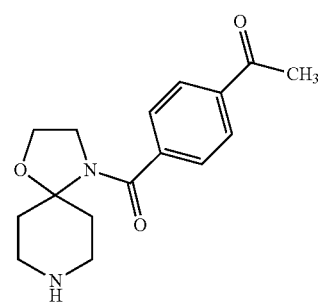

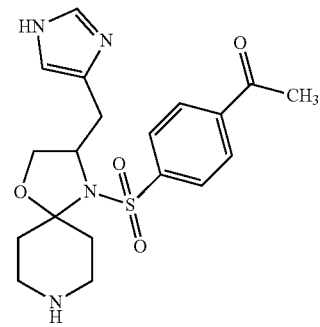

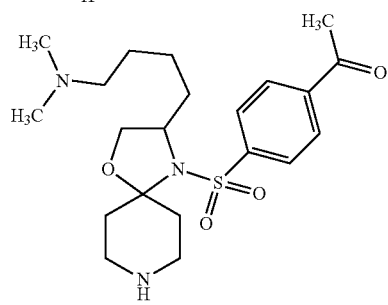

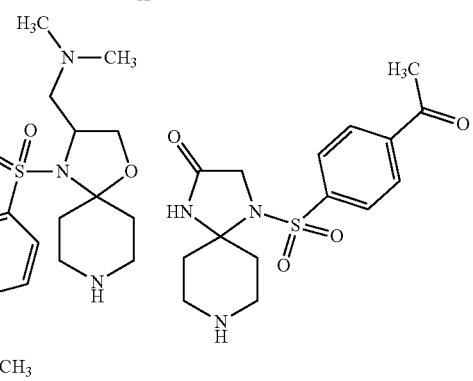

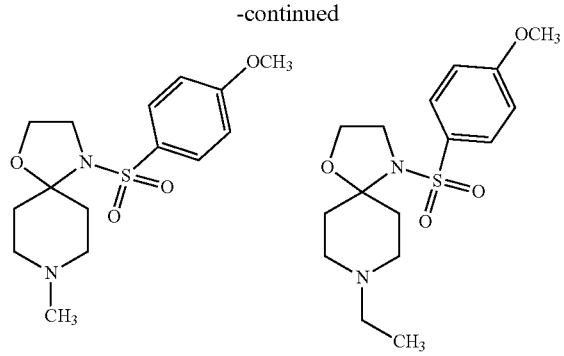
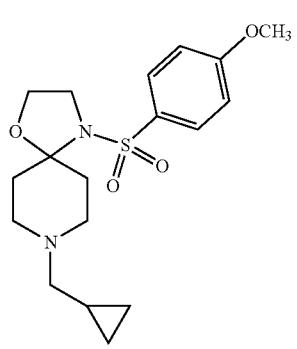
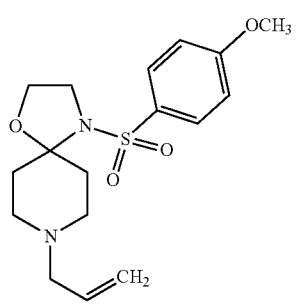
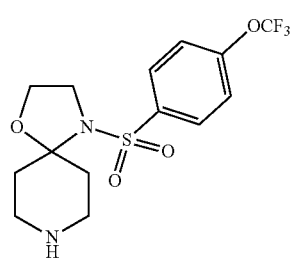
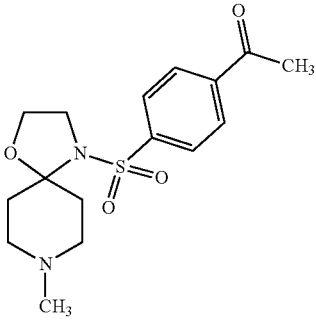
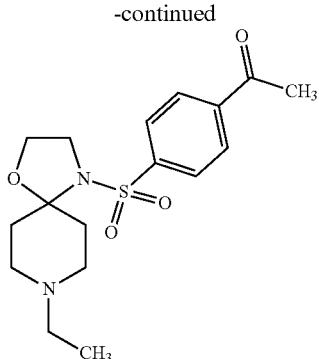
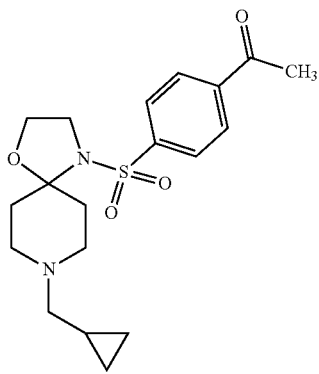
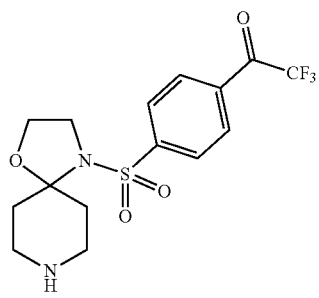
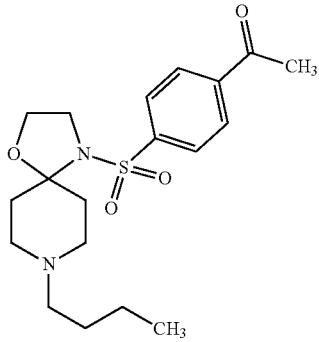
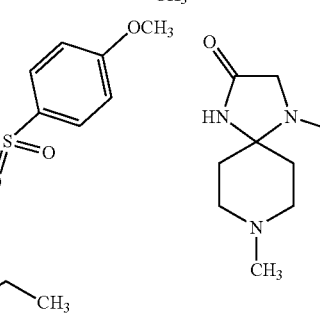

201
-continued
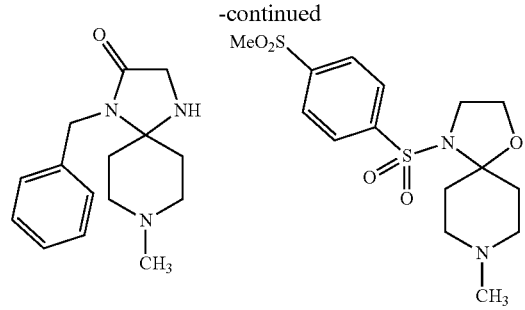
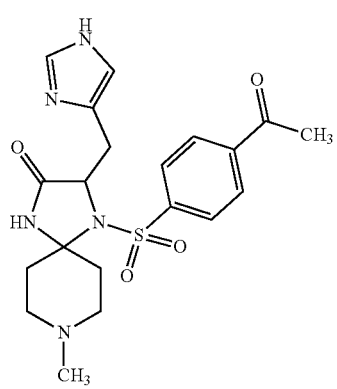
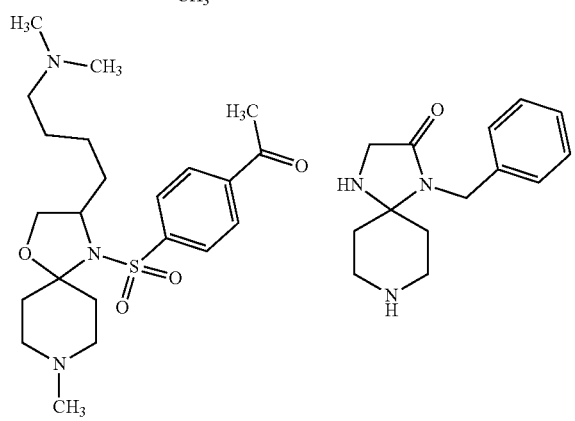
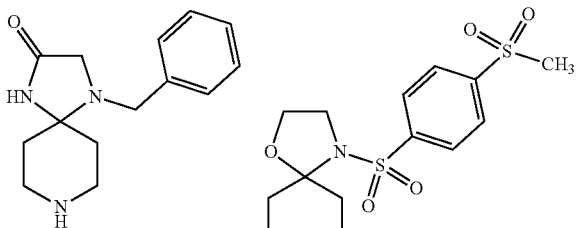
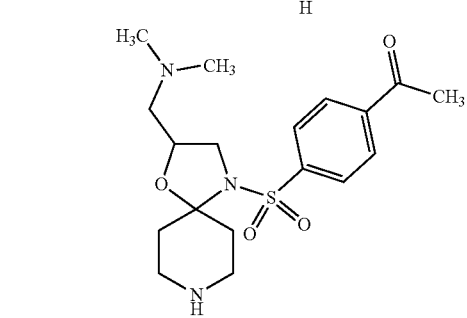
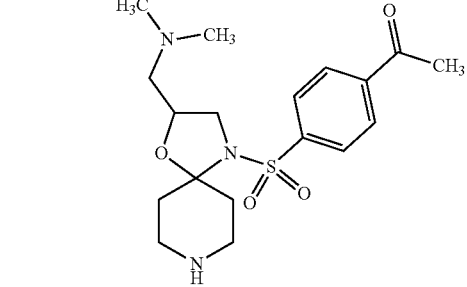
202
-continued
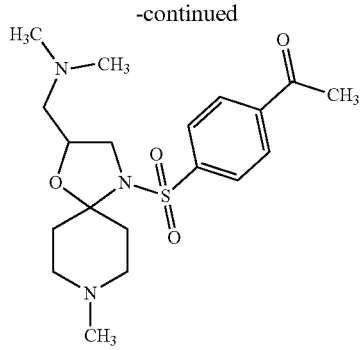
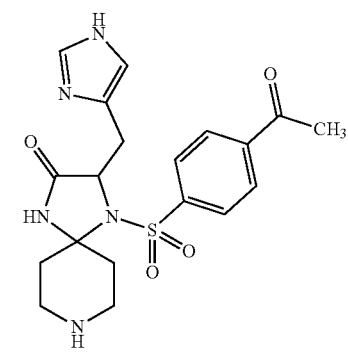
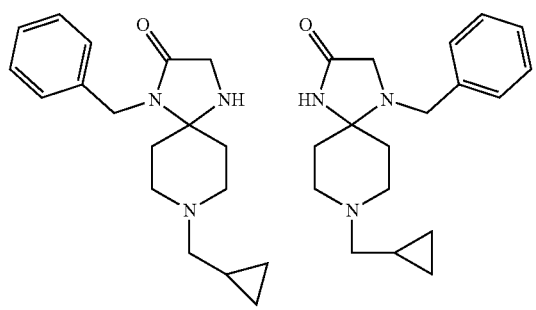
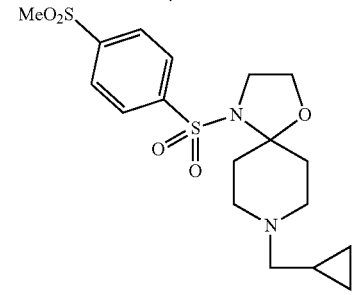
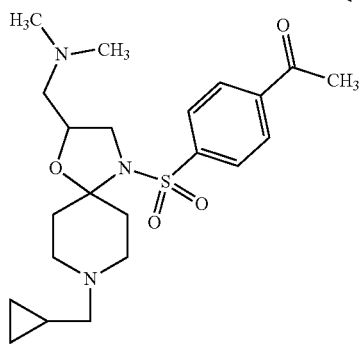

-continued
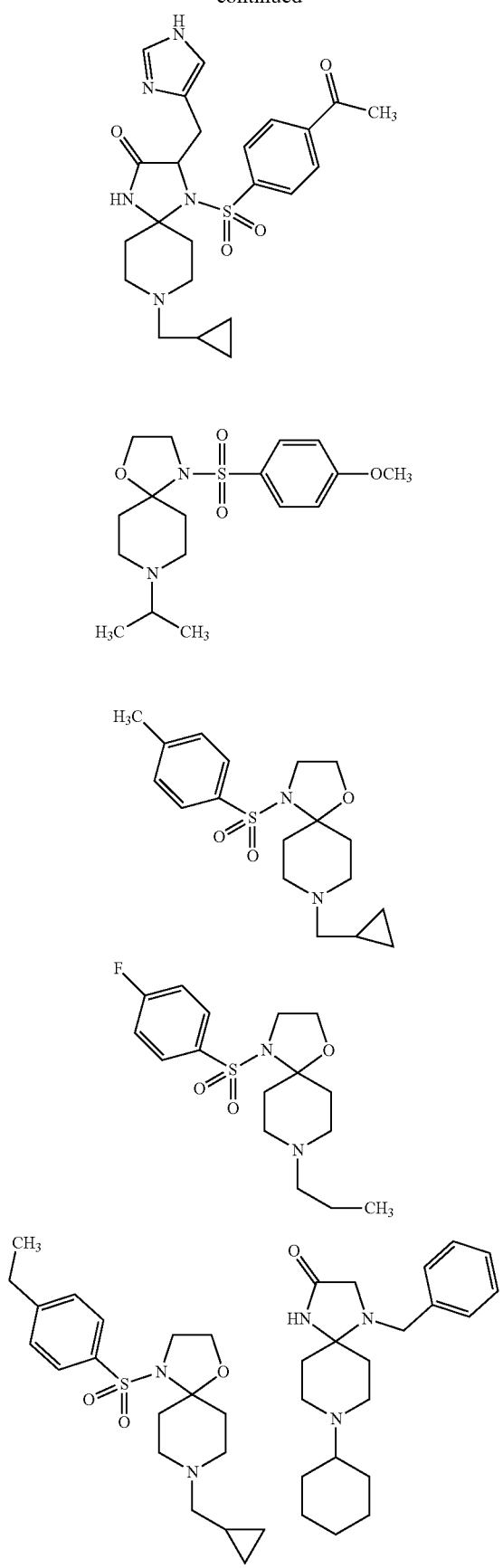
-continued
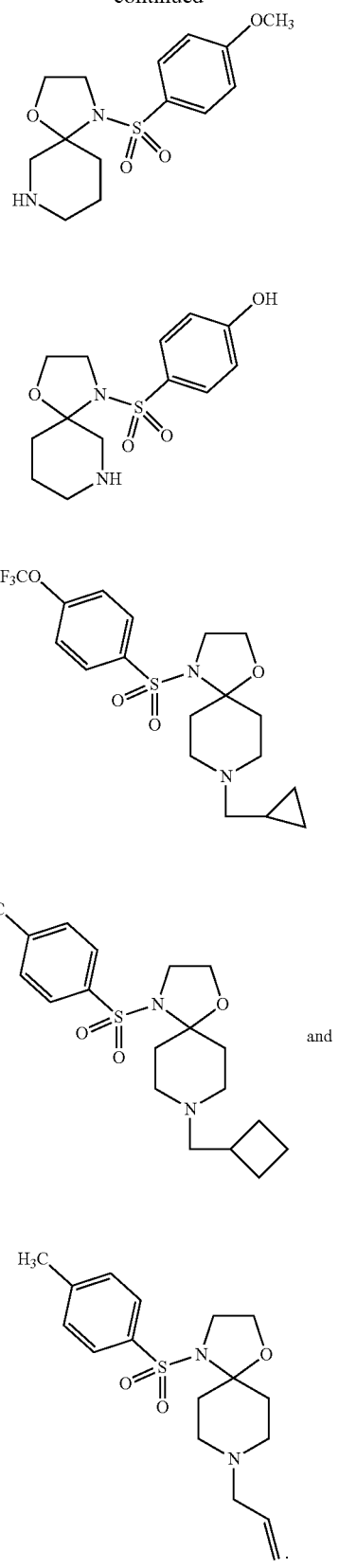
and
5. The method according to claim 1, wherein said compound has the structure

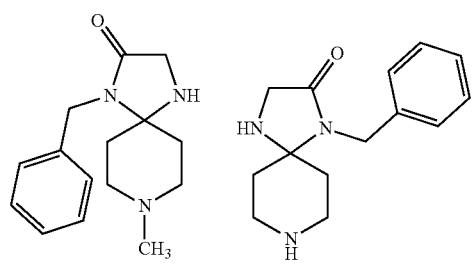
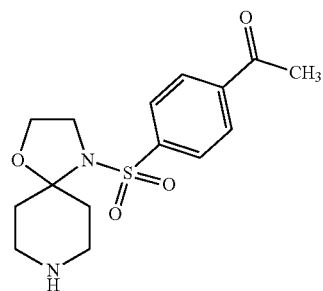
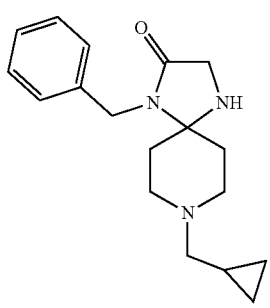
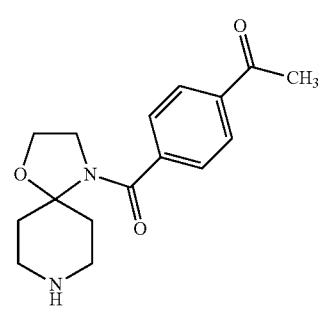
6. The method according to claim 1, wherein d is zero when f is zero.
7. The method according to claim 6, wherein the sum of m+n+p is 2.
8. The method according to claim 7, wherein said compound has a structure selected from the group consisting of one or more of
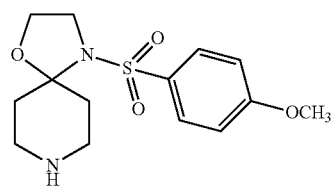
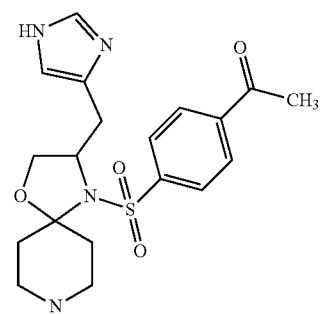
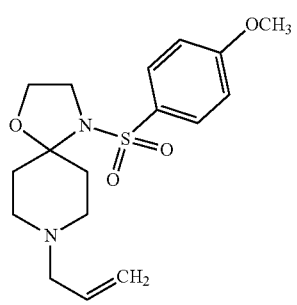
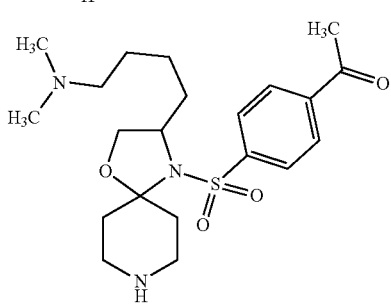
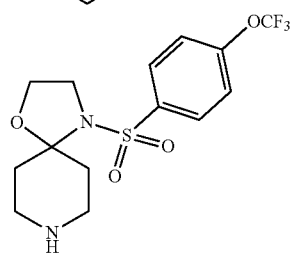
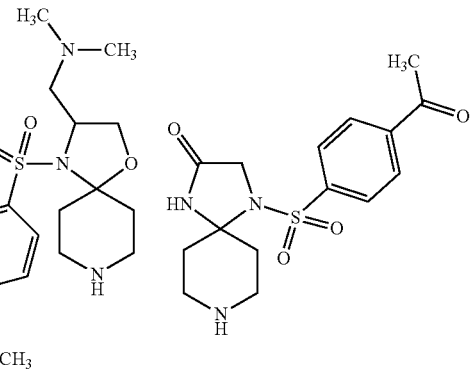

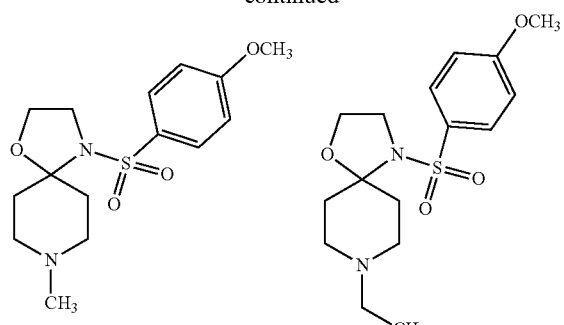
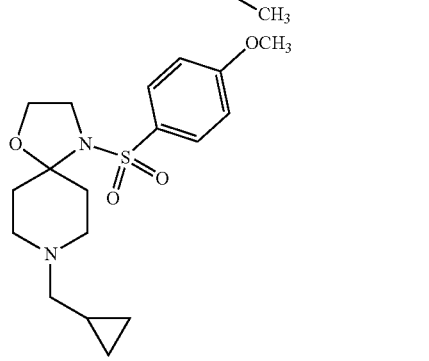
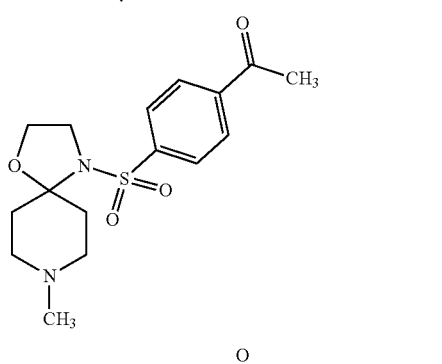
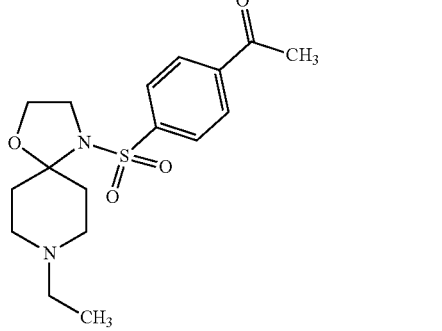
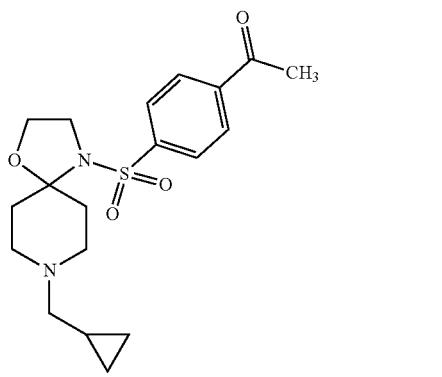
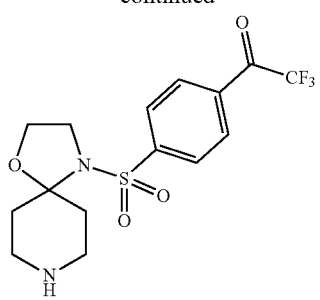
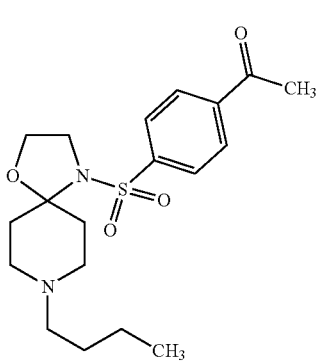
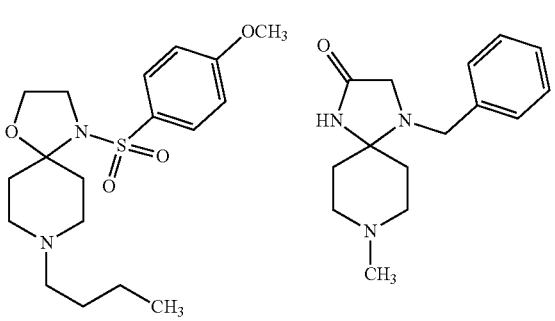
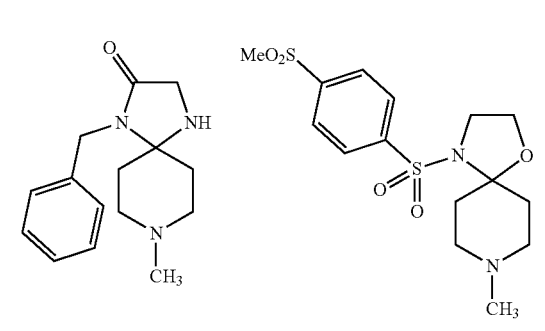
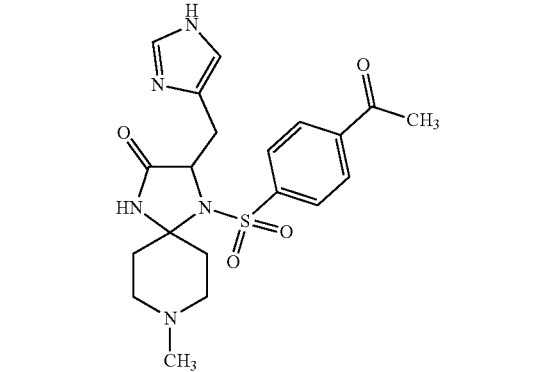

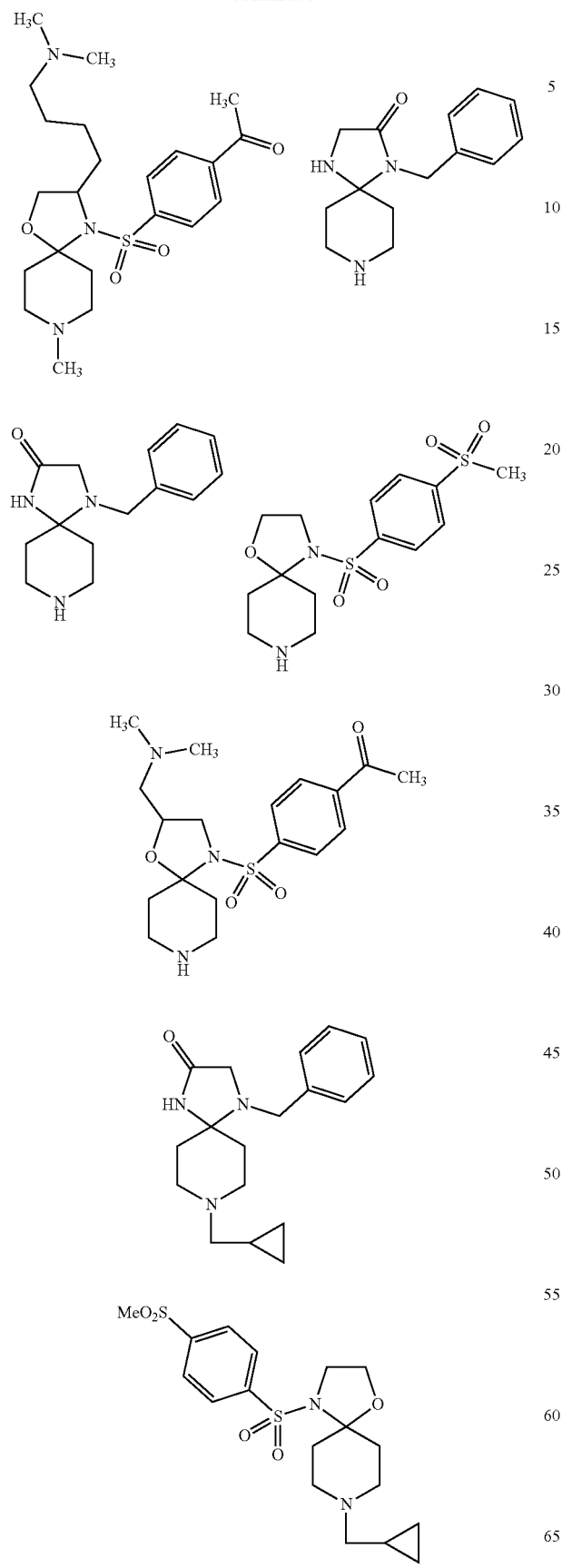
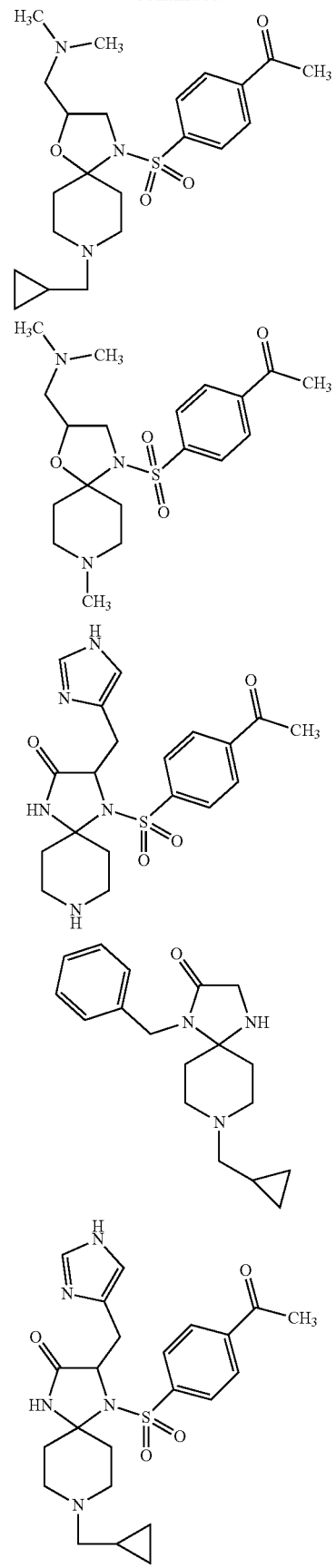

211
-continued
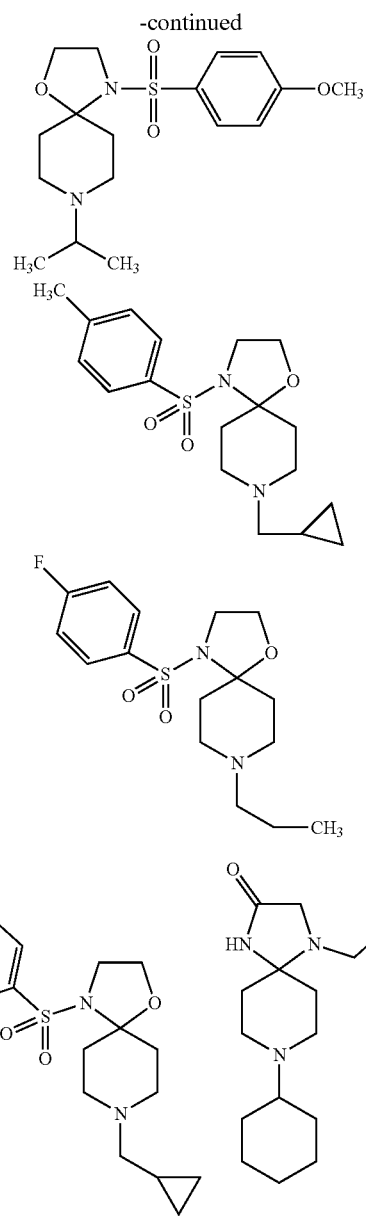
212
-continued
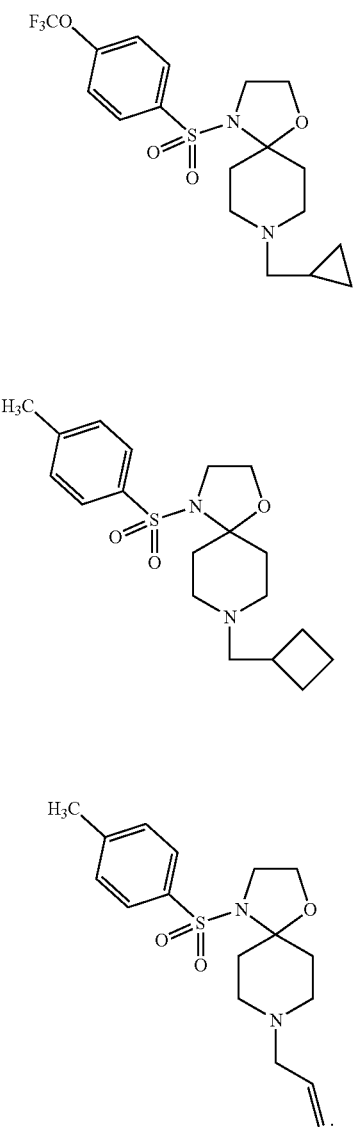
* * * * *

UNITED STATES PATENT AND TRADEMARK OFFICE
CERTIFICATE OF CORRECTION

PATENT NO. : 10,222,368 B2
APPLICATION NO. : 15/167370
DATED : March 5, 2019
INVENTOR(S) : Hoau-Yan Wang and Lindsay Burns Barbier Page 1 of 1

It is certified that error appears in the above-identified patent and that said Letters Patent is hereby corrected as shown below:

On the Title Page

Item (60), should read:
(60) Provisional application No. 61/789,180, filed on Mar. 15, 2013, provisional application No. 61/671,445, filed on Jul. 13, 2012.

Signed and Sealed this
Twenty-fourth Day of May, 2022

Katherine Kelly Vidal
*Director of the United States Patent and Trademark Office*